(12) United States Patent
Albrecht et al.

(10) Patent No.: US 11,912,701 B2
(45) Date of Patent: Feb. 27, 2024

(54) PROTEIN KINASE INHIBITORS FOR PROMOTING LIVER REGENERATION OR REDUCING OR PREVENTING HEPATOCYTE DEATH

(71) Applicant: HEPAREGENIX GMBH, Tübingen (DE)

(72) Inventors: Wolfgang Albrecht, Ulm (DE); Stefan Laufer, Tübingen (DE); Roland Selig, Ulm (DE); Phillip Klövekorn, Pliezhausen (DE); Bent Präfke, Tübingen (DE)

(73) Assignee: HepaRegeniX GmbH, Tübingen (DE)

( * ) Notice: Subject to any disclaimer, the term of this patent is extended or adjusted under 35 U.S.C. 154(b) by 319 days.

(21) Appl. No.: 17/260,519

(22) PCT Filed: Jul. 16, 2019

(86) PCT No.: PCT/EP2019/069150
§ 371 (c)(1),
(2) Date: Jan. 14, 2021

(87) PCT Pub. No.: WO2020/016243
PCT Pub. Date: Jan. 23, 2020

(65) Prior Publication Data
US 2022/0281864 A1   Sep. 8, 2022

(30) Foreign Application Priority Data
Jul. 16, 2018   (EP) .................................... 18183712

(51) Int. Cl.
*C07D 471/04*   (2006.01)
(52) U.S. Cl.
CPC .................. *C07D 471/04* (2013.01)
(58) Field of Classification Search
CPC .................................................. C07D 471/04
See application file for complete search history.

(56) References Cited

U.S. PATENT DOCUMENTS

| | | |
|---|---|---|
| 6,514,981 B1 | 2/2003 | Tang et al. |
| 11,040,027 B2 | 6/2021 | Albrecht et al. |
| 2020/0399241 A1 | 12/2020 | Scheidt et al. |
| 2021/0078995 A1 | 3/2021 | Praefke et al. |
| 2021/0261545 A1 | 8/2021 | Juchum et al. |
| 2022/0281864 A1 | 9/2022 | Albrecht et al. |
| 2022/0340561 A1 | 10/2022 | Pfaffenrot et al. |
| 2023/0088395 A1 | 3/2023 | Selig et al. |

FOREIGN PATENT DOCUMENTS

| | | |
|---|---|---|
| CA | 3075477 A1 | 2/2019 |
| CN | 112778311 A | 5/2021 |
| CN | 113072497 A | 7/2021 |
| EP | 2161271 A1 | 3/2010 |
| FR | 2876377 A1 | 4/2006 |
| JP | 2006282745 A | 10/2006 |
| RU | 2678455 C1 | 1/2019 |
| WO | 2003035621 A1 | 5/2003 |
| WO | 2003037898 A1 | 5/2003 |
| WO | 2004058764 A1 | 7/2004 |
| WO | 2007002325 A1 | 1/2007 |
| WO | 2007002433 A1 | 1/2007 |
| WO | 2007013896 A2 | 2/2007 |
| WO | 2008063888 A2 | 5/2008 |
| WO | 2008064255 A2 | 5/2008 |
| WO | 2008064265 A2 | 5/2008 |
| WO | 2008079903 A1 | 7/2008 |
| WO | 2008079906 A1 | 7/2008 |
| WO | 2010104945 A1 | 9/2010 |
| WO | 2010111527 A1 | 9/2010 |
| WO | 2010129567 A1 | 11/2010 |
| WO | 2010129570 A1 | 11/2010 |
| WO | 2011047432 A1 | 4/2011 |
| WO | 2011079133 A2 | 6/2011 |
| WO | 2012109075 A1 | 8/2012 |
| WO | 2012129562 A2 | 9/2012 |
| WO | 2012135631 A1 | 10/2012 |
| WO | 2012136859 A1 | 10/2012 |
| WO | 2013032951 A1 | 3/2013 |
| WO | 2014035846 A2 | 3/2014 |
| WO | 2014047648 A1 | 3/2014 |

(Continued)

OTHER PUBLICATIONS

Vemurafenib, PubChem CID 42611257. https://pubchem.ncbi.nlm.nih.gov/compound/Vemurafenib. Accessed Dec. 13, 2022, create date Jun. 22, 2009 (Year: 2009).*

(Continued)

*Primary Examiner* — Michael Barker
*Assistant Examiner* — Jed A Kucharczk
(74) *Attorney, Agent, or Firm* — Viksnins Harris Padys Malen LLP

(57) ABSTRACT

The invention relates to compounds of formula (I) which are inhibitors of MKK4 (mitogen-activated protein kinase kinase 4) and their use in promoting liver regeneration or reducing or preventing hepatocyte death. The compounds selectively inhibit protein kinase MKK4 over protein kinases JNK and MKK7. (I), wherein $R^x$, $R^y$, $R^z$ and $R^{zz}$ are selected from: a) $R^x$ and $R^y$ are F and $R^z$ and $R^{zz}$ are H; b) $R^x$, $R^y$ and $R^{zz}$ are independently halogen and $R^z$ is H; c) $R^x$ $R^z$ and $R^{zz}$ are independently halogen and $R^y$ is H; and d) $R^x$ $R^y$ and $R^z$ are independently halogen and $R^{zz}$ is H.

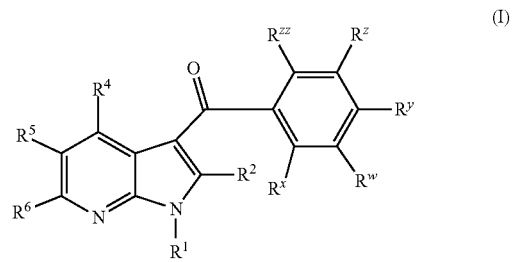

18 Claims, No Drawings

(56) References Cited

FOREIGN PATENT DOCUMENTS

| WO | 2014194127 A1 | 12/2014 |
|---|---|---|
| WO | 2017066193 A1 | 4/2017 |
| WO | 2018134254 A1 | 7/2018 |
| WO | 2019031990 A1 | 2/2019 |
| WO | 2019149738 A1 | 8/2019 |
| WO | 2019243315 A1 | 12/2019 |
| WO | 2020051207 A2 | 3/2020 |
| WO | 2020123675 A1 | 6/2020 |
| WO | 2021018820 A1 | 2/2021 |
| WO | 2021144287 A1 | 7/2021 |

OTHER PUBLICATIONS

Wermuth, Molecular Variations Based on Isosteric Replacements, The Practice of Medicinal Chemistry, (1996), 203-237 (Year: 1996).*

Ibrahim et al., "Case History: Vemurafenib, a Potent, Selective, and First-in-Class Inhibitor of Mutant BRAF for the Treatment of Metastatic Melanoma" Annual Reports in Medicinal Chemistry, vol. 48, Chapter 26, pp. 435-449, 2013 (Year: 2013).*

Chem Abstract, Registry No. 1246614-25-4, 1 page (Oct. 20, 2010).

U.S. Appl. No. 16/965,912, 2021-0078995.

U.S. Appl. No. 17/254,071, 2021-0261545.

U.S. Appl. No. 16/478,006, U.S. Pat. No. 11,040,027.

Deibler, K, et al., "A Chemical Probe Strategy for Interrogating Inhibitor Selectivity Across the MEK Kinase Family", ACS Chem Biol 12, 1245-1256, Supporting Information, 82 pages (2017).

Deibler, K, et al., "Synthesis and Biological Evaluation of 3-Arylindazoles as Selective MEK4 Inhibitors", ChemMedChem 14, 615-620 (2019).

Erion, M, et al., "Liver-Targeted Drug Delivery Using HepDirect1 Prodrugs", Journal of Pharmacology and Experimental Therapeutics 312(2), 554-560 (2005).

Grueninger, F, et al., "Novel screening cascade identifies MKK4 as key kinase regulating Tau phosphorylation at Ser422", Mol Cell Biochem 357, 199-207 (2011).

Hu, G, et al., "MicroRNA-145 attenuates TNF-α-driven cartilage matrix degradation in osteoarthritis via direct suppression of MKK4", Cell Death and Disease 8, e3140, 13 pages (2017).

Kim, D, et al., "Novel Small Molecule Raf Kinase Inhibitors for Targeted Cancer Therapeutics", Arch Pharm Res 35(4), 605-612 (2012).

Krishna, S, et al., "A Fluorescence-Based Thermal Shift Assay Identifies Inhibitors of Mitogen Activated Protein Kinase Kinase 4", PLoS One 8(12), e81504, 11 pages (2013).

Ogura, M, et al., "Prenylated quinolinecarboxylic acid derivative prevents neuronal cell death through inhibition of MKK4", Biochemical Pharmacology 1-37, doi: https://doi.org/10.1016/j.bcp.2018.10.008 (2018).

Patent Cooperation Treaty, International Searching Authority, Search Report and Written Opinion for PCT/EP2019/069150, 10 pages, dated Sep. 18, 2019.

Schneider, C, et al., "Synthesis of 6-Substituted Pyrido[2,3-b]indoles by Electrophilic Substitution", Synlett 14, 2237-2241 (2007).

Vin, H, et al., "BRAF inhibitors suppress apoptosis through off-target inhibition of JNK signaling", eLife 2, e00969, DOI: 10.755/4/eLife.00969, 1-25 (2013).

Vin, H, et al., "BRAF inhibitors suppress apoptosis through off-target inhibition of JNK signaling", eLife 2, e00969, DOI: 10.7554/eLife.00969, 1-25, Supporting Information—Figures and Supplements (2013).

Wadsworth, A, et al., "A review of the synthesis of a-carbolines", European Journal of Medicinal Chemistry 97, 816-829 (2015).

Willenbring, H, et al., "A Therapy for Liver Failure Found in the JNK Yard", Cell 153, 283-284 (2013).

Wuestefeld, T, et al., "A Direct in Vivo RNAi Screen Identifies MKK4 as a Key Regulator of Liver Regeneration", Cell 153, 389-401 (2013).

Merriam-Webster, "Prevent", https:/www.merriam-webster.com/dictionary/prevent, 2022.

U.S. Appl. No. 17/630,105, 2022-0340561.

U.S. Appl. No. 17/792,685.

Asaoka, Y, "Diverse physiological functions of JNK signaling networks during early embryogenesis", Comparative Physiology and Biochemistry 30 (2), 59-67 (2013). [English Abstract].

* cited by examiner

PROTEIN KINASE INHIBITORS FOR PROMOTING LIVER REGENERATION OR REDUCING OR PREVENTING HEPATOCYTE DEATH

The present invention relates to protein kinase inhibitors which inhibit mitogen-activated protein kinase kinase 4 (MKK4) and in particular, selectively inhibit MKK4 over protein kinases JNK1 and MKK7.

BACKGROUND OF THE INVENTION

Liver diseases may be caused by infection, injury, exposure to toxic compounds, like alcohol or drugs, autoimmune processes, genetic defects, and other factors. Liver has a remarkable regenerative capacity which, however, may be impaired in disease state and may therefore be insufficient to compensate for the loss of hepatocytes and organ function.

WO 2007/002433 describes compounds which are protein kinase inhibitors useful to treat diseases and conditions associated with aberrant activity of protein kinases. These compounds are inhibitors of Raf protein kinase, in particular B-Raf and c-Raf and mutations thereof and are therefore useful for cancer treatment. Further, they are said to inhibit a large variety of other protein kinases, among them c-Jun N-terminal kinases (JNK) and in particular JNK1. WO 2010/002325 has a similar disclosure and WO 2012/109075 and WO 2014/194127 disclose modified compounds having Raf protein kinase inhibiting activity. H. Vin et al. refer to two compounds of WO 2007/002433 as B-Raf inhibitors that suppress apoptosis through off-target inhibition of JNK signaling. WO 2010/111527 describes pyrazolo[3,4-b]pyridine compounds which are protein kinase inhibitors useful to treat a Raf protein kinase mediated disease or condition, like cancer. Further, they are said to inhibit a large variety of other protein kinases, among them c-Jun N-terminal kinases (JNK) and in particular JNK1. WO 2012/136859 discloses some compounds which are described as inhibitors of mitogen-activated protein kinase kinase 4 (MKK4) and as being useful in the treatment of liver failure, for the protection of hepatocytes against apoptosis and for the regeneration of hepatocytes. Wuestefeld et al. (Cell 153:389-401, 2013) describe a functional genetic approach for the identification of gene targets that can be exploited to increase the regenerative capacity of hepatocytes. In particular, Wuestefeld et al. identify protein kinase MKK4 as a key regulator of liver regeneration and report that MKK4 suppression increased hepatocyte regeneration via compensatory upregulation of MKK7 and a JNK1-dependent activation of ATF2 and ELK1. On the basis of the findings of the prior art it has been concluded that MKK4 and JNK1 inhibitors could be useful to treat JNK1-mediated diseases.

However, it has been recognized in clinical treatments that treatment of liver diseases with such compounds failed.

SUMMARY OF THE INVENTION

The problem underlying the invention was to provide useful compounds that are MKK4 inhibitors, in particular MKK4 inhibitors which selectively inhibit MKK4 over MKK7 and JNK1. A further problem was to provide compounds that are MKK4 inhibitors which selectively inhibit MKK4 over MKK7 and JNK1, and which are useful for treating liver diseases and especially for promoting liver regeneration or reducing or preventing hepatocyte death.

This problem was solved by providing the compounds of formula (I).

Thus, the invention relates to the following embodiments:
1. A compound having formula (I)

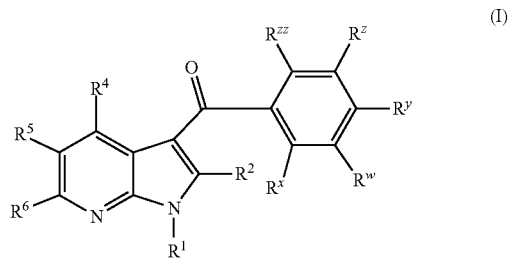

wherein
$R^1$ is H or alkyl;
$R^2$ is H or alkyl;
$R^4$ is H, halogen, CN or alkyl;
$R^6$ is H, alkoxy or alkyl;
$R^w$ is —$NR^{10}SO_2R^{12}$;
$R^{10}$ is H, alkyl, or phenylalkyl;
$R^{12}$ is selected from
  H,
  alkyl, wherein the alkyl group is optionally substituted with 1 or 2 hydroxy groups or with an acetyl group,
  haloalkyl or
  phenylalkyl, wherein the phenyl group is optionally substituted with 1 or 2 groups independently selected from alkyl and halogen;
$R^x$, $R^y$, $R^z$ and $R^{zz}$ are selected from:
a) $R^x$ and $R^y$ are F and $R^z$ and $R^{zz}$ are H;
b) $R^x$, $R^y$ and $R^{zz}$ are independently halogen and $R^z$ is H;
c) $R^x$, $R^z$ and $R^{zz}$ are independently halogen and $R^y$ is H; and
d) $R^x$, $R^y$ and $R^z$ are independently halogen and $R^{zz}$ is H;
$R^5$ is selected from
  (a) phenyl which is substituted with 1, 2 or 3 groups independently selected from
    halogen,
    alkyl,
    alkoxy,
    alkoxy wherein the alkyl group is substituted with 1, 2 or 3 hydroxy groups,
    alkoxy wherein the alkyl group is substituted with 1, 2 or 3 halogen atoms,
    haloalkyl,
    hydroxy,
    —$SO_2NR^{10}R^{10}$,
    —$CO_2R^{10}$,
    —CN,
    —$SF_5$,
    —($NR^{10}$=)S(=O)-alkyl (S-alkylsulfonimidoyl),
    1H- or 2H-tetrazolyl,
    —$SO_2$alkyl, wherein the alkyl group is optionally substituted with 1, 2 or 3 halogen atoms,
    —SOalkyl,
    alkylsulfanyl, wherein the alkyl group is optionally substituted with —$NR^{10}R^{10}$ or 1, 2 or 3 halogen atoms,
    —POdi(alkyl),
    —$NO_2$,
    —$NR^{10}R^{10}$, $R^{10}R^{10}N-CO-$,
—$NR^{10}CO$alkyl,
hydroxyalkyl-ONH—CO—,
cycloalkyl,
a non-aromatic heterocyclic 5- or 6-membered monocyclic group having 1, 2 or 3 heteroatoms independently selected from O, N and S which group is optionally substituted with 1 or 2 groups independently selected from alkyl and $C_2$-$C_5$-alkanoyl, and
alkoxy wherein the alkyl group is substituted with a non-aromatic heterocyclic 5- or 6-membered monocyclic group having 1, 2 or 3 heteroatoms independently selected from O, N and S which monocyclic group is optionally substituted with 1 or 2 groups independently selected from alkyl and halogen;
(b) naphthyl;
(c) a heteroaromatic 5- or 6-membered monocyclic group having 1, or 2 heteroatoms independently selected from O, N and S, wherein the heteroaromatic group is optionally substituted with 1, 2 or 3 groups independently selected from
alkyl,
haloalkyl,
cycloalkyl,
—$NR^{10}R^{10}$,
halogen,
hydroxy,
alkoxy, which is optionally substituted with —$NR^{10}R^{10}$,
—CN,
alkenyl,
alkinyl,
$R^{10}R^{10}N-CO-$,
—$SO_2NR^{10}R^{10}$,
—$SO_2$alkyl,
—$(NR^{10}=)S(=O)$-alkyl,
cycloalkyl-$NR^{10}$—,
alkyl-$NR^{10}$—, wherein the alkyl group is substituted with hydroxy or alkoxy,
alkylsulfanyl,
benzimidazolyl,
and
a non-aromatic heterocyclic 4-, 5- or 6-membered monocyclic group having 1 or 2 heteroatoms independently selected from O, N, S, SO and $SO_2$, which heterocyclic group is optionally substituted with alkyl, hydroxyalkyl or hydroxy,
(d) $C_2$-$C_5$-alkinyl;
(e) $C_2$-$C_5$-alkenyl;
(f) halogen;
(g) cycloalkyl;
(h) phenyl which is fused with a heteroaromatic 5- or 6-membered monocyclic group having 1, 2 or 3 heteroatoms independently selected from O, N and S;
i) 1,3-dialkylyl-1-oxido-1l4-benzo[e][1,2]thiazin;
j) a saturated or unsaturated non-aromatic heterocyclic 4-, 5- or 6-membered monocyclic group having 1, 2 or 3 heteroatoms independently selected from O, N, S, SO and $SO_2$ which heterocyclic group is optionally substituted with 1 or 2 groups independently selected from alkyl, $C_2$-$C_5$-alkanoyl, benzoyl, hydroxy, —$CO_2R^{10}$ or carbonyl (one of the ring carbon atoms is a >C=O group);
k) oxetanamino;
and the pharmaceutically acceptable salts, solvates and optical isomers thereof.

2. A compound of embodiment 1, wherein
$R^1$ is H or alkyl;
$R^2$ is H or alkyl;
$R^4$ is H, or alkyl;
$R^6$ is H, or alkyl;
$R^w$ is —$NR^{10}SO_2R^{12}$;
$R^{10}$ is H, alkyl, or phenylalkyl;
$R^{12}$ is H, alkyl, haloalkyl or phenylalkyl, wherein the phenyl group is optionally substituted with 1 or 2 groups independently selected from alkyl and halogen;
$R^x$, $R^y$, $R^z$ and $R^{zz}$ are selected from:
a) $R^x$ and $R^y$ are F and $R^z$ and $R^{zz}$ are H;
b) $R^x$, $R^y$ and $R^{zz}$ are independently halogen and $R^z$ is H;
c) $R^x$, $R^z$ and $R^{zz}$ are independently halogen and $R^y$ is H; and
d) $R^x$, $R^y$ and $R^z$ are independently halogen and $R^{zz}$ is H;
$R^5$ is selected from
(a) phenyl which is substituted with 1, 2 or 3 groups independently selected from
halogen,
alkyl,
alkoxy,
alkoxy wherein the alkyl group is substituted with 1, 2 or 3 hydroxy groups,
haloalkyl,
hydroxy,
—$SO_2NR^{10}R^{10}$,
—$CO_2R^{10}$,
—CN.
—$SF_5$,
—$(NR^{10}=)S(=O)$-alkyl (S-alkylsulfonimidoyl), and
1H- or 2H-tetrazolyl;
(b) naphthyl;
(c) a heteroaromatic 5- or 6-membered monocyclic group having 1 or 2 heteroatoms independently selected from O, N and S, wherein the heteroaromatic group is optionally substituted with 1, 2 or 3 groups independently selected from
alkyl,
haloalkyl,
cycloalkyl,
—$NR^{10}R^{10}$,
halogen,
hydroxy,
alkoxy, which is optionally substituted with —$NR^{10}R^{10}$,
—CN,
alkenyl,
alkinyl,
$R^{10}R^{10}N-CO-$,
alkyl-$S(=O)(=NR^{10})$—,
cycloalkyl-$NR^{10}$—,
alkyl-$NR^{10}$—, wherein the alkyl group is substituted with hydroxy or alkoxy,
alkylsulfanyl,
benzimidazolyl,
and
a non-aromatic heterocyclic 4-, 5- or 6-membered monocyclic group having 1 or 2 heteroatoms independently selected from O, and N, which heterocyclic group is optionally substituted with alkyl, hydroxyalkyl or hydroxy,d) $C_2$-$C_5$-alkinyl,
(e) $C_2$-$C_5$-alkenyl
(f) halogen, and
(g) cycloalkyl
and the pharmaceutically acceptable salts, solvates and optical isomers thereof.

3. A compound of embodiment 2, wherein $R^5$ is selected from
   (a) phenyl which is substituted with 1, 2 or 3 groups independently selected from
      halogen,
      alkyl,
      alkoxy,
      alkoxy wherein the alkyl group is substituted with 1 or 2 hydroxy groups,
      hydroxy,
      —$SO_2NR^{10}R^{10}$,
      —$CO_2R^{10}$,
      —CN,
      —$SF_5$,
      —($NR^{10}$=)S(=O)-alkyl (S-alkylsulfonimidoyl), and
      1H- or 2H-tetrazolyl;
   (b) naphthyl;
   (c) a heteroaromatic 5- or 6-membered monocyclic group having 1 or 2 heteroatoms independently selected from O, N and S, wherein the heteroaromatic group is optionally substituted with 1, 2 or 3 groups independently selected from alkyl,
      haloalkyl,
      cycloalkyl,
      —$NR^{10}R^{10}$,
      halogen,
      alkoxy, which is optionally substituted with —$NR^{10}R^{10}$,
      —CN,
      alkenyl,
      alkinyl,
      $R^{10}R^{10}$N—CO—,
      alkyl-S(=O)(=$NR^{10}$)—,
      cycloalkyl-$NR^{10}$—,
      alkyl-$NR^{10}$—, wherein the alkyl group is substituted with hydroxy or alkoxy,
      alkylsulfanyl,
      benzimidazolyl,
      and
      a non-aromatic heterocyclic 4-, 5- or 6-membered monocyclic group having 1 or 2 heteroatoms independently selected from 0, and N, which heterocyclic group is optionally substituted with alkyl, hydroxyalkyl or hydroxy,
   (f) halogen, and
   (g) cycloalkyl,
   and the pharmaceutically acceptable salts, solvates and optical isomers thereof.
4. A compound of any one of embodiments 1 to 3, wherein, if $R^5$ is substituted with 1, 2 or 3 halogens, the halogen is independently selected from F or Cl,
   and the pharmaceutically acceptable salts, solvates and optical isomers thereof.
5. A compound of any one of embodiments 1 to 3, wherein $R^5$ is phenyl which is substituted with 1, 2 or 3 groups independently selected from
   halogen,
   alkyl,
   alkoxy,
   alkoxy wherein the alkyl group is substituted with 1 or 2 hydroxy groups,
   hydroxy,
   —$SO_2NR^{10}R^{10}$,
   —$CO_2R^{10}$,
   —CN,
   —$SF_5$,
   —($NR^{10}$=)S(=O)-alkyl (S-alkylsulfonimidoyl), and
   1H- or 2H-tetrazolyl.
6. A compound of any one of embodiments 1 to 3, wherein $R^5$ is a heteroaromatic 5- or 6-membered monocyclic group having 1 or 2 heteroatoms independently selected from O and N, wherein the heteroaromatic group is optionally substituted with 1, 2 or 3 groups independently selected from
   alkyl,
   haloalkyl,
   cycloalkyl,
   —$NR^{10}R^{10}$,
   halogen,
   alkoxy, which is optionally substituted with —$NR^{10}R^{10}$,
   —CN,
   alkenyl,
   alkinyl,
   $R^{10}R^{10}$N—CO—,
   alkyl-S(=O)(=$NR^{10}$)—,
   cycloalkyl-$NR^{10}$—,
   alkyl-$NR^{10}$—, wherein the alkyl group is substituted with hydroxy or alkoxy,
   alkylsulfanyl,
   benzimidazolyl,
   and
   a non-aromatic heterocyclic 4-, 5- or 6-membered monocyclic group having 1 or 2 heteroatoms independently selected from O, and N, which heterocyclic group is optionally substituted with alkyl, hydroxyalkyl or hydroxyl.
7. A compound of embodiment 6, wherein the heteroaromatic 5- or 6-membered monocyclic group is selected from pyrrolyl, pyrazolyl, triazolyl, thiadiazolyl, pyridyl, pyridazinyl, pyrimidinyl and pyrazinyl, which group is optionally substituted as defined in any one of embodiments 1 to 3 or 6 and in particular as defined in embodiment 6.
8. A compound of embodiment 7, wherein the heteroaromatic 5- or 6-membered monocyclic group is selected from pyridyl, pyridazinyl, pyrimidinyl and pyrazinyl which group is optionally substituted as defined in embodiment 6.
9. A compound of embodiment 8, wherein the heteroaromatic 5- or 6-membered monocyclic group is selected from pyridyl and pyrimidinyl which group is optionally substituted as defined in embodiment 6.
10. A compound of embodiment 9, wherein the heteroaromatic 5- or 6-membered monocyclic group is pyridyl which is optionally substituted with 1, 2 or 3 groups independently selected from halogen, in particular F or Cl, alkyl, alkoxy, haloalkyl, in particular $CF_3$, cycloalkyl, —$NR^{10}R^{10}$, cycloalkyl-$NR^{10}$—, alkenyl, in particular vinyl, and alkyl-S(=O)(=$NR^{10}$)—.
11. A compound of embodiment 9, wherein the heteroaromatic 5- or 6-membered monocyclic group is pyrimidinyl which is optionally substituted with 1 or 2 groups independently selected from
   alkyl,
   alkoxy which is optionally substituted with —$NR^{10}R^{10}$,
   halogen, in particular F or Cl,
   alkyl-$NR^{10}$—, wherein the alkyl group is substituted with hydroxy or alkoxy,
   —$NR^{10}R^{10}$,
   haloalkyl, in particular $CF_3$,
   cycloalkyl,
   alkenyl,
   —CN,
   alkylsulfanyl,

—NR$^{10}$R$^{10}$.

R$^{10}$R$^{10}$N—CO—, cycloalkyl-NR$^{10}$—, benzimidazolyl and a non-aromatic heterocyclic 4-, 5- or 6-membered monocyclic group having 1 or 2 heteroatoms independently selected from O, and N, which heterocyclic group is optionally substituted with alkyl, hydroxyalkyl or hydroxy.

12. A compound of embodiment 11, wherein the pyrimidinyl is substituted with a non-aromatic heterocyclic 4-, 5- or 6-membered monocyclic group selected from azetidinyl which is optionally substituted with hydroxy, pyrrolidinyl which is optionally substituted with hydroxy, piperidinyl, morpholinyl and piperazidinyl which is optionally substituted with alkyl, hydroxy or hydroxyalkyl.

13. A compound of embodiment 11, wherein the pyrimidinyl is substituted with cycloalkyl, in particular C$_3$-C$_6$-cycloalkyl.

14. A compound of embodiment 12 or 13, wherein the pyrimidinyl is bound in 5-position to the 1H-pyrrolo[2,3-b]pyridine and is substituted in 2-position.

15. A compound of embodiment 3, wherein R$^5$ is selected from C$_3$-C$_6$-cycloalkyl.

16. A compound of any one of the preceding embodiments, wherein R$^{12}$ is C$_1$-C$_4$-alkyl, C$_1$-C$_4$-haloalkyl, in particular —CH$_2$CH$_2$CF$_3$, or benzyl.

17. A compound of embodiment 12, wherein R$^{12}$ is C$_1$-C$_4$-alkyl and preferably methyl, ethyl, or propyl.

18. A compound of any one of the preceding embodiments having formula (Ia)

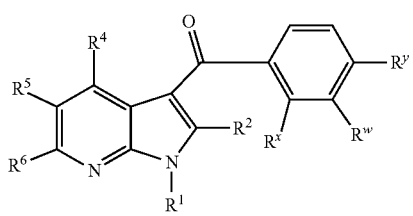

(Ia)

and the pharmaceutically acceptable salts, solvates and optical isomers thereof.

19. A compound of any one of embodiments 1 to 17 having formula (Ib)

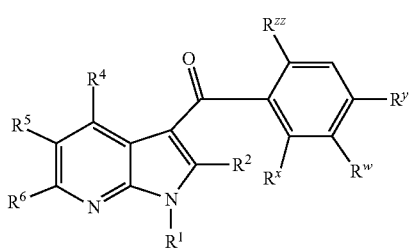

(Ib)

and the pharmaceutically acceptable salts, solvates and optical isomers thereof.

20. A compound of any one of embodiments 1 to 17 having formula (Ic)

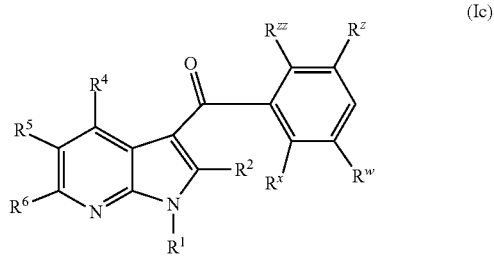

(Ic)

and the pharmaceutically acceptable salts, solvates and optical isomers thereof.

21. A compound of any one of embodiments 1 to 17 having formula (Id)

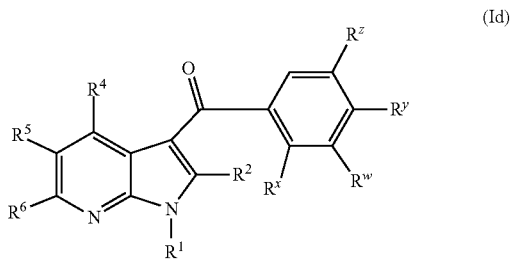

(Id)

and the pharmaceutically acceptable salts, solvates and optical isomers thereof.

22. A compound of any one of the preceding embodiments, wherein R$^1$, R$^2$, R$^3$, R$^4$, and R$^6$ are H or alkyl, in particular H.

23. A compound of any one of the preceding embodiments, wherein R$^{10}$ is H or alkyl, in particular H.

Further embodiments are:

24. A compound having formula (I)

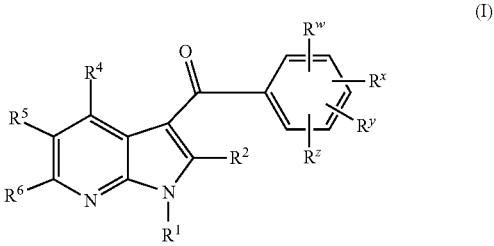

(I)

wherein

R$^1$ is H or alkyl;

R$^2$ is H or alkyl;

R$^4$ is H, halogen, CN or alkyl;

R$^6$ is H, alkoxy or alkyl;

R$^w$ is —NR$^{10}$SO$_2$R$^{12}$ or —N=S(=O)R$^{10}$NR$^{10}$R$^{10}$;

R$^{10}$ is H, alkyl, or phenylalkyl;

R$^{12}$ is H, alkyl, hydroxyalkyl, alkoxyalkyl, haloalkyl or phenylalkyl, wherein the phenyl group is optionally substituted with 1 or 2 groups independently selected from alkyl, halogen;

$R^x$ is H, halogen, CN or alkyl;
$R^y$ is H, halogen, CN or alkyl;
$R^z$ is H, halogen, CN or alkyl;
$R^5$ is selected from
  (a) phenyl substituted with 1, 2 or 3 groups independently selected from
    alkyl,
    alkoxy,
    alkoxy wherein the alkyl group is substituted with 1, 2 or 3 hydroxy groups,
    alkoxy wherein the alkyl group is substituted with a non-aromatic heterocyclic 5- or 6-membered monocyclic group having 1, 2 or 3 heteroatoms independently selected from O, N and S which monocyclic group is optionally substituted with 1 or 2 groups independently selected from alkyl, and halogen,
    haloalkyl,
    hydroxy,
    $NR^{10}R^{10}$,
    alkylsulfonyl-$NR^{10}$—,
    —$SO_2NR^{10}R^{10}$,
    alkylsulfanyl wherein the alkyl group is optionally substituted with $NR^{10}R^{10}$ or 1, 2 or 3 halogen atoms,
    alkylsulfinyl,
    alkylsulfonyl, wherein the alkyl group is optionally substituted with 1, 2 or 3 halogen atoms,
    haloalkoxy,
    cycloalkyl,
    thioguanidino ($H_2NC(=NH)$—S—),
    $R^{10}R^{10}N$—CO—,
    $R^{10}R^{11}NSO_2$—,
    alkylcarbonyl-$NR^{10}$—,
    CN, and
    a non-aromatic heterocyclic 5- or 6-membered monocyclic group having 1, 2 or 3 heteroatoms independently selected from O, N and S which is optionally substituted with 1 or 2 groups independently selected from alkyl, $C_2$-$C_5$-alkanoyl, and benzoyl,
  (b) phenyl which is fused with a heteroaromatic 5- or 6-membered monocyclic group having 1, 2 or 3 heteroatoms independently selected from O, N and S,
  (c) a heteroaromatic 5- or 6-membered monocyclic or heteroaromatic 9- or 10-membered bicyclic group wherein the heteroaromatic groups have 1, 2 or 3 heteroatoms independently selected from O, N and S, the heteroaromatic group being optionally substituted with
    alkyl,
    haloalkyl,
    cycloalkyl,
    —$NR^{10}R^{10}$,
    halogen,
    alkoxy,
    —$CO_2R^{10}$ and
    a non-aromatic heterocyclic 5- or 6-membered monocyclic group having 1, 2 or 3 heteroatoms independently selected from O, N, S, SO and $SO_2$ which heterocyclic group is optionally substituted with alkylsulfanyl or 1 or 2 hydroxy groups,
  (d) non-aromatic heterocyclic 5- or 6-membered monocyclic group having 1, 2 or 3 heteroatoms independently selected from O, N, S, SO and $SO_2$ which heterocyclic group is optionally substituted with 1 or 2 groups independently selected from
    alkyl,
    $C_2$-$C_5$-alkanoyl,
    benzoyl,
    hydroxy,
    —$CO_2R^{10}$ and
    carbonyl (one of the ring carbon atoms is a >C=O group),
  (e) $C_2$-$C_5$-alkinyl,
  (f) $C_2$-$C_5$-alkenyl
  (g) halogen;
  (h) cycloalkyl and
the pharmaceutically acceptable salts, solvates and optical isomers thereof.

25. A compound of embodiment 24, wherein $R^5$ is selected from
  (a) phenyl substituted with 1, 2 or 3 groups independently selected from
    alkyl,
    alkoxy,
    alkoxy wherein the alkyl group is substituted with 1, 2 or 3 hydroxy groups,
    alkoxy wherein the alkyl group is substituted with a non-aromatic heterocyclic 5- or 6-membered monocyclic group having 1 or 2 heteroatoms independently selected from O and N and which monocyclic group is optionally substituted with 1 or 2 alkyl groups, —$SO_2NR^{10}R^{10}$,
    alkylsulfanyl wherein the alkyl group is optionally substituted with $NR^{10}R^{10}$ or 1, 2 or 3 halogen atoms,
    alkylsulfinyl,
    alkylsulfonyl, wherein the alkyl group is optionally substituted with 1, 2 or 3 halogen atoms,
    cycloalkyl,
    thioguanidino,
    $NR^{10}R^{10}$, and
    a non-aromatic heterocyclic 5- or 6-membered monocyclic group having 1, or 2 heteroatoms independently selected from O and N which is optionally substituted with 1 or 2 groups independently selected from alkyl and $C_2$-$C_5$-alkanoyl,
  (b) phenyl which is fused with a a heteroaromatic 5- or 6-membered monocyclic group having 1, 2 or 3 heteroatoms independently selected from O, N and S,
  (c) a heteroaromatic 5- or 6-membered monocyclic group having 1, 2 or 3 heteroatoms independently selected from O, N and S which heteroaromatic group is optionally substituted with
    alkyl,
    cycloalkyl,
    —$NR^{10}R^{10}$,
    —$CO_2R^{10}$ and
    a non-aromatic heterocyclic 5- or 6-membered monocyclic group having 1, 2 or 3 heteroatoms independently selected from O, N, S, SO and $SO_2$ which heterocyclic group is optionally substituted with alkylsulfanyl or 1 or 2 hydroxy groups,
  (d) a non-aromatic heterocyclic 5- or 6-membered monocyclic group having 1 or 2 heteroatoms independently selected from O, N, S, SO and $SO_2$ which heterocyclic group is optionally substituted with 1 or 2 groups independently selected from
    alkyl,
    $C_2$-$C_5$-alkanoyl,
    hydroxy,
    —$CO_2R^{10}$ and
    carbonyl, (e) $C_2$-$C_5$-alkinyl,
(f) halogen, and
(g) cycloalkyl.

26. A compound of embodiment 24 or 25, wherein $R^5$ is selected from
(a) phenyl substituted with 1, 2 or 3 groups independently selected from
alkyl,
alkoxy,
alkoxy wherein the alkyl group is substituted with 1, 2 or 3 hydroxy groups,
alkoxy wherein the alkyl group is substituted with a non-aromatic heterocyclic 5- or 6-membered monocyclic group having 1 or 2 oxygen heteroatoms which monocyclic group is optionally substituted with 1 or 2 alkyl groups,
—$SO_2NR^{10}R^{10}$,
alkylsulfanyl wherein the alkyl group is optionally substituted with $NR^{10}R^{10}$ or 1, 2 or 3 halogen atoms,
alkylsulfinyl,
alkylsulfonyl, wherein the alkyl group is optionally substituted with 1, 2 or 3 halogen atoms,
cycloalkyl,
thioguanidino,
$NR^{10}R^{10}$, and
a non-aromatic heterocyclic 6-membered monocyclic group having 1 or 2 heteroatoms independently selected from O and N which is optionally substituted with 1 or 2 groups independently selected from alkyl and $C_2$-$C_5$-alkanoyl,
(b) phenyl which is fused with a heteroaromatic 5-membered monocyclic group having 1 or 2 heteroatoms independently selected from N, O and S,
(c) a heteroaromatic 5- or 6-membered monocyclic group having 1, 2 or 3 heteroatoms independently selected from O, N and S which is optionally substituted with
alkyl,
haloalkyl,
cycloalkyl,
—$NR^{10}R^{10}$,
—$CO_2R^{10}$ or
a non-aromatic heterocyclic 5- or 6-membered monocyclic group having 1, 2 or 3 heteroatoms independently selected from O, N, S, SO and $SO_2$ which heterocyclic group is optionally substituted with alkylsulfanyl or 1 or 2 hydroxy groups,
(d) non-aromatic heterocyclic 5- or 6-membered monocyclic group having 1 or 2 heteroatoms independently selected from O, N, S, SO and $SO_2$ which heterocyclic group is optionally substituted with 1 or 2 groups independently selected from alkyl, $C_2$-$C_5$-alkanoyl, and hydroxy,
(e) $C_2$-$C_5$-alkinyl,
(f) halogen and
(g) cycloalkyl.

27. A compound of any one embodiments 24 to 26, wherein $R^5$ is selected from
phenyl substituted with 1, 2 or 3 groups independently selected from alkyl, alkoxy, $C_2$-$C_4$-alkoxy wherein the alkyl group is substituted with 1, 2 or 3 hydroxy groups, $C_2$-$C_4$-alkoxy wherein the alkyl group is substituted with a non-aromatic heterocyclic 5- or 6-membered monocyclic group having 1 or 2 oxygen heteroatoms which monocyclic group is optionally substituted with 1 or 2 alkyl groups, —$SO_2NR^{10}R^{10}$, alkylsulfonyl, $NR^{10}R^{10}$, non-aromatic heterocyclic 6-membered monocyclic group having 1 or 2 heteroatoms independently selected from O and N which is optionally substituted with 1 or 2 groups independently selected from alkyl and $C_2$-$C_5$-alkanoyl.

28. A compound of any one of embodiments 24 to 26, wherein $R^5$ is selected from benzothiophen and benzofurane.

29. A compound of any one of embodiments 24 to 26, wherein $R^5$ is selected from furanyl, thiazolyl, alkylsulfanyl substituted thiazolyl, pyrazolyl, triazolyl, thiadiazolyl, alkylsulfanyl substituted thiadiazolyl, pyrimidinyl, pyridinyl, and pyridazinyl.

30. A compound of any one of embodiments 24 to 26, wherein $R^5$ is selected from morpholinyl which is optionally substituted with 1 or 2 alkyl groups, piperazinyl which is optionally substituted with 1 or 2 alkyl groups, oxacycloalkyl, azacycloalkyl which is optionally substituted with 1 or 2 groups independently selected from alkyl, hydroxy, —$COOR^{10}$ and oxoazacycloalkyl.

31. A compound of any one of embodiments 24 to 26, wherein $R^5$ is ethinyl or cycloalkyl.

32. A compound of any one of embodiments 24 to 31, wherein $R^w$ is —$NR^{10}SO_2R^{12}$.

33. A compound of embodiment 32, wherein $R^{12}$ is alkyl, hydroxyalkyl, or phenylalkyl, wherein the phenyl group is optionally substituted with 1 or 2 groups independently selected from alkyl and halogen.

34. A compound of embodiment 33, wherein $R^{12}$ is alkyl.

35. A compound of any one of embodiments 24 to 34 having formula (Ia)

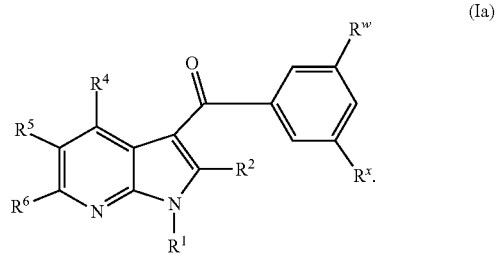

(Ia)

36. A compound of an one of embodiments 24 to 34 having formula (Ib)

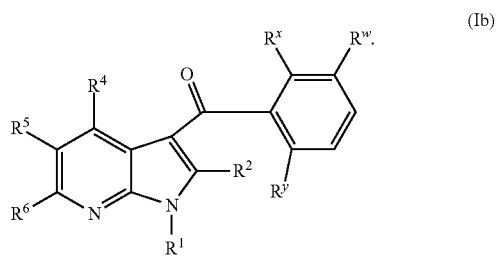

(Ib)

37. A compound of any one of embodiments 24 to 34 having formula (Ic)

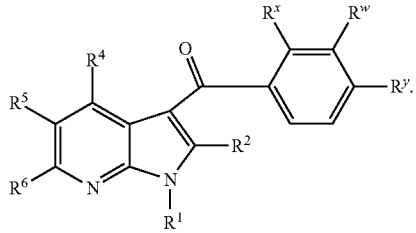

38. A compound of any one of embodiments 24 to 34 having formula (Id)

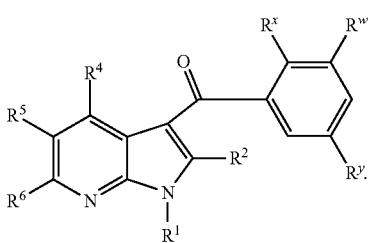

39. A compound of any one of embodiments 24 to 34 having formula (Ie)

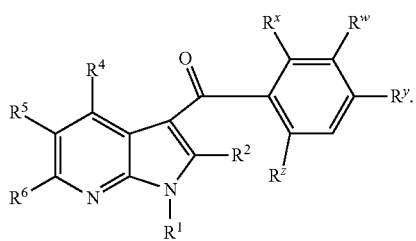

40. A compound of any one of embodiments 24 to 34 having formula (If)

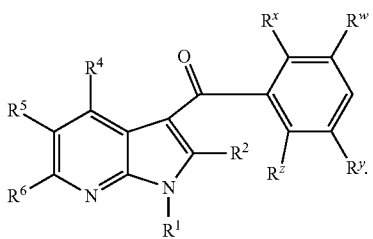

41. A compound of any one of embodiments 24 to 34 having formula (Ig)

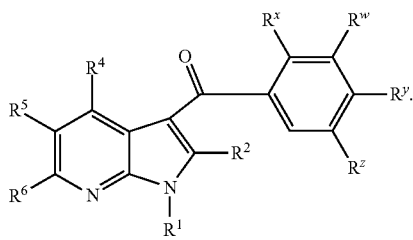

42. A compound of any one of embodiments 24 to 34 having formula (Ih)

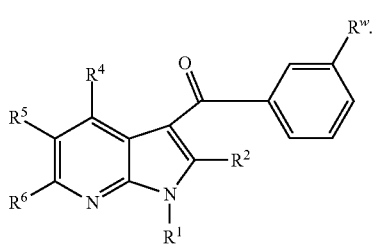

43. A compound of embodiment 35, wherein $R^5$ is phenyl which substituted with halogen and $R^w$ is —$NR^{10}SO_2R^{12}$, wherein $R^{12}$ is alkyl.

44. A compound of embodiment 36, wherein $R^5$ is alkenyl, $R^x$ and $R^y$ are halogen, and $R^w$ is —$NR^{10}SO_2R^{12}$ wherein $R^{12}$ is alkyl.

45. A compound of embodiment 36, wherein
$R^5$ is phenyl which is substituted with a group selected from
a) a non-aromatic heterocyclic 6-membered monocyclic group having 1 or 2 heteroatoms independently selected from O and N which is optionally substituted with 1 or 2 groups independently selected from alkyl and $C_2$-$C_5$-alkanoyl,
b) $C_2$-$C_4$-alkoxy wherein the alkyl group is substituted with a non-aromatic heterocyclic 5- or 6-membered monocyclic group having 1 or 2 oxygen heteroatoms which monocyclic group is optionally substituted with 1 or 2 alkyl groups,
c) alkoxy wherein the alkyl group is substituted with 1, 2 or 3 hydroxy groups, and wherein $R^5$ is optionally substituted with halogen and/or alkyl,
d) alkylsulfonyl which is optionally substituted with 1, 2 or 3 halogen atoms,
e) alkylsulfanyl, wherein the alkyl group is optionally substituted with $NR^{10}R^{10}$ or 1, 2 or 3 halogen atoms,
f) thioguanidino, and
g) cycloalkyl,
$R^x$ and $R^y$ are halogen, and $R^w$ is —$NR^{10}SO_2R^{12}$ wherein $R^{12}$ is alkyl or benzyl which is optionally substituted with 1 or 2 groups independently selected from alkyl and halogen.

46. A compound of embodiment 36, wherein
$R^5$ is phenyl which is substituted with alkoxy, —$SO_2NR^{10}R^{10}$, halogen, alkoxy wherein the alkyl group is substituted with 1, 2 or 3 hydroxy groups, alkyl, a heteroaromatic 5- or 6-membered monocyclic group having 1 or 2 heteroatoms independently selected from N and S which is optionally substituted with alkyl, cycloalkyl, and —$NR^{10}R^{10}$,
$R^x$ and $R^y$ are halogen, and $R^w$ is —$NR^{10}SO_2R^{12}$ wherein $R^{12}$ is benzyl which is optionally substituted with 1 or 2 groups independently selected from alkyl and halogen.

47. A compound of embodiment 36, wherein $R^5$ is a heteroaromatic 5-membered monocyclic group having 1, 2 or 3 heteroatoms independently selected from O, N and S which is optionally substituted with
    a) alkylsulfanyl,
    b) cycloalkyl,
    c) oxacycloalkyl,
    d) azacycloalkyl which is optionally substituted with hydroxy,
    e) —$CO_2R^{10}$,
    f) oxodihydropyrazinyl,
    g) oxopiperidinyl and
    h) morpholinyl which is optionally substituted with 1 or 2 alkyl groups,
    $R^x$ and $R^y$ are halogen, and $R^w$ is —$NR^{10}SO_2R^{12}$ wherein $R^{12}$ is alkyl.

48. A compound of embodiment 36, wherein $R^5$ is selected from
    a) pyrimidine which is optionally substituted with cycloalkyl,
    b) pyridazine,
    c) benzothiophen,
    d) benzofurane,
    e) pyridinyl which is substituted with —$SO_2NR^{10}R^{10}$, morpholinyl, thiomorpholinyl, 1,1-dioxidothiomorpholinyl, alkylsulfonyl,
    f) furane,
    g) thiazole,
    h) pyrazole,
    i) triazole, in particular 1,2,4-triazole,
    j) thiadiazole,
    k) alkylthio substituted thiadiazole, and
    l) alkylthio substituted thiazole,
    $R^x$ and $R^y$ are independently halogen or CN, and $R^w$ is —$NR^{10}SO_2R^{12}$ wherein $R^{12}$ is alkyl or benzyl which is optionally substituted with 1, 2 or 3 groups independently selected from alkyl and halogen.

49. A compound of embodiment 47, wherein $R^5$ is pyridinyl which is substituted with morpholinyl, thiomorpholinyl, or 1,1-dioxidothiomorpholinyl, $R^x$ and $R^y$ are halogen and $R^w$ is —$NR^{10}SO_2R^{12}$ wherein $R^{12}$ is alkyl which is substituted with 1, 2 or 3 halogen atoms.

50. A compound of embodiment 36, wherein $R^5$ is non-aromatic heterocyclic 5- or 6-membered monocyclic group having 1 or 2 heteroatoms independently selected from 0 and N which is optionally substituted with 1 or 2 alkyl groups, $R^x$ and $R^y$ are halogen, and $R^w$ is —$NR^{10}SO_2R^{12}$ wherein $R^{12}$ is alkyl.

51. A compound of embodiment 37, wherein $R^5$ is a heteroaromatic 6-membered monocyclic group having 1, 2 or 3 heteroatoms independently selected from O, N and S which is optionally substituted with
    a) cycloalkyl,
    b) alkyl,
    c) haloalkyl,
    d) —$COOR^{10}$,
    e) oxacycloalkane which is optionally substituted with hydroxyl,
    $R^x$ and $R^y$ are halogen, and $R^w$ is —$NR^{10}SO_2R^{12}$ wherein $R^{12}$ is alkyl, alkoxyalkyl or haloalkyl.

52. A compound of embodiment 51, wherein heteroaromatic 6-membered monocyclic group is pyridyl, pyrimidyl or pyridazyl.

53. A compound of embodiment 38, wherein $R^5$ is phenyl which is substituted with 1 or 2 halogen atoms, $R^x$ and $R^y$ are halogen, and $R^w$ is —$NR^{10}SO_2R^{12}$ wherein $R^{12}$ is alkyl.

54. A compound of embodiment 39, wherein $R^5$ is phenyl which is substituted with 1 or 2 halogen atoms, $R^x$, $R^y$ and $R^z$ are halogen, and $R^w$ is —$NR^{10}SO_2R^{12}$ wherein $R^{12}$ is alkyl.

55. A compound of embodiment 40, wherein $R^5$ is phenyl which is substituted with 1 or 2 halogen atoms, $R^x$, $R^y$ and $R^z$ are halogen, and $R^w$ is —$NR^{10}SO_2R^{12}$ wherein $R^{12}$ is alkyl.

56. A compound of embodiment 41, wherein $R^5$ is phenyl which is substituted with 1 or 2 halogen atoms, $R^x$, $R^y$ and $R^z$ are halogen, and $R^w$ is —$NR^{10}SO_2R^{12}$ wherein $R^{12}$ is alkyl.

57. A compound of embodiment 42, wherein $R^5$ is phenyl which is substituted with 1 or 2 halogen atoms, and $R^w$ is —$NR^{10}SO_2R^{12}$ wherein $R^{12}$ is alkyl.

58. A compound of any one of embodiments 24 to 57, wherein $R^1$, $R^2$, $R^3$, $R^4$, and $R^6$ are H or alkyl, in particular H.

59. A compound of any one of the preceding embodiments, wherein $R^{10}$ is H or alkyl, in particular H.

36. A compound of any one of embodiments 24 to 59, wherein $R^{12}$ is alkyl, in particular $C_1$-$C_4$ alkyl, and most preferably methyl, ethyl, or propyl.

DETAILED DESCRIPTION OF THE INVENTION

In an embodiment, the invention relates to selective MKK4 inhibitor compounds and the pharmaceutically acceptable salts, solvates and optical isomers thereof, wherein the compounds are of the formula I, wherein $R^1$ to $R^6$, $R^{10}$, A and Q are as defined in the above embodiments in any combination.

In an embodiment, the compounds of the invention and the pharmaceutically acceptable salts, solvates and optical isomers thereof selectively inhibit protein kinase MKK4 over protein kinases JNK1 and MKK7.

Further, the invention also relates to said compounds for use in promoting liver regeneration or reducing or preventing hepatocyte death and, at the same time, increasing hepatocyte proliferation.

The invention also includes the pharmaceutically acceptable salts of the compounds mentioned above. The pharmaceutically acceptable salts are especially acid or base addition salts with pharmaceutically acceptable acids or bases. Examples of suitable pharmaceutically acceptable organic and inorganic acids are hydrochloric acid, hydrobromic acid, phosphoric acid, sulfuric acid, sulfamic acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhauser Verlag, Basel and Stuttgart, 1966. Examples of suitable pharmaceutically acceptable organic and inorganic bases are alkali metal hydroxides, such as sodium hydroxide or potassium hydroxide, alkaline earth metal hydroxides such as calcium or magnesium hydroxide, ammonium hydroxide, organic nitrogen bases such as dimethylamine, trimethylamine, ethanolamine, diethanolamine, triethanolamine, choline, 2-amino-2-hydroxymethyl-propane-1,3-diol, meglumine, procaine etc. L-arginine, L-lysine, ethylenediamine, or hydroxyethylpyrrolidine.

The invention also includes any tautomeric, crystal and polymorphic form of the compounds and salts of the present invention and mixtures thereof.

The invention also includes solvates such as hydrates.

The compounds of the invention may contain one or more chiral centers, and exist in different optically active forms such enantiomers and diastereomers.

As used herein, the term "pro-drug" refers to an agent which is converted into the parent drug in vivo by some physiological chemical process. An example, without limitation, of a pro-drug would be a compound of the present invention in the form of an ester.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue. Exemplary pro-drugs include, but are not limited to, compounds with carboxylic acid substituents wherein the free hydrogen is replaced by ($C_1$-$C_4$)alkyl, ($C_1$-$C_{12}$)alkanoyloxy-methyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyl-oxy)ethyl having from 4 to 7 carbon atoms, 1-methyl-1-(alkoxycarbonyloxy)-ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotono-lactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)-alkylcarbamoyl-($C_1$-$C_2$)alkyl and piperidino-, pyrrolidino- or morpholino($C_2$-$C_3$)alkyl. Other exemplary pro-drugs release an alcohol of Formula (I) wherein the free hydrogen of the hydroxyl substituent (e.g., R group contains hydroxyl) is replaced by ($C_1$-$C_6$)alkanoyloxy-methyl, 1-(($C_1$-$C_6$)alkanoyloxy)-ethyl, 1-methyl-1-(($C_1$-$C_6$)alkanoyloxy)ethyl, ($C_1$-$C_{12}$)alkoxy-carbonyloxy-methyl, N—($C_1$-$C_6$)-alkoxy-carbonylaminomethyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, P(O)(OH)$_2$, —P(O)(O($C_1$—$C_6$)alkyl)$_2$ or glycosyl (the radical resulting from detachment of the hydroxyl of the hemiacetal of a carbohydrate).

The expression MKK4 inhibitor means that, upon administration, the kinase activity of MKK4 is inhibited with an $IC_{50}$ of <10 μmol/l, preferably <1 μmol/l, and in particular <0.5 μmol/l. The expression "selectively inhibit protein kinase MKK4 over protein kinases JNK1 and MKK7" as used herein means that the ratio of MKK7 inhibiting activity to MKK4 inhibiting activity or the ratio of JNK1 inhibiting activity to MKK4 inhibiting activity, expressed as either percent of control or Kd, is ≥10, as measured with KINOMEscan™.

The expression "promoting liver regeneration or reducing or preventing hepatocyte death" as used herein means an increase in the relative number of proliferating hepatocytes by at least 30%, preferably at least 50%, as compared to the number of proliferating cells at the beginning of therapy. In particular, the expression means an increase by ≥100% when compared to the number of proliferating cells at the beginning of therapy. In this context, the experimental determination and quantification will be performed using standard methods, e.g. the quantification of the protein Ki67, which is strictly associated with cell proliferation. For quantification of proliferating hepatocytes in a tissue slide, several immunohistochemical standard methods are available, which use a primary anti-Ki67 antibody followed by visualization of anti-Ki67-binding by using, for example, a horseradish peroxidase conjugated secondary antibody. The amount of peroxidase activity, which is visualized by enzymatic conversion of chromogenic substrates, correlates with the amount of Ki67 protein and the number of proliferating cells.

In the experiments described below, hepatocyte proliferation was quantified by Ki67-staining using the primary polyclonal rabbit anti-Ki67 antibody from Abcam (article no. ab15580, Abcam, Cambridge, USA) and the fluorophore tetramethylrhodamine containing secondary goat polyclonal antibody from Invitrogen (article no. 16101, Invitrogen/ThermoFisher). Based on data obtained from several preclinical mouse models it was found that shRNA (small hairpin RNA) mediated suppression of MKK4 in a chronic $CCl_4$ (carbon tetrachloride) mediated liver damage mouse model increased hepatocyte proliferation from 13% to 27% (compared to a control shRNA) and was associated with decreased liver damage (transaminases) and decreased liver fibrosis. According to the definition in the previous chapter, the relative increase of proliferating cells was 108%. In a model of alcohol induced steatohepatitis (ASH), shRNA mediated silencing of MKK4 resulted in a hepatocyte proliferation rate of 4% as compared to 2% when a control shRNA was used (relative increase: 100%). The duplication of hepatocyte proliferation was associated with decreased steatosis (fat deposition) and decreased liver damage as measured by transaminases. Along the same lines, shRNA mediated MKK4 silencing increased hepatocyte proliferation from 16% (control shRNA) to 33% (relative increase: 106%) in a model of partial hepatectomy (48 hrs after surgical removal of two thirds of the liver). Again, increased hepatocyte proliferation was associated with improved liver regeneration and a faster restoration of liver mass.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine or chlorine.

Alkyl is a straight-chain or branched alkyl group which is preferably a $C_1$-$C_6$-alkyl group, i.e. an alkyl group having from 1 to 6 carbon atoms, and more preferably a $C_1$-$C_4$-alkyl group. Examples of an alkyl group are methyl, ethyl, n-propyl, iso-propyl, n-butyl, 2-butyl, iso-butyl, tert-butyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The definition of alkyl is likewise applicable to any group which includes an alkyl group.

Haloalkyl is a halogenated alkyl group as defined above, wherein at least one, e.g. 1, 2, 3, 4 or all of the hydrogen atoms are replaced by 1, 2, 3, 4 or a corresponding number of identical or different halogen atoms, such as trifluoromethyl, chloromethyl, bromomethyl, difluoromethyl, fluoromethyl, difluoroethyl, etc. Particular examples include the fluorinated $C_1$-$C_4$ alkyl groups as defined, such as trifluoromethyl, difluoromethyl, fluoromethyl, difluoroethyl, 2,2,2-trifluoroethyl or 3,3,3-trifluoropropyl.

Cycloalkyl is a cycloaliphatic radical which is preferably $C_3$-$C_8$-cycloalkyl, i.e. a cycloalkyl group having from 3 to 8 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is >C=O.

Aminocarbonyl is $NH_2C(O)$—.

Alkenyl is a singly unsaturated hydrocarbon radical which is preferably a $C_2$-$C_6$-alkenyl group, i.e. an alkenyl group having 2, 3, 4, 5 or 6 carbon atoms, e.g. vinyl, allyl (2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl, 2-hexen-1-yl.

Alkinyl is a singly unsaturated hydrocarbon radical which is preferably a $C_2$-$C_6$-alkinyl group, i.e. an alkinyl group having 2, 3, 4, 5 or 6 carbon atoms, e.g. ethynyl, 2-propyn-1-yl, 1-propyn-1-yl, 2-propyn-2-yl and the like. $C_3$-$C_5$-Alkinyl is, in particular, 2-propyn-1-yl, 2-butyn-1-yl, 3-butyn-1-yl, 2-pentyn-1-yl, 3-pentyn-1-yl, 4-pentyn-1-yl.

A heteroaromatic (or heteroaryl) group is a 5- or 6-membered monocyclic or 9- or 10-membered bicyclic aromatic group having 1, 2 or 3 heteroatoms selected from O, N and S. The heteroaryl or heteroaromatic group may be bound to the neighboring group via a carbon atom (C-bound) or via a nitrogen heteroatom (N-bound). The heterocyclic radicals may be bound via a carbon atom (C-bound) or a nitrogen atom (N-bound). Preferred heteroaromatic radicals comprise 1 nitrogen atom as ring member atom and optionally 1 or 2 further heteroatoms as ring members, which are selected, independently of each other from O, S and N. Examples are:

C-bound, 5-membered, heteroaromatic rings:
2-furyl, 3-furyl, 5-furyl, 2-thienyl, 3-thienyl, 5-thienyl, pyrrol-2-yl, pyrrol-3-yl, pyrrol-5-yl, pyrazol-3-yl, pyrazol-4-yl, pyrazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, oxazol-2-yl, oxazol-4-yl, oxazol-5-yl, thiazol-2-yl, thiazol-4-yl, thiazol-5-yl, 1,2,3-oxadiazol-imidazol-4-yl, 4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl; C-bound, 6-membered, heteroaromatic rings: pyridin-2-yl, pyridin-3-yl (3-pyridyl), pyridin-4-yl (4-pyridyl), pyridin-5-yl, pyridazin-3-yl, pyridazin-4-yl, pyridazin-6-yl, pyrimidin-2-yl, pyrimidin-4-yl, pyrimidin-5-yl, pyrazin-2-yl, pyrazin-5-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings:
pyrrol-1-yl, pyrazol-1-yl, imidazol-1-yl, 1,2,3-triazol-1-yl, 1,2,4-triazol-1-yl.

Bicyclic heteroaromatic groups include one of the described 5- or 6-membered heteroaromatic rings and a further anellated, saturated or unsaturated or aromatic carbocycle, such as a benzene, cyclohexane, cyclohexene or cyclohexadiene ring. Examples are quinolinyl, isoquinolinyl, indolyl, indolizinyl, isoindolyl, 4-, 5-, 6- or 7-azaindole, indazolyl, benzofuryl, benzthienyl, benzo[b]thiazolyl, benzoxazolyl, benzthiazolyl, benzimidazolyl, imidazo[b]thiazolyl, thieno[b]pyridyl, imidazo[a]pyridyl, pyrazo[a]pyridyl and pyrrol[d]pyrimidyl. Examples of 5- or 6-membered heteroaromatic compounds comprising an anellated cycloalkenyl ring include dihydroindolyl, dihydroindolizinyl, dihydroisoindolyl, dihydroquinolinyl, dihydroisoquinolinyl, dihydrobenzofuryl, chromenyl, chromanyl, dihydropyrrol[a]imidazolyl and tetrahydrobenzothiazolyl.

A non-aromatic 5- or 6-membered group (heterocyclic group) may be saturated or partially unsaturated and includes 1, 2 or 3 heteroatoms selected from O, N and S. The heterocyclic radicals may be bound via a carbon atom (C-bound) or a nitrogen atom (N-bound). Preferred heterocyclic groups comprise 1 nitrogen atom as ring member atom and optionally 1 or 2 further heteroatoms as ring members, which are selected, independently of each other from O, S and N. Examples are:

C-bound, 4-membered, saturated rings, such as azetidin-2-yl, azetidin-3-yl, oxetan-2-yl, oxetan-3-yl;

C-bound, 5-membered, saturated rings, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 4-membered, saturated rings, such as
azetidin-1-yl;

N-bound, 5-membered, saturated rings, such as
tetrahydropyrrol-1-yl (pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as
piperidin-1-yl, hexahydropyrimidin-1-yl, hexahydropyrazin-1-yl (piperazin-1-yl), hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholin-1-yl), tetrahydro-1,2-oxazin-2-yl;

C-bound, 5-membered, partially unsaturated rings, such as
2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydroxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetra-hydropyridin-3-yl, 1,2,3,4-tetrahydropyridin-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydro-pyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyrdazin-4-yl, 2,3,4,5-tetrahydropyrdazin-5-yl, 2,3,4,5-tetrahydro-pyridazin-6-yl, 3,4,5,6-tetrahydropyrdazin-3-yl, 3,4,5,6-tetrahydropyrdazin-4-yl, 1,2,5,6-tetrahydropyrdazin-3-yl, 1,2,5,6-tetrahydropyrdazin-4-yl, 1,2,5,6-tetra-hydropyridazin-5-yl, 1,2,5,6-tetrahydropyrdazin-6-yl, 1,2,3,6-tetrahydropyridazin-3-yl, 1,2,3,6-tetrahydropyrdazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin- 5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyrdazin-1-yl, 1,2,5,6-tetrahydropyrdazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Any group containing heteroatoms may contain 1, 2 or 3 heteroatoms which may be the same or different.

The compounds of the invention including the pharmaceutically acceptable salts, prodrugs, biologically active metabolites, solvates and stereoisomers thereof, can be prepared as disclosed in WO 2007/002433 which is incorporated herein in its entirety by reference or according to analogous procedures. The acid or base addition salts are prepared in a customary manner by mixing the free base with a corresponding acid or by mixing the free acid with the desired base. Optionally, the reaction is carried out in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as EtOAc.

The compounds of the invention are useful for promoting liver regeneration or reducing or preventing hepatocyte death and, at the same time, increasing hepatocyte proliferation. The compounds are therefore useful in treating, modulating, improving or preventing diseases which involve acute or chronic damages to the liver that may be caused by infection, injury, exposure to toxic compounds, an abnormal build-up of normal substances in the blood, an autoimmune process, a genetic defect or unknown causes.

Such liver diseases comprise all diseases where increased liver regeneration and reduction or prevention of hepatocyte death may be helpful to achieve a potential therapeutic effect, i.e. partial or complete restoration of liver functions. Such diseases comprise acute and chronic or acute on chronic liver diseases such as acute and chronic viral hepatitis like hepatitis B, C, E, hepatitis caused by Epstein-Barr virus, cytomegalovirus, herpes simplex virus and other viruses, all types of autoimmune hepatitis, primary sclerosing hepatitis, alcoholic hepatitis;

metabolic liver diseases such as metabolic syndrome, fatty liver like non-alcoholic fatty liver (NAFL), non-alcoholic steatohepatitis (NASH), alcoholic steatohepatitis (ASH), Morbus Wilson, Hemochromatosis, alpha1-antitrypsin deficiency, glycogen storage diseases;

all types of liver cirrhosis, such as primary biliary cirrhosis, ethyl toxic liver cirrhosis, cryptogenic cirrhosis;

acute (fulminant) or chronic liver failure such as toxic liver failure like acetaminophen (paracetamol) induced liver failure, alpha-amanitin induced liver failure, drug induced hepatotoxicity, liver failure caused, for example, by antibiotics, nonsteroidal anti-inflammatory drugs and anticonvulsants, acute liver failure induced by herbal supplements (kava, ephedra, skullcap, pennyroyal etc), liver disease and failure due to vascular diseases such as Budd-Chiari syndrome, acute liver failure of unknown origin, chronic liver disease due to right heart failure;

galactosemia, cystic fibrosis, porphyria, hepatic ischemia perfusion injury, small for size syndrome after liver transplantation, primary sclerosing cholangitis or hepatic encephalopathy.

For promoting liver regeneration or reducing or preventing hepatocyte death the compounds of the invention are administered to a patient in need thereof in a therapeutically effective amount. Various diagnostic methods are available to detect the presence of a liver disease. Blood levels of alanine aminotransferase (ALT) and aspartate aminotransferase (AST), above clinically accepted normal ranges, are known to be indicative of on-going liver damage. Blood bilirubin levels or other liver enzymes may be used as detection or diagnostic criteria. Routine monitoring of liver disease patients for blood levels of ALT and AST is used to measure progress of the liver disease while on medical treatment. Reduction of elevated ALT and AST levels to within the accepted normal range is taken as clinical evidence reflecting a reduction in the severity of the patients' liver damage. Commercial assays such as FibroTest/FibroSURE, HepaScore®, FibroMeter or Cirrhometer evaluate the combined results of five and more biochemical parameters for the detection of liver steatosis, fibrosis and cirrhosis. Furthermore, non-invasive, innovative physical imaging techniques such as magnetic resonance imaging, sonography and, in particular, elastography techniques are available to detect and monitor the status and progression of liver diseases.

It has further been found that shRNA mediated MKK4 suppression attenuate TNF-α-driven cartilage matrix degradation in osteoarthritis (Cell Death and Disease (2017) 8, e3140). Therefore, inhibition of the activity of MKK4 using the compounds of the invention are further useful for treating osteoarthritis and rheumatoid arthritis.

The compounds of the invention are customarily administered in the form of pharmaceutical compositions which comprise at least one compound according to the invention, optionally together with an inert carrier (e.g. a pharmaceutically acceptable excipient) and, where appropriate, other drugs. These compositions can, for example, be administered orally, rectally, transdermally, subcutaneously, intraperitoneally, intravenously, intramuscularly or intranasally.

Examples of suitable pharmaceutical compositions are solid medicinal forms, such as powders, granules, tablets, in particular film tablets, lozenges, sachets, cachets, sugar-coated tablets, capsules, such as hard gelatin capsules and soft gelatin capsules, or suppositories, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resins; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Cantor-Verlag, 1996.

The compounds of the invention may also be suitable for combination with other therapeutic agents. The invention therefore further relates to a combination comprising a compound of the invention with one or more further therapeutic agents, in particular for use in promoting liver regeneration or reducing or preventing hepatocyte death. The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of the invention and at least one further therapeutic agent are within the scope of the current invention. In one embodiment of adjunctive therapeutic administration as described herein, a patient is typically stabilized on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

Suitable agents for use in combination with the compounds of the inventions include for example:
  ACC inhibitors such as TOFA (5-(tetradecyloxy)-2-furoic acid), GS 0976, and ACC inhibitors as disclosed in WO 2016/112305,
  angiotensin II receptor antagonists,
  angiotensin converting enzyme (ACE) inhibitors, such as enalapril,
  caspase inhibitors, such as emricasan,
  cathepsin B inhibitors, such as a mixed cathepsin B/hepatitis C virus NS3 protease inhibitor. like VBY-376,
  CCR2 chemokine antagonists, such as a mixed CCR2/CCR5 chemokine antagonist like cenicriviroc,
  CCR5 chemokine antagonists,
  chloride channel stimulators, such as cobiprostone,
  cholesterol solubilizers,
  diacylglycerol O-acyltransferase 1 (DGAT1) inhibitors, such as LCQ908,
  dipeptidyl peptidase IV (DPPIV) inhibitors, such as linagliptin,
  farnesoid X receptor (FXR) agonists, such as INT-747 (obeticholic acid) or GS-9674 (PX-102),
  FXR/TGR5 dual agonists, such as INT-767,
  galectin-3 inhibitors, such as GR-MD-02,
  glucagon-like peptide 1 (GLP1) agonists, such as liraglutide or exenatide,
  glutathione precursors,
  hepatitis C virus NS3 protease inhibitors, such as a mixed cathepsin B/hepatitis C virus NS3 protease inhibitor like VBY-376,
  HMG CoA reductase inhibitors, such as a statin like atorvastatin,
  11ß-hydroxysteroid dehydrogenase (11ß-HSD1) inhibitors, such as R05093151,
  IL-1ßantagonists,
  IL-6 antagonists, such as a mixed IL-6/IL-1ß/TNFα ligand inhibitor like BLX-1002,
  IL-10 agonists, such as peg-ilodecakin,
  IL-17 antagonists, such as KD-025,
  ileal sodium bile acid cotransporter inhibitors, such as SHP-626,
  leptin analogs, such as metreleptin,
  5-lipoxygenase inhibitors, such as a mixed 5-lipoxygenase/PDE3/PDE4/PLC inhibitor like tipelukast,
  LPL gene stimulators, such as alipogene tiparvovec,
  lysyl oxidase homolog 2 (LOXL2) inhibitors, such as an anti-LOXL2 antibody like GS-6624, PDE3 inhibitors, such as a mixed 5-lipoxygenase/PDE3/PDE4/PLC inhibitor like tipelukast, PDE4 inhibitors, such as ASP-9831 or a mixed 5-lipoxygenase/PDE3/PDE4/PLC inhibitor like tipelukast, phospholipase C (PLC) inhibitors, such as a mixed 5-lipoxygenase/PDE3/PDE4/PLC inhibitor like tipelukast, PPARα agonists, such as a mixed PPARα/δ agonist like GFT505 (elafibranor), PPARγ agonists, such as pioglitazone, PPARδ agonists, Rho associated protein kinase 2 (ROCK2) inhibitors, such as KD-025, sodium glucose transporter-2 (SGLT2) inhibitors, such as remogliflozin etabonate, stearoyl CoA desaturase-1 inhibitors, such as aramchol or CVT-12805, thyroid hormone receptor ß agonists, such as MGL-3196, tumor necrosis factor α (TNFα) ligand inhibitors, transglutaminase inhibitors and transglutaminase inhibitor precursors, such as mercaptamine, PTPIb inhibitors, such as A119505, A220435, A321842, CPT633, ISIS-404173, JTT-551, MX-7014, MX-7091, MX-7102, NNC-521246, OTX-001, OTX-002, or TTP814 and ASK1 inhibitors such as GS4977 (selonsertib).

In some embodiments, the one or more further therapeutic agents are selected from acetylsalicylic acid, alipogene tiparvovec, aramchol, atorvastatin, BLX-1002, cenicriviroc, cobiprostone, colesevelam, emricasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, GS-9674, remogliflozin etabonate, SHP-626, solithromycin, tipelukast, TRX-318, ursodeoxycholic acid, and VBY-376.

In some embodiments, one of the one or more further therapeutic agents is selected from acetylsalicylic acid, alipogene tiparvovec, aramchol, atorvastatin, BLX-1 002, and cenicriviroc.

In an embodiment the invention relates to a method of
inhibiting protein kinase MKK4,
selectively inhibiting protein kinase MKK4 over protein kinases JNK1 and MKK7, promoting liver regeneration or preventing hepatocyte death,
treating acute, acute-on-chronic or chronic liver disease,
treating acute and chronic or acute on chronic liver diseases such as acute and chronic viral hepatitis like hepatitis B, C, E, hepatitis caused by Epstein-Barr virus, cytomegalovirus, herpes simplex virus and other viruses, all types of autoimmune hepatitis, primary sclerosing hepatitis, alcoholic hepatitis;
treating metabolic liver diseases such as metabolic syndrome, fatty liver like non-alcoholic fatty liver (NAFL), non-alcoholic steatohepatitis (NASH), alcoholic steatohepatitis (ASH), Morbus Wilson, hemochromatosis, alpha1-antitrypsin deficiency, glycogen storage diseases;
treating all types of liver cirrhosis, such as primary biliary cirrhosis, ethyl toxic liver cirrhosis, cryptogenic cirrhosis;
treating acute (fulminant) or chronic liver failure such as toxic liver failure like acetaminophen (paracetamol) induced liver failure, alpha-amanitin induced liver failure, drug induced hepatotoxicity and liver failure caused, for example, by antibiotics, nonsteroidal anti-inflammatory drugs, anticonvulsants, acute liver failure induced by herbal supplements (kava, ephedra, skullcap, pennyroyal etc.), liver disease and failure due to vascular diseases such as Budd-Chiari syndrome, acute liver failure of unknown origin, chronic liver disease due to right heart failure;
treating galactosemia, cystic fibrosis, porphyria, hepatic ischemia perfusion injury, small for size syndrome after liver transplantation, primary sclerosing cholangitis or hepatic encephalopathy, or
treating osteoarthritis or rheumatoid arthritis,
which comprises administering an effective amount of a compound or a composition as defined above to a subject in need thereof.

In an embodiment, the compounds of the invention are administered in a dosage of 0.2 to 15 mg/kg or 0.5 to 12 mg/kg of the subject being treated. The compounds can be administered once or several times a day. The compounds are administered over 4 to 12 weeks.

The following examples illustrate the invention without limiting it.

EXAMPLES

Abbreviations

AcOH acetic acid
ATP adenosintriphosphate
Boc$_2$O di-tert.-butyloxycarbonate
CDE 1,2-dimethyl-propylamine
CPME cyclopentylmethyl ether
DCE dichloroethane
DCM dichloromethane
DEA diethylether
DIPEA diisopropylethyl amine
4-DMAP (4-)dimethylaminopyridine
DMA dimethylacetamide
DME dimethyl ether
DMF dimethylformamide
DMSO dimethylsulfoxide
DPPA diphenylphosphoryl azide
DTT dithiothreitol
EtOH ethanol
EtOAc ethyl acetate
HEPES 2-(4-(2-hydroxyethyl)-1-piperazinyl)-ethansulfonsäure
HOBt hydroxybenzotriazole
HPLC high performance liquid chromatography
IPA isopropylalcohol (or iPrOH)
KOAc potassium acetate
LAH lithium aluminium hydride
LCMS liquid chromatography mass spectroscopy
LDA lithium diisopropylamide
LiHDMS lithium bis(trimethylsilyl)amide
mCPBA m-perchlorobenzoic acid
MeCN acetonitrile
MeOH methanol
nhex n-hexane
NIS N-iodosuccinimide
NMP N-methylpyrrolidone
Pd$_2$(dba$_3$) tris(dibenzylideneacetone)dipalladium(0)
Pd(dppf)Cl$_2$ [1,1'-Bis(diphenylphosphino)ferrocene]palladium(II)dichloride
PE petrolether
pMBCl p-methoxybenzyl chloride
rt or RT RT
Ruphos 2-dicyclohexylphosphino-2',6'-diisopropylbiphenyl
SFC supercritical fluid chromatography
Sol. solution TEA triethylamine
TfOH triflic acid
THF tetrahydrofurane
TLC thin layer chromatography
Xantphos 4,5-bis(diphenylphosphino)-9,9-dimethylxanthine

EXAMPLES

Example 1: Synthesis of Substituted Benzoic Acid Sulfonamide Derivatives (General Procedure)

Example 1a

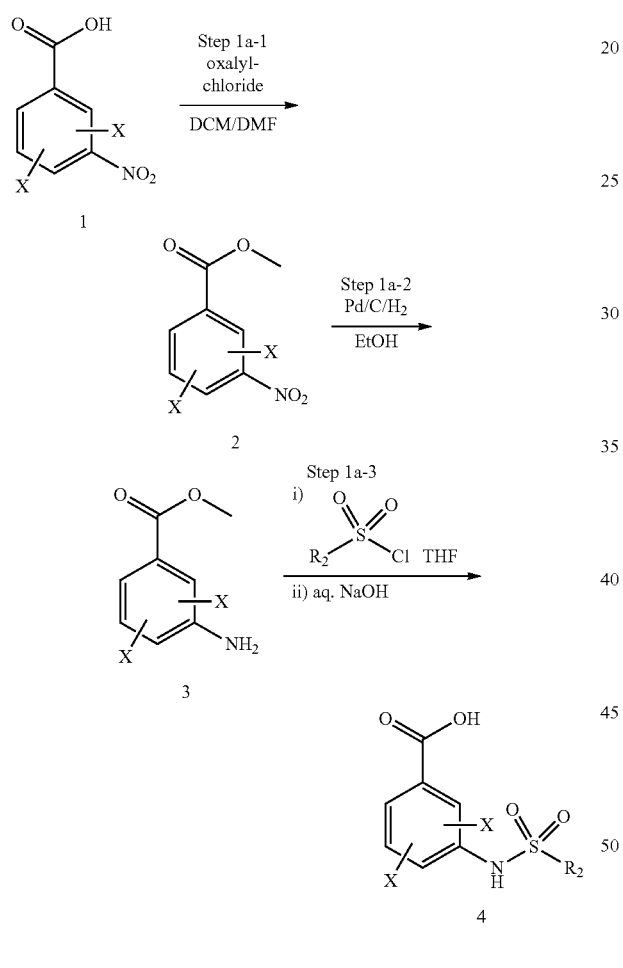

Step 1a-1

Oxalyl chloride (1.1 eq.) was added to a suspension of 1 eq. of the benzoic acid derivative (1) in dry DCM (0.5 M). Some drops of DMF were added and the resulting mixture was stirred at room temperature (RT) until the gas formation was complete. An excess of MeOH was added to the solution and the solvent was evaporated under reduced pressure. The residual was dried in vacuo and the product was used without further purification. (X is H or the substituent as defined in the examples, description and claims).

Step 1a-2

Pd/C (0.1 eq.) was added to a solution of the methyl 3-nitrobenzoate derivative (2, 1.0 eq.) in EtOH (0.2 M). The suspension was purged with $H_2$ and stirred at RT upon complete consumption of the starting material. Then, the mixture was passed through a Celite pad and the filtrate was concentrated in vacuum. The product was used without further purification.

Step 1a-3

A solution of the methyl 3-aminobenzoate derivative (3, 1.0 eq.) and $Et_3N$ (2.2 eq.) in dry DCM (0.25 M) was cooled to 0° C. and the corresponding sulfonyl chloride (1.1 eq., 2.2 eq. for di-sulfonamides, respectively) was added dropwise. After completion, the ice bath was removed and the solution was stirred at RT for ~1 h. The solution was then diluted with water, extracted with EtOAc and the combined organic layers were dried over $Na_2SO_4$. The solvent was removed under reduced pressure and the product was purified via flash chromatography ($SiO_2$, nHex/EtOAc 9/1).

The ester/mono-/disulfonamide was dissolved in THF/MeOH (1 M, 4:1), cooled to 0° C. and treated with $NaOH^{aq}$ (2 M, 2-3 eq.). After 10 min. the ice bath was removed and the reaction was stirred at RT until complete hydrolysis. THF/MeOH was removed in vacuo, the residual was treated with $HCl^{aq}$ (2 M) upon precipitating of the product. The precipitate was filtered of, dried and was used without any further purification.

Example 1b

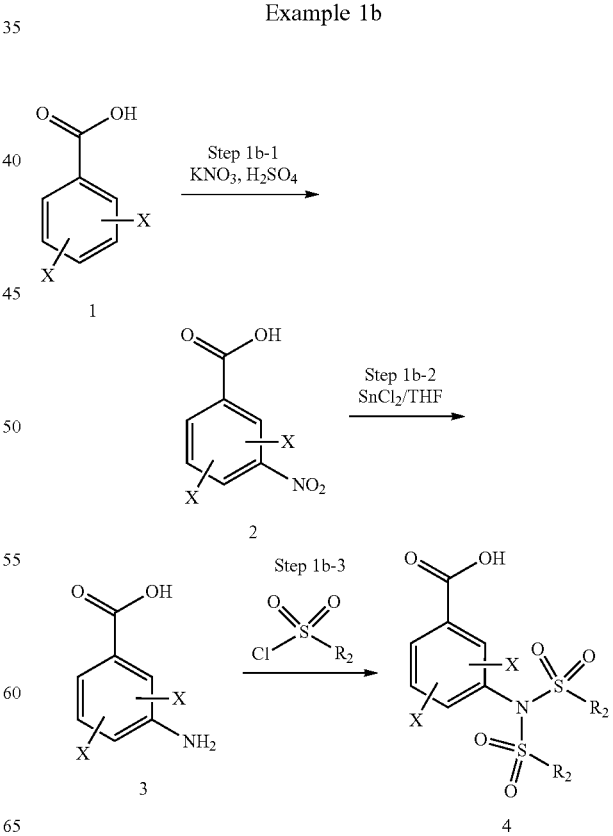

Step 1b-1: (Substituted) 3-nitrobenzoic acid (2)

To a solution of 1 eq. of the benzoic acid derivative (1) in conc. sulfuric acid (20 mL), stirred and cooled in an ice-bath, 1 eq. potassium nitrate was added in portions within 15 min. The reaction mixture was stirred at 0° C. for 1 h and thereafter poured into 50 mL of ice water and extracted with EtOAc (15 mL×3). The combined organic layers were washed with brine, dried over $Na_2SO_4$, filtered and concentrated under reduced pressure to obtain the corresponding 3-nitrobenzoic acid derivative (2) in >80% yield.

Step 1b-2 and 1b-3: 2,6-dibromo-3-(N-(propylsulfonyl)propylsulfonamido)benzoic acid (4)

To a stirred solution of 1 eq. of the 3-nitrobenzoic acid (2) in THF (20 mL), 3 eq. stannous chloride were added at RT. The mixture was stirred at 80° C. for 3 h. The progress of the reaction was monitored by TLC (30% EtOAc in hexane). After completion, the reaction mixture was quenched with aq. ammonia solution (10 mL) and the product was extracted with EtOAc (20 mL×3). The combined organic layers were washed with brine, dried over $Na_2SO_4$, filtered, and concentrated under reduced pressure to get the 3-amino-benzoic acid derivative (3) as crude material, which was used in the next step without further purification.

To a stirred solution of the 3-amino-benzoic acid (3) in dichloromethane (DCM, 20 mL), 4 eq. TEA were added and the mixture was cooled to 0° C. 2 eq. 1-alkylsulfonyl chloride were added and the reaction was monitored by TLC. After completion (approx. 12 h), the reaction was quenched with 2N HCl (10 mL) and the product was extracted with DCM (10 mL×2). The combined organic layers were washed with brine, dried over anhydrous $Na_2SO_4$ and concentrated under reduced pressure to get the crude 3-(N-(alkylsulfonyl)-propylsulfonamido)benzoic acid derivative (4) which was used in the next step without further purification. (X is H or the substituent as defined in the examples, description and claims).

Example 2

Example 2a: (General Procedure)

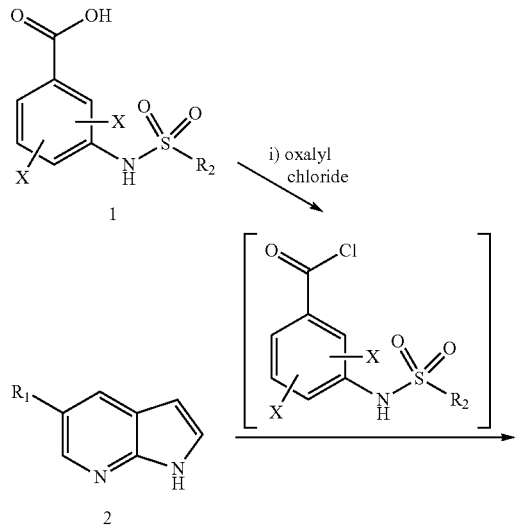

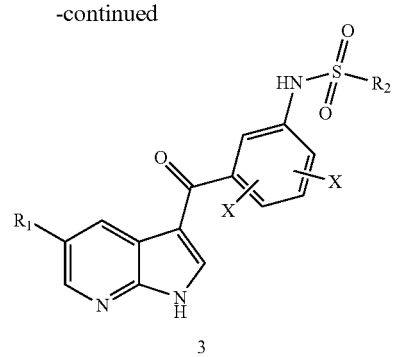

The benzoic acid derivative, prepared according to Example 1a (1) (1.1 eq.) was suspended in dry DCM (0.5 M), oxalyl chloride (1.05 eq.) and a few drops of DMF were added successively. After the gas formation stopped the resulting solution was added dropwise to a suspension of 1 eq. azaindole (2) and $AlCl_3$ (5 eq.) in dry DCM (0.5 M). The mixture was stirred at RT for 0.5-3 h. Saturated, aqueous $NH_4Cl$ solution was added to quench the reaction. The water phase was extracted with EtOAc (3×), the combined organic layers were dried over $Na_2SO_4$ and the solvent was evaporated under reduced pressure. The product (3) was purified via flash chromatography ($SiO_2$, nHex/EtOAc 1:1 or DCM/MeOH 1-3%) to yield the titled compound.

The following compounds were prepared according to this procedure:

Expl. 13-Step 2, Expl. 14-Step 2, Expl. 15-Step 2, Expl. 16-Step 2, Expl. 17-Step 2.

Example 2b: Synthesis of N-(2,4-dibromo-3-(5-(4-chlorophenyl)-1H-pyrrolo[2,3-b]pyridine-3-carbonyl)phenyl)propane-1-sulfonamide

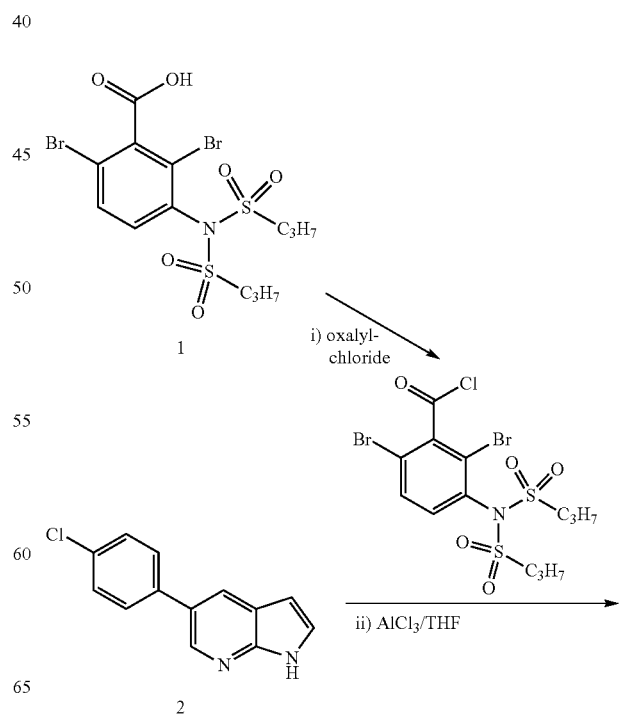

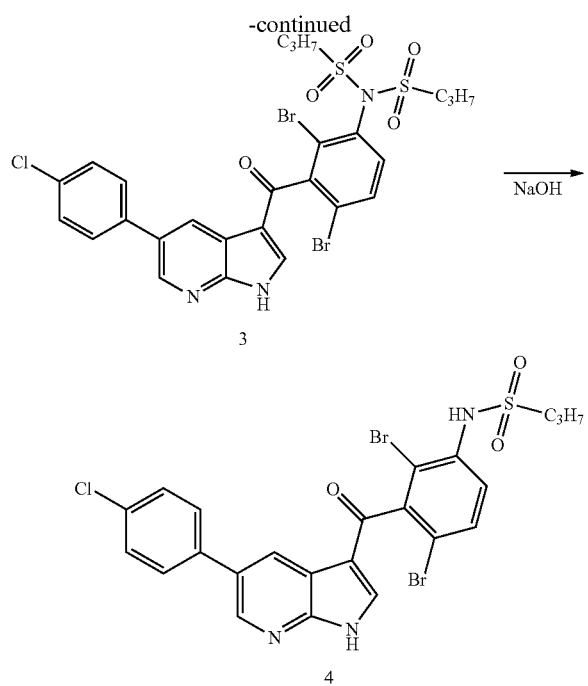

To a stirred solution of 2,6-dibromo-3-(N-(propylsulfonyl)propylsulfonamido)benzoic acid (1) (1 eq., 900 mg, crude), in DCM (10 mL) at 0° C. was added oxalyl chloride (2 eq, 450.6 mg, 3.55 mmol) followed by a catalytic amount of DMF. The reaction mixture was stirred at RT for 4 h. After completion of the reaction (TLC) the solvent was removed under reduced pressure and the obtained residue was dissolved in DCM (10 mL). Hereinbelow, this reactant is denominated as solution A AlCl$_3$ (1.18 g, 8.87 mmol) was added to DCM (40 mL) and the mixture was stirred for 10 min at RT followed by cooling to 0° C. 5-(4-chlorophenyl)-1H-pyrrolo[2,3-b]pyridine (2) (1 eq., 405.92 mg, 1.77 mmol) was added and the mixture was stirred for 30 min then warmed to RT for 3 h. solution A was slowly added to the above suspension at 0° C. and the reaction was stirred for 2 days at RT. After complete conversion, the reaction was quenched with methanol (MeOH, 10 mL) and concentrated to give a dark brown residue. Cold water (50 mL) was added to the residue and the pH of the solution was adjusted to 7 (neutral) with aq. ammonia. EtOAc (50 mL) was added and the mixture was stirred for 30 min. It was then filtered through celite, the filtrate was extracted with EtOAc (20 mL×3) and the combined organic layers were washed with brine, dried over anhydrous Na$_2$SO$_4$ and concentrated under reduced pressure to get crude N-(2,4-dibromo-3-(5-(4-chlorophenyl)-1H-pyrrolo[2,3-b]pyridine-3-carbonyl)-phenyl)propane-1-sulfonamide (900 mg, crude) which was used in the next step without further purification.

The crude N-(2,4-dibromo-3-(5-(4-chlorophenyl)-1H-pyrrolo[2,3-b]pyridine-3-carbonyl)-phenyl)propane-1-sulfonamide (900 mg) was dissolved in THF (5 mL) and to this was added aq. NaOH (2 eq., 238.9 mg, 7.09 mmol) in water (5 mL) and the reaction mixture was stirred at RT for 4 h. After completion of the reaction, the pH was brought to pH-6 with 5N HCl and the mixture was extracted with EtOAc (20 mL×3). The combined organic layers were washed with brine, dried over anhydrous Na$_2$SO$_4$ and concentrated under reduced pressure to get a crude material which was purified by FCC (flash chromatography) to obtain N-(2,4-dibromo-3-(5-(4-chlorophenyl)-1H-pyrrolo[2,3-b]pyridine-3-carbonyl)phenyl)propane-1-sulfonamide (5) (400 mg, 0.65 mmol, 36% yield).

According to Example 2b, the following compounds given in table 1 were prepared:

TABLE 1

| Ex. | Reactand | Chemical structure | Analytical data |
|---|---|---|---|
| 2c | [structure] | [structure] | $^1$H NMR (400 MHz, DMSO) δ 12.93 (s, 1H), 9.66 (s, 1H), 8.69 (dd, J = 8.2, 2.2 Hz, 2H), 8.09 (s, 1H), 7.79 (d, J = 8.5 Hz, 2H), 7.65 (d, J = 6.1 Hz, 1H), 7.58 (d, J = 8.5 Hz, 2H), 7.35 (t, J = 8.8 Hz, 1H), 3.20-3.03 (m, 2H), 1.81 (dd, J = 15.2, 7.6 Hz, 3H), 1.00 (t, J = 7.4 Hz, 3H). Calculated 489.92 for C23H18ClF2N3O3S. Measured 490.05 for [M + H]$^+$. |
| 2d | [structure] | [structure] | $^1$H NMR (400 MHz, DMSO) δ 12.94 (s, 1H), 9.69 (s, 1H), 8.69 (dd, J = 6.8, 2.1 Hz, 2H), 8.08 (s, 1H), 7.79 (d, J = 8.5 Hz, 2H), 766-7.51 (m, 4H), 3.24-3.13 (m, 2H), 1.90-1.76 (m, 2H), 1.00 (t, J = 7.4 Hz, 3H). Calculated 506.37 for C23H18Cl2FN3O3S. Measured 507.05 for [M + H]$^+$. |

TABLE 1-continued

| | | | |
|---|---|---|---|
| 2e | | | ¹H NMR (400 MHz, DMSO) δ 13.04 (s, 1H), 9.63 (s, 1H), 8.72 (d, J = 2.2 Hz, 1H), 8.65 (s, 1H), 8.29 (s, 1H), 7.80 (d, J = 8.5 Hz, 2H), 7.55 (dd, J = 20.8, 8.6 Hz, 3H), 3.18-3.09 (m, 2H), 1.79 (dq, J = 14.9, 7.4 Hz, 2H), 0.98 (t, J = 7.4 Hz, 3H). Calculated 507.91 for C23H17ClF3N3O3S. Measured 508.1 for [M + H]⁺. |
| 2f | | | ¹H NMR (400 MHz, DMSO) δ 12.95 (s, 1H), 10.09 (s, 1H), 8.68 (dt, J = 11.5, 5.8 Hz, 2H), 8.18 (s, 1H), 7.77 (t, J = 10.0 Hz, 1H), 7.58 (d, J = 8.5 Hz, 2H), 7.43 (ddd, J = 9.3, 6.0, 3.1 Hz, 1H), 7.34-7.25 (m, 1H), 3.25-3.18 (m, 2H), 1.75 (dq, J = 14.9, 7.4 Hz, 2H), 0.98 (t, J = 7.4 Hz, 3H). Calculated 489.92 for C23H18ClF2N3O3S. Measured 488.10 for [M + H]⁻. |
| 2g | | | ¹H NMR (400 MHz, DMSO) δ 13.09 (s, 1H), 10.03 (s, 1H), 8.70 (d, J = 18.1 Hz, 2H), 8.41 (s, 1H), 7.81 (d, J = 8.1 Hz, 2H), 7.61 (dd, J = 25.9, 8.9 Hz, 3H), 3.24-3.13 (m, 2H), 1.74 (d, J = 7.3 Hz, 2H), 0.97 (t, J = 7.2 Hz, 3H). Calculated 507.91 for C23H17ClF3N3O3S. Measured 508.1 for [M + H]⁺. |
| 2h | | | ¹H NMR (400 MHz, DMSO) δ 8.66 (d, J = 2.0 Hz, 2H), 8.12 (s, 1H), 7.79-7.65 (m, 3H), 7.60-7.51 (m, 2H), 3.20-3.10 (m, 2H), 1.84-1.69 (m, 2H), 0.96 (t, J = 7.4 Hz, 3H). Calculated 507.91 for C23H17ClF3N3O3S. Measured 508.1 for [M + H]⁺. |

Example 3: Synthesis of halogen-substituted (=X) N-(3-(5-bromo-1H-pyrrolo[2,3-b]pyridine-3-carbonyl)phenyl) alkyl-1-sulfonamides (alkyl=R₂)

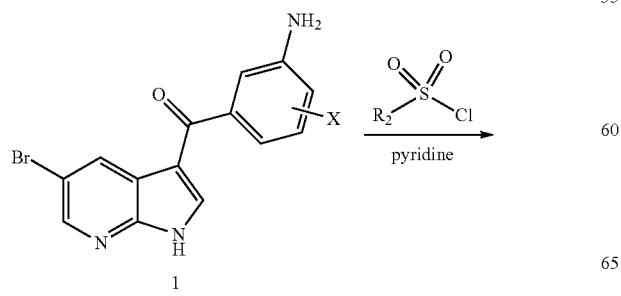

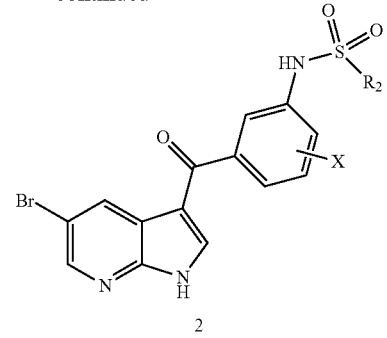

The 3-aminophenyl derivative (1, 1 eq.) was dissolved in pyridine (1 M) and sulfonyl chloride (1.5 eq.) was added in portions. The mixture was heated to 60° C. and stirred for 1-6 h. After complete consumption of the starting material, the crude was diluted with aqueous 1N HCl solution and extracted three times with EtOAc. The organic layers were dried over sodium sulfate and the solvent was evaporated. Purification of the product was performed by flash chromatography using the following solvent gradient: DCM/EtOAc/MeOH (95/5/0-92/5/3).

Example 4: Synthesis of halogen-substituted (=X) N-(3-(1H-pyrrolo[2,3-b]pyridine-3-carbonyl)phenyl) alkyl-1-sulfonamides (alkyl=$R_2$)

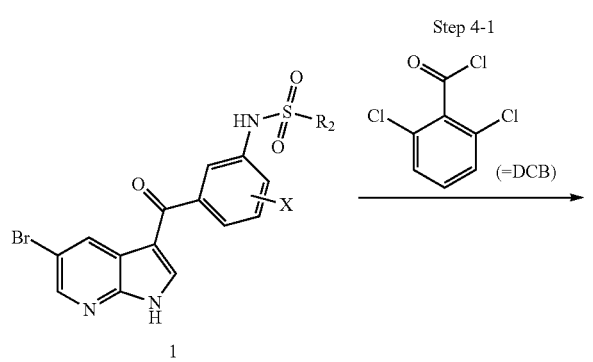

Step 4-1

To a solution of 1 eq. 1H-pyrrolo[2,3-b]pyridine derivative (1), prepared according to Example 3, in THF (0.1 M), triethylamine (1.05 eq.) was added. The resulting solution was cooled to 0° C., 2,6-dichlorobenzoyl chloride (1.01 eq.) was added dropwise followed by the addition of 0.1 eq. 4-DMAP. The ice bath was removed and the reaction was stirred at RT until TLC showed complete consumption of the starting material (about 30 min). The crude material was poured on water and extracted with EtOAc three times. The combined organic layers were dried over sodium sulfate, the solvent was removed in vacuo and the product was purified via flash chromatography ($SiO_2$, PE/EtOAc 15-25%).

Step 4-2

1 eq. of intermediate 2, $B_2Pin_2$ (bis(pinacolato)diboron) (1.05 eq.) and KOAc (3.0 eq.) were suspended in dry 1,4-dioxane (0.5 M) and degassed with argon for 5 min. $Pd(PPh_3)_2Cl_2$ (0.05 eq.) was added and the mixture was stirred for 5 h at 80° C. The crude material was passed through a pad of Celite and the pad was flushed with EtOAc. The organic phase was washed with brine and water, successively. After the organic phase was dried over sodium sulfate, the solvent was removed. Applying flash chromatography ($SiO_2$, PE/EtOAc 25%) gave the pure product.

Step 4-3

Pinacolester ($B_2Pin_2$) (1 eq.), arylbromid (1.5 eq.) and potassium carbonate (2 eq.) were dissolved in 1,4-dioxane/water (2:1, 1 M) and the mixture was degassed with argon. $Pd(dppf)Cl_2$ (0.06 eq.) was added and the mixture was heated to 60° C. for 2 h. The crude mixture was passed through a Celite pad, flushed with MeOH and EtOAc and the solvent was removed in vacuo. The residue was redissolved in MeOH, potassium carbonate (1 g) was added and the suspension was stirred for 3 h at rt. Water was added, the pH adjusted to 6-8 with 1 M HCl$_q$. and the aqueous phase was extracted with EtOAc, the layers were separated and the organic layers were combined, dried over sodium sulfate and the solvent was removed under reduced pressure. The product was pre-purified via flash chromatography using DCM/EtOAc/aceton (70/25/5) as eluent. The pre-purified product was redissolved in DCM/iPrOH (9:1) and precipitated with n-pentane, filtered and dried in vacuo.

According to Example 4, the compounds of examples 20, 21, 22, 23, 24, 25, 29, 35, 36, 39, 45, 46, 47, 48, 49, 50, and 51 were prepared.

Example 5: Synthesis of 5-(4-chlorophenyl)-1H-pyrrolo[2,3-b]pyridine

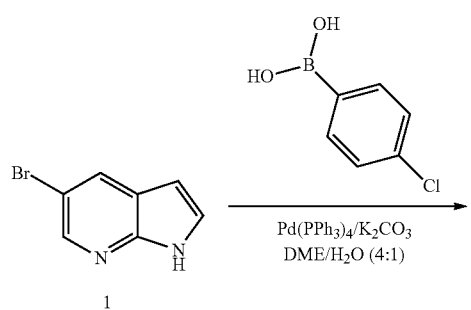

Procedure: 5-bromo-1H-pyrrolo[2,3-b]pyridine (1, 2 g, 10.2 mmol, 1.0 eq.), K$_2$CO$_3$ (2.8 g, 20.3 mmol, 2 eq.) and (4-chlorphenyl)boronic acid (1.8 g, 11.2 mmol, 1.1 eq.) was suspended in DME/H$_2$O (30 ml, 4:1) and degassed with argon. Pd(PPh$_3$)$_4$ (587 mg, 508 μmol, 0.05 eq.) was added and the reaction mixture was heated under reflux until complete consumption of the starting material. The resulting solution was passed through a Celite pad, diluted with EtOAc and washed with water. The combined organic layers were dried over Na$_2$SO$_4$ and the solvent was evaporated under reduced pressure. The crude product was purified via flash chromatography (SiO$_2$, nHex/EtOAc 6:4).

Yield: 2.23 g, 9.4 mmol, 92% (white solid).

TLC: PE/EtOAc 1:1

$^1$H NMR (DMSO-d$_6$, 200 MHz, ppm): δ 11.76 (s, 1H), 8.51 (d, J=2.1 Hz, 1H), 8.20 (d, J=1.9 Hz, 1H), 7.72 (d, J=8.5 Hz, 2H), 7.57-7.43 (m, 3H), 6.50 (dd, J=3.2, 1.7 Hz, 1H). $^{13}$C NMR (DMSO-d$_6$, 50 Hz, ppm): δ 148.2, 141.4, 138.0, 131.7, 128.9, 128.6, 127.1, 126.9, 126.1, 119.7, 100.2.

Example 6

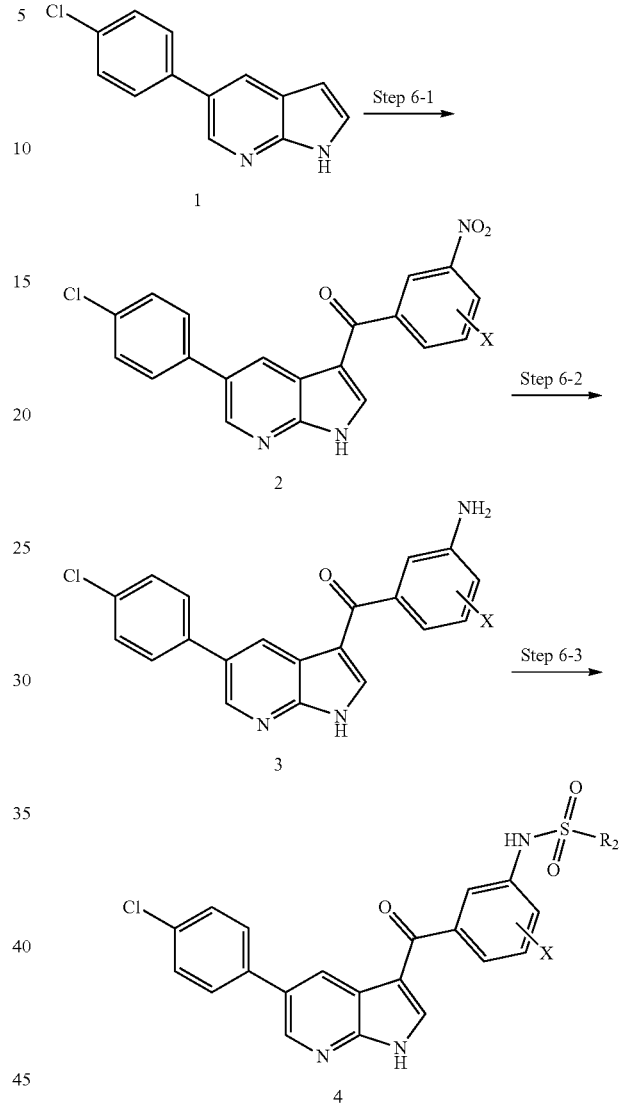

The staring material, 1, was prepared according to Example 5.

Step 6-1 and Step 6-2 were carried out in analogy to the method disclosed by Zhang et al. (Nature, 256, 583-586. Supplementary material: doi: 10.1038/nature14982).

Step 6-3

One equivalent (1 eq.) 3-aminophenyl-1H-pyrrolo[2,3-b] pyridine derivative (3) was dissolved in pyridine (1 M) and the sulfonyl chloride (1.5 eq.) was added in portions. The mixture was heated to 60° C. and stirred for 1-6 h. After complete consumption of the starting material, the crude product was diluted with aq. 1N HCl and extracted three times with EtOAc. The organic layers were combined and dried over sodium sulfate. After solvent evaporation, the product was purified by flash chromatography using the following solvent gradient: DCM/EtOAc/MeOH (95/5/0-92/5/3).

According to Example 6, the compounds of examples 37, 38, 42, 43 and 44 were prepared.

Example 7

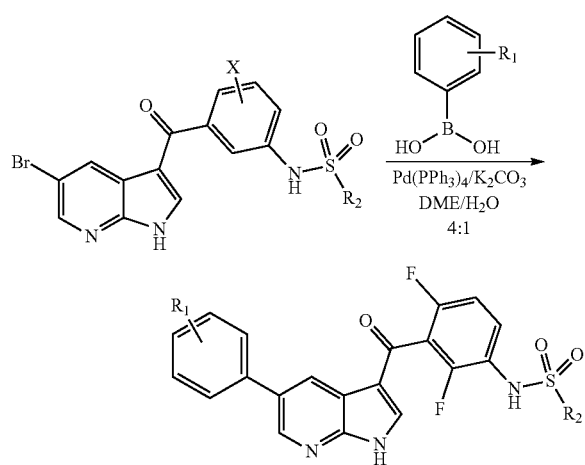

1 eq. of the 5-bromo-1H-pyrrolo[2,3-b]pyridine, K$_2$CO$_3$ (2 eq.) and boronic acid/pinacol ester (1.5 eq.) were suspended in DME/H$_2$O (0.15 M, 4:1) or 1,4-dioxane/H$_2$O (0.15 M, 2:1) and degassed with argon for 10 min. Pd(PPh$_3$)$_4$ (0.1 eq.) was added and the suspension was then irradiated in a microwave oven at 130° C. for 30 min (pw). The resulting mixture was passed through a Celite pad and the solvent was removed under reduced pressure. The crude mixture was purified via flash chromatography (SiO$_2$, DCM/EtOAc/MeOH 95/5/0 to 92/5/3) to yield the titled compound.

According to Example 7, the compounds of examples 21, 26, 27, 32, 33, and 34 were prepared.

Example 8: Synthesis of (3-amino)(5-bromo-1H-pyrrolo[2,3-b]pyridin-3-yl)methanone derivatives

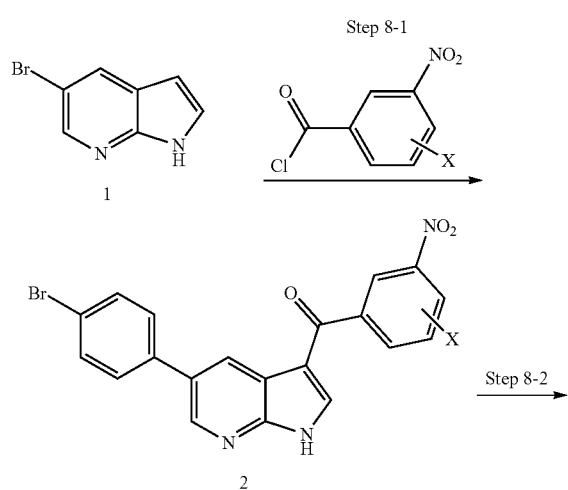

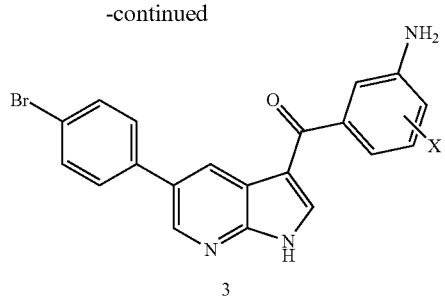

Step 8-1: (5-bromo-1H-pyrrolo[2,3-b]pyridin-3-yl)(3-nitrophenyl)methanone (2)

At RT and under argon atmosphere, 5 eq. AlCl$_3$ were stirred in 300 ml anhydrous DCM. After 1 h, 1 eq. 5-bromo-1H-pyrrolo[2,3-b]pyridine (1) was added. The reaction mixture was further stirred at RT for 1 h, then cooled to 0° C. Freshly prepared 3-nitrobenzoyl chloride derivative was dissolved in 150 mL DCM and added dropwise to the reaction mixture. After completion, the mixture was stirred at RT for 3 days. The progress of the reaction was monitored by TLC (40% EtOAc in hexane). The resulting mixture was then cautiously quenched at 0° C. with acetonitrile:H$_2$O (1:1, 300 mL). The precipitated solid was filtered, washed with MeOH and dried to afford (5-bromo-1H-pyrrolo[2,3-b]pyridin-3-yl)(3-nitrophenyl)methanone derivative 2 (20.0 g, crude), which was used in the next reaction without further purification.

Step 8-2: (3-aminophenyl)(5-bromo-1H-pyrrolo[2,3-b]pyridin-3-yl)methanone derivative (3)

To a stirred solution of 1 eq. (5-bromo-1H-pyrrolo[2,3-b]pyridin-3-yl)(3-nitrophenyl)-methanone derivative (2) in 2-methyl-THF, stannous chloride (3 eq, 29.77 g, 157.02 mmol) was added at RT. The reaction mixture was stirred at 60° C. for 16 h. The progress of the reaction was monitored by TLC (30% EtOAc in hexane). After completion, the reaction mixture was quenched with 20% aq. K$_2$CO$_3$ solution (100 mL) and stirred for 10 min, filtered through a pad of Celite and the Celite bed was washed with THF (250 mL). The resulting organic layer was washed with brine, dried over Na$_2$SO$_4$, filtered, and concentrated under reduced pressure to get a crude compound. To the crude compound was added MeOH to obtain a solid which was filtered and dried to afford (3-aminophenyl)(5-bromo-1H-pyrrolo[2,3-b]pyridin-3-yl)methanone derivative 3 as off-white solid, which was used in the next reaction without further purification.

Example 9: Synthesis of halogen-substituted (=X) N-(3-(5-bromo-1H-pyrrolo[2,3-b]pyridine-3-carbonyl)phenyl) alkyl-1-sulfonamides (alkyl=R$_2$)

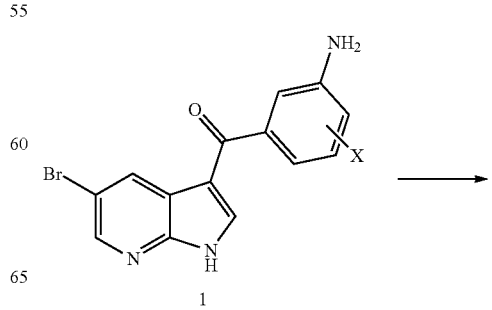

-continued

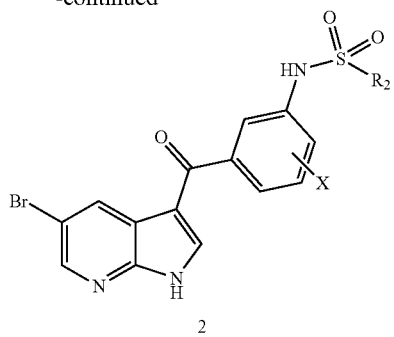

2

The (3-aminophenyl)(5-bromo-1H-pyrrolo[2,3-b]pyridin-3-yl)methanone derivative (1) (1 eq.), prepared according to Example 8, was dissolved in pyridine (1 M) and the corresponding sulfonyl chloride (1.5 eq.) was added in portions. The mixture was heated to 60° C. and stirred for 1-6 h. After complete consumption of the starting material, the crude was diluted with aqueous 1N HCl solution and extracted three times with EtOAc. The organic layers were dried over sodium sulfate and the solvent was evaporated. Purification of (2) was performed by flash chromatography using the following solvent gradient: DCM/EtOAc/MeOH (95/5/0-92/5/3).

Example 10

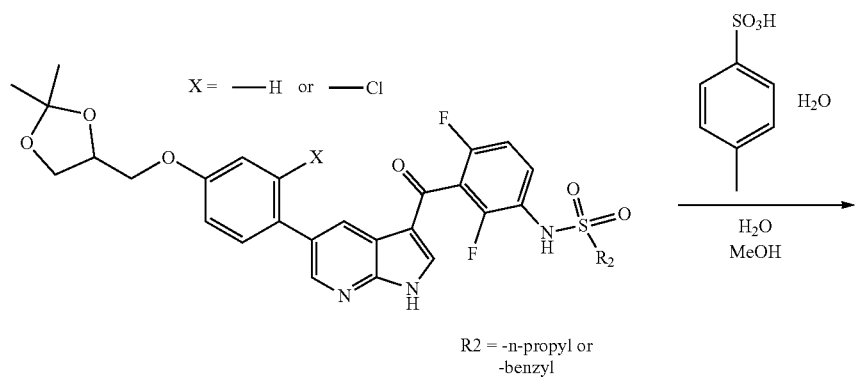

p-Toluenesulfonic acid monohydrate (0.6 eq.) was added to a solution of the acetal (1 eq.) in ethanol (EtOH, 0.05 M) and water (0.21 M). The mixture was heated to 50° C. for 6 h, then concentrated to dryness and the residue was taken up in EtOAc and the organics were washed twice with aqueous sodium bicarbonate solution (5%). The organic phase was dried over sodium sulfate and concentrated under reduced pressure. The residue was redissolved in EtOAc and precipitated with n-pentan, the solid was filtered off and dried in vacuo to obtain the desired product.

According to Example 10, the compounds of examples 30, 31, 40 and 41 were prepared.

Example 11

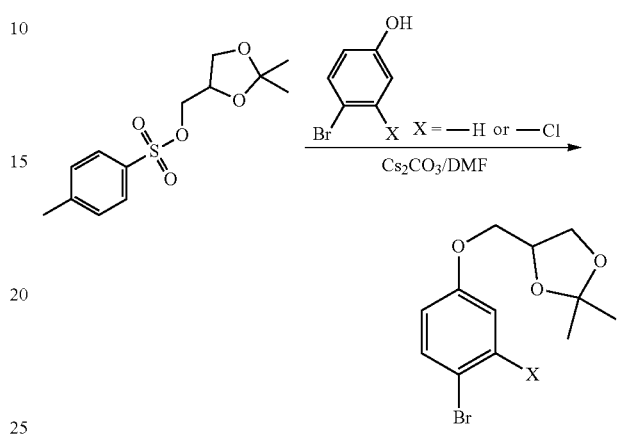

A solution of the corresponding phenol (1.0 eq) and K$_2$CO$_3$ or Cs$_2$CO$_3$ (1.5 eq.) in DMF (0.4 M) was stirred for 30 min at rt. The particular halogenalkane (1.5 eq.) and KI

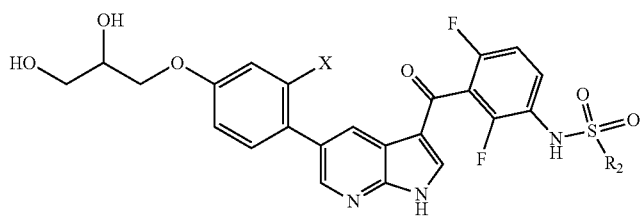

(1.0 eq.) were added to the suspension and the mixture was stirred for 2 h at 80° C. The mixture was cooled to rt and diluted with saturated, aqueous NH$_4$Cl solution. The aqueous phase was extracted with Et$_2$O, the organic extracts were dried over sodium sulfate and the solvent was removed under reduced pressure. The crude product was purified via flash chromatography (SiO2, PE/EtOAc 0-5%).

According to Example 11, the compounds of examples 25 (step 1) and 29 (step 1) were prepared.

Example 12

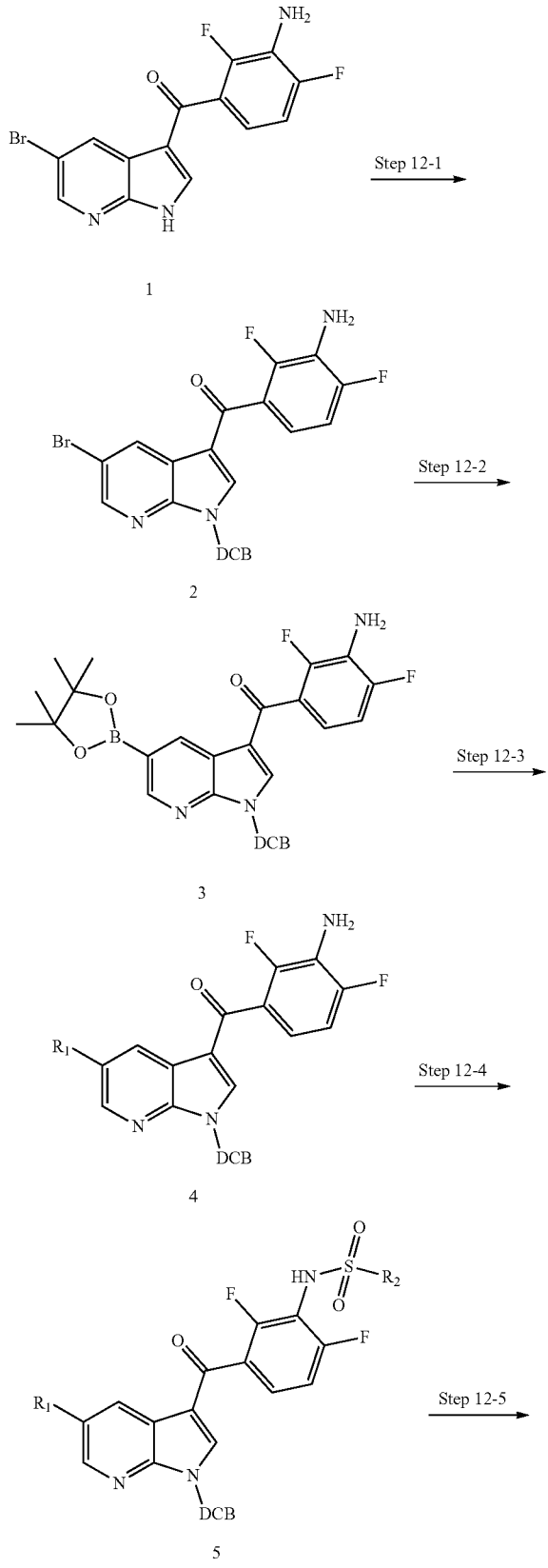

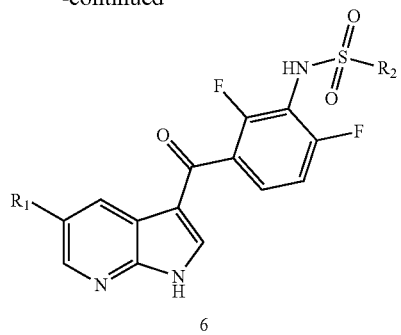

6

The starting reactant (1) was prepared according to Example 8.

Step 12-1: (3-(3-amino-2,4-difluorobenzoyl)-5-bromo-1H-pyrrolo[2,3-b]pyridin-1-yl)(2,6-dichlorophenyl)methanone (2)

To a stirred solution of (3-amino-2,4-difluorophenyl)(5-bromo-1H-pyrrolo[2,3-b]pyridin-3-yl)methanone (1, 1 eq, 11.0 g, 31.24 mmol) in 2-methyl-THF (200 mL), Et₃N (1.1 eq, 3.47 g, 34.36 mmol) was added followed by addition of 4-DMAP (0.1 eq, 0.38 g, 3.12 mmol) at 0° C. and the reaction mixture was stirred for 5 min. To this mixture 2,6-dichlorobenzoyl chloride (1 eq, 6.54 g, 31.24 mmol) was added dropwise over a period of 2 h at 0° C. The reaction mixture was stirred at RT for 1 h. The progress of the reaction was monitored by TLC (20% EtOAc in hexane). After completion of the reaction, the reaction mixture was quenched with water (100 mL) and extracted with EtOAc (500 mL×2). The organic layers were washed with brine, dried over Na₂SO₄, filtered and concentrated under reduced pressure. Trituration of the crude residue with MeOH followed by filtration afforded (3-(3-amino-2,4-difluorobenzoyl)-5-bromo-1H-pyrrolo[2,3-b]pyridin-1-yl)(2,6-dichlorophenyl)methanone (2, 14.0 g, 85%) as an off-white solid.

Analytical Data: $^1$H NMR (400 MHz, DMSO-d₆) δ 8.69 (d, J=1.96 Hz, 1H), 8.53 (br s, 1H), 8.31 (br s, 1H), 7.67 (m, 3H), 7.11 (t, J=9.29 Hz, 1H), 6.88-6.96 (m, 1H), 5.59 (s, 2H).

Step 12-2: (3-(3-amino-2,4-difluorobenzoyl)-5-(4,4,5,5-tetramethyl-1,3,2-dioxaborolan-2-yl)-1H-pyrrolo[2,3-b]pyridin-1-yl)(2,6-dichlorophenyl)methanone derivative (3)

To a stirred solution of (3-(3-aminobenzoyl)-5-bromo-1H-pyrrolo[2,3-b]pyridin-1-yl)(2,6-dichlorophenyl)methanone derivative (2, 1 eq., 7.0 g, 13.33 mmol) in dry 1,4-dioxane (100 mL), bis(pinacolato)diboron (1.20 eq, 4.06 g, 16.00 mmol) was added followed by addition of potassium acetate (fused, 2.50 eq, 3.28 g, 33.33 mmol). PdCl₂(dppf)Cl₂ (0.05 eq, 0.54 g, 0.67 mmol) was added and the reaction mixture was stirred at 80° C. for 3 h. The progress of the reaction was monitored by TLC (20% EtOAc in hexane) and LCMS. After completion, the reaction mixture was cooled to RT and filtered through a pad of Celite. The resulting organic layer was concentrated under reduced pressure. The crude product obtained was dissolved in Et₂O (200 mL), filtered and the organic layer was concentrated under reduced pressure. Trituration of the crude residue from acetonitrile followed by filtration afforded (3-(3-amino-2,4-difluorobenzoyl)-5-(4,4,5,5-tetramethyl-1,3,2-dioxaborolan-2-yl)-1H- pyrrolo[2,3-b]pyridin-1-yl)(2,6-dichlorophenyl)methanone (3, 7.0 g,) as light brown solid Analytical Data: LCMS (ESI) m/z=572.20 [M+H]$^+$
$^1$H NMR (400 MHz, DMSO-d$_6$) δ 8.81 (d, J=1.47 Hz, 1H), 8.49 (br s, 1H), 8.29 (br s, 1H), 7.66 (s, 3H), 7.11 (t, J=9.54 Hz, 1H), 6.95-6.88 (m, 1H), 5.58 (s, 2H), 1.31 (s, 12H).

Step 12-3: This reaction is being performed in analogy to Example 4, Step 3.

Step 12-4: This reaction is being performed in analogy to Example 6, Step 3.

Step 12-5: The removal of the 2,6-dichlorophenylmethanone protection group was achieved by dissolving intermediate 5 in MeOH followed by addition of potassium carbonate and stirring the mixture at RT for 3 h.

In analogy to Example 12, the compounds of examples 75 and 76 were prepared.

Synthesis of Individual Compounds

Example 13: Synthesis of N-(3-bromo-5-(5-(4-chlorophenyl)-1H-pyrrolo[2,3-b]pyridine-3-carbonyl)-phenyl)propane-1-sulfonamide

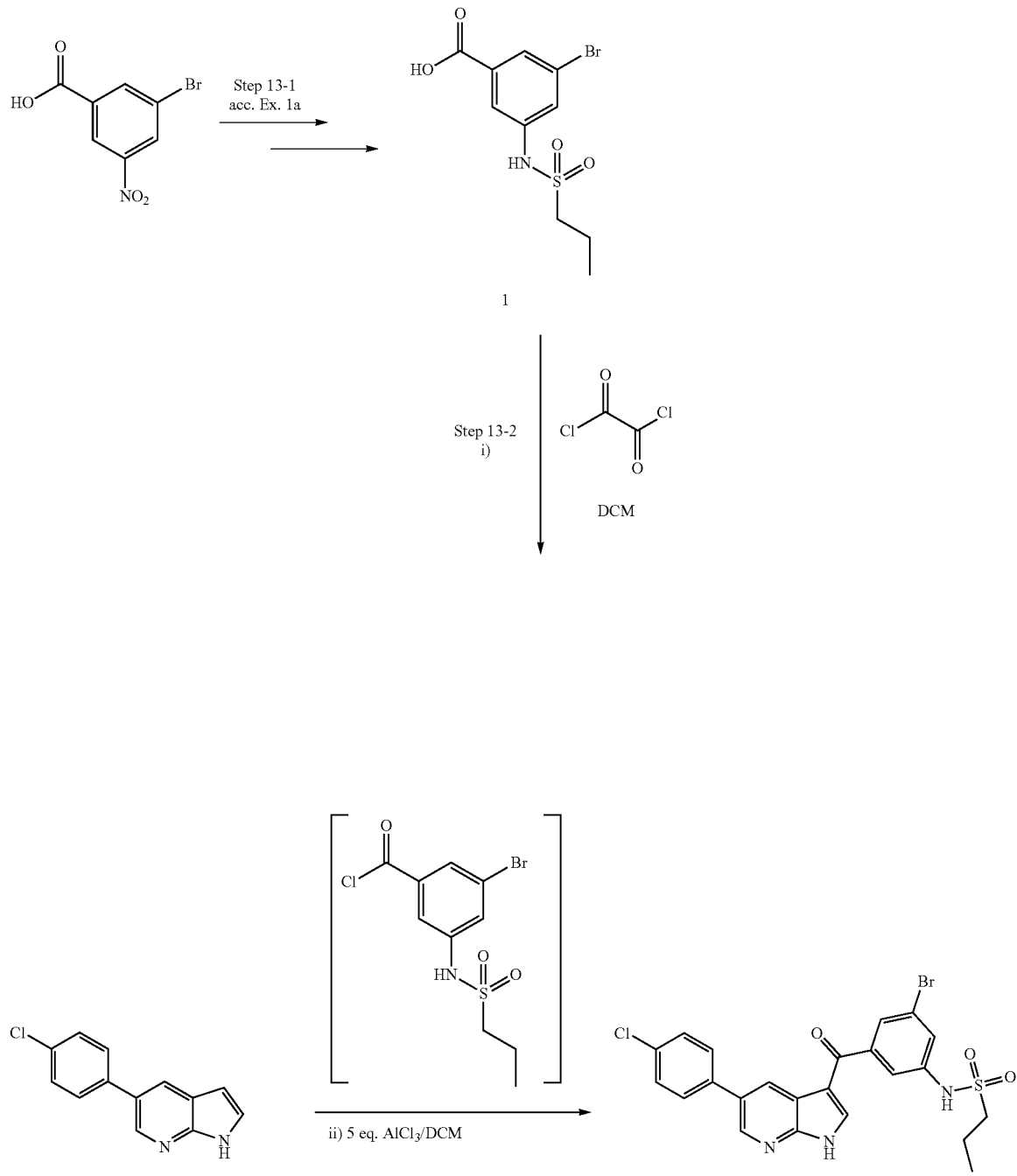

Step 13-1: Compound 1 was prepared according to Example 1a.

Analytical data: $^1$H NMR (DMSO-d$_6$, 200 MHz, ppm): δ 8.06 (d, J=2.3 Hz, 1H), 7.66 (dd, J=8.8, 2.5 Hz, 1H), 7.49 (d, J=8.8 Hz, 1H), 3.23-3.09 (m, 2H), 1.75-1.52 (m, 2H), 0.91 (t, J=7.4 Hz, 3H).

$^{13}$C NMR (DMSO-d$_6$, 50 MHz, ppm): δ 168.4, 140.5, 135.5, 133.6, 121.3, 119.4, 113.5, 52.7, 16.8, 12.4.

TLC-MS: m/z calculated for C$_{10}$H$_{12}$BrNO$_4$S ([M−H]$^-$): 320.0, found: 320.0.

Step 13-2: Synthesis of N-(3-bromo-5-(5-(4-chlorophenyl)-1H-pyrrolo[2,3-b]pyridine-3-carbonyl)-phenyl)propane-1-sulfonamide (2)

The title compound was prepared according to Example 2a.

Yield: 71 mg, 133 µmol, 38% (white solid).
TLC: nHex/EE (1:1)

Analytical data: $^1$H NMR (DMSO-d$_6$, 400 MHz, ppm): δ 12.88 (s, 1H), 9.48 (s, 1H), 8.69 (d, J=2.2 Hz, 1H), 8.67 (d, J=2.2 Hz, 1H), 8.10 (s, 1H), 7.81 (d, J=2.3 Hz, 1H), 7.77 (d, J=8.5 Hz, 3H), 7.57 (d, J=8.5 Hz, 2H), 7.50 (d, J=8.7 Hz, 1H), 3.13-3.07 (m, 2H), 1.58 (dq, J=14.9, 7.4 Hz, 2H), 0.80 (t, J=7.4 Hz, 3H);

$^{13}$C NMR (DMSO-d$_6$, 101 MHz, ppm): 188.5, 148.9, 143.5, 138.3, 137.1, 135.1, 134.2, 133.9, 132.4, 132.2, 129.8, 129.1, 128.8, 127.4, 125.7, 118.5, 116.9, 114.6, 53.6, 16.8, 12.3. TLC-MS: m/z calculated for C$_{23}$H$_{19}$BrClN$_3$O$_3$S ([M−H]$^-$): 530.0, found: 529.9.

Purity: 95%

Example 14: Synthesis of 3-(5-bromo-1H-pyrrolo[2,3-b]pyridine-3-carbonyl)-N-propyl benzene sulfonamide Step 14-1

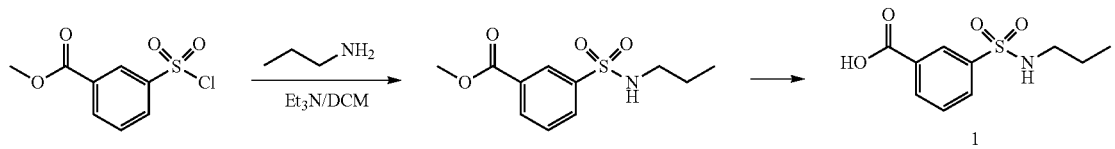

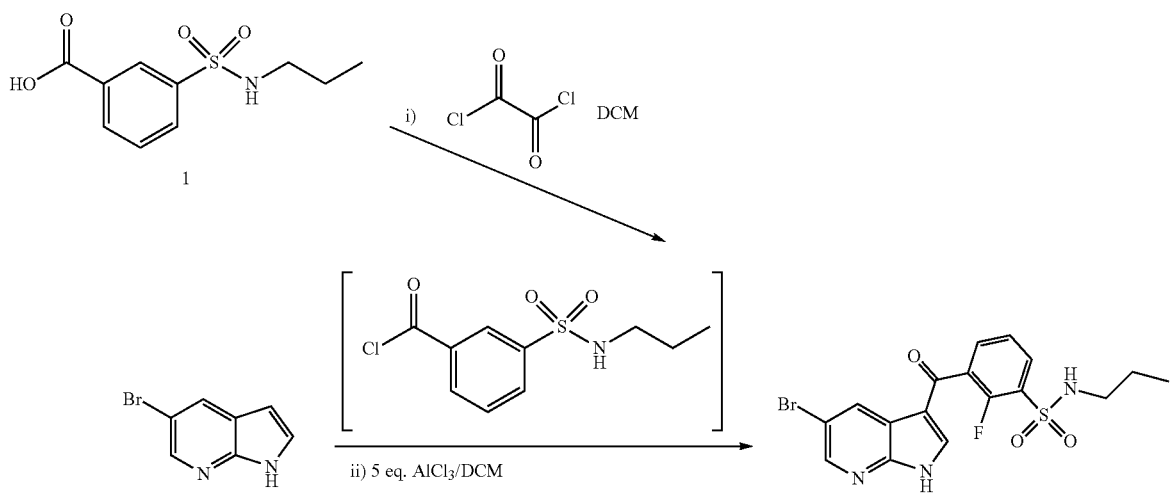

Step 14-1: 3-(N-propylsulfamoyl)benzoic acid (1) was prepared according to Example 1(Step 3), with the following deviation: The sulfonyl chloride was dissolved in DCM, followed by adding propylamine and trimethylamine. The mixture was stirred overnight at rt.

Analytical data: $^1$H NMR (DMSO-$d_6$, 200 MHz, ppm): δ 8.32 (s, 1H), 8.16 (d, J=7.6 Hz, 1H), 8.01 (d, J=7.8 Hz, 1H), 7.82-7.64 (m, 1H), 2.69 (dd, J=13.0, 6.8 Hz, 1H), 1.48-1.23 (m, 1H), 0.76 (t, J=7.3 Hz, 1H).

$^{13}$C NMR (DMSO-$d_6$, 50 MHz, ppm): δ 166.3, 141.3, 133.0, 131.9, 130.7, 130.0, 127.2, 44.5, 22.5, 11.2.

Step 14-2: 3-(5-bromo-1H-pyrrolo[2,3-b]pyridine-3-carbonyl)-N-propyl benzene sulfonamide Procedure: The titled compound was prepared according to Example 2a.
Yield: 317 mg, 750 μmol, 73% (off-white solid).
TLC: nHex/EE (1:1)

Analytical data: $^1$H NMR (DMSO-$d_6$, 400 MHz, ppm): δ 13.02 (s, 1H), 8.65 (d, J=2.3 Hz, 1H), 8.48 (d, J=2.3 Hz, 1H), 8.22 (s, 1H), 8.16 (t, J=1.4 Hz, 1H), 8.07 (m, 2H), 7.84-7.71 (m, 2H), 2.74 (dd, J=13.0, 6.7 Hz, 2H), 1.39 (h, J=7.0 Hz, 2H), 0.80 (t, J=7.3 Hz, 3H);

$^{13}$C NMR (DMSO-$d_6$, 101 MHz, ppm): 188.2, 147.6, 145.0, 141.1, 139.8, 137.7, 132.3, 131.6, 129.8, 129.4, 126.2, 120.3, 113.8, 112.8, 44.4, 22.5, 11.2.

TLC-MS: m/z calculated for $C_{17}H_{16}BrN_3O_3S$ ([M–H]$^-$): 420.0, found: 419.7.

Example 15: Synthesis of N-(3-(5-(4-chlorophenyl)-1H-pyrrolo[2,3-b]pyridine-3-carbonyl)phenyl)-propane-1-sulfonamide Step 1: 3-(Propylsulfonamido)benzoic acid

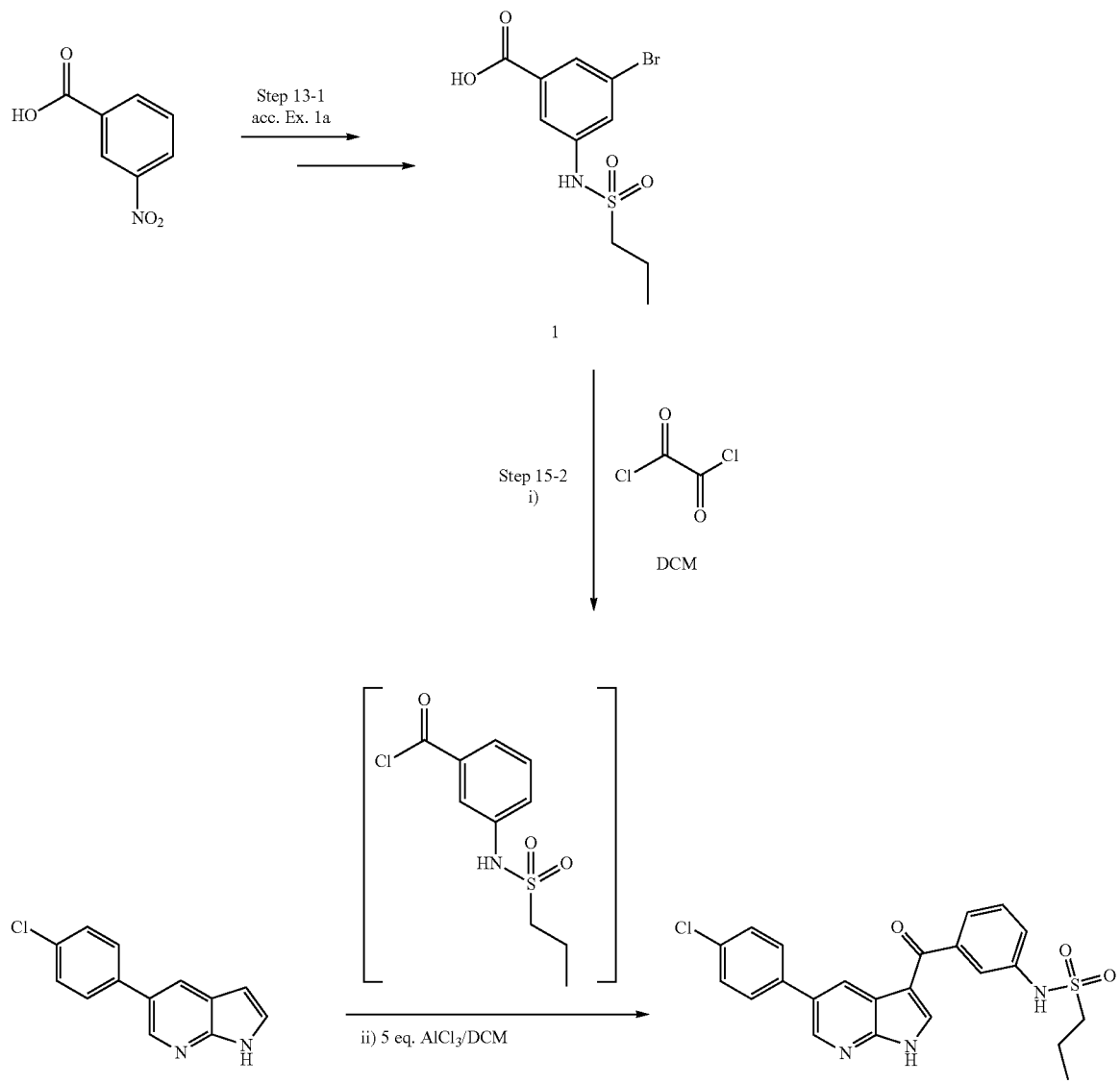

Step 15-1: 3-(Propylsulfonamido)benzoic acid (1) was prepared according to Example 1a.

Analytical data: $^1$H NMR (DMSO-$d_6$, 200 MHz, ppm): δ 13.05 (s, 1H), 10.01 (s, 1H), 7.81 (s, 1H), 7.65 (t, J=4.1 Hz, 1H), 7.44 (d, J=4.8 Hz, 2H), 3.08 (dd, J=8.6, 6.7 Hz, 2H), 1.79-1.55 (m, 2H), 0.92 (t, J=7.3 Hz, 3H).
$^{13}$C NMR (DMSO-$d_6$, 50 MHz, ppm): δ 166.9, 138.8, 131.9, 129.7, 124.4, 123.4, 119.8, 52.5, 16.8, 12.5.

TLC-MS: m/z calculated for $C_{10}H_{13}NO_4S$ ([M−H]$^−$): 242.1, found: 241.8.

Step 15-2: N-(3-(5-(4-chlorophenyl)-1H-pyrrolo[2,3-b]pyridine-3-carbonyl)phenyl)-propane-1-sulfonamide (2) was prepared according to General Procedure 2a Yield: 62 mg, 137 μmol, 52% (off-white solid).
TLC: nHex/EE (1:1)

Analytical data: $^1$H NMR (DMSO-$d_6$, 400 MHz, ppm): δ 11.40 (s, 1H), 8.73 (d, J=2.2 Hz, 1H), 8.68 (d, J=2.2 Hz, 1H), 8.16 (s, 1H), 7.77 (d, J=8.5 Hz, 2H), 7.68 (s, 1H), 7.52 (m, 5H), 3.17-3.08 (m, 2H), 1.77-1.63 (m, 2H), 0.95 (t, J=7.4 Hz, 3H); $^{13}$C NMR (DMSO-$d_6$, 101 MHz, ppm): 189.0, 148.7, 143.4, 140.4, 138.8, 137.3, 136.6, 132.3, 129.6, 129.6, 129.0, 128.8, 127.6, 123.5, 122.2, 119.3, 118.7, 113.7, 52.7, 16.8, 12.5. TLC-MS: m/z calculated for $C_{23}H_{20}ClN_3O_3S$ ([M−H]$^−$): 452.1, found: 451.9.

Purity: 96%

Example 16: Synthesis of N-(3-chloro-5-(5-(4-chlorophenyl)-1H-pyrrolo[2,3-b]pyridine-3-carbonyl)phenyl)propane-1-sulfonamide

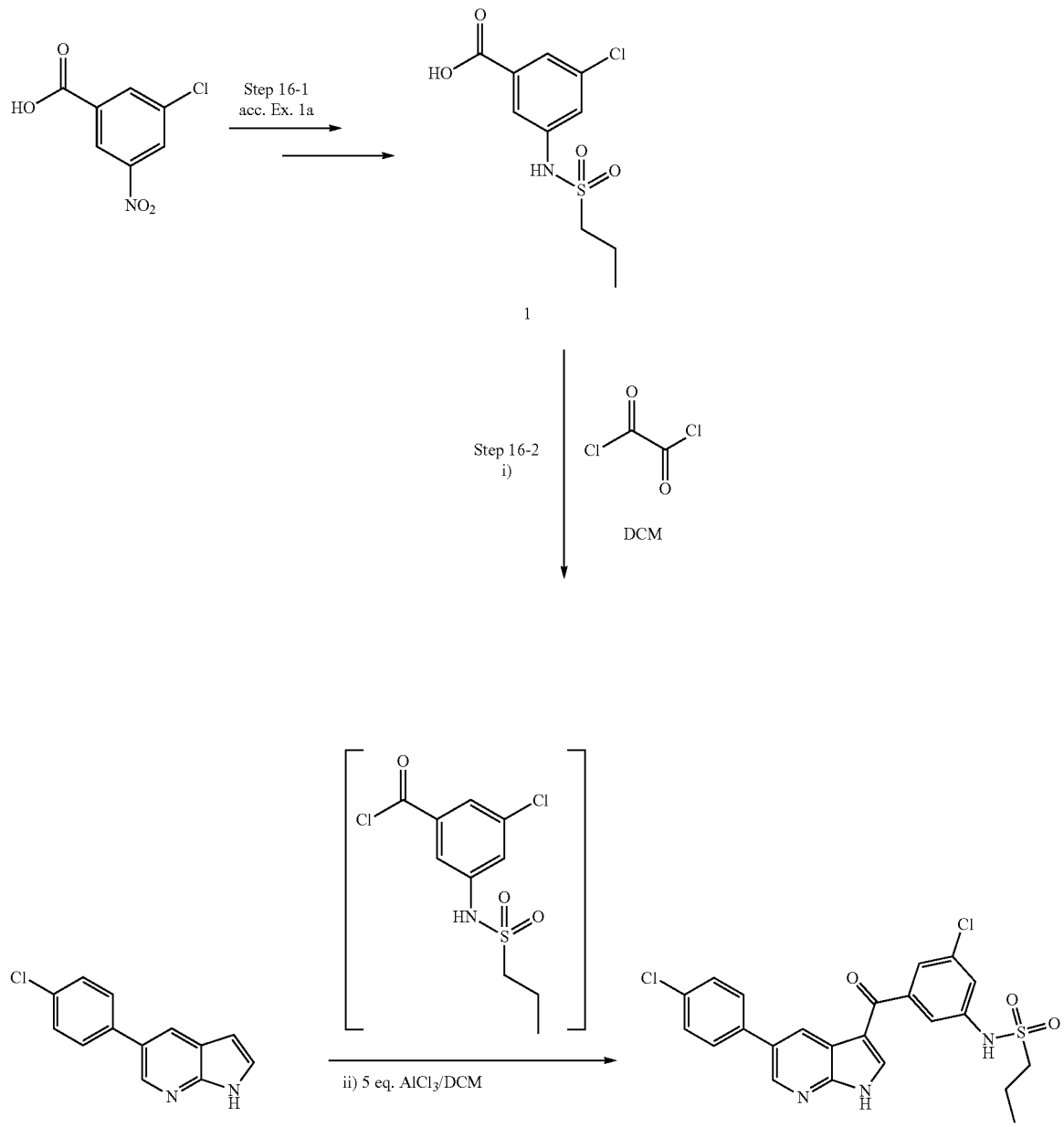

Step 16-1: 3-Chloro-5-(propylsulfonamido)benzoic acid (1) was prepared in analogy to Example 1a. The reduction of the nitro group was not performed according to Example 1a (Step 2) but carried out as follows: Methyl 3-chloro-5-nitrobenzoate (1.0 eq.) was suspended in EtOH/H$_2$O (4:1, 0.5 M), fine powdered Fe$^0$ (1.5 eq.) and solid NH$_4$Cl (3 eq.) was added. The mixture was heated to reflux for 3 h. The crude was poured through a pad of Celite and the solvent was concentrated to a minimum. The residue was diluted with EtOAc and washed with brine, the combined organic extracts were dried over sodium sulfate and the solvent was removed under reduced pressure. The product was used without any further purification for Step 3.

Analytical data: $^1$H NMR (DMSO-d$_6$, 200 MHz, ppm): δ 10.86 (s, 1H), 7.94 (d, J=2.1 Hz, 1H), 7.72-7.52 (m, 2H), 3.34-3.18 (m, 2H), 1.78-1.51 (m, 2H), 0.92 (t, J=7.4 Hz, 3H).

$^{13}$C NMR (DMSO-d$_6$, 50 MHz, ppm): δ 168.7, 139.5, 134.1, 130.8, 126.4, 119.6, 118.3, 53.0, 16.8, 12.4.

TLC-MS: m/z calculated for C$_{10}$H$_{12}$ClNO$_4$S ([M−H]$^-$): 276.0, found: 275.9.

Step 16-2: N-(3-chloro-5-(5-(4-chlorophenyl)-1H-pyrrolo[2,3-b]pyridine-3-carbonyl) phenyl)propane-1-sulfonamide (2) was prepared in analogy to Example 2a.

Yield: 78 mg, 160 μmol, 61% (white solid).

TLC: nHex/EE (1:1)

Analytical data: $^1$H NMR (DMSO-d$_6$, 400 MHz, ppm): δ 12.89 (s, 1H), 9.49 (s, 1H), 8.68 (dd, J=5.4, 2.2 Hz, 2H), 8.12 (d, J=3.0 Hz, 1H), 7.77 (d, J=8.5 Hz, 2H), 7.71 (d, J=2.5 Hz, 1H), 7.65 (dd, J=8.7, 2.5 Hz, 1H), 7.57 (dd, J=8.7, 3.0 Hz, 3H), 3.14-3.06 (m, 2H), 1.64-1.52 (m, 2H), 0.80 (t, J=7.4 Hz, 3H);

$^{13}$C NMR (DMSO-d$_6$, 101 MHz, ppm): 188.5, 148.8, 143.5, 138.3, 137.1, 134.5, 133.7, 132.4, 131.2, 129.8, 129.4, 129.0, 128.9, 128.7, 127.4, 125.5, 118.5, 114.6, 53.6, 16.7, 12.3.

TLC-MS: m/z calculated for C$_{23}$H$_{19}$Cl$_2$N$_3$O$_3$S ([M−H]$^-$): 486.1, found: 486.1.

Purity: >99%

Example 17: Synthesis of N-(3-(5-(4-chlorophenyl)-1H-pyrrolo[2,3-b]pyridine-3-carbonyl)-5-fluorophenyl) propane-1-sulfonamide

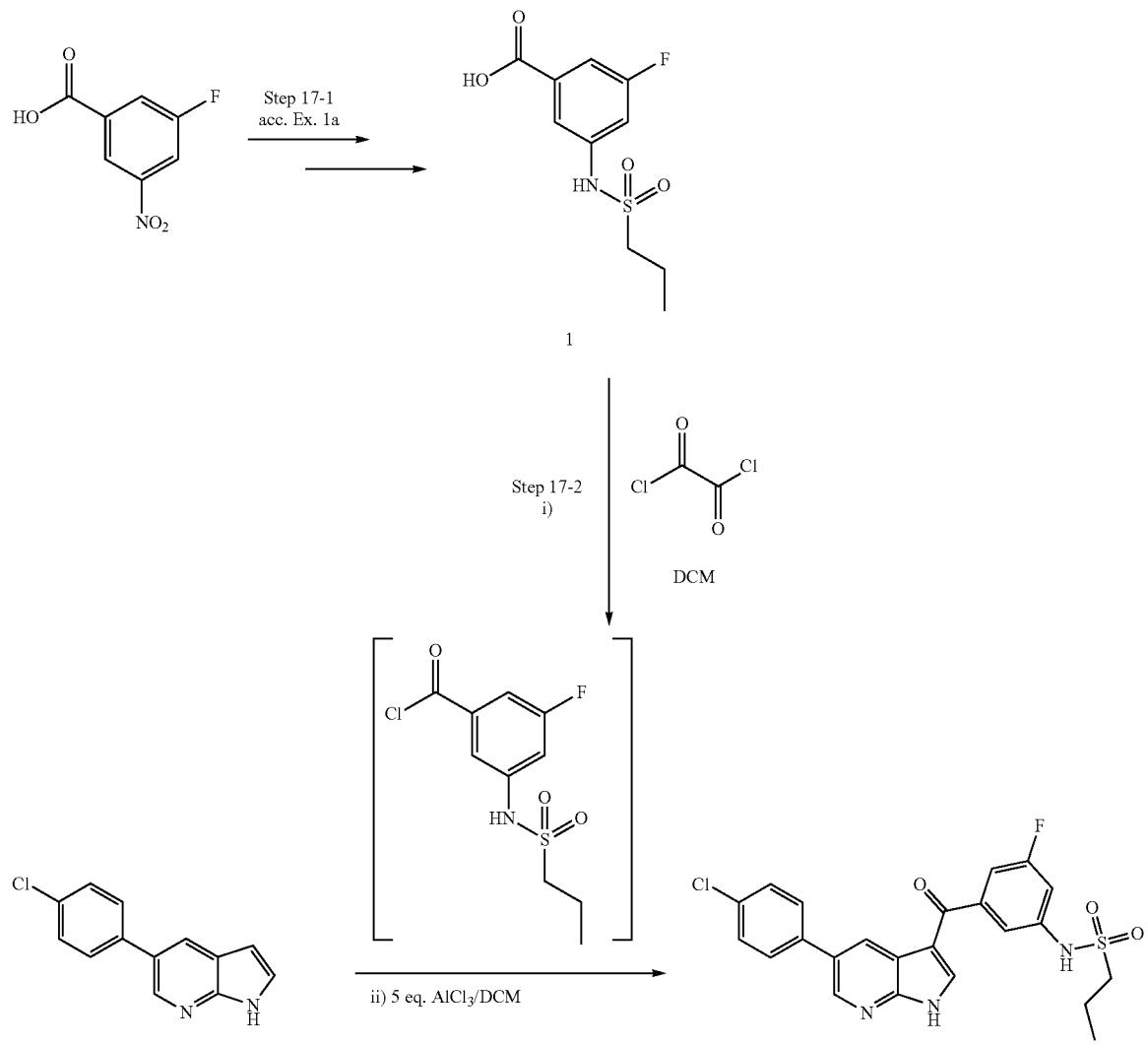

Step 17-1: 3-Fluoro-5-(propylsulfonamido)benzoic acid was prepared according to Example 1a.

Analytical data: $^1$H NMR (DMSO-d$_6$, 200 MHz, ppm): δ 13.47 (br. s., 1H), 10.47 (s, 1H), 7.85-7.36 (m, 2H), 3.41-3.05 (m, 2H), 1.83-1.46 (m, 2H), 0.92 (t, J=7.3 Hz, 3H).

$^{13}$C NMR (DMSO-d$_6$, 50 MHz, ppm): δ 168.72 (d, J=2.3 Hz), 157.12 (d, J=241.1 Hz), 136.86 (d, J=2.5 Hz), 121.74 (d, J=22.8 Hz), 120.50 (d, J=7.7 Hz), 118.23 (d, J=6.9 Hz), 117.42 (d, J=23.9 Hz), 53.0, 16.8, 12.4.

TLC-MS: m/z calculated for $C_{10}H_{12}FNO_4S$ ([M−H]$^−$): 260.1, found: 260.0.

Step 17-2: N-(3-(5-(4-chlorophenyl)-1H-pyrrolo[2,3-b]pyridine-3-carbonyl)-5-fluorophenyl) propane-1-sulfonamide (2) was prepared according to Example 2a.

Yield: 113 mg, 239 µmol, 55% (white solid).

TLC: nHex/EE (1:1)

Analytical data: $^1$H NMR (DMSO-d$_6$, 400 MHz, ppm): δ 12.88 (s, 1H), 9.33 (s, 1H), 8.69 (s, 2H), 8.10 (s, 1H), 7.77 (d, J=8.5 Hz, 2H), 7.60-7.50 (m, 4H), 7.44 (td, J=8.5, 3.0 Hz, 1H), 3.08-2.98 (m, 2H), 1.62-1.49 (m, 2H), 0.76 (t, J=7.4 Hz, 3H);

$^{13}$C NMR (DMSO-d$_6$, 101 MHz, ppm): 188.6, 158.8 (d, J=244.5 Hz), 148.9, 143.5, 138.4, 137.1, 135.1 (d, J=6.2 Hz), 132.4, 131.5 (d, J=2.4 Hz), 129.8, 129.1, 128.8, 127.4, 127.2 (d, J=8.4 Hz), 118.4, 118.0 (d, J=22.5 Hz), 116.4 (d, J=24.0 Hz), 114.6, 53.5, 16.7, 12.3.

TLC-MS: m/z calculated for $C_{23}H_{19}ClFN_3O_3S$ ([M−H]$^−$): 470.1, found: 470.1.

Purity: 91%

Example 18: Synthesis of N-(3-(5-ethynyl-1H-pyrrolo[2,3-b]pyridine-3-carbonyl)-2,4-difluorophenyl)propane-1-sulfonamide

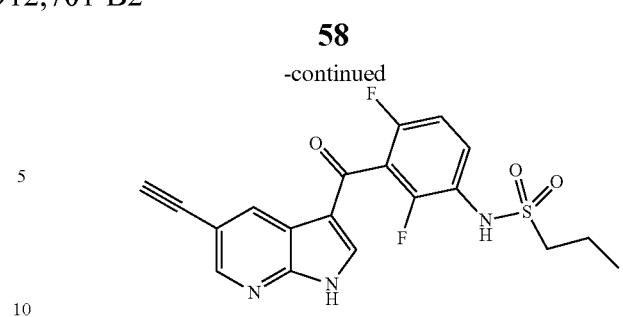

Procedure: N-(3-(5-bromo-1H-pyrrolo[2,3-b]pyridine-3-carbonyl)-2,4-difluorophenyl)propane-1-sulfonamide (100 mg, 218 µmol, 1.0 eq.), CuI (8 mg, 44 µmol, 0.2 eq.) and Pd(PPh$_3$)$_2$Cl$_2$ (31 mg, 44 µmol, 0.2 eq.) were suspended in MeCN. Triethylamine (76 µL, 546 µmol 2.5 eq.) and ethynyltrimethylsilane (93 µL, 655 µmol, 3.0 eq.) were added and the mixture was heated in a microwave oven for 2 h at 130° C. The crude was poured over a Celite pad, which was flushed with EtOAc, the organic phase was washed with brine and dried over sodium sulfate. After the solvent was removed, the left overs were solved in MeOH and 0.5 g K$_2$CO$_3$ was added. The mixture was stirred at Rt until TMS was completely cleaved and the solvent was removed under reduced pressure. Subsequent flash chromatography (SiO$_2$, DCM/MeOH 0-2%) yielded the desired product in sufficient purity.

Yield: 45 mg, 112 µmol, 51% (beige solid).

TLC: nHex/EE (1:1)

PKL440: $^1$H NMR (DMSO-d$_6$, 400 MHz, ppm): δ 13.15 (s, 1H), 9.79 (s, 1H), 8.52 (d, J=1.6 Hz, 1H), 8.50 (s, 1H), 8.30 (d, J=2.2 Hz, 1H), 7.59 (td, J=9.0, 6.0 Hz, 1H), 7.28 (t, J=8.4 Hz, 1H), 4.34 (s, 1H), 3.16-3.06 (m, 2H), 1.79-1.67 (m, 2H), 0.96 (t, J=7.4 Hz, 3H).

TLC-MS: m/z calculated for $C_{19}H_{15}F_2N_3O_3S$ ([M−H]$^−$): 402.1, found: 402.0.

Purity: 97%

Example 19: Synthesis of N-(2,4-difluoro-3-(5-(4-fluoro-2-methylphenyl)-1H-pyrrolo[2,3-b]pyridine-3-carbonyl)phenyl)butane-1-sulfonamide

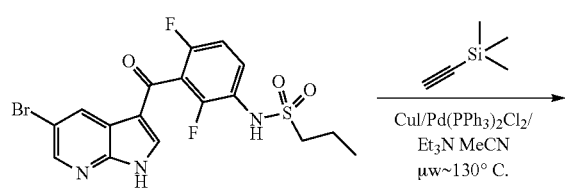

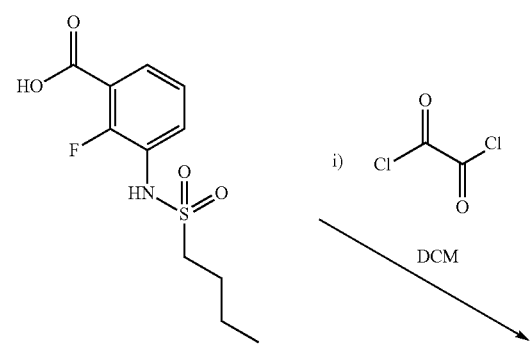

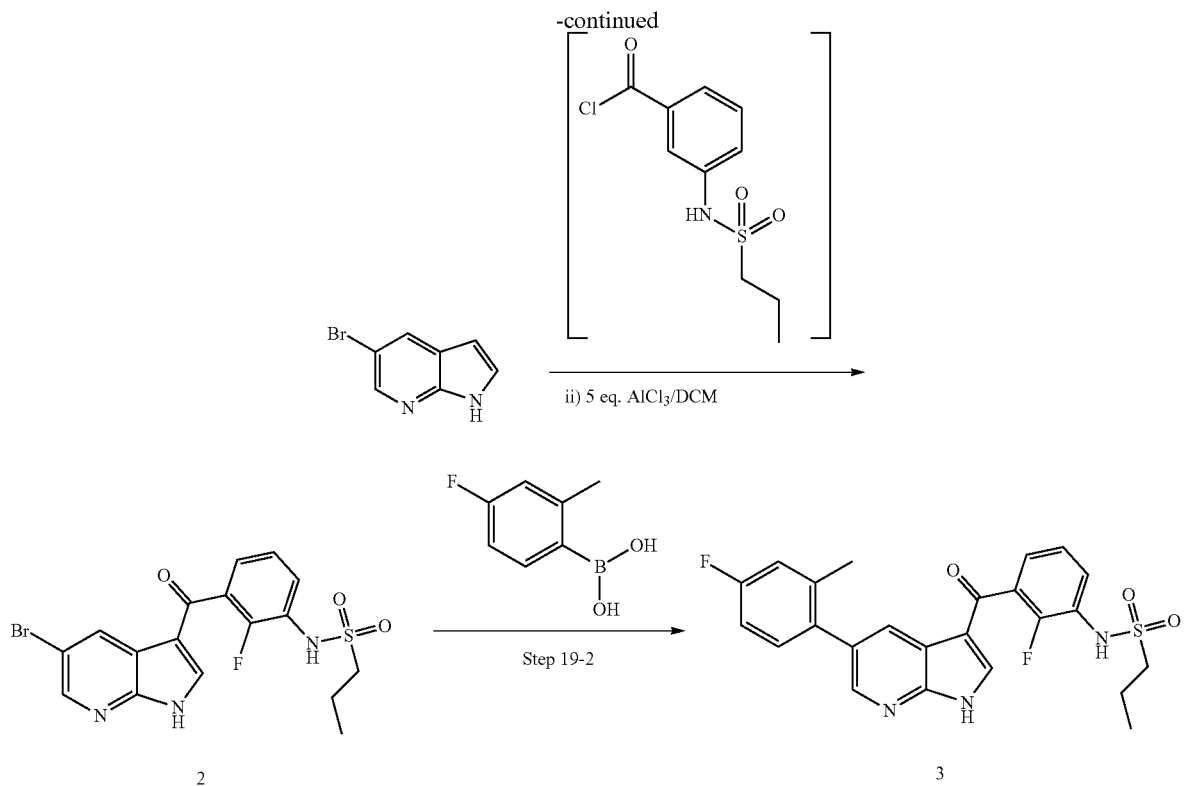

Step 19-1: N-(3-(5-bromo-1H-pyrrolo[2,3-b]pyridine-3-carbonyl)-2-fluorophenyl)propane-1-sulfonamide (2) was prepared according to Example 2a.

Yield: 1.4 g, 3 mmol, 84% (white solid).
TLC: nHex/EE (1:1)
Analytical data: $^1$H NMR (DMSO-$d_6$, 400 MHz, ppm): δ 12.99 (s, 1H), 9.80 (s, 1H), 8.59 (d, J=1.4 Hz, 1H), 8.47 (d, J=1.6 Hz, 1H), 8.08 (s, 1H), 7.60 (t, J=7.2 Hz, 1H), 7.37 (m, 2H), 3.23-3.09 (m, 2H), 1.81-1.59 (m, 2H), 1.38 (dq, J=14.0, 7.0 Hz, 2H), 0.85 (t, J=7.1 Hz, 3H).
TLC-MS: m/z calculated for $C_{18}H_{17}BrFN_3O_3S$ ([M−H]$^−$): 452.0, found: 452.4.

Step 19-2: N-(2,4-difluoro-3-(5-(4-fluoro-2-methylphenyl)-1H-pyrrolo[2,3-b]pyridine-3-carbonyl)phenyl)butane-1-sulfonamide (3) was prepared according to Example 7.

Yield: 37 mg, 73 µmol, 49% (off-white solid).
TLC: nHex/EE (1:1)
Analytical data: $^1$H NMR (DMSO-$d_6$, 400 MHz, ppm): δ 13.02 (s, 1H), 9.78 (s, 1H), 8.37 (d, J=2.0 Hz, 1H), 8.34 (s, 1H), 8.26 (s, 1H), 7.58 (td, J=8.9, 6.0 Hz, 1H), 7.36 (dd, J=8.3, 6.1 Hz, 1H), 7.28 (t, J=8.7 Hz, 1H), 7.23 (dd, J=10.1, 2.5 Hz, 1H), 7.14 (td, J=8.5, 2.6 Hz, 1H), 3.18-3.07 (m, 2H), 2.26 (s, 3H), 1.69 (dt, J=15.2, 7.6 Hz, 2H), 1.43-1.32 (m, 2H), 0.85 (t, J=7.4 Hz, 3H).
TLC-MS: m/z calculated for $C_{25}H_{22}F_3N_3O_3S$ ([M−H]$^−$): 500.1, found: 500.0.
Purity: 97%

Example 20: Synthesis of N-(3-(5-(4-(tert-butoxy)-2-chlorophenyl)-1H-pyrrolo[2,3-b]pyridine-3-carbonyl)-2,4-difluorophenyl)propane-1-sulfonamide

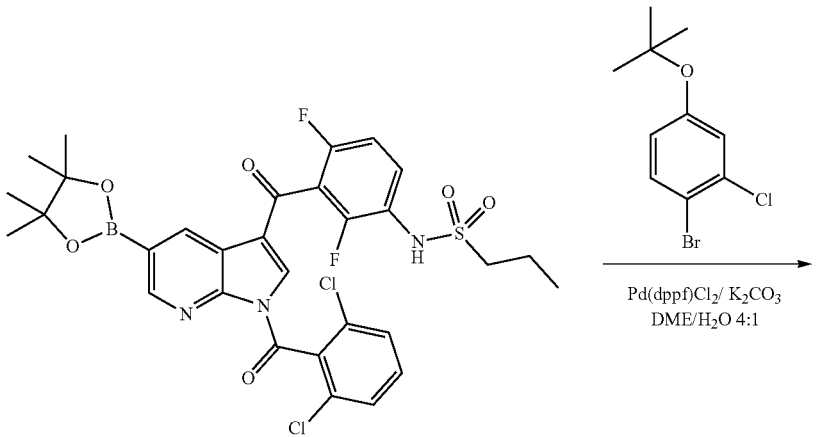

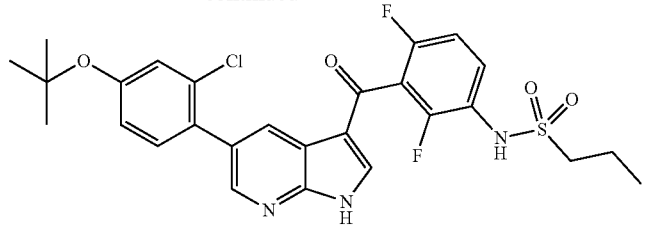

Procedure: The title compound was prepared according to Example 4, Step 3.

Yield: 52 mg, 93 μmol, 63% (off-white solid).

TLC: nHex/EE (1:1)

Analytical data: $^1$H NMR (DMSO-d$_6$, 400 MHz, ppm): δ 13.04 (d, J=1.7 Hz, 1H), 9.78 (s, 1H), 8.47 (s, 1H), 8.45 (d, J=2.1 Hz, 1H), 8.27 (d, J=1.9 Hz, 1H), 7.59 (td, J=9.0, 6.0 Hz, 1H), 7.47 (d, J=8.4 Hz, 1H), 7.28 (t, J=8.3 Hz, 1H), 7.22 (d, J=2.3 Hz, 1H), 7.12 (dd, J=8.4, 2.4 Hz, 1H), 3.15-3.09 (m, 2H), 1.80-1.67 (m, 2H), 1.37 (s, 9H), 0.96 (t, J=7.4 Hz, 3H).

TLC-MS: m/z calculated for C$_{27}$H$_{26}$ClF$_2$N$_3$O$_4$S ([M−H]$^−$): 560.1, found: 559.9.

Purity: >99%

Example 21: Synthesis of N-(3-(5-(2-chloro-4-methoxyphenyl)-1H-pyrrolo[2,3-b]pyridine-3-carbonyl)-2,4-difluorophenyl)butane-1-sulfonamide

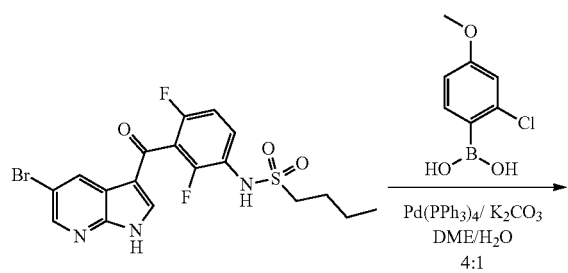

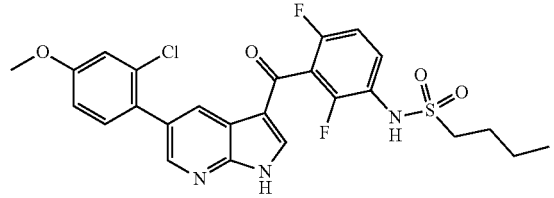

Procedure: The title compound was prepared according to Example 7.

Yield: 37 mg, 69 μmol, 47% (off-white solid).

TLC: nHex/EE (1:1)

Analytical data: $^1$H NMR (DMSO-d$_6$, 400 MHz, ppm): δ 13.04 (s, 1H), 9.78 (s, 1H), 8.44 (s, 1H), 8.41 (d, J=2.1 Hz, 1H), 8.26 (d, J=0.7 Hz, 1H), 7.58 (td, J=9.0, 6.0 Hz, 1H), 7.47 (d, J=8.5 Hz, 1H), 7.31-7.25 (m, 1H), 7.22 (d, J=2.6 Hz, 1H), 7.07 (dd, J=8.6, 2.6 Hz, 1H), 3.85 (s, 3H), 3.18-3.08 (m, 2H), 1.69 (dt, J=15.2, 7.6 Hz, 2H), 1.43-1.30 (m, 2H), 0.85 (t, J=7.4 Hz, 3H).

TLC-MS: m/z calculated for C$_{25}$H$_{22}$ClF$_2$N$_3$O$_4$S ([M−H]$^−$): 532.1, found: 531.9.

Purity: 97%

Example 22: Synthesis of N-(2,4-difluoro-3-(5-(4-morpholinophenyl)-1H-pyrrolo[2,3-b]pyridine-3-carbonyl)phenyl)propane-1-sulfonamide

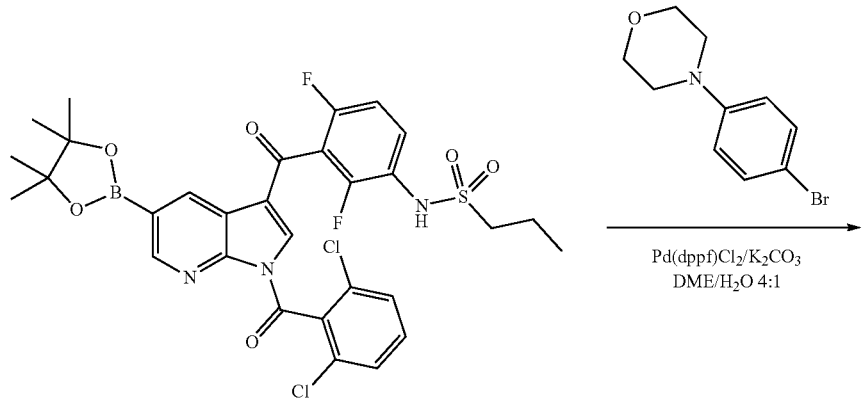

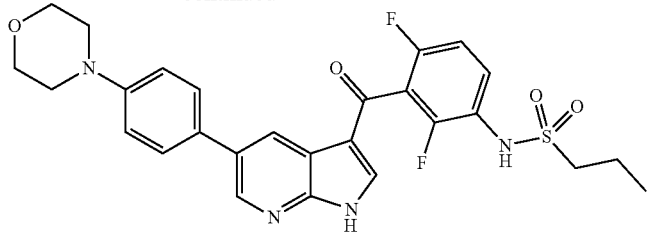

Procedure: The title compound was prepared according to Example 4, Step 3.

Yield: 18 mg, 32 μmol, 22% (beige solid).

TLC: nHex/EE (1:1)

PKL503: $^1$H NMR (DMSO-d$_6$, 400 MHz, ppm): δ 12.91 (s, 1H), 9.77 (s, 1H), 8.66 (d, J=1.8 Hz, 1H), 8.55 (s, 1H), 8.19 (s, 1H), 7.66-7.54 (m, 3H), 7.28 (t, J=8.6 Hz, 1H), 7.09 (d, J=8.6 Hz, 2H), 3.82-3.72 (m, 4H), 3.21-3.15 (m, 4H), 3.14-3.09 (m, 2H), 1.79-1.67 (m, 2H), 0.96 (t, J=7.4 Hz, 3H). TLC-MS: m/z calculated for $C_{27}H_{26}F_2N_4O_4S$ ([M−H]$^-$): 539.2, found: 539.0.

Purity: 97%

Example 23: Synthesis of N-(2,4-difluoro-3-(5-(4-(4-methylpiperazin-1-yl)phenyl)-1H-pyrrolo[2,3-b]-pyridine-3-carbonyl)phenyl)propane-1-sulfonamide

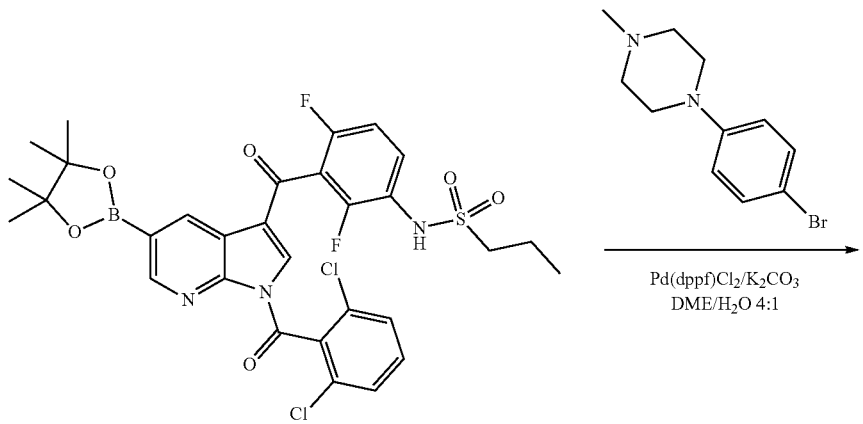

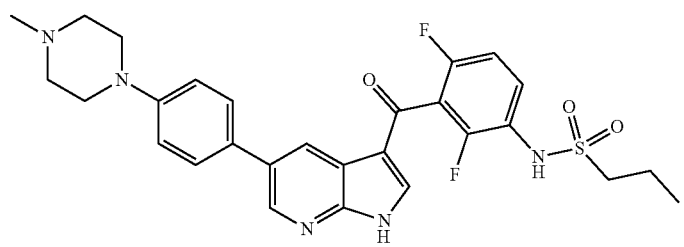

Procedure: The title compound was prepared according to Example 4, Step 3.

Yield: 38 mg, 68 μmol, 46% (beige solid).

TLC: nHex/EE (1:1)

Analytical data: $^1$H NMR (DMSO-$d_6$, 400 MHz, ppm): δ 12.96 (s, 1H), 9.92 (s, 1H), 8.66 (d, J=1.8 Hz, 1H), 8.55 (s, 1H), 8.19 (s, 1H), 7.66-7.53 (m, 3H), 7.28 (t, J=8.6 Hz, 1H), 7.09 (d, J=8.6 Hz, 2H), 3.31 (s, 4H), 3.17-3.07 (m, 2H), 2.74 (s, 4H), 2.42 (s, 3H), 1.74 (dq, J=14.8, 7.4 Hz, 2H), 0.96 (t, J=7.4 Hz, 3H). TLC-MS: m/z calculated for $C_{28}H_{29}F_2N_5O_3S$ ([M−H]$^-$): 552.2, found: 551.9.

Purity: 96%

Example 24: Synthesis of N-(3-(5-(4-(4-acetylpiperazin-1-yl)phenyl)-1H-pyrrolo[2,3-b]pyridine-3-carbonyl)-2,4-difluorophenyl)propane-1-sulfonamide Step 1: N-(3-(5-bromo-1-(2,6-dichlorobenzoyl)-1H-pyrrolo[2,3-b]pyridine-3-carbonyl)-2,4-difluorophenyl)propane-1-sulfonamide

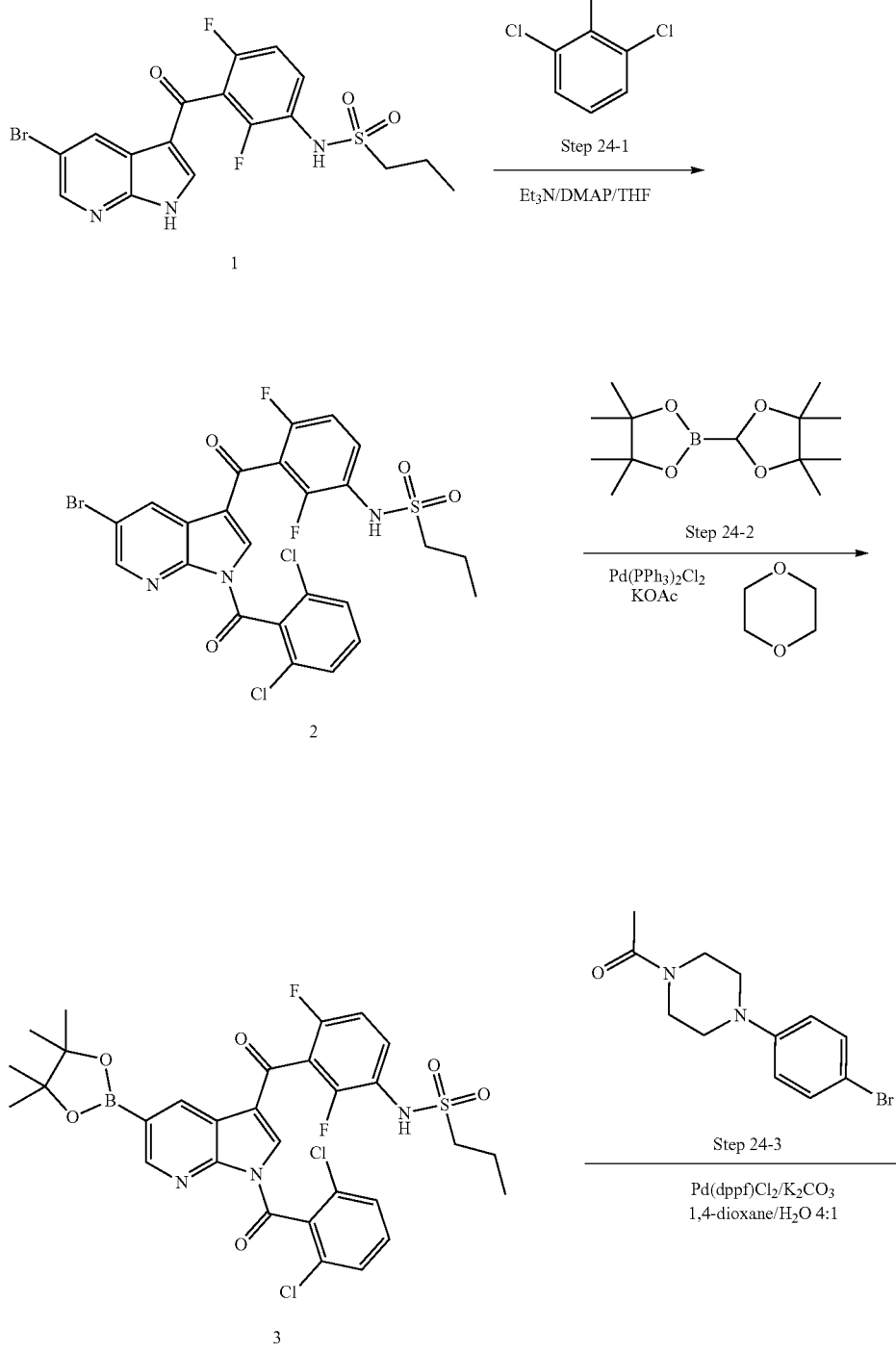

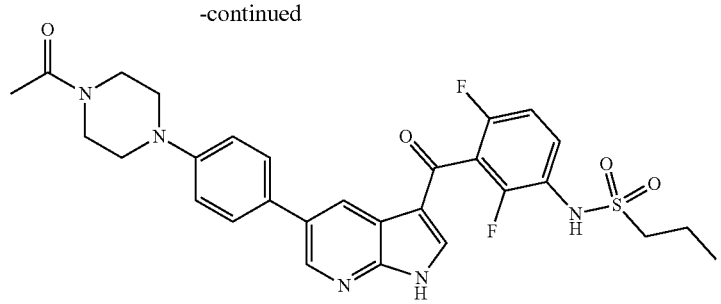

4

Step 24-1: N-(3-(5-bromo-1-(2,6-dichlorobenzoyl)-1H-pyrrolo[2,3-b]pyridine-3-carbonyl)-2,4-difluorophenyl)propane-1-sulfonamide (2) was prepared according to Example 4, Step 1.

Yield: 5.1 g, 8.1 mmol, 74% (light beige solid).

TLC: nHex/EE 25%

Analytical data: $^1$H NMR (DMSO-$d_6$, 400 MHz, ppm): δ 9.84 (s, 1H), 8.90 (s, 1H), 8.72 (d, J=2.0 Hz, 1H), 8.31 (s, 1H), 7.72-7.62 (m, 4H), 7.33 (t, J=8.9 Hz, 1H), 3.21-3.10 (m, 2H), 1.83-1.68 (m, 2H), 0.97 (t, J=7.4 Hz, 3H). TLC-MS: m/z calculated for $C_{24}H_{16}BrCl_2F_2N_3O_4S$ ([M–H]$^-$): 627.9, found: 628.0.

Step 24-2: N-(3-(1-(2,6-dichlorobenzoyl)-5-(4,4,5,5-tetramethyl-1,3,2-dioxaborolan-2-yl)-1H-pyrrolo[2,3-b]pyridine-3-carbonyl)-2,4-difluorophenyl)propane-1-sulfonamide (3) was prepared according to Example 4, Step 2.

Yield: 2.8 g, 4.1 mmol, 88% (beige solid).

TLC: nHex/EE 25%

Analytical data: $^1$H NMR (DMSO-$d_6$, 400 MHz, ppm): δ 9.06 (d, J=1.6 Hz, 1H), 8.48 (s, 1H), 8.37 (s, 1H), 7.77 (td, J=8.9, 5.6 Hz, 1H), 7.45-7.32 (m, 3H), 7.09 (t, J=8.5 Hz, 1H), 6.74 (s, 1H), 3.18-3.05 (m, 2H), 1.90 (dp, J=10.3, 7.5 Hz, 2H), 1.33 (s, 12H), 1.07 (t, J=7.4 Hz, 3H).

TLC-MS: m/z calculated for $C_3H_{28}BCl_2F_2N_3O_6S$ ([M–H]$^-$): 676.1, found: 676.5.

Step 24-3: N-(3-(5-(4-(4-acetylpiperazin-1-yl)phenyl)-1H-pyrrolo[2,3-b]pyridine-3-carbonyl)-2,4-difluorophenyl)propane-1-sulfonamide (4) was prepared according to Example 4, Step 3.

Yield: 29 mg, 49 μmol, 33% (off-white solid).

TLC: nHex/EE (1:1)

Analytical Data:
$^1$H NMR (DMSO-$d_6$, 400 MHz, ppm): δ 12.73 (s, 1H), 9.52 (s, 1H), 8.66 (d, J=1.9 Hz, 1H), 8.56 (s, 1H), 8.19 (s, 1H), 7.68-7.53 (m, 3H), 7.28 (t, J=8.6 Hz, 1H), 7.10 (d, J=8.6 Hz, 2H), 3.61 (s, 4H), 3.28-3.22 (m, 2H), 3.22-3.15 (m, 2H), 3.15-3.08 (m, 2H), 2.06 (s, 3H), 1.80-1.67 (m, 2H), 0.96 (t, J=7.4 Hz, 3H).

TLC-MS: m/z calculated for $C_{29}H_{29}F_2N_5O_4S$ ([M–H]$^-$): 580.2, found: 579.8.

Purity: >99%

Example 25: Synthesis of N-(3-(5-(2-chloro-4-((2,2-dimethyl-1,3-dioxolan-4-yl)methoxy)phenyl)-1H-pyrrolo[2,3-b]pyridine-3-carbonyl)-2,4-difluorophenyl)propane-1-sulfonamide

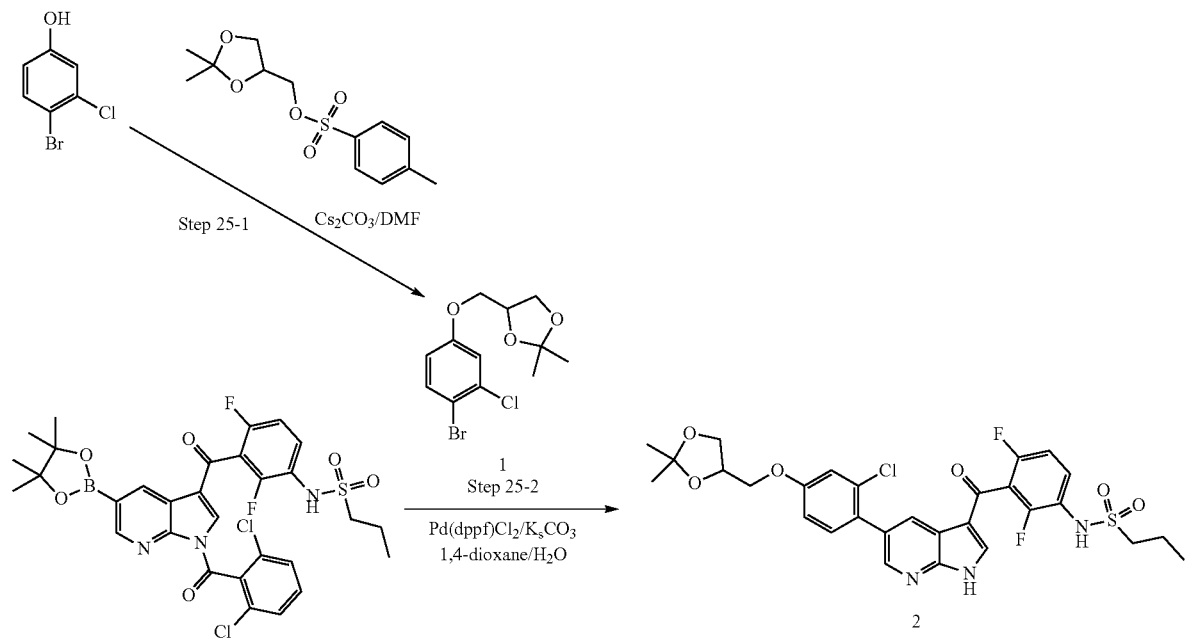

Step 25-1: 4-((4-Bromo-3-chlorophenoxy)methyl)-2,2-dimethyl-1,3-dioxolane (1) was prepared according to Example 11.

Yield: 447 mg, 1.4 μmol, 96% (white solid).
TLC: nHex/EE 25%
Analytical data: $^1$H NMR (DMSO-d$_6$, 200 MHz, ppm): δ 7.63 (d, J=8.9 Hz, 1H), 7.27 (d, J=2.9 Hz, 1H), 6.91 (dd, J=8.9, 2.9 Hz, 1H), 4.46-4.31 (m, 1H), 4.13-3.92 (m, 3H), 3.73 (dd, J=8.3, 6.3 Hz, 1H), 1.34 (s, 3H), 1.29 (s, 3H).
$^{13}$C NMR (DMSO-d$_6$, 50 MHz, ppm): δ 158.5, 134.1, 133.6, 116.4, 115.9, 112.0, 108.9, 73.5, 69.4, 65.5, 26.5, 25.3.

Step 25-2: N-(3-(5-(2-chloro-4-((2,2-dimethyl-1,3-dioxolan-4-yl)methoxy)phenyl)-1H-pyrrolo[2,3-b]pyridine-3-carbonyl)-2,4-difluorophenyl)propane-1-sulfonamide (2) was prepared according to Example 4, Step 3.

Yield: 97 mg, 156 μmol, 70% (off-white solid).
TLC: nHex/EE (1:1)
Analytical data: $^1$H NMR (DMSO-d$_6$, 400 MHz, ppm): δ 12.99 (s, 1H), 9.76 (s, 1H), 8.44 (s, 1H), 8.41 (d, J=1.9 Hz, 1H), 8.26 (s, 1H), 7.58 (td, J=9.0, 6.0 Hz, 1H), 7.47 (d, J=8.5 Hz, 1H), 7.32-7.23 (m, J=14.0, 5.6 Hz, 2H), 7.09 (dd, J=8.6, 2.5 Hz, 1H), 4.50-4.38 (m, 1H), 4.19-4.03 (m, 3H), 3.78 (dd, J=8.3, 6.4 Hz, 1H), 3.17-3.08 (m, 2H), 1.82-1.67 (m, 2H), 1.38 (s, 3H), 1.32 (s, 3H), 0.96 (t, J=7.4 Hz, 3H).
TLC-MS: m/z calculated for C$_{29}$H$_{28}$ClF$_2$N$_3$O$_6$S ([M−H]): 618.1, found: 617.8
Purity: 95%

Example 26: Synthesis of N-(2,4-difluoro-3-(5-(4-methoxyphenyl)-1H-pyrrolo[2,3-b]pyridine-3-carbonyl) phenyl)-1-phenylmethanesulfonamide

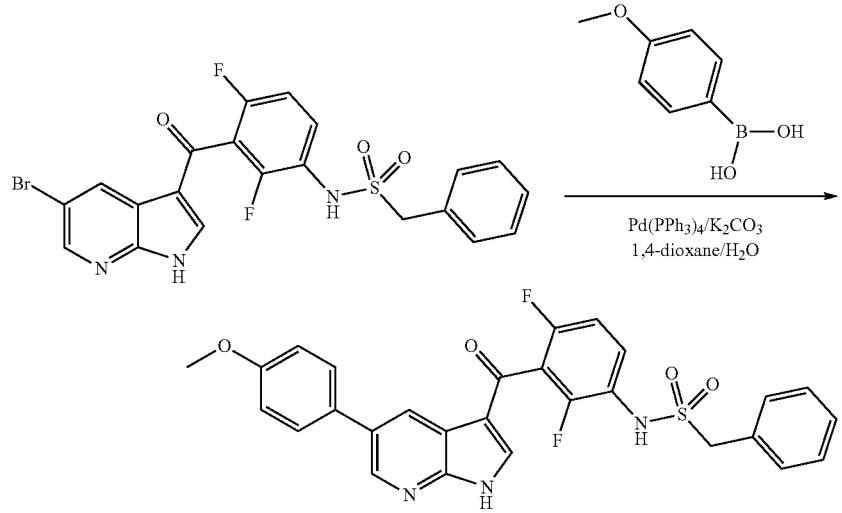

Procedure: The title compound was prepared according to Example 7.
Yield: 11 mg, 21 μmol, 15% (off-white solid).
TLC: nHex/EE (1:1)
Analytical data: $^1$H NMR (DMSO-d$_6$, 400 MHz, ppm): δ 12.97 (s, 1H), 9.83 (s, 1H), 8.67 (s, 1H), 8.59 (s, 1H), 8.19 (s, 1H), 7.69 (d, J=8.2 Hz, 2H), 7.51 (dd, J=14.7, 8.7 Hz, 1H), 7.43-7.30 (m, J=9.6 Hz, 5H), 7.24 (t, J=8.7 Hz, 1H), 7.09 (d, J=8.4 Hz, 2H), 4.53 (s, 2H), 3.82 (s, 3H).
TLC-MS: m/z calculated for C$_{28}$H$_{21}$F$_2$N$_3$O$_4$S ([M−H]): 532.1, found: 531.8.
Purity: 99%

Example 27: Synthesis of 4-(3-(2,6-difluoro-3-((phenylmethyl)sulfonamido) benzoyl)-1H-pyrrolo[2,3-b]pyridin-5-yl)benzenesulfonamide

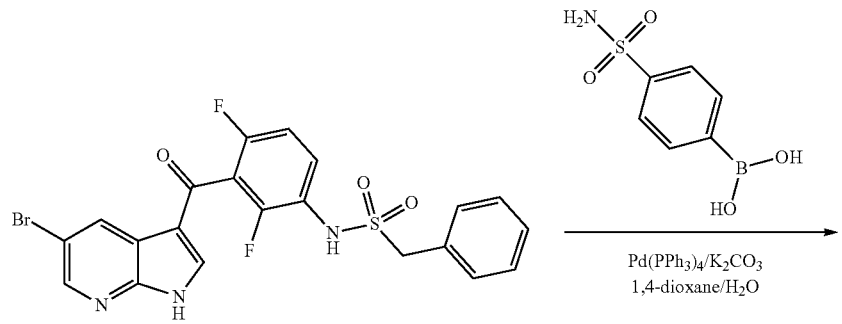

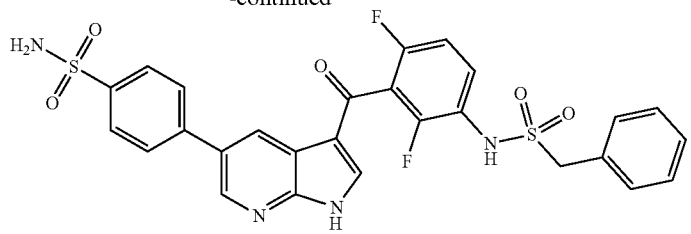

Procedure: The title compound was prepared according to Example 7.

Yield: 75 mg, 129 μmol, 65% (off-white solid).

TLC: nHex/EE (1:1)

Analytical data: $^1$H NMR (DMSO-$d_6$, 400 MHz, ppm): δ 13.10 (s, 1H), 9.85 (s, 1H), 8.80 (s, 1H), 8.75 (s, 1H), 8.27 (d, J=1.8 Hz, 1H), 7.98 (q, J=8.5 Hz, 4H), 7.52 (dd, J=14.9, 9.0 Hz, 1H), 7.46 (s, 2H), 7.43-7.32 (m, 5H), 7.25 (t, J=8.7 Hz, 1H), 4.55 (s, 2H).

TLC-MS: m/z calculated for $C_{27}H_{20}F_2N_4O_5S_2$ ([M−H]): 581.1, found: 580.7.

Purity: 93%

Example 28: Synthesis of N-(2,4-difluoro-3-(5-(4-fluorophenyl)-1H-pyrrolo[2,3-b]pyridine-3-carbonyl) phenyl)-1-phenylmethanesulfonamide

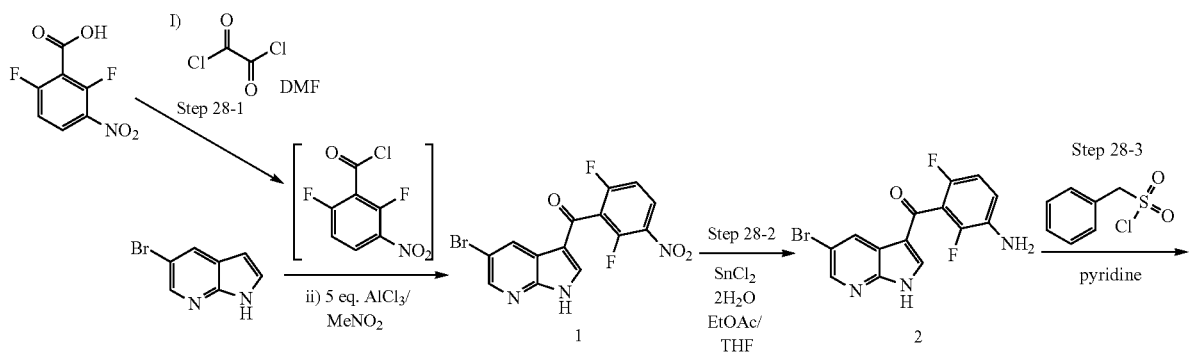

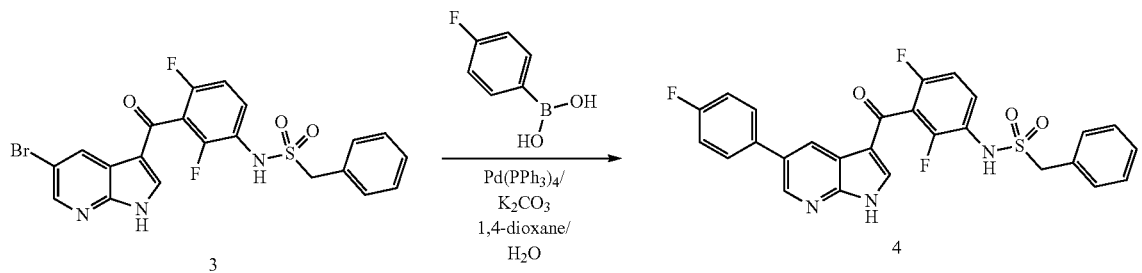

Step 28-1: (5-Bromo-1H-pyrrolo[2,3-b]pyridin-3-yl)(2,6-difluoro-3-nitrophenyl)methanone (1) was prepared according to Example 6, Step 1 (Lit.: Zhang et al [doi: 10.1038/nature14982]).

Yield: 17.3 g, 45.3 mmol, 59% (beige solid).

TLC: PE/EtOAc 1:1

Analytical data: $^1$H NMR (DMSO-$d_6$, 200 MHz, ppm): δ 13.16 (s, 1H), 8.64 (d, J=2.3 Hz, 1H), 8.51 (d, J=2.3 Hz, 1H), 8.49-8.37 (m, 2H), 7.54 (ddd, J=9.5, 8.3, 1.6 Hz, 1H). $^{13}$C NMR (DMSO-$d_6$, 50 Hz, ppm): δ 178.9, 161.5 (dd, J=257.6, 7.5 Hz), 152.8 (dd, J=264.4, 9.3 Hz), 147.9, 145.5, 140.3, 134.4 (dd, J=7.9, 3.8 Hz), 131.2, 129.1 (dd, J=11.4, 1.2 Hz), 119.2 (dd, J=25.1, 23.0 Hz), 119.0, 114.7, 114.5, 113.3 (dd, J=24.0, 4.2 Hz).

TLC-MS: m/z calculated for $C_{14}H_6BrF_2N_3O_3$ ([M−H]$^−$): 380.0, found: 380.1.

Step 28-2: (3-Amino-2,6-difluorophenyl)(5-bromo-1H-pyrrolo[2,3-b]pyridin-3-yl) methanone (2) was prepared according to Example 6, Step 2 (Lit.: Zhang et al [doi: 10.1038/nature14982]).

Yield: 16.8 g, 44.4 mmol, 98% (beige solid).

TLC: PE/EtOAc 1:1

Analytical data: $^1$H NMR (DMSO-$d_6$, 200 MHz, ppm): δ 13.04 (s, 1H), 8.56 (d, J=2.2 Hz, 1H), 8.49 (d, J=2.3 Hz, 1H), 8.15 (s, 1H), 7.03-6.81 (m, 2H), 5.22 (s, 2H).

$^{13}$C NMR (DMSO-$d_6$, 50 Hz, ppm): δ 182.27 (s), 150.0 (dd, J=157.3, 7.2 Hz), 147.7, 145.2 (dd, J=163.6, 7.1 Hz), 145.1, 138.7, 133.48 (dd, J=13.1, 2.4 Hz), 131.1, 119.1, 117.88-116.41 (m), 115.2, 114.1, 111.44 (dd, J=22.0, 3.3 Hz).

TLC-MS: m/z calculated for $C_{14}H_8BrF_2N_3O$ ([M−H]$^−$): 350.0, found: 349.9.

Step 28-3: N-(3-(5-bromo-1H-pyrrolo[2,3-b]pyridine-3-carbonyl)-2,4-difluorophenyl)-1-phenylmethanesulfonamide (2) was prepared according to Example 6, Step 3.

Yield: 1.7 g, 3.4 mmol, 79% (off-white solid).

TLC: nHex/EE (1:1)

Analytical data: $^1$H NMR (DMSO-$d_6$, 400 MHz, ppm): δ 13.15 (s, 1H), 9.86 (s, 1H), 8.61 (s, 1H), 8.50 (d, J=2.0 Hz, 1H), 8.24 (d, J=2.0 Hz, 1H), 7.51 (td, J=8.9, 6.3 Hz, 1H), 7.43-7.30 (m, 5H), 7.23 (t, J=8.7 Hz, 1H), 4.53 (s, 2H).

TLC-MS: m/z calculated for $C_{21}H_{14}BrF_2N_3O_3S$ ([M−H]$^−$): 504.0, found: 503.8.

Step 28-4: N-(2,4-difluoro-3-(5-(4-fluorophenyl)-1H-pyrrolo[2,3-b]pyridine-3-carbonyl) phenyl)-1-phenylmethanesulfonamide (4) was prepared according to Example 7.

Yield: 27 mg, 51 μmol, 37% (off-white solid).

TLC: nHex/EE (1:1)

Analytical data: $^1$H NMR (DMSO-$d_6$, 400 MHz, ppm): δ 13.02 (s, 1H), 9.84 (s, 1H), 8.70 (s, 1H), 8.64 (s, 1H), 8.22 (d, J=2.3 Hz, 1H), 7.81 (dd, J=8.1, 5.6 Hz, 2H), 7.51 (dd, J=14.7, 8.9 Hz, 1H), 7.41-7.31 (m, 7H), 7.24 (t, J=8.7 Hz, 1H), 4.54 (s, 2H).

TLC-MS: m/z calculated for $C_{27}H_{18}F_3N_3O_3S$ ([M−H]): 520.1, found: 519.8

Purity: 93%

Example 29: Synthesis of N-(3-(5-(4-((2,2-dimethyl-1,3-dioxolan-4-yl)methoxy) phenyl)-1H-pyrrolo[2,3-b]pyridine-3-carbonyl)-2,4-difluorophenyl) propane-1-sulfonamide

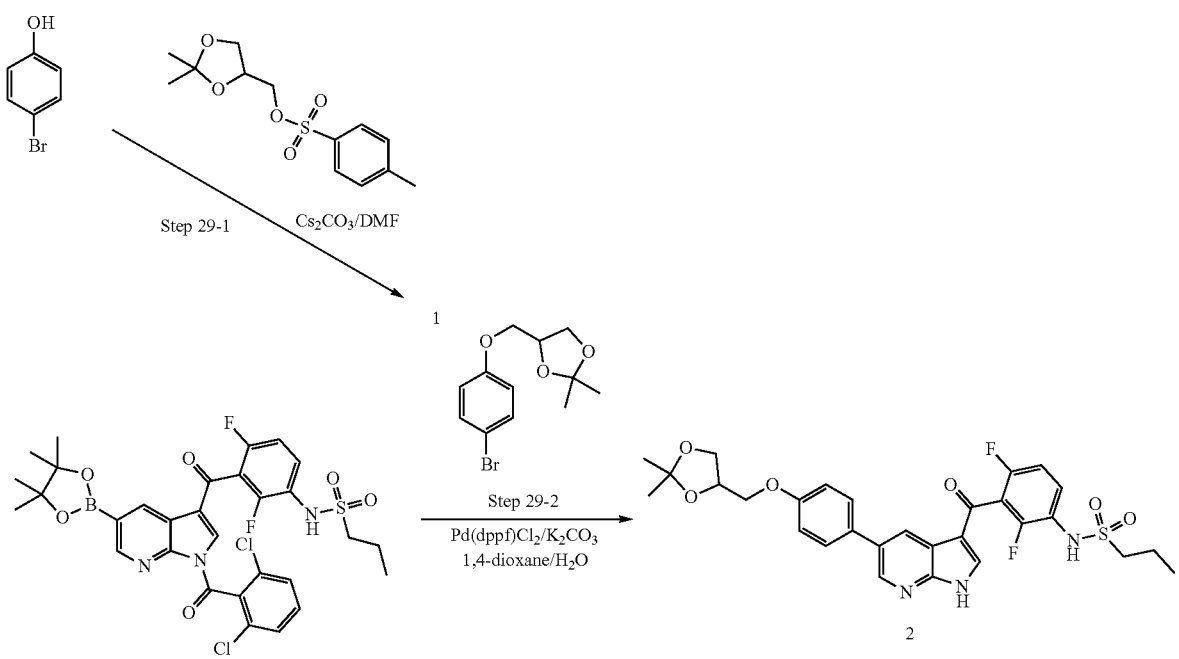

Step 29-1: 4-((4-Bromophenoxy)methyl)-2,2-dimethyl-1,3-dioxolane (1) was prepared according to Example 11.

Yield: 474 mg, 1.7 μmol, 95% (colorless oil).

TLC: nHex/EE 25%

Analytical data: ¹H NMR (DMSO-d₆, 200 MHz, ppm): δ 7.43 (d, J=9.1 Hz, 2H), 6.92 (d, J=9.1 Hz, 2H), 4.46-4.31 (m, 1H), 4.13-3.92 (m, 3H), 3.73 (dd, J=8.3, 6.3 Hz, 1H), 1.34 (s, 3H), 1.29 (s, 3H).

¹³C NMR (DMSO-d₆, 50 MHz, ppm): δ 157.8, 132.2, 116.9, 112.3, 109.0, 73.7, 69.0, 65.7, 26.7, 25.4.

Step 29-2: N-(3-(5-(4-((2,2-dimethyl-1,3-dioxolan-4-yl)methoxy) phenyl)-1H-pyrrolo[2,3-b]pyridine-3-carbonyl)-2,4-difluorophenyl)propane-1-sulfonamide (2) was prepared according to Example 4, Step 3.

Yield: 67 mg, 114 μmol, 52% (off-white solid).

TLC: nHex/EE (1:1)

Analytical data: ¹H NMR (DMSO-d₆, 400 MHz, ppm): δ 12.96 (s, 1H), 9.77 (s, 1H), 8.67 (d, J=2.2 Hz, 1H), 8.57 (s, 1H), 8.21 (s, 1H), 7.68 (d, J=8.7 Hz, 2H), 7.59 (td, J=9.0, 6.0 Hz, 1H), 7.28 (t, J=8.4 Hz, 1H), 7.11 (d, J=8.8 Hz, 2H), 4.51-4.39 (m, 1H), 4.16-4.00 (m, 3H), 3.79 (dd, J=8.3, 6.4 Hz, 1H), 3.18-3.03 (m, 2H), 1.80-1.66 (m, 2H), 1.38 (s, 3H), 1.32 (s, 3H), 0.96 (t, J=7.4 Hz, 3H).

TLC-MS: m/z calculated for $C_{29}H_{29}F_2N_3O_6S$ ([M−H]): 584.2, found: 583.7.

Purity: 95%

Example 30: Synthesis of N-(3-(5-(2-chloro-4-(2,3-dihydroxypropoxy)phenyl)-1H-pyrrolo[2,3-b]pyridine-3-carbonyl)-2,4-difluorophenyl)propane-1-sulfonamide

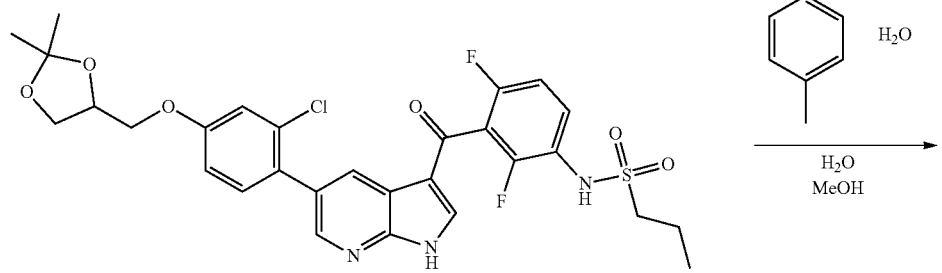

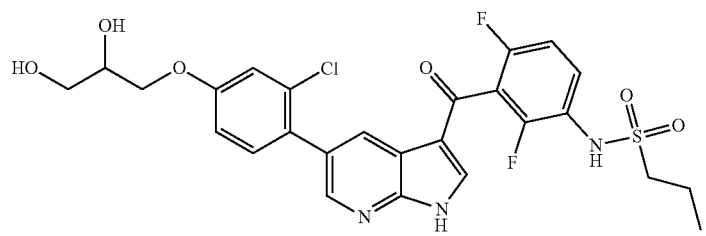

Procedure: The title compound was prepared according to Example 10.

Yield: 18 mg, 31 μmol, 38% (off-white solid).

TLC: DCM/MeOH 5%

Analytical data: ¹H NMR (DMSO-d₆, 400 MHz, ppm): δ 13.03 (s, 1H), 9.78 (s, 1H), 8.44 (s, 1H), 8.41 (d, J=2.0 Hz, 1H), 8.26 (s, 1H), 7.58 (td, J=9.0, 6.0 Hz, 1H), 7.46 (d, J=8.5 Hz, 1H), 7.28 (t, J=8.7 Hz, 1H), 7.21 (d, J=2.5 Hz, 1H), 7.07 (dd, J=8.6, 2.5 Hz, 1H), 5.03 (d, J=5.1 Hz, 1H), 4.72 (t, J=5.6 Hz, 1H), 4.11 (dd, J=10.1, 4.0 Hz, 1H), 3.97 (dd, J=10.0, 6.2 Hz, 1H), 3.87-3.79 (m, 1H), 3.47 (t, J=5.6 Hz, 2H), 3.17-3.06 (m, 2H), 1.81-1.65 (m, 2H), 0.96 (t, J=7.4 Hz, 3H).

TLC-MS: m/z calculated for $C_{26}H_{24}ClF_2N_3O_6S$ ([M−H]): 578.1, found: 577.7.

Purity: >99%

Example 31: Synthesis of N-(3-(5-(4-(2,3-dihydroxypropoxy)phenyl)-1H-pyrrolo[2,3-b]pyridine-3-carbonyl)-2,4-difluorophenyl)propane-1-sulfonamide

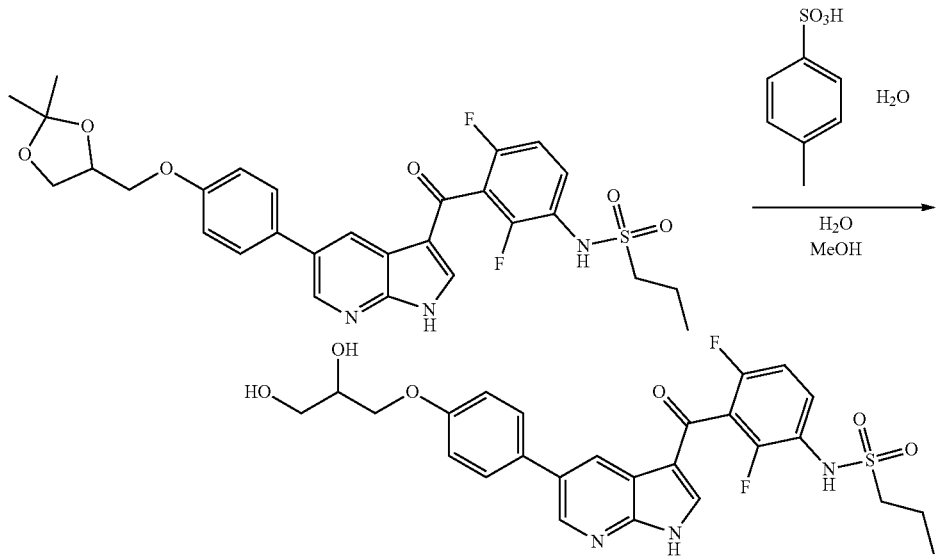

Procedure: The title compound was prepared according to Example 10.

Yield: 25 mg, 45 μmol, 66% (off-white solid).

TLC: DCM/MeOH 5%

Analytical data: $^1$H NMR (DMSO-$d_6$, 400 MHz, ppm): δ 12.92 (s, 1H), 9.81 (s, 1H), 8.67 (d, J=2.1 Hz, 1H), 8.57 (s, 1H), 8.21 (s, 1H), 7.67 (d, J=8.6 Hz, 2H), 7.58 (td, J=9.0, 6.1 Hz, 1H), 7.27 (t, J=8.4 Hz, 1H), 7.09 (d, J=8.7 Hz, 2H), 5.00 (d, J=4.5 Hz, 1H), 4.71 (s, 1H), 4.07 (dd, J=9.8, 4.1 Hz, 1H), 3.93 (dd, J=9.8, 6.2 Hz, 1H), 3.83 (td, J=10.7, 5.7 Hz, 1H), 3.48 (s, 2H), 3.17-3.06 (m, 2H), 1.74 (dq, J=14.9, 7.4 Hz, 2H), 0.96 (t, J=7.4 Hz, 3H).

TLC-MS: m/z calculated for $C_{26}H_{25}F_2N_3O_6S$ ([M–H]$^-$): 544.1, found: 543.8.

Purity: 95%

Example 32: Synthesis of N-(3-(5-(3-chlorophenyl)-1H-pyrrolo[2,3-b]pyridine-3-carbonyl)-2,4-difluorophenyl)propane-1-sulfonamide Procedure: The title compound was prepared according to Example 7.

Yield: 50 mg, 102 μmol, 47% (beige solid).

TLC: nHex/EE (1:1)

Analytical data: 1H NMR (DMSO-$d_6$, 400 MHz, ppm): δ 13.04 (s, 1H), 9.78 (s, 1H), 8.74 (d, J=1.9 Hz, 1H), 8.66 (s, 1H), 8.27 (s, 1H), 7.83 (s, 1H), 7.73 (d, J=7.6 Hz, 1H), 7.64-7.52 (m, 2H), 7.48 (d, J=7.9 Hz, 1H), 7.29 (t, J=8.6 Hz, 1H), 3.18-3.07 (m, 2H), 1.74 (dq, J=14.8, 7.4 Hz, 2H), 0.96 (t, J=7.4 Hz, 3H). TLC-MS: m/z calculated for $C_{23}H_{18}ClF_2N_3O_3S$ ([M–H]$^-$): 488.1, found: 487.8.

Purity: 92%

Example 33: Synthesis of N-(3-(5N-(2,4-difluorophenyl)-1H-pyrrolo[2,3-b]pyridine-3-carbonyl)-2,4-difluorophenyl)propane-1-sulfonamide

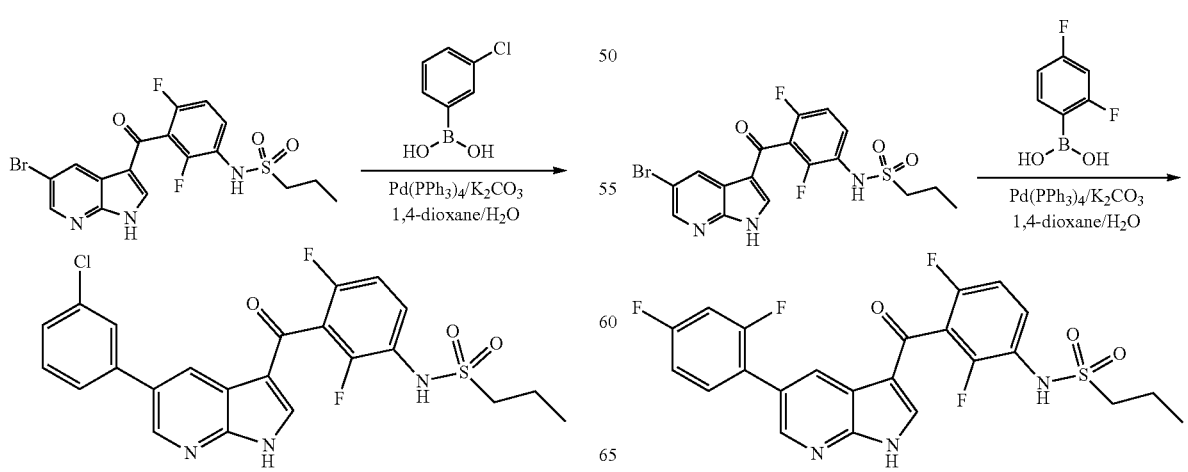

Procedure: The title compound was prepared according to Example 7.

Yield: 50 mg, 101 μmol, 46% (off-white solid).

TLC: nHex/EE (1:1)

Analytical data: $^1$H NMR (DMSO-d$_6$, 400 MHz, ppm): δ 13.07 (s, 1H), 9.78 (s, 1H), 8.57 (s, 1H), 8.55 (s, 1H), 8.28 (d, J=1.6 Hz, 1H), 7.73 (dd, J=15.5, 8.7 Hz, 1H), 7.59 (td, J=8.9, 6.1 Hz, 1H), 7.48-7.39 (m, 1H), 7.32-7.21 (m, 2H), 3.17-3.06 (m, 2H), 1.80-1.67 (m, 2H), 0.96 (t, J=7.4 Hz, 3H).

TLC-MS: m/z calculated for C$_2$H$_{17}$F$_4$N$_3$O$_3$S ([M−H]$^-$): 490.1, found: 489.9.

Purity: 99%

Example 34: Synthesis of N-(2,4-difluoro-3-(5-(2-fluorophenyl)-1H-pyrrolo[2,3-b]pyridine-3-carbonyl) phenyl)propane-1-sulfonamide

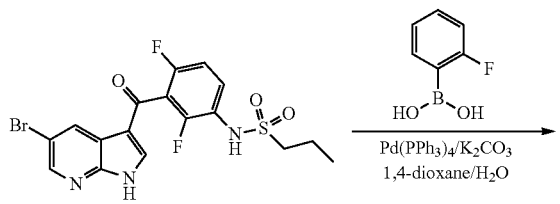

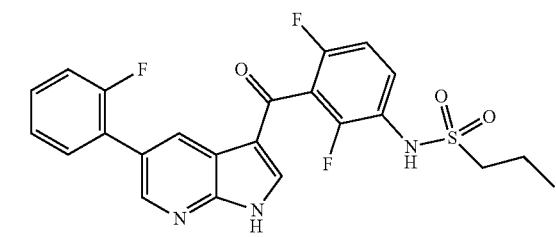

Procedure: The title compound was prepared according to Example 7.

Yield: 31 mg, 66 μmol, 30% (off-white solid).

TLC: nHex/EE (1:1)

Analytical data: $^1$H NMR (DMSO-d$_6$, 400 MHz, ppm): δ 13.06 (s, 1H), 9.78 (s, 1H), 8.59 (s, 2H), 8.27 (s, 1H), 7.67 (t, J=7.7 Hz, 1H), 7.59 (dd, J=14.7, 8.8 Hz, 1H), 7.49 (dd, J=12.3, 6.3 Hz, 1H), 7.38 (dd, J=16.4, 8.7 Hz, 2H), 7.29 (t, J=8.5 Hz, 1H), 3.18-3.07 (m, 2H), 1.74 (dq, J=14.1, 7.0 Hz, 2H), 0.96 (t, J=7.3 Hz, 3H).

TLC-MS: m/z calculated for C$_{23}$H$_{18}$F$_3$N$_3$O$_3$S ([M−H]$^-$): 472.1, found: 471.9.

Purity: 99%

Example 35: Synthesis of N-(2,4-difluoro-3-(5-(4-hydroxyphenyl)-1H-pyrrolo[2,3-b]pyridine-3-carbonyl) phenyl)propane-1-sulfonamide

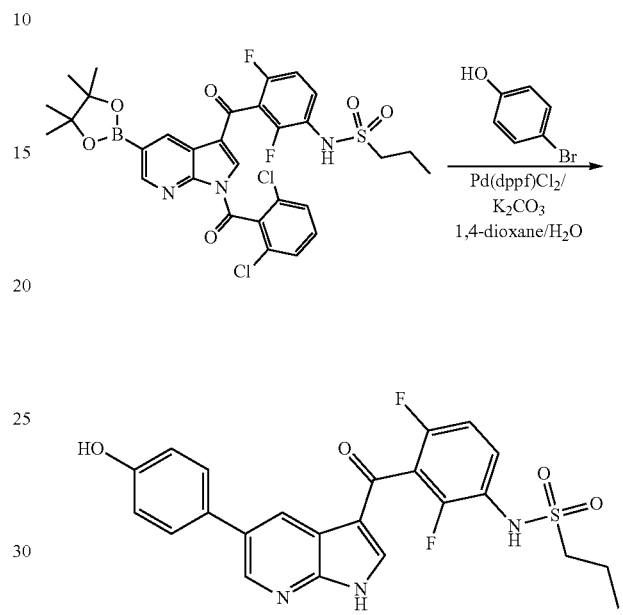

Procedure: The title compound was prepared according to Example 4, Step 3.

Yield: 54 mg, 115 μmol, 52% (off-white solid).

TLC: nHex/EE (1:1)

Analytical data: $^1$H NMR (DMSO-d$_6$, 400 MHz, ppm): δ 12.93 (s, 1H), 9.77 (s, 1H), 9.63 (s, 1H), 8.63 (d, J=1.7 Hz, 1H), 8.53 (s, 1H), 8.19 (s, 1H), 7.64-7.50 (m, 3H), 7.28 (t, J=8.7 Hz, 1H), 6.91 (d, J=8.4 Hz, 2H), 3.19-3.05 (m, 2H), 1.81-1.65 (m, 2H), 0.96 (t, J=7.4 Hz, 3H).

TLC-MS: m/z calculated for C$_{23}$H$_{19}$F$_2$N$_3$O$_4$S ([M−H]$^-$): 470.1, found: 469.9.

Purity: 97%

Example 36: Synthesis of N-(2,4-difluoro-3-(5-(2-fluoro-4-methoxyphenyl)-1H-pyrrolo[2,3-b]pyridine-3-carbonyl)phenyl)propane-1-sulfonamide

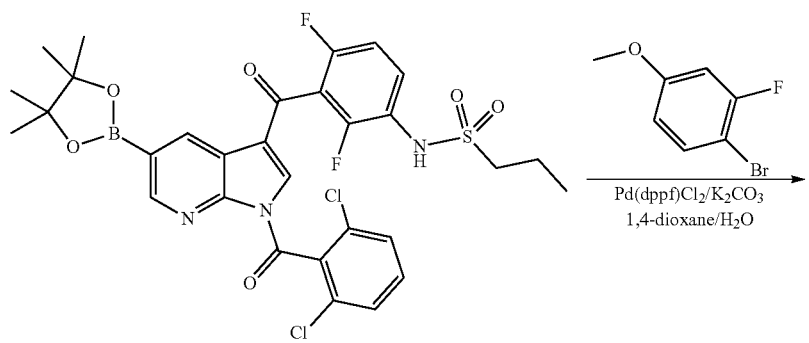

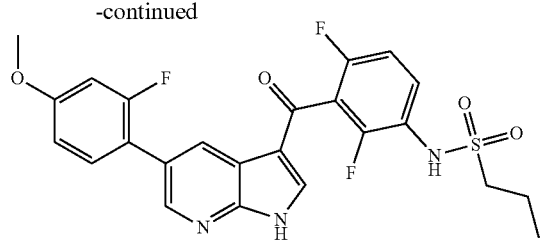

Procedure: The title compound was prepared according to Example 4, Step 3.

Yield: 54 mg, 107 μmol, 48% (off-white solid).

TLC: nHex/EE (1:1)

Analytical data: $^1$H NMR (DMSO-$d_6$, 400 MHz, ppm): δ 13.02 (s, 1H), 9.78 (s, 1H), 8.53 (s, 2H), 8.25 (s, 1H), 7.64-7.54 (m, 2H), 7.28 (t, J=8.7 Hz, 1H), 7.02 (dd, J=12.8, 2.1 Hz, 1H), 6.95 (dd, J=8.6, 2.1 Hz, 1H), 3.84 (s, 3H), 3.19-3.06 (m, 2H), 1.74 (dq, J=14.9, 7.4 Hz, 2H), 0.96 (t, J=7.4 Hz, 3H).

TLC-MS: m/z calculated for $C_{24}H_{20}F_3N_3O_4S$ ([M−H]$^-$): 502.1, found: 502.0.

Purity: >99%

Example 37: Synthesis of N-(3-(5-(4-chlorophenyl)-1H-pyrrolo[2,3-b]pyridine-3-carbonyl)-2,4-difluorophenyl)-1-(m-tolyl)methanesulfonamide

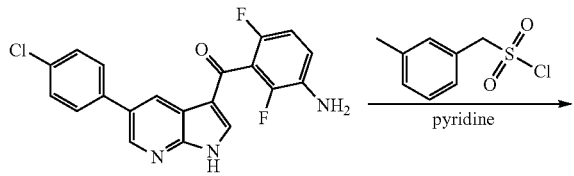

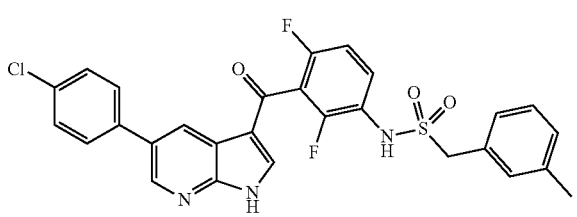

Procedure: The title compound was prepared according to Example 6, Step 3.

Yield: 31 mg, 57 μmol, 27% (off-white solid).

TLC: nHex/EE (1:1)

Analytical data: $^1$H NMR (DMSO-$d_6$, 400 MHz, ppm): δ 13.04 (s, 1H), 9.82 (s, 1H), 8.72 (s, 1H), 8.66 (s, 1H), 8.24 (s, 1H), 7.80 (d, J=8.3 Hz, 2H), 7.61-7.50 (m, 3H), 7.28-7.12 (m, 5H), 4.49 (s, 2H), 2.24 (s, 3H). TLC-MS: m/z calculated for $C_{28}H_{20}ClF_2N_3O_3S$ ([M−H]$^-$): 550.1, found: 549.6.

Purity: 93%

Example 38: Synthesis of N-(3-(5-(4-chlorophenyl)-1H-pyrrolo[2,3-b]pyridine-3-carbonyl)-2,4-difluorophenyl)-1-(p-tolyl)methanesulfonamide

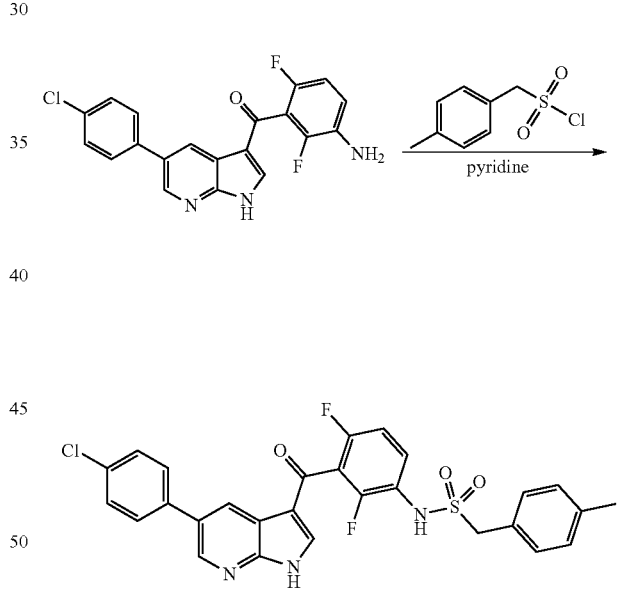

Procedure: The title compound was prepared according to Example 6, Step 3.

Yield: 31 mg, 56 μmol, 27% (off-white solid).

TLC: nHex/EE (1:1)

Analytical data: $^1$H NMR (DMSO-$d_6$, 400 MHz, ppm): δ 13.04 (s, 1H), 9.78 (s, 1H), 8.72 (d, J=2.2 Hz, 1H), 8.66 (s, 1H), 8.24 (s, 1H), 7.80 (d, J=8.5 Hz, 2H), 7.57 (d, J=8.5 Hz, 2H), 7.52 (td, J=9.0, 6.0 Hz, 1H), 7.29-7.21 (m, 3H), 7.16 (d, J=7.9 Hz, 2H), 4.48 (s, 2H), 2.28 (s, 3H). TLC-MS: m/z calculated for $C_{28}H_{20}ClF_2N_3O_3S$ ([M−H]$^-$): 550.1, found: 549.9.

Purity: 94%

Example 39: Synthesis of N-(2,4-difluoro-3-(5-(4-methoxy-2-methylphenyl)-1H-pyrrolo[2,3-b]pyridine-3-carbonyl)phenyl)propane-1-sulfonamide

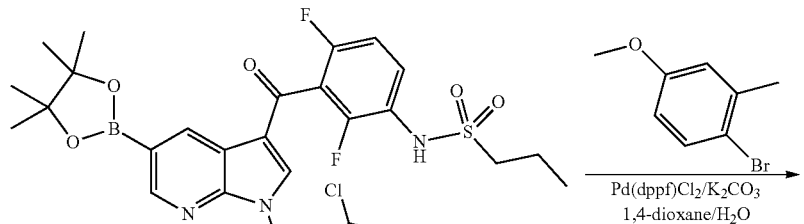

Procedure: The title compound was prepared according to Example 4, Step 3.

Yield: 61 mg, 122 µmol, 55% (white solid).

TLC: nHex/EE (1:1)

Analytical data: $^1$H NMR (DMSO-$d_6$, 200 MHz, ppm): δ 12.97 (s, 1H), 9.76 (s, 1H), 8.35 (d, J=1.9 Hz, 1H), 8.31 (s, 1H), 8.22 (s, 1H), 7.58 (td, J=9.0, 6.0 Hz, 1H), 7.27 (t, J=8.8 Hz, 1H), 7.23 (d, J=8.4 Hz, 1H), 6.94 (d, J=2.4 Hz, 1H), 6.88 (dd, J=8.4, 2.5 Hz, 1H), 3.80 (s, 3H), 3.15-3.08 (m, 2H), 2.24 (s, 3H), 1.81-1.67 (m, 2H), 0.96 (t, J=7.4 Hz, 3H).

TLC-MS: m/z calculated for $C_{25}H_{23}F_2N_3O_4S$ [M−H]$^-$: 498.1, found: 498.0.

Purity: >99%

Example 40: Synthesis of N-(3-(5-(4-(2,3-dihydroxypropoxy)phenyl)-1H-pyrrolo [2,3-b]pyridine-3-carbonyl)-2,4-difluorophenyl)-1-phenylmethanesulfonamide

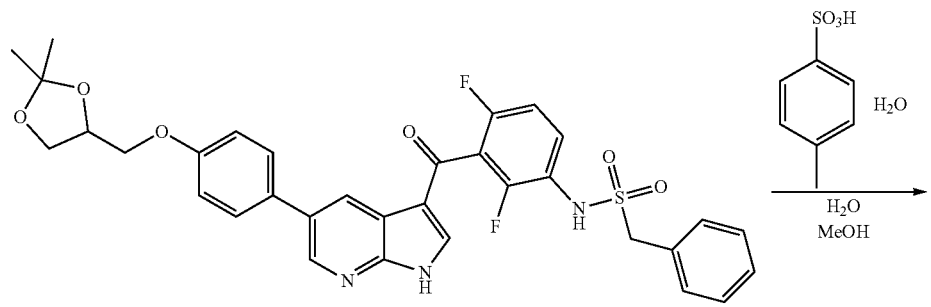

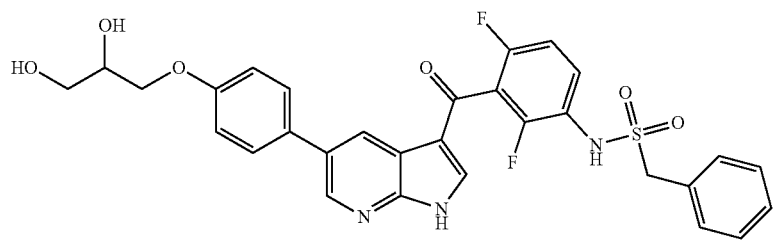

Procedure: The title compound was prepared according to Example 10.

Yield: 54 mg, 92 µmol, 80% (white solid).

TLC: nHex/EE (1:1)

Analytical data: $^1$H NMR (DMSO-d$_6$, 400 MHz, ppm): δ 12.96 (s, 1H), 9.83 (s, 1H), 8.67 (d, J=1.8 Hz, 1H), 8.60 (s, 1H), 8.18 (s, 1H), 7.68 (d, J=8.5 Hz, 2H), 7.51 (dd, J=15.0, 9.0 Hz, 1H), 7.43-7.30 (m, 5H), 7.23 (t, J=8.7 Hz, 1H), 7.09 (d, J=8.7 Hz, 2H), 5.01 (d, J=4.9 Hz, 1H), 4.72 (s, 1H), 4.53 (s, 2H), 4.08 (dd, J=9.8, 4.1 Hz, 1H), 3.94 (dd, J=9.8, 6.2 Hz, 1H), 3.84 (dq, J=10.6, 5.3 Hz, 1H), 3.49 (t, J=5.2 Hz, 2H).

TLC-MS: m/z calculated for C$_3$OH$_{25}$F$_2$N$_3$O$_6$S ([M−H]$^-$): 592.1, found: 592.0.

Purity: 94%

Example 41: Synthesis of N-(3-(5-(2-chloro-4-(2,3-dihydroxypropoxy)phenyl)-1H-pyrrolo[2,3-b]pyridine-3-carbonyl)-2,4-difluorophenyl)-1-phenylmethane-sulfonamide

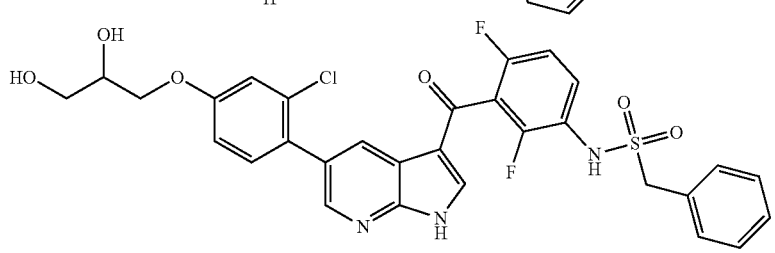

Procedure: The title compound was prepared according to Example 10.

Yield: 76 mg, 121 µmol, 77% (white solid).

TLC: nHex/EE (1:1)

Analytical data: $^1$H NMR (DMSO-d$_6$, 400 MHz, ppm): δ 13.04 (s, 1H), 9.83 (s, 1H), 8.47 (s, 1H), 8.43 (d, J=2.0 Hz, 1H), 8.23 (s, 1H), 7.55-7.44 (m, 2H), 7.43-7.30 (m, 5H), 7.27-7.17 (m, 2H), 7.08 (dd, J=8.6, 2.4 Hz, 1H), 5.04 (d, J=4.9 Hz, 1H), 4.73 (s, 1H), 4.53 (s, 2H), 4.12 (dd, J=10.1, 3.9 Hz, 1H), 3.98 (dd, J=10.0, 6.2 Hz, 1H), 3.84 (dq, J=10.7, 5.3 Hz, 1H), 3.48 (t, J=5.2 Hz, 2H).

TLC-MS: m/z calculated for C$_3$OH$_{24}$ClF$_2$N$_3$O$_6$S ([M−H]$^-$): 626.1, found: 625.9.

Purity: >99%

Example 42: Synthesis of N-(3-(5-(4-chlorophenyl)-1H-pyrrolo[2,3-b]pyridine-3-carbonyl)-2,4-difluorophenyl)-1-(4-fluorophenyl)methanesulfonamide

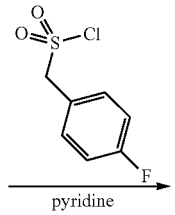

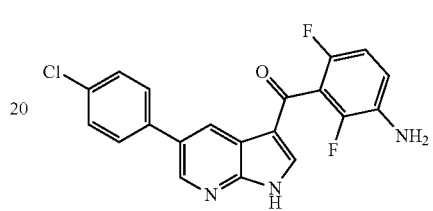

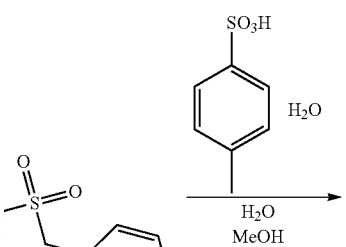

-continued

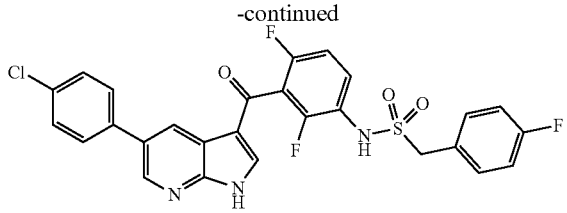

Procedure: The title compound was prepared according to Example 6, Step 3.

Yield: 36 mg, 66 µmol, 31% (white solid).

TLC: nHex/EE (1:1)

Analytical data: $^1$H NMR (DMSO-d$_6$, 400 MHz, ppm): δ 13.04 (s, 1H), 9.83 (s, 1H), 8.72 (s, 1H), 8.67 (s, 1H), 8.24 (s, 1H), 7.80 (d, J=7.8 Hz, 2H), 7.61-7.48 (m, 3H), 7.46-7.39 (m, 2H), 7.25 (t, J=8.8 Hz, 1H), 7.19 (t, J=8.4 Hz, 2H), 4.55 (s, 2H).

TLC-MS: m/z calculated for $C_{27}H_{17}ClF_3N_3O_3S$ ([M−H]$^-$): 554.1, found: 553.8.
Purity: 96%

Example 43: Synthesis of N-(3-(5-(4-chlorophenyl)-1H-pyrrolo[2,3-b]pyridine-3-carbonyl)-2,4-difluorophenyl)-1-(3-fluorophenyl)methanesulfonamide

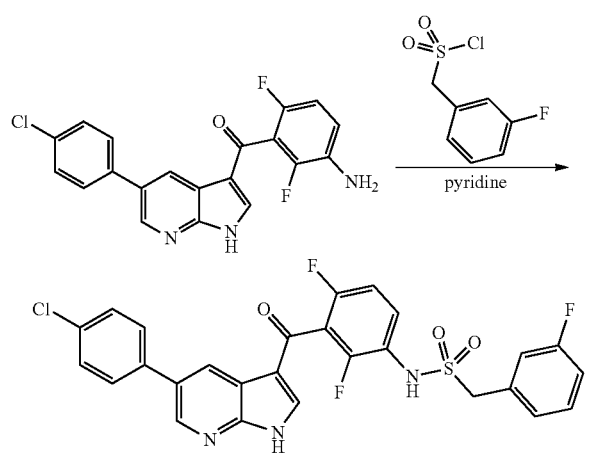

Procedure: The title compound was prepared according to Example 6, Step 3.
Yield: 53 mg, 66 μmol, 45% (off-white solid).
TLC: nHex/EE (1:1)
Analytical data: $^1$H NMR (DMSO-d$_6$, 400 MHz, ppm): δ 13.04 (s, 1H), 9.83 (s, 1H), 8.72 (s, 1H), 8.67 (s, 1H), 8.24 (s, 1H), 7.80 (d, J=7.8 Hz, 2H), 7.61-7.48 (m, 3H), 7.46-7.39 (m, 2H), 7.25 (t, J=8.8 Hz, 1H), 7.19 (t, J=8.4 Hz, 2H), 4.55 (s, 2H).
TLC-MS: m/z calculated for $C_{27}H_{17}ClF_3N_3O_3S$ ([M−H]$^-$): 554.1, found: 553.9.
Purity: 97%

Example 44: Synthesis of N-(3-(5-(4-chlorophenyl)-1H-pyrrolo[2,3-b]pyridine-3-carbonyl)-2,4-difluorophenyl)-1-(2-fluorophenyl)methanesulfonamide

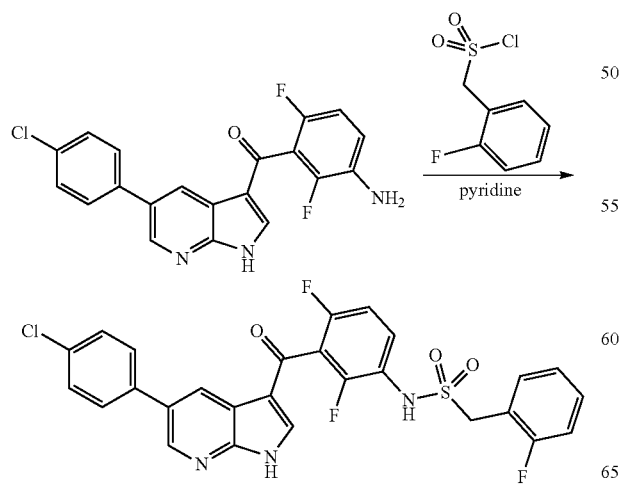

Procedure: The title compound was prepared according to to Example 6, Step 3.
Yield: 52 mg, 93 μmol, 44% (white solid).
TLC: nHex/EE (1:1)
Analytical data: $^1$H NMR (DMSO-d$_6$, 400 MHz, ppm): δ 13.04 (s, 1H), 10.02 (s, 1H), 8.72 (d, J=2.1 Hz, 1H), 8.67 (s, 1H), 8.21 (s, 1H), 7.80 (d, J=8.5 Hz, 2H), 7.61-7.52 (m, 3H), 7.51-7.38 (m, 2H), 7.31-7.15 (m, 3H), 4.60 (s, 2H).
TLC-MS: m/z calculated for $C_{27}H_{17}ClF_3N_3O_3S$ ([M−H]$^-$): 554.1, found: 553.9.
Purity: 95%

Example 45: Synthesis of N-(3-(5-(2-cyclopropylpyrimidin-5-yl)-1H-pyrrolo[2,3-b]pyridine-3-carbonyl)-2,4-difluorophenyl)propane-1-sulfonamide Step 1: 5-Bromo-2-cyclopropylpyrimidine

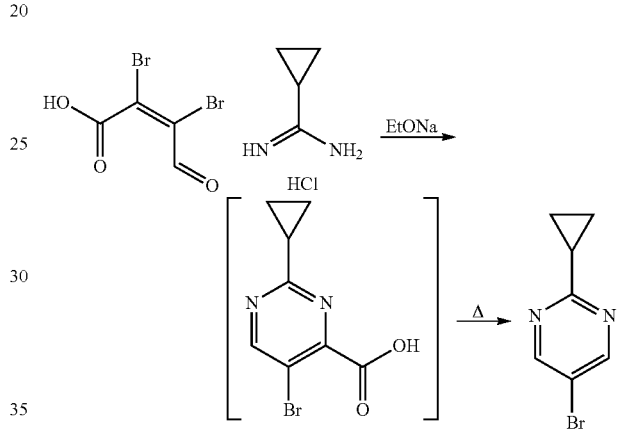

Procedure: The title compound was prepared according to Gabos et al. [WO 2006004532 A1].
Yield: 403 mg, 2.2 mmol, 13% over two steps (colorless oil).
TLC: nHex/EE 10%
Analytical data: $^1$H NMR (CDCl$_3$, 200 MHz, ppm): δ 8.58 (s, 2H), 2.31-2.12 (m, 1H), 1.13-1.05 (m, 4H). $^{13}$C NMR (CDCl$_3$ 50 MHz, ppm): δ. 170.7, 157.5, 116.7, 18.0, 11.4.

Step 2: N-(3-(5-(2-cyclopropylpyrimidin-5-yl)-1H-pyrrolo[2,3-b]pyridine-3-carbonyl)-2,4-difluorophenyl)propane-1-sulfonamide

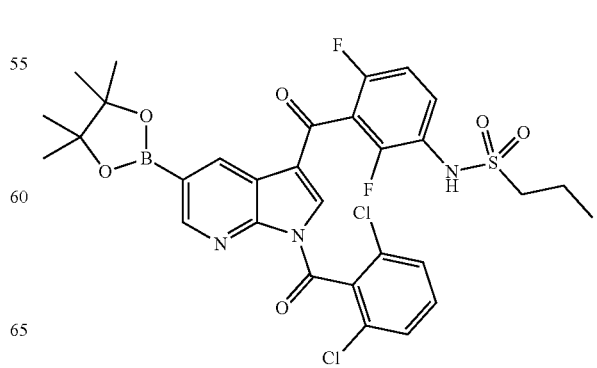

-continued

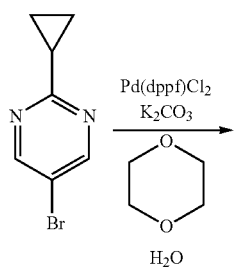
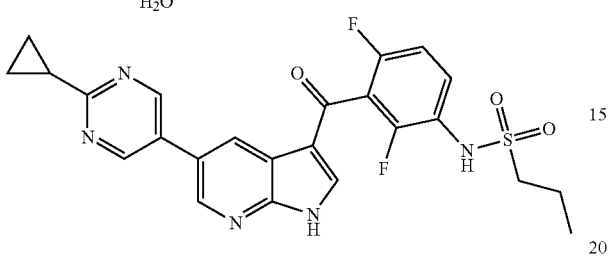

Procedure: The title compound was prepared according to Example 4, Step 3.

Yield: 51 mg, 103 μmol, 47% (white solid).

TLC: nHex/EE (1:1)

Analytical data: $^1$H NMR (DMSO-$d_6$ 400 MHz, ppm): δ 13.08 (s, 1H), 9.77 (s, 1H), 9.03 (s, 2H), 8.75 (d, J=1.9 Hz, 1H), 8.70 (s, 1H), 8.28 (s, 1H), 7.59 (td, J=8.9, 6.2 Hz, 1H), 7.28 (t, J=8.6 Hz, 1H), 3.17-3.09 (m, 2H), 2.28 (ddd, J=12.6, 7.9, 5.0 Hz, 1H), 1.80-1.68 (m, 2H), 1.14-1.02 (m, 4H), 0.96 (t, J=7.4 Hz, 3H).

TLC-MS: m/z calculated for $C_{24}H_{21}F_2N_5O_3S$ ([M−H]): 496.1, found: 496.1.

Purity: 97%

Example 46: Synthesis of N-(3-(5-(2-cyclopropylpyrimidin-5-yl)-1H-pyrrolo[2,3-b]pyridine-3-carbonyl)-2,4-difluorophenyl)-1-phenylmethanesulfonamide

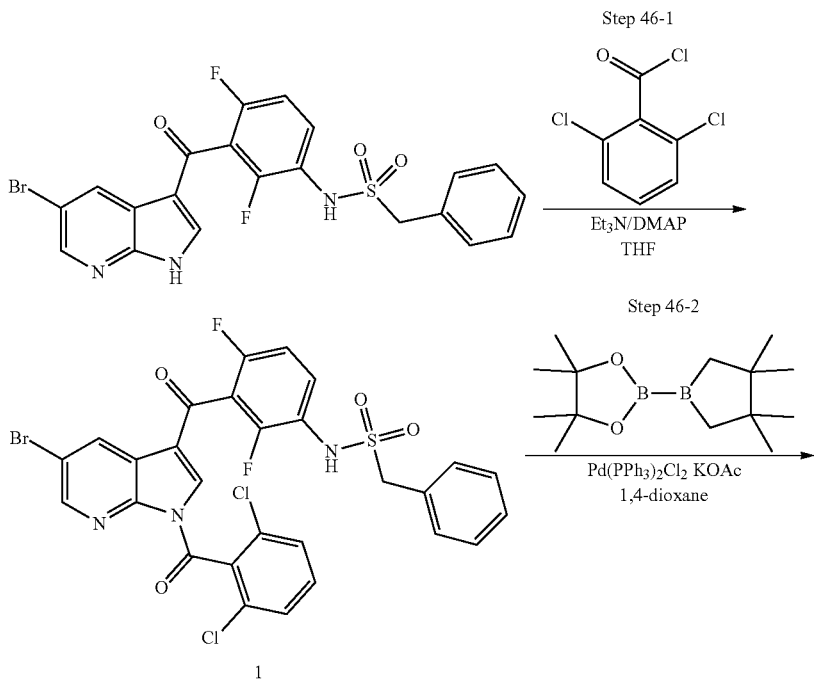

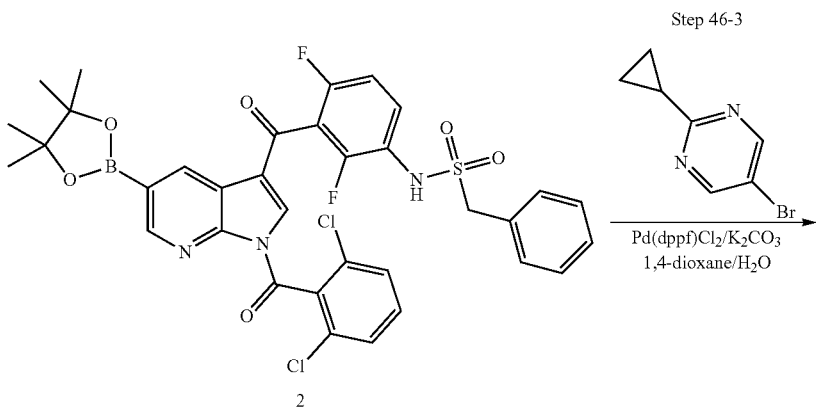

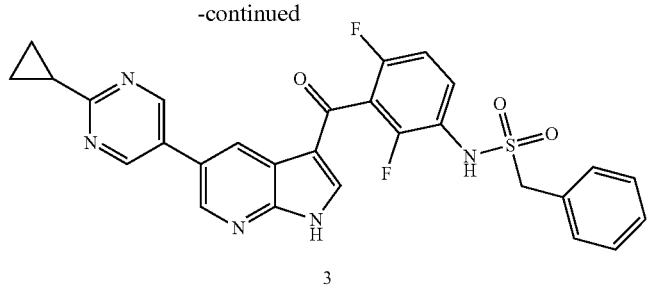

3

Step 46-1: N-(3-(5-bromo-1-(2,6-dichlorobenzoyl)-1H-pyrrolo[2,3-b]pyridine-3-carbonyl)-2,4-difluorophenyl)-1-phenylmethanesulfonamide was prepared according to Example 4, Step 1.

Yield: 2.1 g, 3.12 mmol, 93% (white solid).

TLC: nHex/EE 25%

Analytical data: $^1$H NMR (DMSO-d$_6$, 400 MHz, ppm): δ 9.93 (s, 1H), 8.88 (s, 1H), 8.75 (d, J=1.8 Hz, 1H), 8.34 (s, 1H), 7.66 (s, 3H), 7.60 (dd, J=14.6, 8.6 Hz, 1H), 7.41 (d, J=3.7 Hz, 2H), 7.36-7.33 (m, 3H), 7.28 (t, J=9.0 Hz, 1H), 4.57 (s, 2H).

TLC-MS: m/z calculated for $C_{28}H_{16}BrCl_2F_2N_3O_4S$ ([M−H]$^-$): 675.9, found: 675.4.

Step 46-2: N-(3-(1-(2,6-dichlorobenzoyl)-5-(4,4,5,5-tetramethyl-1,3,2-dioxaborolan-2-yl)-1H-pyrrolo[2,3-b]pyridine-3-carbonyl)-2,4-difluorophenyl)-1-phenyl methane sulfonamide was prepared according to Example 4, Step 2.

Yield: 1.2 g, 1.7 mmol, 75% (off-white solid).

TLC: nHex/EE 25%

Analytical data: $^1$H NMR (DMSO-d$_6$, 400 MHz, ppm): δ 9.91 (s, 1H), 8.86 (d, J=1.6 Hz, 1H), 8.83 (s, 1H), 8.33 (s, 1H), 7.65 (s, 3H), 7.63-7.55 (m, 1H), 7.43-7.32 (m, 5H), 7.28 (t, J=8.9 Hz, 1H), 4.57 (s, 2H), 1.30 (s, 12H).

TLC-MS: m/z calculated for $C_{34}H_{28}BCl_2F_2N_3O_6S$ ([M−H]$^-$): 724.1, found: 723.6.

Step 46-3: N-(3-(5-(2-cyclopropylpyrimidin-5-yl)-1H-pyrrolo[2,3-b]pyridine-3-carbonyl)-2,4-difluorophenyl)-1-phenylmethanesulfonamide was prepared according to Example 4, Step 3.

Yield: 53 mg, 97 μmol, 47% (off-white solid).

TLC: nHex/EE (1:1)

Analytical data: $^1$H NMR (DMSO-d$_6$, 400 MHz, ppm): δ 13.10 (s, 1H), 9.83 (s, 1H), 9.04 (s, 2H), 8.76 (s, 1H), 8.72 (s, 1H), 8.25 (s, 1H), 7.51 (dd, J=14.8, 8.8 Hz, 1H), 7.43-7.31 (m, 5H), 7.24 (t, J=8.6 Hz, 1H), 4.54 (s, 2H), 2.33-2.24 (m, 1H), 1.14-1.03 (m, 4H).

TLC-MS: m/z calculated for $C_{28}H_{21}F_2N_5O_3S$ ([M−H]$^-$): 544.1, found: 544.0.

Purity: 97%

According to the Example 4, Steps 2 and 3, illustrated by the following reaction scheme, the compounds given in Table 2 were prepared.

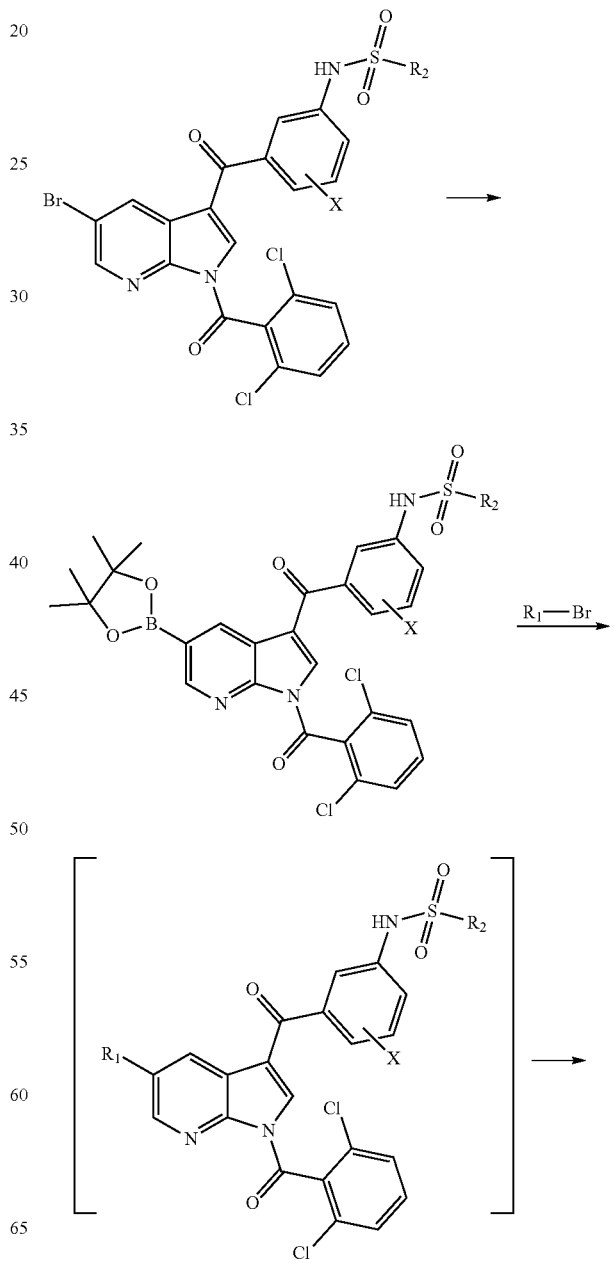

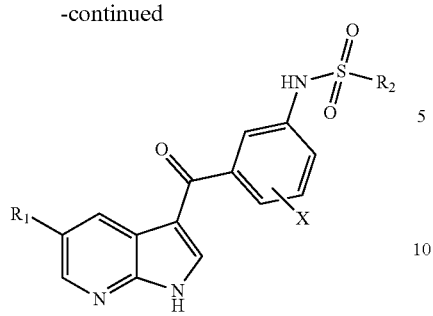
TABLE 2
Examples 47-57, prepared in analogy to Example 4, Steps 2 and 3.
| Expl. | R₁—Br | Product |
|---|---|---|
| 47 | | |
| 48 | | |
| 49 | | |
| 50 | | |

TABLE 2-continued
Examples 47-57, prepared in analogy to Example 4, Steps 2 and 3.
51 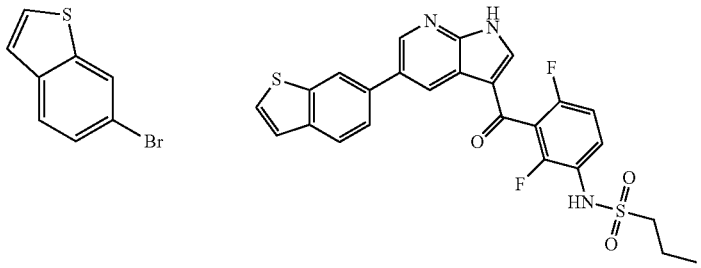
52 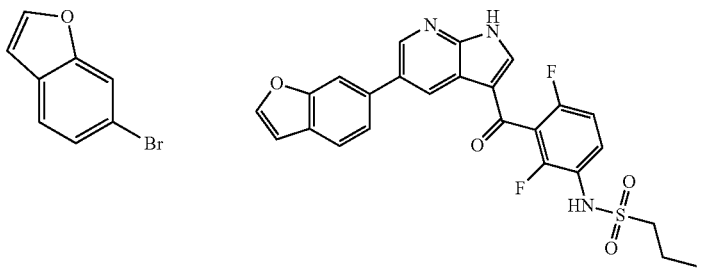
53 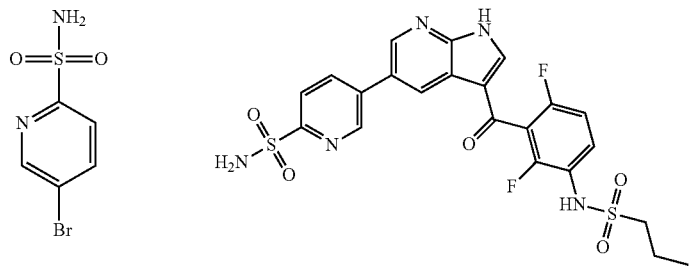
54 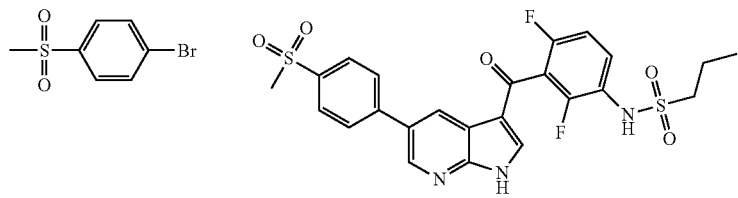
55 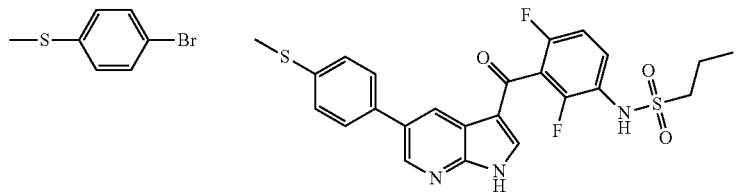
56 

TABLE 2-continued

Examples 47-57, prepared in analogy to Example 4, Steps 2 and 3.

| 57 | 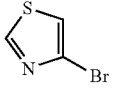 |  |
|---|---|---|

| Expl. | Analytical Data |
|---|---|
| 47 | $^1$H NMR (400 MHz, DMSO-d$_6$) δ 13.03 (s, 1H), 9.77 (s, 1H), 9.12 (s, 2H), 8.73 (d, J = 4.1 Hz, 1H), 8.25 (s, 1H), 8.10 (d, J = 8.0 Hz, 1H), 7.93 (t, J = 6.9 Hz, 1H), 7.59 (dd, J = 14.9, 9.0 Hz, 1H), 7.41 (dd, J = 7.3, 4.9 Hz, 1H), 7.29 (t, J = 8.6 Hz, 1H), 3.19-3.06 (m, 2H), 1.74 (dq, J = 15.0, 7.4 Hz, 2H), 0.96 (t, J = 7.4 Hz, 3H). Calculated exact mass for C22H18F2N4O3S: 456.1 MS(ESI$^+$): 457.05 for [M + H]$^+$. |
| 48 | $^1$H NMR (400 MHz, DMSO-d$_6$) δ 13.12 (s, 1H), 9.79 (s, 1H), 9.26 (dd, J = 4.9, 1.4 Hz, 1H), 9.21 (s, 1H), 9.17 (d, J = 2.1 Hz, 1H), 8.40 (dd, J = 8.6, 1.3 Hz, 1H), 8.32 (s, 1H), 7.84 (dd, J = 8.6, 4.9 Hz, 1H), 7.60 (dd, J = 14.9, 9.0 Hz, 1H), 7.29 (t, J = 8.4 Hz, 1H), 3.19-3.06 (m, 2H), 1.74 (dd, J = 15.1, 7.5 Hz, 2H), 0.96 (t, J = 7.4 Hz, 3H). Calculated exact mass for C21H17F2N5O3S: 457.46. MS(ESI$^+$): 458.10 for [M + H]$^+$. |
| 49 | $^1$H NMR (400 MHz, DMSO-d$_6$) δ 13.16 (s, 1H), 9.75 (s, 2H), 9.31 (d, J = 5.5 Hz, 1H), 8.94 (d, J = 2.2 Hz, 1H), 8.89 (s, 1H), 8.33 (s, 1H), 8.15 (dd, J = 5.4, 2.5 Hz, 1H), 7.60 (dd, J = 15.0, 9.0 Hz, 1H), 7.29 (t, J = 8.6 Hz, 1H), 3.20-3.06 (m, 2H), 1.74 (dd, J = 15.2, 7.5 Hz, 2H), 0.97 (t, J = 7.4 Hz, 3H). Calculated exact mass: 457.10 (C21H17F2N5O3S); MS(ESI$^+$): 458.05 for [M + H]$^+$. |
| 50 | $^1$H NMR (400 MHz, DMSO-d$_6$) δ 12.94 (s, 1H), 8.61 (d, J = 1.9 Hz, 1H), 8.50 (s, 1H), 8.28 (s, 1H), 8.19 (s, 1H), 8.16 (s, 1H), 7.77 (d, J = 8.6 Hz, 1H), 7.58 (dd, J = 14.8, 8.9 Hz, 1H), 7.28 (t, J = 8.8 Hz, 1H), 6.58 (d, J = 8.6 Hz, 1H), 6.14 (s, 2H), 3.18-3.06 (m, 2H), 1.74 (dd, J = 15.1, 7.5 Hz, 2H), 0.96 (t, J = 7.4 Hz, 3H). Calculated 471.48 for C22H19F2N5O3S. Measured 472.05 for [M + H]$^+$. |
| 51 | $^1$H NMR (400 MHz, DMSO-d$_6$) δ 13.00 (s, 1H), 9.79 (s, 1H), 8.79 (d, J = 2.0 Hz, 1H), 8.72 (s, 1H), 8.43 (s, 1H), 8.24 (s, 1H), 8.02 (d, J = 8.3 Hz, 1H), 7.81 (d, J = 5.4 Hz, 1H), 7.77 (d, J = 8.3 Hz, 1H), 7.58 (dd, J = 14.8, 8.9 Hz, 1H), 7.51 (d, J = 5.4 Hz, 1H), 7.28 (t J = 8.6 Hz, 1H), 3.17-3.07 (m, 2H), 1.73 (dq, J = 14.9, 7.4 Hz, 2H), 0.95 (t, J = 7.4 Hz, 3H). Calculated 511.56 for C25H19F2N3O3S2. Measured 512.05 for [M + H]$^+$. |
| 52 | $^1$H NMR (400 MHz, DMSO-d$_6$) δ 12.98 (s, 1H), 9.76 (s, 1H), 8.76 (s, 1H), 8.66 (s, 1H), 8.22 (s, 1H), 8.05 (s, 1H), 7.99 (s, 1H), 7.79 (d, J = 8.0 Hz, 1H), 7.68-7.52 (m, 2H), 7.27 (t, J = 8.7 Hz, 1H), 7.02 (s 1H), 3.16-3.05 (m, 2H), 1.73 (dd, J = 15.0, 7.5 Hz, 2H), 0.95 (t, J = 7.3 Hz, 3H). Calculated exact mass for C25H19F2N3O4S: 495.11; MS(ESI$^+$): 496.10 for [M + H]$^+$. |
| 53 | $^1$H NMR (400 MHz, DMSO-d$_6$) δ 13.28-12.91 (m, 1H), 10.04-9.62 (m, 1H), 9.14 (d, J = 1.8 Hz, 1H), 8.85 (d, J = 2.2 Hz, 1H), 8.79 (s, 1H), 8.46 (dd, J = 8.2, 2.2 Hz, 1H), 8.31 (s, 1H), 8.04 (d, J = 8.2 Hz, 1H), 7.65-7.51 (m, 3H), 7.29 (t, J = 8.3 Hz, 1H), 3.18-3.07 |

TABLE 2-continued

Examples 47-57, prepared in analogy to Example 4, Steps 2 and 3.

| | |
|---|---|
| | (m, 2H), 1.74 (dq, J = 15.0, 7.5 Hz, 2H), 0.97 (t, J = 7.4 Hz, 3H). Calculated exact mass for C22H19F2N5O5S2: 535.08 for. MS(ESI+): 536.1 for [M + H]⁺. |
| 54 | ¹H NMR (400 MHz, DMSO-d₆) δ 8.79 (d, J = 2.1 Hz, 2H), 8.72 (s, 2H), 8.33 (s, 1H), 8.23 (s, 2H), 8.05 (s, 6H), 7.55 (dd, J = 15.1, 9.1 Hz, 2H), 7.20 (t, J = 8.6 Hz, 2H), 3.28 (s, 5H), 3.09-2.99 (m, 4H), 1.72 (dq, J = 15.0, 7.5 Hz, 4H), 0.95 (t, J = 7.4 Hz, 5H). |
| 55 | ¹H NMR (400 MHz, DMSO-d₆) δ 13.03-12.77 (m, 1H), 10.25-10.00 (m, 1H), 8.69 (d, J = 2.2 Hz, 1H), 8.60 (s, 1H), 8.19 (s, 1H), 7.71 (d, J = 8.3 Hz, 2H), 7.56 (dd, J = 15.1, 9.0 Hz, 1H), 7.40 (d, J = 8.4 Hz, 2H), 7.23 (t, J = 8.8 Hz, 1H), 3.13-3.00 (m, 2H), 2.53 (d J = 4.5 Hz, 3H), 1.73 (dt, J = 15.2, 7.4 Hz, 2H), 0.95 (t, J = 7.4 Hz, 3H). Calculated exact mass for C24H21F2N3O3S2: 501.57; MS(ESI+): 502.2 for [M + H]⁺. |
| 56 | ¹H NMR (400 MHz, cdcl₃) δ 10.20-10.05 (m, 1H), 8.85 (s, 1H), 8.62 (s, 1H), 7.87 (s, 1H), 7.72 (t, J = 11.8 Hz, 2H), 7.57 (s, 1H), 7.08 (t, J = 8.6 Hz, 1H), 6.83 (s, 1H), 6.48 (s, 1H), 3.13 (dd, J = 9.1, 6.6 Hz, 2H), 1.91 (dt, J = 15.1, 7.6 Hz, 2H), 1.08 (t, J = 7.4 Hz, 3H). Calculated exact mass for C21H17F2N3O4S: 445.09. MS(ESI⁺): 446 for [M + H]⁺. |
| 57 | ¹H NMR (400 MHz, DMSO-d₆) δ 12.98 (s, 1H), 9.84 (s, 1H), 9.28 (s, 1H), 9.05 (d, J = 12.3 Hz, 2H), 8.36 (d, J = 11.8 Hz, 1H), 8.20 (d, J = 14.4 Hz, 1H), 7.58 (dd, J = 14.8, 8.7 Hz, 1H), 7.27 (t, J = 8.6 Hz, 1H), 3.12 (dd, J = 18.6, 11.1 Hz, 2H), 1.72 (dt, J = 14.7, 7.4 Hz, 2H), 0.91 (dd, J = 39.4, 32.0 Hz, 3H). Calculated exact mass for C20H16F2N4O3S2: 462.06. MS(ESI⁺): 463.15 for [M + H]⁺. |

Compounds 58 and 59 were prepared in analogy to Example 7.

| Expl. | Reactand | Product | ¹H-NMR/MS |
|---|---|---|---|
| 58 | 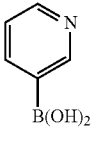 | 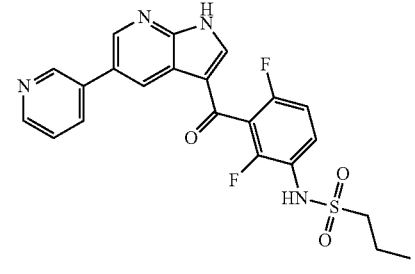 [SMILES: CCCS(=O)(=O)Nc1ccc(F)c(C(=O)c2c[nH]c3ncc(-c4cccnc4)cc23)c1F] | ¹H NMR (400 MHz, DMSO) δ 13.06 (s, 1H), 9.77 (s, 1H), 8.98 (s, 1H), 8.76 (d, J = 2.1 Hz, 1H), 8.69 (s, 1H), 8.64 (d, J = 4.3 Hz, 1H), 8.27 (d, J = 2.7 Hz, 1H), 8.21 (d, J = 7.9 Hz, 1H), 7.66-7.50 (m, 2H), 7.29 (t, J = 8.8 Hz, 1H), 3.17-3.08 (m, 2H), 1.73 (dt, J = 14.9, 7.5 Hz, 2H), 0.96 (t, J = 7.4 Hz, 3H). Calculated exact mass for C22H18F2N4O3S: 456.11, MS(ESI⁺): 457.10 for [M + H]⁺. |
| 59 | 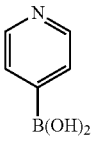 | 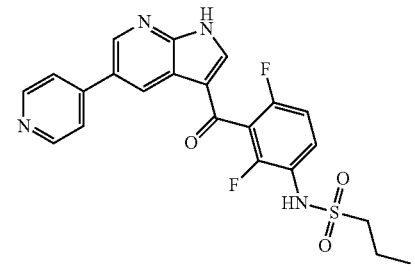 [SMILES: CCCS(=O)(=O)Nc1ccc(F)c(C(=O)c2c[nH]c3ncc(-c4ccncc4)cc23)c1F] | ¹H NMR (400 MHz, DMSO) δ 8.85 (d, J = 2.0 Hz, 1H), 8.77 (s, 1H), 8.69 (d, J = 5.8 Hz, 2H), 8.29 (s, 1H), 7.83 (d, J = 5.7 Hz, 2H), 764-7.54 (m, 1H), 7.28 (t, J = 8.4 Hz, 1H), 3.18-3.06 (m, 2H), 1.74 (dd, J = 15.3, 7.6 Hz, 2H), 0.96 (t, J = 7.4 Hz, 3H). Calculated exact mass for C22H18F2N4O3S: 456.11. MS(ESI⁺): 457.10 for [M + H]⁺. |

Example 60: Synthesis of N-(4-bromo-3-(5-(4-chlorophenyl)-1H-pyrrolo[2,3-b]pyridine-3-carbonyl)-2-fluorophenyl)propane-1-sulfonamide
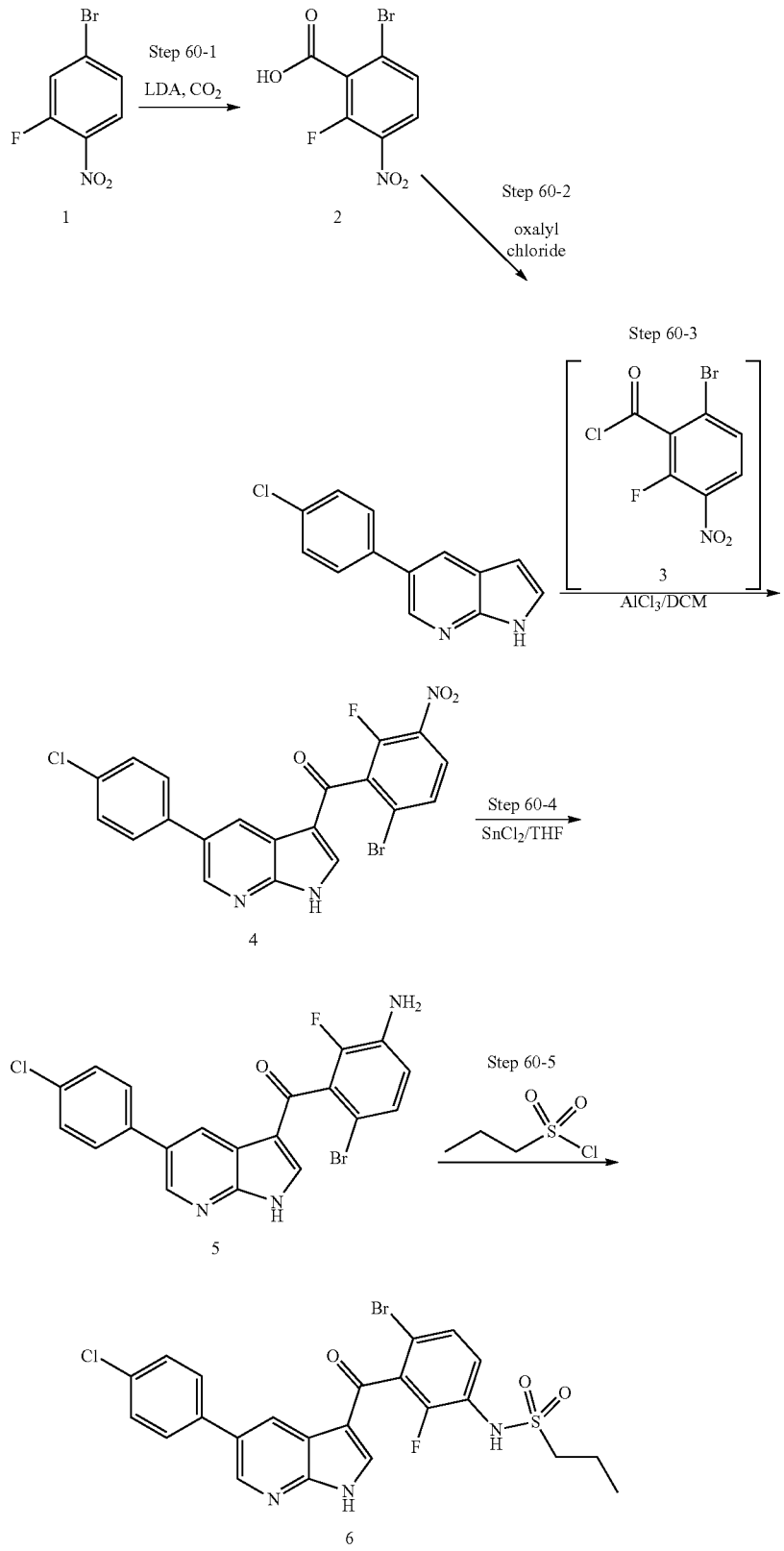

Step 60-1: Synthesis of 6-bromo-2-fluoro-3-nitrobenzoic acid (2)

4-Bromo-2-fluoro-1-nitrobenzene (1, 1 eq., 4 g, 18.18 mmol) was dissolved in anhydrous tetrahydrofuran (THF, 100 mL) and cooled to −78° C. Lithium diisopropylamide (2M in THF, 2 eq., 18.18 mL, 36.36 mmol) was added dropwise and the reaction was stirred at −78° C. for 1 hour, and then was quenched with gaseous carbon dioxide. The reaction mixture was warmed to RT and the solvents were removed under vacuum. The obtained residue was extracted with 0.5 M aqueous sodium hydroxide (20 mL×3). The combined aqueous layers were washed with ethyl acetate (EtOAc, 30 mL×2), acidified to about pH 1 with concentrated hydrochloric acid and then extracted with diethyl ether (30 mL×2). The combined organic layer was dried over magnesium sulfate and concentrated under reduced pressure to yield the desired product 6-bromo-2-fluoro-3-nitrobenzoic acid (1.3 g, 4.92 mmol, 27% yield) as a white solid that was used without further purification in the next step.

Step 60-2: Synthesis of 6-bromo-2-fluoro-3-nitrobenzoic acid chloride (2)

To a solution of 6-bromo-2-fluoro-3-nitrobenzoic acid (1 eq., 1.3 g, 4.92 mmol) in DCM (25 mL), oxalyl chloride (2.5 eq., 1.55 g, 12.3 mmol) was added at 0° C. followed by addition of dimethylformamide (0.5 mL). The resulting reaction mixture was stirred for about 3 hours at an ambient temperature. Solvents were evaporated under reduced pressure to afford the acid chloride (3, 1.3 g, crude) which was used without further purification.

Step 60-3: Synthesis of (6-bromo-2-fluoro-3-nitrophenyl)(5-(4-chlorophenyl)-1H-pyrrolo[2,3-b]pyridin-3-yl)methanone (4)

At RT and under argon, 5 eq. AlCl$_3$ (4.39 g, 32.94 mmol) was stirred in 30 ml anhydrous DCM. After 1 h, 5-(4-chlorophenyl)-1H-pyrrolo[2,3-b]pyridine 2 (1 eq, 1.5 g, 6.588 mmol) was added. The mixture was stirred at RT for another hour, then cooled to 0° C. Freshly prepared 6-bromo-2-fluoro-3-nitrobenzoyl chloride (3, 1.3 g, crude) was dissolved in 15 mL DCM and added dropwise to the reaction mixture. The reaction mixture was stirred at RT for 3 days. The progress of the reaction was monitored by TLC (40% EtOAc in hexane). The resulting mixture was then cautiously quenched at 0° C. with cold acetonitrile:H$_2$O (1:1, 30 mL). The precipitated solid was filtered, and filtrate was extracted with DCM (25 mL). The filtered precipitate and DCM extract were combined and purified by FCC using 20% EtOAc/hexanes to afford (3-nitro-6-bromo-2-fluorophenyl)(5-(4-chlorophenyl)-1H-pyrrolo[2,3-b]pyridin-3-yl)methanone (4, 610 mg, 1.29 mmol, 19.50% yield) as an off-white solid.

Step 60-4: Synthesis of (3-amino-6-bromo-2-fluorophenyl)(5-(4-chlorophenyl)-1H-pyrrolo[2,3-b]pyridin-3-yl)methanone (5)

To a stirred solution of 3-nitro-6-bromo-2-fluorophenyl)(5-(4-chlorophenyl)-1H-pyrrolo[2,3-b]pyridin-3-yl)methanone (4, 1 eq., 610 mg, 1.285 mmol) in THF (15 mL), stannous chloride (3 eq, 731 mg, 3.85 mmol) was added at RT. The reaction mixture was stirred at 60° C. for 16 h. The progress of the reaction was monitored by TLC (30% EtOAc in hexane). After completion, the reaction mixture was quenched with 20% aq. K$_2$CO$_3$ solution (10 mL) and stirred for 10 min. It was filtered through a pad of celite and the celite bed was washed with THF (25 mL). The resulting organic layer was evaporated under vacuum and the obtained residue was dissolved in EtOAc (20 mL). It was washed with brine, dried over Na$_2$SO$_4$, filtered, and concentrated under reduced pressure to get (3-amino-6-bromo-2-fluorophenyl)(5-(4-chlorophenyl)-1H-pyrrolo[2,3-b]pyridin-3-yl)methanone 3 (560 mg, crude) which was used in the next reaction without further purification.

Step 60-5: Synthesis of N-(4-bromo-3-(5-(4-chlorophenyl)-1H-pyrrolo[2,3-b]pyridine-3-carbonyl)-2-fluorophenyl)propane-1-sulfonamide (6)

To a stirred solution of compound (3-amino-6-bromo-2-fluorophenyl)(5-(4-chlorophenyl)-1H-pyrrolo[2,3-b]pyridin-3-yl)methanone 5 (1 eq., 400 mg, 0.90 mmol) was added pyridine (5 mL) and DMAP (0.05 eq., 5.48 mg, 0.045 mmol). Propanesulfonyl chloride (1.5 eq., 202 mg, 1.35 mmol) was added to it dropwise with stirring at RT. The reaction mixture was stirred at RT for 16 h. The progress of the reaction was monitored by TLC. After completion of the reaction, the solvent was removed under vacuum, water was added (5 mL) and extracted with DCM (10 mL×2). The combined organic layer was washed with brine, dried over anhydrous Na$_2$SO$_4$ and concentrated under reduced pressure to get a crude compound which was purified by FCC to obtain desired product N-(4-bromo-3-(5-(4-chlorophenyl)-1H-pyrrolo[2,3-b]pyridine-3-carbonyl)-2-fluorophenyl)propane-1-sulfonamide (6, 120 mg, 0.22 mmol, 24.4%).

Example 61: Synthesis of N-(3-(5-(4-chlorophenyl)-1H-pyrrolo[2,3-b]pyridine-3-carbonyl)-4-cyano-2-fluorophenyl)propane-1-sulfonamide

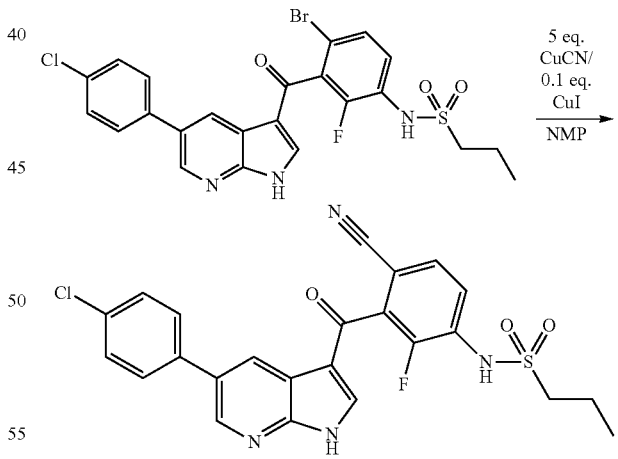

To a microwave vial was added N-(4-bromo-3-(5-(4-chlorophenyl)-1H-pyrrolo[2,3-b]pyridine-3-carbonyl)-2-fluorophenyl)propane-1-sulfonamide (1 eq., 50 mg, 0.09 mmol) and it was dissolved in NMP (2 mL). The mixture was degassed with argon for 10 min and CuCN (5 eq., 40.64 mg, 0.045 mmol), CuI (0.1 eq., 1.73 mg, 0.009 mmol) was added to it. The reaction mixture was heated at 120° C. under microwave for 2 h. The reaction mixture was filtered through celite and concentrated under vacuum to provide crude product which was purified through SFC to obtained N-(3-(5-(4-chlorophenyl)-1H-pyrrolo[2,3-b]pyridine-3-carbonyl)-4-cyano-2-fluorophenyl)propane-1-sulfonamide (17 mg, 0.03 mmol, 37.69%) as off-white solid.

Analytical data: $^1$H NMR (400 MHz, DMSO) δ 13.12 (s, 1H), 10.51 (s, 1H), 8.74 (s, 1H), 8.68 (s, 1H), 8.34 (s, 1H), 7.80 (dt, J=16.0, 10.1 Hz, 4H), 7.58 (d, J=8.3 Hz, 2H), 1.74 (dd, J=15.1, 7.2 Hz, 2H), 0.98 (t, J=7.3 Hz, 3H).

Calculated exact mass for $C_{24}H_{18}ClFN_4O_3S$: 496.08. MS(ESI+): 497.05 for [M+H]$^+$.

Example 62: Synthesis of N-(3-(5-(4-chlorophenyl)-1H-pyrrolo[2,3-b]pyridine-3-carbonyl)-2,4-dicyanophenyl)propane-1-sulfonamide

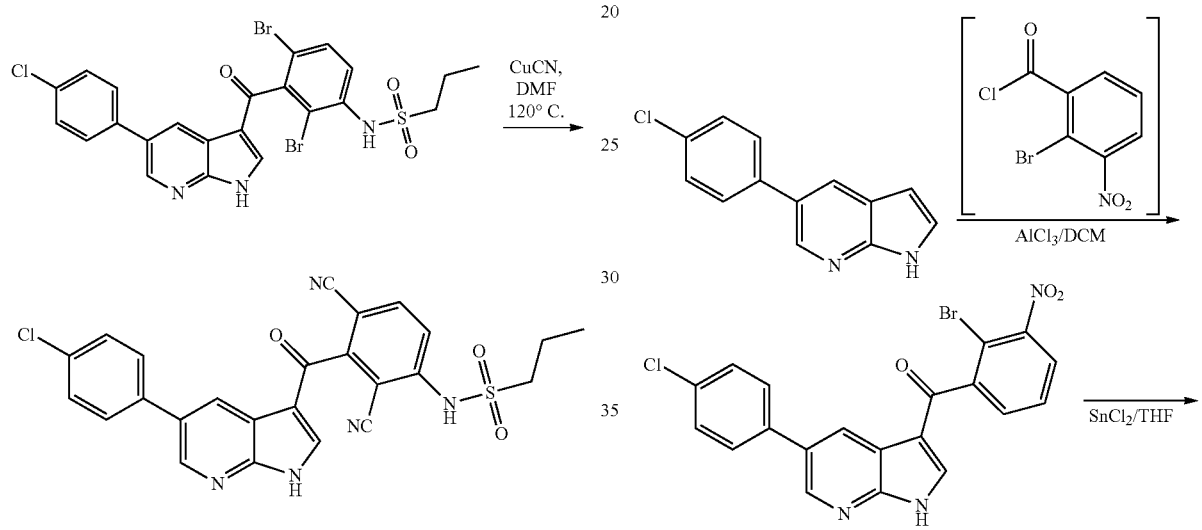

To a stirred solution of N-(2,4-dibromo-3-(5-(4-chlorophenyl)-1H-pyrrolo[2,3-b]pyridine-3-carbonyl)phenyl)propane-1-sulfonamide (5) (1 eq., 100 mg, 0.16 mmol), in DMF (2 mL) was added copper cyanide (4 eq., 58.48 mg, 0.65 mmol) and the reaction was heated at 120° C. in sealed tube for 5 h. After completion of the reaction, the reaction mixture was poured into ice-cold water (20 mL) and obtained precipitate was filtered, washed with water (10 mL×3) followed by dilute aqueous ammonia (5 mL×2). It was dried under vacuum and the crude product was purified by preparative HPLC to obtain N-(3-(5-(4-chlorophenyl)-1H-pyrrolo[2,3-b]pyridine-3-carbonyl)-2,4-dicyanophenyl)propane-1-sulfonamide (15 mg, 0.03 mmol, 18% yield) as a white solid.

Analytical data: $^1$H NMR (400 MHz, DMSO) δ 13.14 (s, 1H), 8.71 (d, J=47.9 Hz, 2H), 8.29 (s, 1H), 7.95 (s, 1H), 7.82 (d, J=8.1 Hz, 2H), 7.67 (s, 1H), 7.57 (d, J=8.3 Hz, 2H), 3.12 (s, 2H), 1.76 (d, J=7.1 Hz, 2H), 0.98 (t, J=7.3 Hz, 3H).

Calculated exact mass for $C_{25}H_{18}ClN_5O_3S$: 503.08. MS(ESI$^+$): 504.10 for [M+H]$^+$.

Example 63: Synthesis of N-(3-(5-(4-chlorophenyl)-1H-pyrrolo[2,3-b]pyridine-3-carbonyl)-2-cyanophenyl)propane-1-sulfonamide The synthesis was performed as illustrated in the scheme below. The individual steps were performed in analogy to those described in Example 60 and 61.

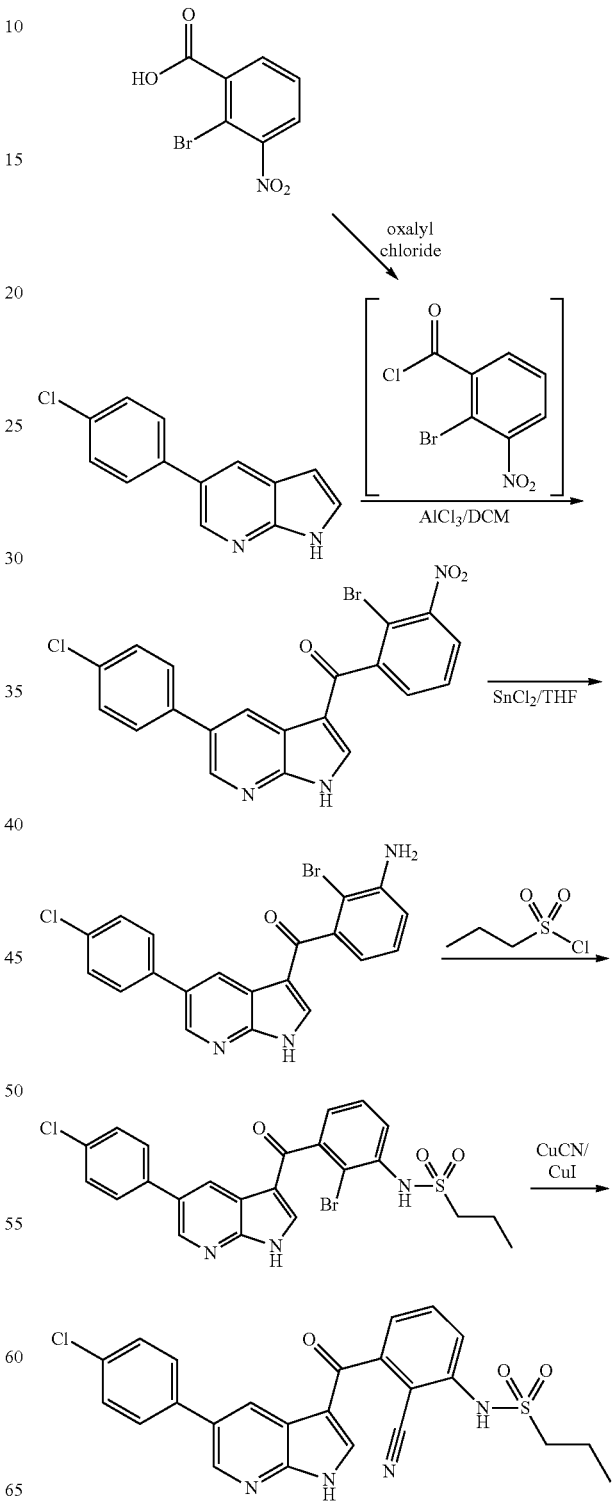

Example 64: Synthesis of N-(3-(4-chloro-5-(4-chlorophenyl)-1H-pyrrolo[2,3-b]pyridine-3-carbonyl)-2,4-difluorophenyl)propane-1-sulfonamide

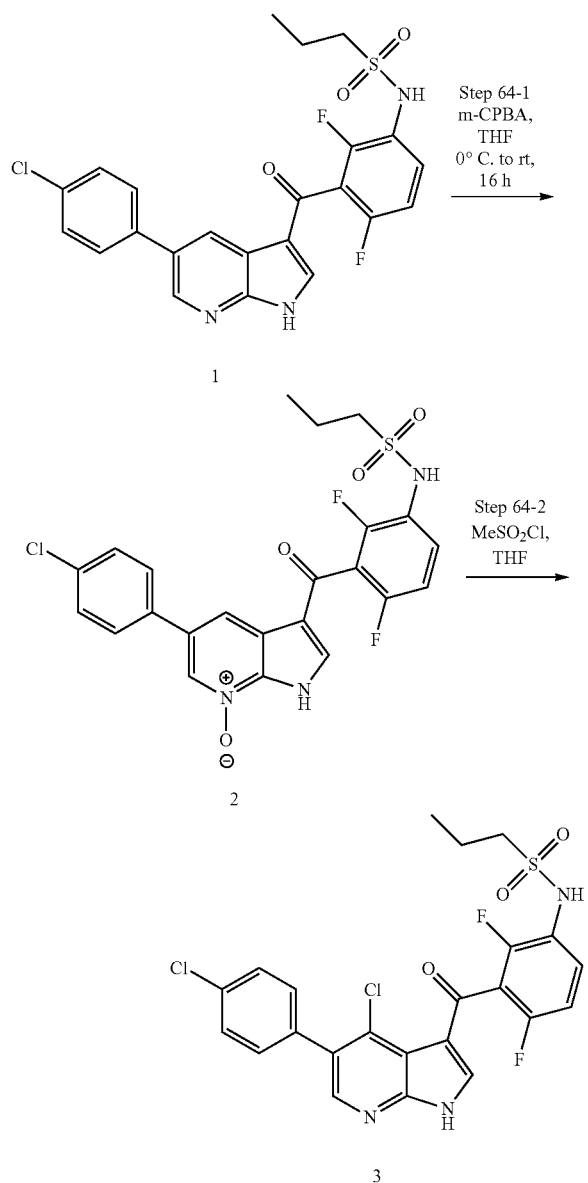

Step 64-1: 5-(4-chlorophenyl)-3-(2,6-difluoro-3-(propylsulfonamido)benzoyl)-1H-pyrrolo[2,3-b] pyridine 7-oxide (2)

To a solution of 1 (1 eq., 500 mg, 1.02 mmol) in THF (10 mL) was portionwise added m-CPBA (211.31 mg, 1.22 mmol) at 0° C. The resulting suspension was allowed to reach rt. and stirred at the same temperature for 16 h. The reaction mixture was concentrated to dryness by rotary evaporation under reduced pressure. To the obtained crude product was added sat. aq. NaHCO₃ (20 mL) which was extracted with DCM (3×60 mL). The combined organic layer was dried and concentrated under vacuum to provide 5-(4-chlorophenyl)-3-(2,6-difluoro-3-(propylsulfonamido) benzoyl)-1H-pyrrolo[2,3-b]pyridine 7-oxide (500 mg crude) as a white solid which was used in the next step without purification.

Step 64-2: N-(3-(4-chloro-5-(4-chlorophenyl)-1H-pyrrolo[2,3-b]pyridine-3-carbonyl)-2,4-difluorophenyl)propane-1-sulfonamide (3)

To a stirred solution of 5-(4-chlorophenyl)-3-(2,6-difluoro-3-(propylsulfonamido)benzoyl)-1H-pyrrolo[2,3-b] pyridine 7-oxide (2) (1 eq., 250 mg, 0.49 mmol) in THF (10 mL), was added Methanesulfonyl chloride (1.5 eq., 84.9 mg, 0.74 mmol) dropwise at 0° C. After completion of the addition, the reaction was heated to 70° C. and stirred for 12 h. The reaction was monitored by LCMS. After completion of the reaction, the volatiles were removed under reduced pressure to provide a residue. The residue was diluted with water (20 mL) and extracted with DCM (50 mL×3). The combined organic layer was washed with brine, dried over anhydrous Na₂SO₄ and concentrated under reduced pressure to get a crude which was purified by preparative HPLC to obtained N-(3-(4-chloro-5-(4-chlorophenyl)-1H-pyrrolo[2,3-b]pyridine-3-carbonyl)-2,4-difluorophenyl)propane-1-sulfonamide (70 mg, 0.13 mmol, 26.5% yield).

Analytical data: $^1$H NMR (400 MHz, DMSO) δ 13.45-12.72 (m, 1H), 10.09-9.49 (m, 1H), 8.40 (s, 1H), 8.32 (s, 1H), 7.64-7.51 (m, 5H), 7.28 (t, J=8.7 Hz, 1H), 3.17-3.06 (m, 2H), 1.81-1.66 (m, 2H), 0.96 (t, J=7.4 Hz, 3H).

Example 65: Synthesis of N-(3-(5-(4-chlorophenyl)-4-cyano-1H-pyrrolo[2,3-b]pyridine-3-carbonyl)-2,4-difluorophenyl)propane-1-sulfonamide

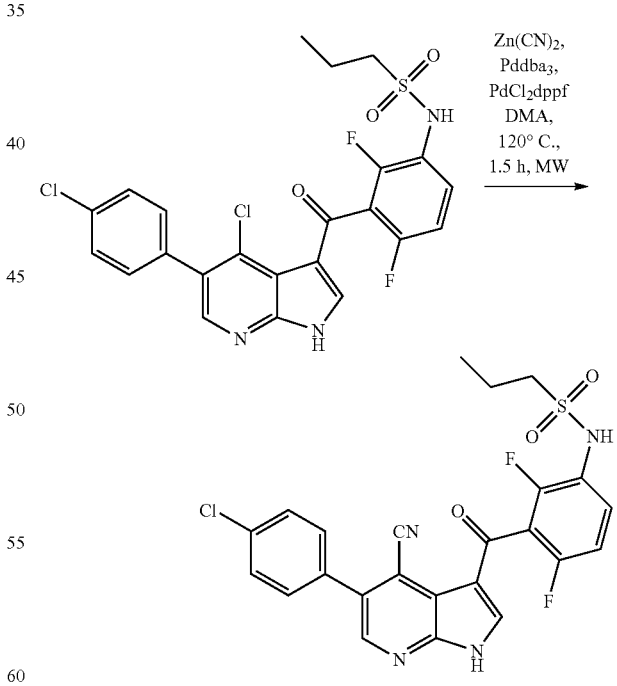

N-(3-(4-chloro-5-(4-chlorophenyl)-1H-pyrrolo[2,3-b] pyridine-3-carbonyl)-2,4-difluorophenyl)propane-1-sulfonamide (Example 50) (1 eq., 300 mg, 0.57 mmol) was dissolved in DMA (3 mL). Zinc (0.1 eq, 3.74 mg, 0.057 mmol), zinc cyanide (2 eq., 134.38 mg, 1.14 mmol), Pd(dppf)Cl₂ (0.035 eq., 16.74 mg, 0.02 mmol) and Pd₂

(dba)₃ (0.0175 eq., 10.48 mg, 0.01 mmol) were added, the reaction mixture was degassed with argon for 20 min and stirred under microwave heating at 120° C. for 1.5 h. After completion of the reaction, the reaction mixture was filtered through a pad of Celite. The Celite pad was washed with EtOAc (20 mL) and filtrate was concentrated under vacuum and to obtain a residue which was dissolved in EtOAc (50 mL), washed with water, dried over Na₂SO₄ concentrated under reduced pressure to obtained crude compound. The crude compound was purified by reverse phase preparative HPLC to obtain N-(3-(5-(4-chlorophenyl)-4-cyano-1H-pyrrolo[2,3-b]pyridine-3-carbonyl)-2,4-difluorophenyl)propane-1-sulfonamide (100 mg, 0.19 mmol, 34% yield).

Analytical data: ¹H NMR (400 MHz, DMSO) δ 13.19 (s, 1H), 9.78 (s, 1H), 8.41 (s, 1H), 8.33 (s, 1H), 7.64-7.52 (m, 5H), 7.28 (t, J=8.4 Hz, 1H), 3.18-3.06 (m, 2H), 1.74 (dq, J=15.1, 7.5 Hz, 2H), 0.96 (t, J=7.4 Hz, 3H).

Calculated exact mass for C₂₄H₁₇ClF₂N₄O₃S: 514.07. MS(ESI⁺): 515.0 for [M+H]⁺.

Example 66: Synthesis of N-(3-(5-(4-chlorophenyl)-6-methoxy-1H-pyrrolo[2,3-b]pyridine-3-carbonyl)-2,4 difluorophenyl)propane-1-sulfonamide

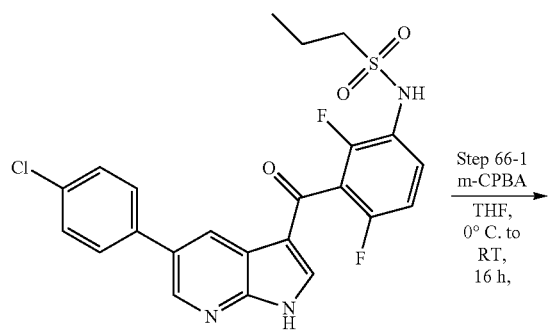

1

Step 66-1
m-CPBA
THF,
0° C. to RT,
16 h,

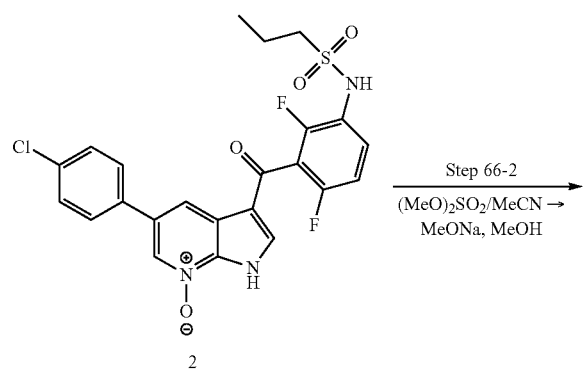

2

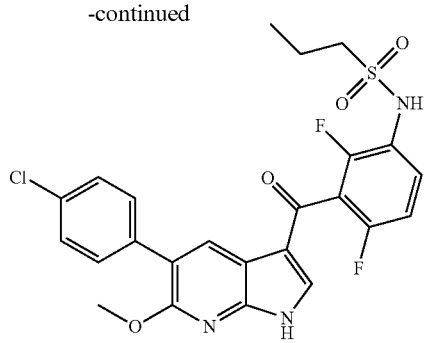

3

Step 66-1: 5-(4-chlorophenyl)-3-(2,6-difluoro-3-(propylsulfonamido)benzoyl)-1H-pyrrolo[2,3-b]pyridine 7-oxide (2)

To a solution of 1 (1 eq., 1 g, 2.04 mmol) in THF (20 mL) was added m-CPBA (1.2 eq., 422.61 mg, 2.45 mmol) at 0° C. The resulting suspension was allowed to reach RT and was stirred overnight. The reaction mixture was concentrated to dryness using rotary evaporator under reduced pressure. Thus obtained crude product was triturated with DCM to provide a solid which was filtered and dried to obtain 5-(4-chlorophenyl)-3-(2,6-difluoro-3-(propylsulfonamido)benzoyl)-1H-pyrrolo[2,3-b]pyridine 7-oxide 2 (700 mg, 1.38 mmol, 68% yield) as a white solid.

Step 66-2: N-(3-(5-(4-chlorophenyl)-6-methoxy-1H-pyrrolo[2,3-b]pyridine-3-carbonyl)-2,4 difluorophenyl)propane-1-sulfonamide (3)

A suspension of N-oxide 2 (1 eq., 500 mg, 0.988 mmol) and dimethyl sulfate (1.1 eq., 137.11 mg, 1.08 mmol) in anhydrous acetonitrile (15 mL) was stirred overnight under nitrogen at 60 to 65° C. After cooling to RT, a solution of NaOMe in MeOH (25 wt %, 4 mL) was added, and the turbid mixture was stirred overnight at 60 to 65° C. After neutralization with AcOH and diluting with MeOH (5 mL), the mixture was evaporated to dryness. The obtained residue was dissolved in EtOAc (40 mL) and washed with aq. NaHCO₃ (5 mL×2). The aqueous layer was extracted with EtOAc (10 mL). The combined organic phases were dried (Na₂SO₄) and evaporated to dryness. Purification by preparative HPLC yielded 22 (30 mg, 0.0576 mmol, 5.85%) as a white solid.

Analytical data: ¹H NMR (400 MHz, DMSO) δ 12.80 (s, 1H), 9.75 (s, 1H), 8.30 (s, 1H), 7.94 (s, 1H), 7.60 (d, J=8.5 Hz, 2H), 7.55 (dd, J=8.9, 3.0 Hz, 1H), 7.51 (d, J=8.5 Hz, 2H), 7.24 (t, J=8.6 Hz, 1H), 3.94 (s, 3H), 3.15-3.04 (m, 2H), 1.73 (dq, J=15.0, 7.5 Hz, 2H), 0.96 (t, J=7.4 Hz, 3H).

Example 67: Synthesis of N-(3-(5-(4-chlorophenyl)-1H-pyrrolo[2,3-b]pyridine-3-carbonyl)-2,4-difluorophenyl)-3-hydroxypropane-1-sulfonamide

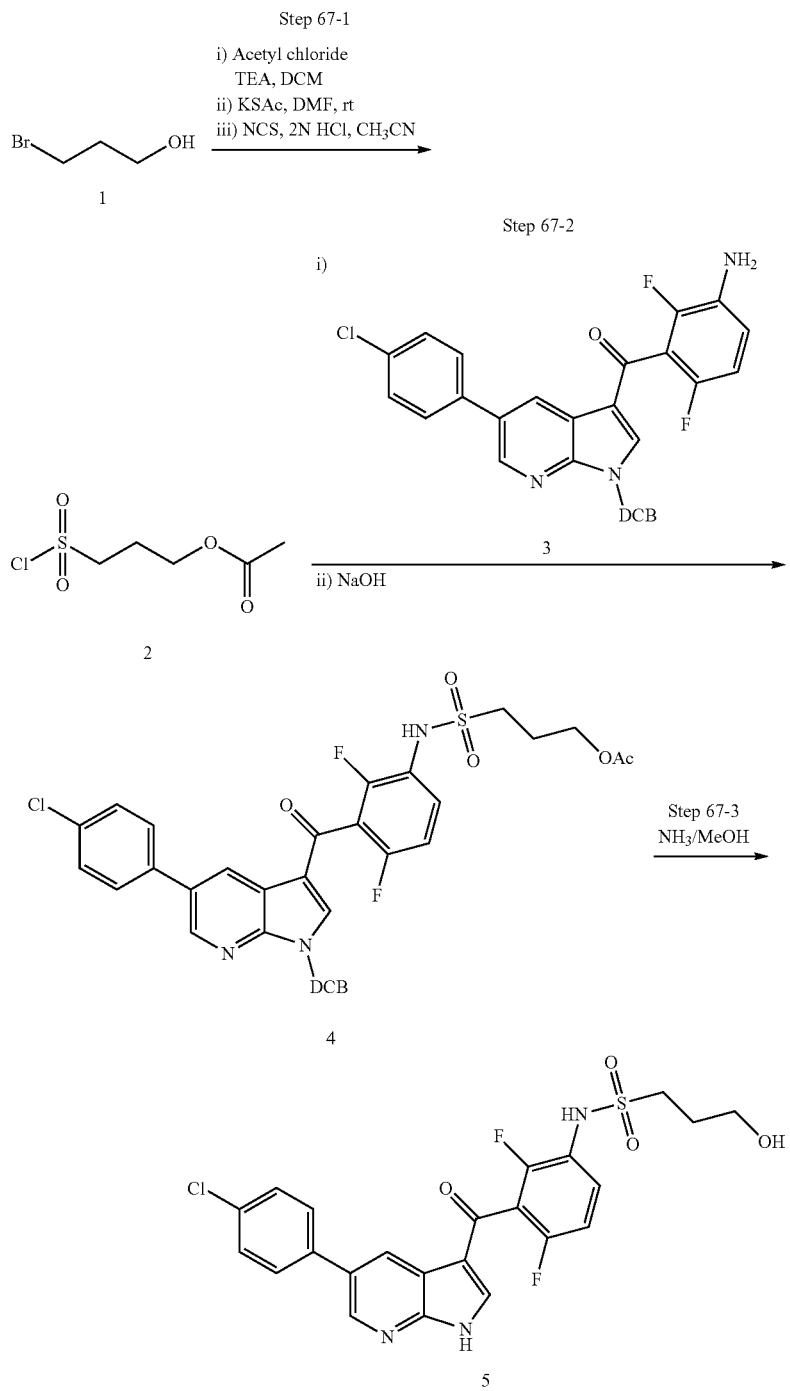

Step 67-1: 3-(chlorosulfonyl)propyl acetate (2)

Step 67-1i: To a stirred solution of 3-bromopropan-1-ol 1 (1 eq., 3.0 g, 21.6 mmol) in DCM (50 mL) was added TEA (3 eq., 6.5 g, 64.8 mmol) and 4-DMAP (0.1 eq., 0.264 g, 2.15 mmol) and the reaction mixture was cooled to 0° C. Acetyl chloride (1.5 eq., 2.54 g, 32.4 mmol) was added to the solution at the same temperature dropwise over 15 minutes. The progress of the reaction was monitored by TLC. After completion of the reaction (TLC), water (100 mL) was added and the reaction mixture was extracted with DCM (20 mL×2). The organic layer was separated, washed with 2N HCl (10 mL) solution and brine. The organic layer was dried over anhydrous $Na_2SO_4$ and concentrated under reduced pressure to get step-1 product (4 g, crude) which was used as such in the next step without further purification.

Step 67-1ii: To a stirred solution of step-1 product (1 eq., 4.0 g, crude) in DMF (50 mL) was added potassium thioacetate (1.2 eq., 3.02 g, 26.51 mmol) and the reaction mixture was stirred for 4 h at RT. The progress of the reaction was monitored by TLC. After completion of the reaction, ice-cold water (150 mL) was added and the reaction mixture was extracted with diethyl ether (20 mL×3). The combined organic layer was washed with brine solution, dried over anhydrous $Na_2SO_4$ and concentrated under reduced pressure to get Step-2 product (3 g, crude) which was used in the next step without any further purification.

Step 67-1iii: To a stirred solution of Step-2 product (1 eq., 3.0 g, 17.023 mmol) in acetonitrile (30 mL) was added 2N HCl (4 mL) at 0° C. NCS (4 eq., 9 g, 68.09 mmol) was added portionwise over 30 min. The reaction mixture was stirred for 3 h at RT. The progress of the reaction was monitored by TLC. After completion of the reaction, acetonitrile was evaporated in vacuum and water (100 mL) was added and the reaction mixture was extracted with diethylether (50 mL×3). The combined organic layer was washed with brine solution, dried over anhydrous $Na_2SO_4$ and concentrated under reduced pressure to get 3-(chlorosulfonyl)propyl acetate 2 (2 g, crude) which was used in next step without any further purification.

Step 67-2: 3-(N-(3-(5-(4-chlorophenyl)-1-(2,6-dichlorobenzoyl)-1H-pyrrolo[2,3-b]pyridine-3-carbonyl)-2,4-difluorophenyl)sulfamoyl)propyl acetate (4)

To a stirred solution of (3-(3-amino-2,6-difluorobenzoyl)-5-(4-chlorophenyl)-1H-pyrrolo[2,3-b]pyridin-1-yl)(2,6-dichlorophenyl)methanone 3 (1 eq., 199.8 mg, 0.359 mmol) in DCM (10 mL) was added TEA (10 eq., 362.59 mg, 3.59 mmol) and DMAP (0.1 eq., 4.38 mg, 0.0359 mmol) and the reaction mixture was cooled to 0° C. 3-(chlorosulfonyl) propyl acetate 2 (4 eq., 287.2 mg, 1.436 mmol) was added to it. The progress of the reaction was monitored by TLC. After completion of the reaction (16 h), the reaction was quenched with 1N HCl (2 mL) and the reaction mixture was extracted with DCM (10 mL×2). The combined organic layer was washed with brine, dried over anhydrous $Na_2SO_4$ and concentrated under reduced pressure to get a crude residue which was purified by FCC to provide disulfonamide intermediate as a step-4 product (150 mg).

To a stirred solution of the step-4 product (1 eq., 150 mg, 0.169 mmol) in THF (2.5 mL) was added aq. NaOH (4 eq., 27.08 mg, 0,677 mmol) and the reaction mixture was stirred at RT for 2 h. The progress of the reaction was monitored by TLC. After completion of the reaction, THF was removed in vacuum, water was added (5 mL) and reaction was neutralized with 5N HCl. The mixture was extracted with EtOAc (10 mL×3). The combined organic layer was washed with brine, dried over anhydrous $Na_2SO_4$ and concentrated under reduced pressure to get 4 (100 mg, crude) which was used in next step without any further purification.

Step 67-3: N-(3-(5-(4-chlorophenyl)-1H-pyrrolo[2,3-b]pyridine-3-carbonyl)-2,4-difluoro-phenyl)-3-hydroxypropane-1-sulfonamide To a stirred solution of 3-(N-(3-(5-(4-chlorophenyl)-1-(2,6-dichlorobenzoyl)-1H-pyrrolo[2,3-b]pyridine-3-carbonyl)-2,4-difluorophenyl)sulfamoyl)propyl acetate 4 (100 mg, 0.147 mmol, crude) in THF (2 mL) was added aq. ammonia (2 mL) and the reaction mixture was stirred at rt for 12 h. The solvent was evaporated under vacuum to provide a residue which was further purified by preparative HPLC to obtain the product (25 mg, 0.05 mmol, 34% yield) as a white solid.

Analytical data: $^1$H NMR (400 MHz, DMSO) δ 13.12-12.92 (m, 1H), 9.87-9.70 (m, 1H), 8.71 (d, J=2.2 Hz, 1H), 8.65 (s, 1H), 8.22 (s, 1H), 7.80 (d, J=8.5 Hz, 2H), 7.59 (t, J=10.0 Hz, 3H), 7.28 (t, J=8.8 Hz, 1H), 4.64 (s, 1H), 3.47 (t, J=5.9 Hz, 2H), 3.17 (dd, J=10.3, 5.2 Hz, 2H), 1.87 (dd, J=15.5, 6.2 Hz, 2H).

Calculated exact mass for $C_{23}H_{18}ClF_2N_3O_4S$: 505.07. MS(ESI$^+$): 506.0 for [M+H]$^+$.

Example 68: Synthesis of N-(3-(5-(4-chlorophenyl)-1H-pyrrolo[2,3-b]pyridine-3-carbonyl)-2,4-difluorophenyl)-2-hydroxypropane-1-sulfonamide

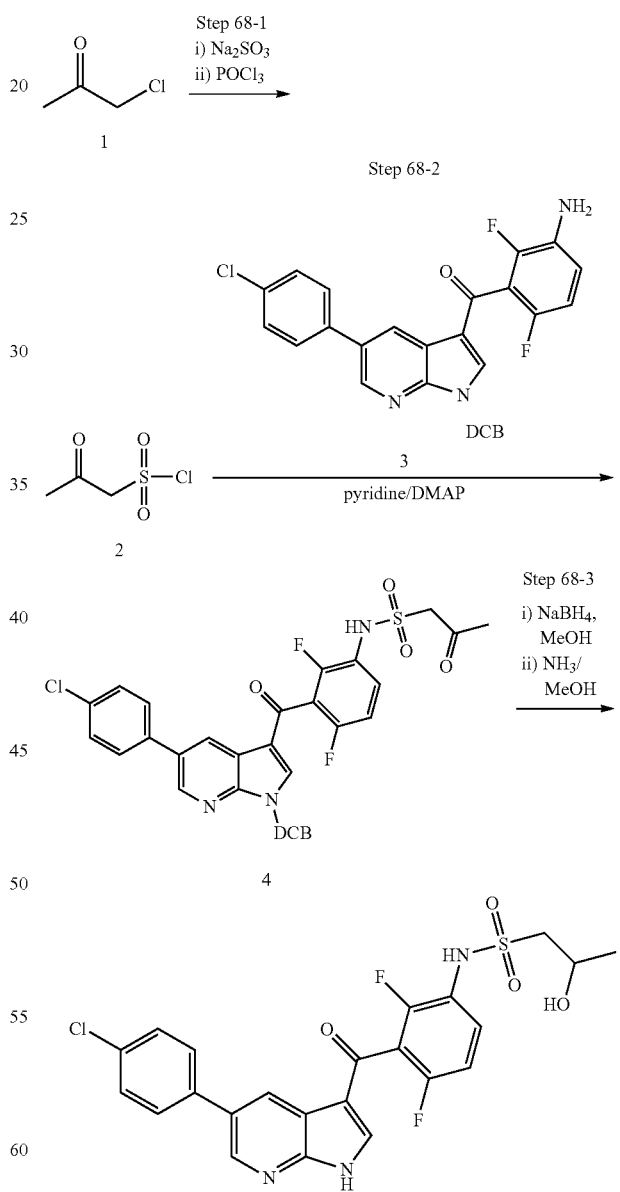

Step 68-1: 2-oxopropane-1-sulfonyl chloride (2)

Chloroacetone (1 eq., 3 g, 32.425 mmol), $Na_2SO_3$ (1 eq., 4.085 g, 32.425 mmol) and water (30 mL) were mixed in a flask equipped with a refluxed condenser. The mixture was refluxed with stirring for 20 h, after which the mixture was evaporated to dryness. The obtained white solid (step-1 product) was used in the next step without further purification.

To a stirred solution of step-1 product (3 g, crude) in toluene (15 mL) was added POCl₃ (15 mL) and the reaction mixture was stirred at 110° C. for 4 h. The solvent was removed by rotary evaporation, diethyl ether (50 mL) was added and mixture was further stirred for 10 min. It was filtered and the filtrate was concentrated under reduced pressure to yield the title compound (2) as a dark brown liquid (3 g, crude), which was used in the next step without further purification.

Step 68-2: N-(3-(5-(4-chlorophenyl)-1-(2,6-dichlorobenzoyl)-1H-pyrrolo[2,3-b]pyridine-3-carbonyl)-2, 4-difluorophenyl)-2-oxopropane-1-sulfonamide (4)

To a stirred solution of compound 3 (1 eq., 200 mg, 0.359 mmol) in dioxane (4 mL) was added pyridine (1 mL) and 4-DMAP (0.1 eq., 4.38 mg, 0.0359 mmol). 2-Oxopropanesulfonyl chloride 2 (4 eq., 224.32 mg, 1.438 mmol) was added dropwise with stirring at RT. The reaction mixture was stirred at RT for 8 h. The progress of the reaction was monitored by TLC. After completion of the reaction, the solvent was removed in vacuum, water was added (5 mL) and extracted with EtOAc (3×10 mL). The combined organic layer was washed with brine, dried over anhydrous Na₂SO₄ and concentrated under reduced pressure to get a crude compound which was purified by FCC to obtain 4 (199.75 mg, 0.295 mmol, 82% yield).

Step 68-3: N-(3-(5-(4-chlorophenyl)-1H-pyrrolo[2, 3-b]pyridine-3-carbonyl)-2,4-difluoro-phenyl)-2-hydroxypropane-1-sulfonamide Step 68-3i: To a stirred solution of N-(3-(5-(4-chlorophenyl)-1-(2,6-dichlorobenzoyl)-1H-pyrrolo[2,3-b]pyridine-3-carbonyl)-2,4-difluorophenyl)-2-oxopropane-1-sulfonamide 4 (1 eq., 200 mg, 0.295 mmol) in MeOH (2 mL) was added methanolic solution of sodium borohydride (1 eq., 11.22 mg, 0.295 mmol, 1 mL), dropwise at 0° C. and the reaction mixture was stirred for 1 h. The progress of the reaction was monitored by TLC. After completion, the reaction mixture was added to water (20 mL) and extracted with EtOAc (3×5 mL). The combined organic layer dried over anhydrous Na₂SO₄ and concentrated under reduced pressure to afford crude product which was purified by FCC using 25% EtOAc/Hexane to obtain step-4 product (70 mg, 0.1 mmol, 33.89%).

Step 68-3ii: To a stirred solution of step 71-4i product (70 mg, 0.103 mmol) in THF:MeOH (2 mL, 1:1) was added aq. ammonia (1 mL) and the reaction mixture was stirred at rt for 4 h. The solvent was evaporated under vacuum and water (10 mL) was added. The mixture was neutralized to pH 7 with 5 N HCl and extracted with EtOAc (3×5 mL). The combined organic layer was dried over anhydrous Na₂SO₄ and concentrated under reduced pressure to afford crude product which was purified by SFC to obtain the desired product N-(3-(5-(4-chlorophenyl)-1H-pyrrolo[2,3-b]pyridine-3-carbonyl)-2,4-difluorophenyl)-2-hydroxypropane-1-sulfonamide (15.99 mg, 0.0316 mmol, 21.50%).

Analytical data: ¹H NMR (400 MHz, DMSO) δ 13.02 (s, 1H), 9.66 (s, 1H), 8.71 (d, J=2.1 Hz, 1H), 8.64 (s, 1H), 8.22 (s, 1H), 7.80 (d, J=8.5 Hz, 2H), 7.66-7.53 (m, 3H), 7.28 (t, J=8.7 Hz, 1H), 5.01 (d, J=4.7 Hz, 1H), 4.12 (d, J=5.7 Hz, 1H), 3.23 (dd, J=10.2, 6.0 Hz, 2H), 1.20 (d, J=6.3 Hz, 3H).

Calculated exact mass for $C_{23}H_{18}ClF_2N_3O_4S$: 505.07. MS(ESI⁺): 506.0 for [M+H]⁺.

Example 69: Synthesis of N-(3-(5-(4-chlorophenyl)-1H-pyrrolo[2,3-b]pyridine-3-carbonyl)-2,4-difluorophenyl)-2-oxopropane-1-sulfonamide

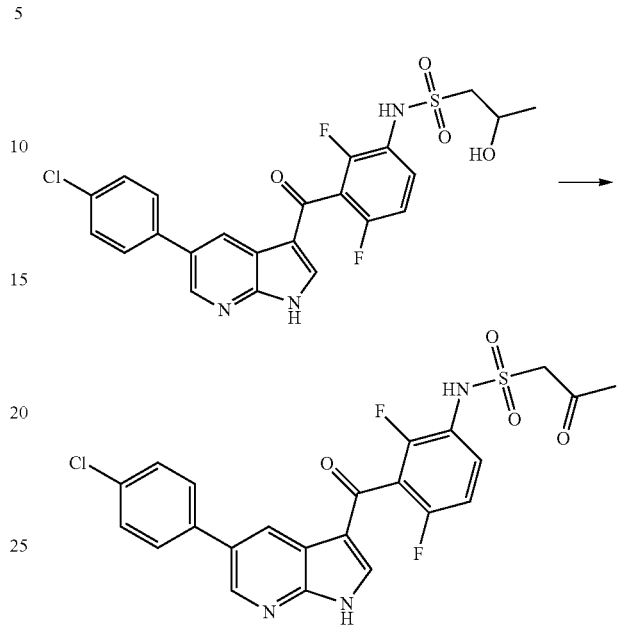

Analytical data: ¹H NMR (400 MHz, DMSO) δ 13.03 (s, 1H), 10.06 (s, 1H), 8.72 (d, J=2.1 Hz, 1H), 8.66 (s, 1H), 8.25 (s, 1H), 7.80 (d, J=8.4 Hz, 2H), 7.59 (t, J=10.2 Hz, 3H), 7.29 (t, J=8.6 Hz, 1H), 4.45 (s, 2H), 2.27 (s, 3H).

Calculated exact mass for $C_{23}H_{16}ClF_2N_3O_4S$: 503.05. MS(ESI+): 504.05 for [M+H]⁺.

Example 70: Synthesis of N-(2,4-difluoro-3-(5-morpholino-1H-pyrrolo[2,3-b]pyridine-3-carbonyl) phenyl)propane-1-sulfonamide

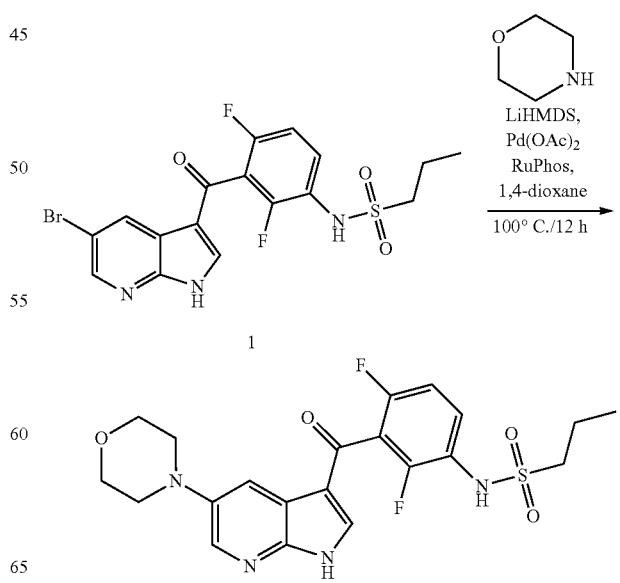

To a degassed stirred solution of RuPhos (0.1 eq., 20.36 mg, 0.04 mmol) in dioxane (2 mL) was added palladium acetate (0.05 eq., 4.89 mg, 0.02 mmol) and the reaction was again degassed with argon for 15 min. To this mixture was added N-(3-(5-bromo-1H-pyrrolo[2,3-b]pyridine-3-carbonyl)-2,4-difluorophenyl)propane-1-sulfonamide (1) (1 eq., 200 mg, 0.44 mmol) and morpholine (2 eq., 76.04 mg, 0.87 mmol) followed by addition of 1M solution of LiHMDS (4 eq., 1.7 mL, 1.7 mmol) in THF. The reaction mixture was further degassed with argon for 10 min and then heated at 100° C. in a sealed tube for 12 h. The reaction mixture was diluted with water (10 mL) and the pH was adjusted to 6 with 5N HCl. The reaction mixture was extracted with EtOAc (10 mL×3). The combined organic layer was dried over Na$_2$SO$_4$ and concentrated under reduced pressure to obtain a crude residue which was further purified by SFC to afford N-(2,4-difluoro-3-(5-morpholino-1H-pyrrolo[2,3-b]pyridine-3-carbonyl)phenyl)propane-1-sulfonamide (35 mg, 0.08 mmol, 17%) as a white solid.

Analytical data: $^1$H NMR (400 MHz, DMSO) δ 12.69 (s, 1H), 9.74 (s, 1H), 8.28 (d, J=2.7 Hz, 1H), 8.02 (d, J=3.0 Hz, 1H), 7.92 (s, 1H), 7.61-7.50 (m, 1H), 7.26 (t, J=8.6 Hz, 1H), 3.99-3.62 (m, 19H), 3.21-3.06 (m, 5H), 1.73 (dt, J=15.0, 7.5 Hz, 2H), 0.96 (t, J=7.4 Hz, 3H).

Example 71: Synthesis of N-(2,4-difluoro-3-(5-(piperazin-1-yl)-1H-pyrrolo[2,3-b]pyridine-3-carbonyl)phenyl)propane-1-sulfonamide Step 71-1: tert-butyl 4-(3-(2,6-difluoro-3-(propylsulfonamido)benzoyl)-1H-pyrrolo[2,3-b]pyridin-5-yl)piperazine-1-carboxylate (2)

To a degassed stirred solution of Ruphos (0.1 eq., 20.36 mg, 0.04 mmol) in NMP (2 mL) was added Pd$_2$dba$_3$ (0.05 eq., 19.97 mg, 0.02 mmol) and the reaction was again degassed with argon for 15 min. To this mixture was added N-(3-(5-bromo-1H-pyrrolo[2,3-b]pyridine-3-carbonyl)-2,4-difluorophenyl)propane-1-sulfonamide 1 (1 eq., 200 mg, 0.436 mmol) and 1-Boc-piperazine (1.5 eq., 121.81 mg, 0.65 mmol) followed by addition of sodium tert-butoxide (3 eq., 125.66 mg, 1.31 mmol). The reaction mixture was further degassed with argon for 10 min and then heated at 100° C. in microwave for 1 h. The reaction mixture was diluted with water (10 mL) and extracted with EtOAc (10 mL×3). The combined organic layer was dried over sodium sulphate and concentrated under reduced pressure to obtain a crude product which was further purified by FCC using 30% EtOAc/Hexanes to afford tert-butyl 4-(3-(2,6-difluoro-3-(propylsulfonamido)benzoyl)-1H-pyrrolo[2,3-b]pyridin-5-yl)piperazine-1-carboxylate (2) (70 mg, 0.12 mmol, 28% yield) as a white solid.

Step 71-2: N-(2,4-difluoro-3-(5-(piperazin-1-yl)-1H-pyrrolo[2,3-b]pyridine-3-carbonyl) phenyl)propane-1-sulfonamide HCl salt HCl in dioxane (3 mL of 4M) was added to the tert-butyl 4-(3-(2,6-difluoro-3-(propylsulfonamido)benzoyl)-1H-pyrrolo[2,3-b]pyridin-5-yl)piperazine-1-carboxylate (2) (70 mg, 0.12 mmol) at 0° C. and the reaction mixture was further stirred at RT for 1 h. After completion of the reaction, dioxane was removed under vacuum to obtain a crude residue. This residue was triturated with diethyl ether to obtain N-(2,4-difluoro-3-(5-(piperazin-1-yl)-1H-pyrrolo[2,3-b]pyridine-3-carbonyl)phenyl)propane-1-sulfonamide as HCl salt (25 mg, 0.05 mmol, 43%) as a white solid.

Analytical data: 1H NMR (400 MHz, DMSO) δ 8.29 (d, J=2.4 Hz, 1H), 8.00 (s, 2H), 7.55 (dd, J=14.8, 8.9 Hz, 1H), 7.25 (t, J=8.7 Hz, 1H), 3.37 (m, 4H), 3.30 (m, 4H), 3.14-3.06 (m, 2H), 1.72 (dd, J=15.0, 7.4 Hz, 2H), 0.94 (t, J=7.4 Hz, 3H).

Synthesis of 5-substituted N-(2,x-difluoro-3-(1H-pyrrolo[2,3-b]pyridine-3-carbonyl)phenyl)alkyl-1-sulfonamide derivatives 5-substituted N-(2,4-difluoro-3-(1H-pyrrolo[2,3-b]pyridine-3-carbonyl)phenyl)alkyl-1-sulfonamide derivatives according to the formula

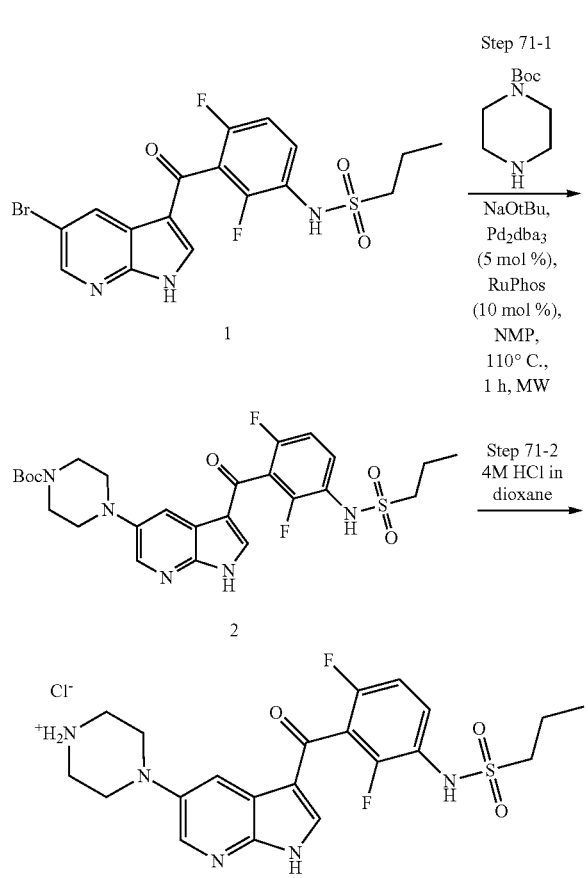

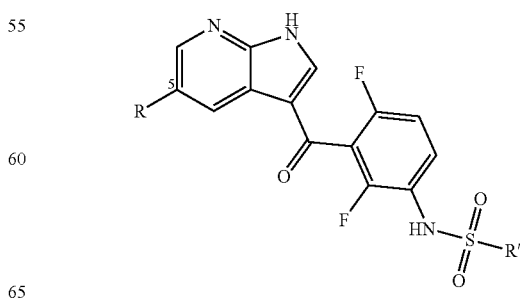

were prepared according to the following examples.

Example 72: N-(2,4-difluoro-3-(5-(2-methoxypyrimidin-5-yl)-1H-pyrrolo[2,3-b]pyridine-3-carbonyl)phenyl)propane-1-sulfonamide

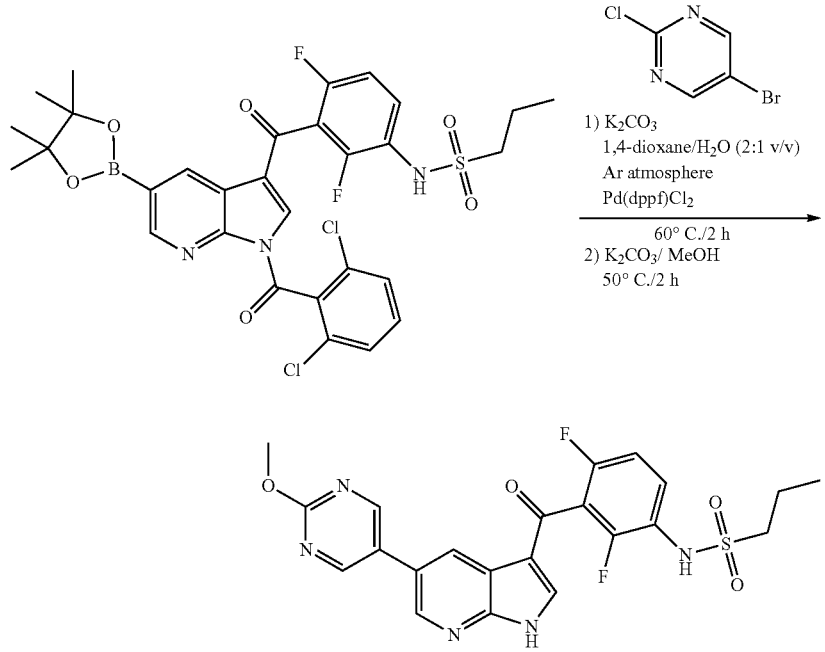

N-[3-[1-(2,6-dichlorobenzoyl)-5-(4,4,5,5-tetramethyl-1,3,2-dioxaborolan-2-yl)pyrrolo[2,3-b]pyridine-3-carbonyl]-2,4-difluorophenyl]propane-1-sulfonamide (150 mg, 0.221 mmol, prepared in analogy to Example 4, Steps 4-1 and 4-2), 5-bromo-2-chloropyrimidine (64.2 mg, 0.332 mmol) and potassium carbonate (62.0 mg, 0.442 mmol) were suspended in 1,4-dioxane (0.600 mL) and water (0.300 mL) and degassed with argon for 5 min. [1,1'-Bis(diphenylphosphino)ferrocene]dichloropalladium (II) (Pd(dppf)Cl$_2$, 8.09 mg, 0.0111 mmol) was added and the mixture was heated to 60° C. for 2 h. The solvent was removed by evaporation and the residue dissolved in 10 mL MeOH. Potassium carbonate (1 g) was added and the mixture was stirred at 50° C. After 2 h, water was added and the pH was adjusted to ~7 with aqueous HCl solution (1N). The aqueous phase was extracted with EtOAc three times, the combined organics were dried over sodium sulfate and the solvent removed in vacuo. The product was purified via flash chromatography using DCM/EtOAc/MeOH (92/8/0-88/8/4) as eluent. Along with the potassium carbonate catalysed removal of the dichlorobenzoyl protection group the chlorine of 5-bromo-2-chloropyrimidine was substituted with the methoxy group.

Analytical Data:

$^1$H NMR (600 MHz, DMSO-d$_6$): δ 13.05 (s, 1H), 9.77 (s, 1H), 9.00 (s, 2H), 8.72 (d, J=1.4 Hz, 1H), 8.67 (s, 1H), 8.24 (s, 1H), 7.59 (dd, J=14.7, 8.8 Hz, 1H), 7.28 (t, J=8.6 Hz, 1H), 3.99 (s, 3H), 3.15-3.07 (m, 2H), 1.74 (dq, J=14.8, 7.3 Hz, 2H), 0.96 (t, J=7.4 Hz, 3H).

Calculated exact mass: 487.1; MS(ESI$^-$): 486.3 for [M−H]$^-$.

In analogy to Example 72, compounds of Examples 73-95, given in Table 3, were prepared.

TABLE 3

Examples 73-95 were prepared according to the procedure described for Example 72.

| Ex. | Reactant | Product |
|---|---|---|
| 73 | ![F₃C-S(O)₂-C₆H₄-Br] | ![product structure] |

TABLE 3-continued
Examples 73-95 were prepared according to the procedure described for Example 72.
| 74 | 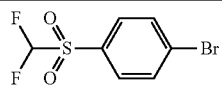 | 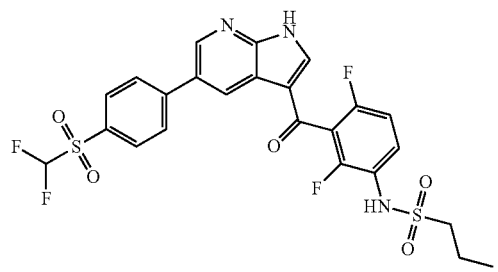 [SMILES: CCCS(=O)(=O)Nc1ccc(F)c(C(=O)c2c[nH]c3ncc(-c4ccc(S(=O)(=O)C(F)F)cc4)cc23)c1F] |
| --- | --- | --- |
| 75 | 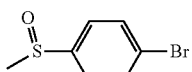 | 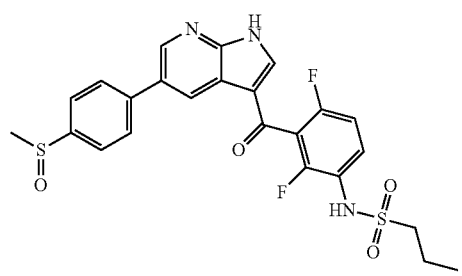 [SMILES: CCCS(=O)(=O)Nc1ccc(F)c(C(=O)c2c[nH]c3ncc(-c4ccc(S(C)=O)cc4)cc23)c1F] |
| 76 |  | 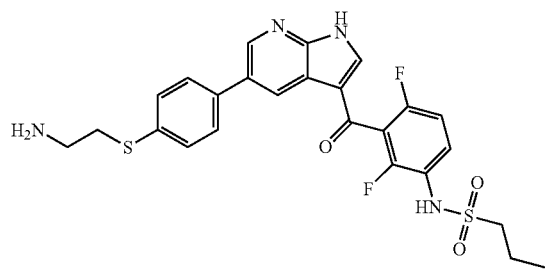 [SMILES: CCCS(=O)(=O)Nc1ccc(F)c(C(=O)c2c[nH]c3ncc(-c4ccc(SCCN)cc4)cc23)c1F] |
| 77 | 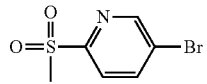 | 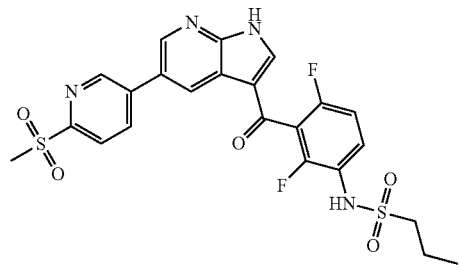 [SMILES: CCCS(=O)(=O)Nc1ccc(F)c(C(=O)c2c[nH]c3ncc(-c4ccc(S(C)(=O)=O)nc4)cc23)c1F] |
| 78 | 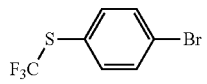 | 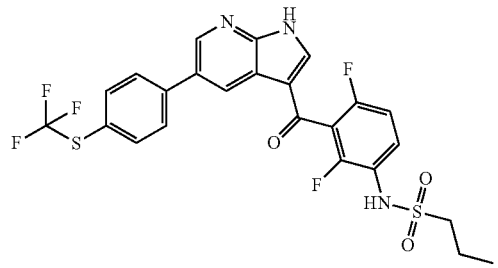 [SMILES: CCCS(=O)(=O)Nc1ccc(F)c(C(=O)c2c[nH]c3ncc(-c4ccc(SC(F)(F)F)cc4)cc23)c1F] |
| 79 | 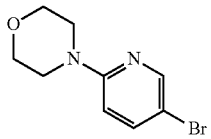 [SMILES: Brc1ccc(N2CCOCC2)nc1] | 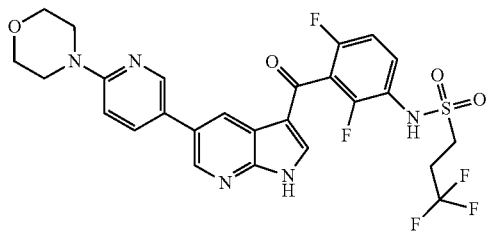 [SMILES: O=C(c1c(F)ccc(NS(=O)(=O)CCC(F)(F)F)c1F)c1c[nH]c2ncc(-c3ccc(N4CCOCC4)nc3)cc12] |

TABLE 3-continued
Examples 73-95 were prepared according to the procedure described for Example 72.
80 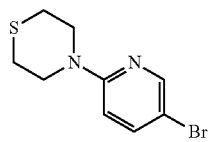 [SMILES: Brc1ccc(N2CCSCC2)nc1] 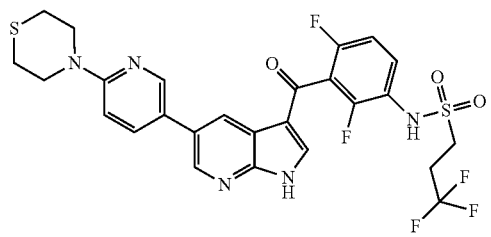 [SMILES: O=C(c1c(F)ccc(NS(=O)(=O)CCC(F)(F)F)c1F)c1c[nH]c2ncc(-c3ccc(N4CCSCC4)nc3)cc12]
81 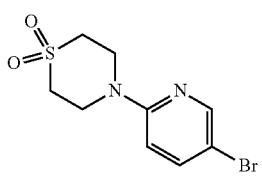 [SMILES: O=S1(=O)CCN(c2ccc(Br)cn2)CC1] 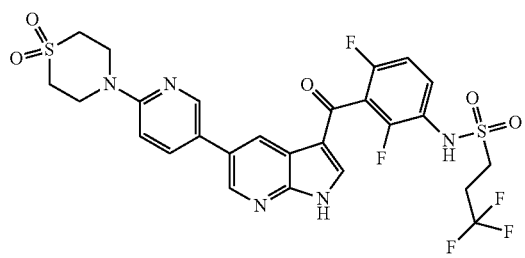 [SMILES: O=C(c1c(F)ccc(NS(=O)(=O)CCC(F)(F)F)c1F)c1c[nH]c2ncc(-c3ccc(N4CCS(=O)(=O)CC4)nc3)cc12]
82 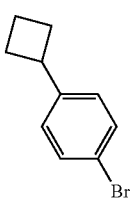 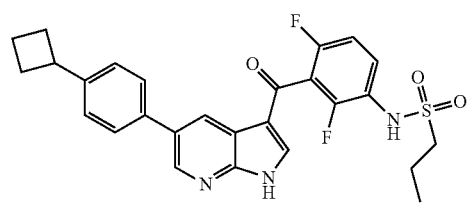 [SMILES: CCCS(=O)(=O)Nc1ccc(F)c(C(=O)c2c[nH]c3ncc(-c4ccc(C5CCC5)cc4)cc23)c1F]
83 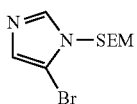 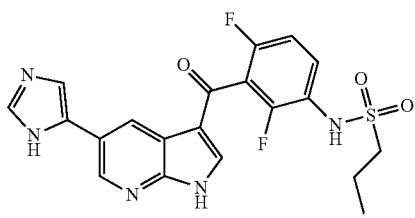 [SMILES: CCCS(=O)(=O)Nc1ccc(F)c(C(=O)c2c[nH]c3ncc(-c4cnc[nH]4)cc23)c1F]
84 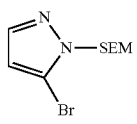 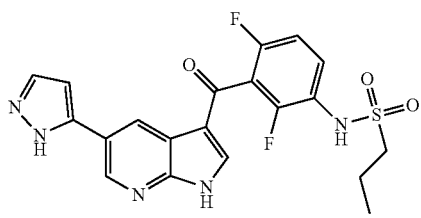 [SMILES: CCCS(=O)(=O)Nc1ccc(F)c(C(=O)c2c[nH]c3ncc(-c4ccn[nH]4)cc23)c1F]
85 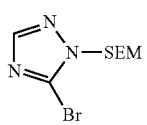 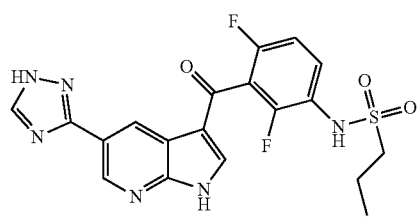 [SMILES: CCCS(=O)(=O)Nc1ccc(F)c(C(=O)c2c[nH]c3ncc(-c4nc[nH]n4)cc23)c1F]

TABLE 3-continued
Examples 73-95 were prepared according to the procedure described for Example 72.
| 86 | 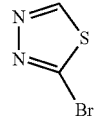 | 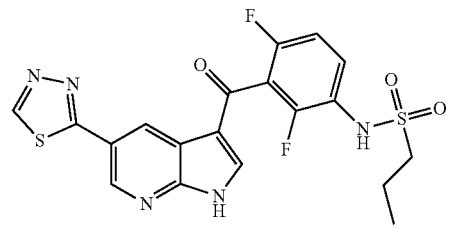 [SMILES: CCCS(=O)(=O)Nc1ccc(F)c(C(=O)c2c[nH]c3ncc(-c4nncs4)cc23)c1F] |
| --- | --- | --- |
| 87 | 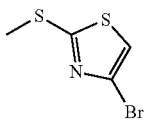 | 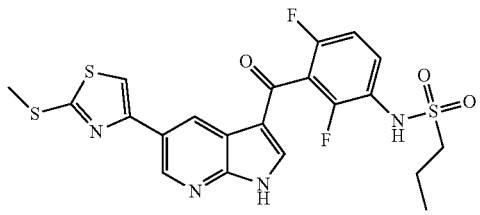 [SMILES: CCCS(=O)(=O)Nc1ccc(F)c(C(=O)c2c[nH]c3ncc(-c4csc(SC)n4)cc23)c1F] |
| 88 | 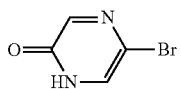 | 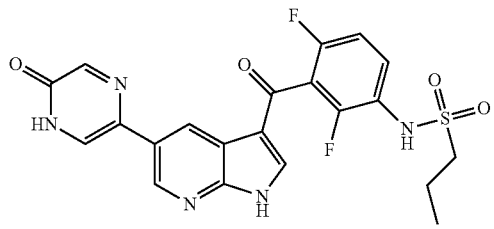 [SMILES: CCCS(=O)(=O)Nc1ccc(F)c(C(=O)c2c[nH]c3ncc(-c4c[nH]c(=O)cn4)cc23)c1F] |
| 89 | 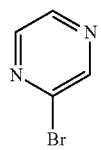 | 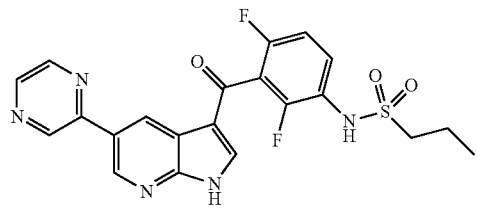 [SMILES: CCCS(=O)(=O)Nc1ccc(F)c(C(=O)c2c[nH]c3ncc(-c4cnccn4)cc23)c1F] |
| 90 | 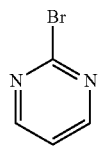 | 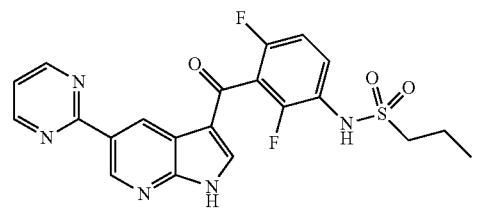 [SMILES: CCCS(=O)(=O)Nc1ccc(F)c(C(=O)c2c[nH]c3ncc(-c4ncccn4)cc23)c1F] |
| 91 | 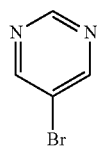 | 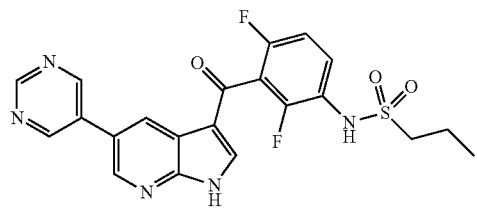 [SMILES: CCCS(=O)(=O)Nc1ccc(F)c(C(=O)c2c[nH]c3ncc(-c4cncnc4)cc23)c1F] |
| 92 | 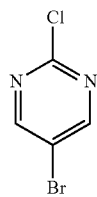 | 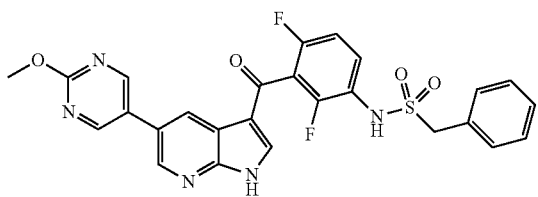 [SMILES: COc1ncc(-c2cnc3[nH]cc(C(=O)c4c(F)ccc(NS(=O)(=O)Cc5ccccc5)c4F)c3c2)cn1] |

TABLE 3-continued

Examples 73-95 were prepared according to the procedure described for Example 72.

| Ex. | | Analytical data |
|---|---|---|
| 73 | N-(2,4-difluoro-3-(5-(4-((trifluoromethyl)sulfonyl)phenyl)-1H-pyrrolo[2,3-b]pyridine-3-carbonyl)phenyl)propane-1-sulfonamide C24H18F5N3O5S2/587.54 | $^1$H NMR (400 MHz, DMSO-d$_6$) δ 13.19-12.82 (m, 1H), 10.03-9.70 (m, 1H), 8.88 (d, J = 2.2 Hz, 1H), 8.82 (s, 1H), 8.31 (s, 1H), 8.26 (q, J = 8.7 Hz, 3H), 7.65-7.54 (m, 1H), 7.28 (t, J = 8.8 Hz, 1H), 3.16-3.06 (m, 2H), 1.74 (dq, J = 14.8, 7.4 Hz, 2H), 0.96 (t, J = 7.4 Hz, 2H). Calculated exact mass: 587.06 MS(ESI$^+$): 588 for [M + H]$^+$. |
| 74 | N-(3-(5-(4-((difluoromethyl)sulfonyl)phenyl)-1H-pyrrolo[2,3-b]pyridine-3-carbonyl)-2,4-difluorophenyl)propane-1-sulfonamide C24H19F4N3O5S2/569.55 | $^1$H NMR (400 MHz, DMSO-d$_6$) δ 13.10 (s, 1H), 9.97-9.66 (m, 1H), 8.82 (d, J = 2.2 Hz, 1H), 8.76 (s, 1H), 8.28 (s, 1H), 8.17 (d, J = 8.5 Hz, 2H), 8.06 (d, J = 8.5 Hz, 2H), 7.56 (td, J = 9.0, 6.0 Hz, 1H), 7.35 (s, 1H), 7.24 (dd, J = 15.3, 6.2 Hz, 1H), 3.15-3.03 (m, 2H), 1.71 (dq, J = 15.0, 7.4 Hz, 2H), 0.93 (t, J = 7.4 Hz, 3H). Calculated exact mass: 569.07; MS(ESI$^+$): 570.15 for [M + H]$^+$. |
| 75 | N-(2,4-difluoro-3-(5-(4-(methylsulfinyl)phenyl)-1H-pyrrolo[2,3-b]pyridine-3-carbonyl)phenyl)propane-1-sulfonamide C24H21F2N3O4S2/517.57 | $^1$H NMR (400 MHz, DMSO-d$_6$) δ 13.06 (s, 1H), 9.78 (s, 1H), 8.77 (d, J = 2.2 Hz, 1H), 8.70 (s, 1H), 8.27 (s, 1H), 7.98 (d, J = 8.4 Hz, 2H), 7.83 (d, J = 8.4 Hz, 2H), 7.59 (td, J = 9.0, 5.9 Hz, 1H), 7.32-7.25 (m, 1H), 3.34 (s, 3H), 3.106-3.144 (m, 2H), 1.73-1.75 (m, 2H), 0.96 (t, J = 7.4 Hz, 3H). Calculated exact mass: 517.09; MS(ESI$^+$): 518.1 |
| 76 | N-(3-(5-(4-((2-aminoethyl)thio)phenyl)-1H-pyrrolo[2,3-b]pyridine-3-carbonyl)-2,4-difluorophenyl)propane-1-sulfonamide C25H24F2N4O3S2/530.61 | $^1$H NMR (400 MHz, dmso) δ 8.70 (d, J = 2.1 Hz, 1H), 8.61 (s, 1H), 8.28 (s, 1H), 8.19 (s, 1H), 7.73 (d, J = 8.3 Hz, 2H), 7.55 (dd, J = 12.1, 6.0 Hz, 1H), 7.50 (d, J = 8.3 Hz, 2H), 7.21 (t, J = 8.5 Hz, 1H), 3.15-3.10 (m, 2H), 3.08-3.03 (m, 2H), 2.87 (t, J = 7.0 Hz, 2H), 1.73 (dt, J = 15.2, 7.5 Hz, 2H), 0.95 (t, J = 7.4 Hz, 3H). Calculated 530.13 for C25H24F2N4O3S2. Measured 531.1 for [M + H]$^+$. |
| 77 | N-(2,4-difluoro-3-(5-(6-(methylsulfonyl)pyridin-3-yl)-1H-pyrrolo[2,3-b]pyridine-3-carbonyl)phenyl)propane-1-sulfonamide C23H20F2N4O5S2/534.55 | $^1$H NMR (400 MHz, dmso) δ 13,16 (s, 1H), 9.76 (s, 1H), 9.22 (d, J = 2.0 Hz, 1H), 8.86 (d, J = 2.2 Hz, 1H), 8.81 (s, 1H), 8.56 (dd, J = 8.2, 2.2 Hz, 1H), 8.31 (s, 1H), 8.16 (d, J = 8.2 Hz, 1H), 7.59 (td, J = 9.0, 6.0 Hz, 1H), 7.29 (t, J = 8.8 Hz, 1H), 3.18-3.09 (m, 2H), 1.74 (dq, J = 15.0, 7.4 Hz, 2H), 0.97 (t, J = 7.4 Hz, 3H). Calculated 534.08 for C23H20F2N4O5S2. Measured 535.15 for [M + H]$^+$. |

TABLE 3-continued

Examples 73-95 were prepared according to the procedure described for Example 72.

| | | |
|---|---|---|
| 78 | N-(2,4-difluoro-3-(5-(4-((trifluoromethyl)thio)phenyl)-1H-pyrrolo[2,3-b]pyridine-3-carbonyl)phenyl)propane-1-sulfonamide<br>C24H18F5N3O3S2/555.54 | $^1$H NMR (400 MHz, dmso) δ 13.07 (s, 1H), 9.78 (s, 1H), 8.78 (d, J = 2.2 Hz, 1H), 8.71 (s, 1H), 8.28 (s, 1H), 7.95 (d, J = 8.4 Hz, 2H), 7.86 (d, J = 8.3 Hz, 2H), 7.59 (td, J = 9.0, 5.9 Hz, 1H), 7.29 (t, J = 8.1 Hz, 1H), 3.13 (dd, J = 14.9, 7.3 Hz, 2H), 1.74 (dq, J = 15.0, 7.4 Hz, 2H), 0.96 (t, J = 7.4 Hz, 3H).<br>Calculated 555.07 for C24H18F5N3O3S2.<br>Measured 556.0 for [M + H]$^+$. |
| 79 | N-(2,4-difluoro-3-(5-(6-morpholinopyridin-3-yl)-1H-pyrrolo[2,3-b]pyridine-3-carbonyl)phenyl)-3,3,3-trifluoropropane-1-sulfonamide<br>C26H22F5N5O4S/595.55 | $^1$H NMR (400 MHz, DMSO-d$_6$) δ 12.86 (d, J = 3.1 Hz, 1H), 10.04 (s, 1H), 8.65 (d, J = 2.3 Hz, 1H), 8.60 (d, J = 2.3 Hz, 1H), 8.51 (d, J = 2.6 Hz, 1H), 8.08 (d, J = 2.9 Hz, 1H), 7.95 (dd, J = 8.8, 2.6 Hz, 1H), 7.69 (td, J = 8.2, 6.1 Hz, 1H), 7.38 (t, J = 8.9 Hz, 1H), 6.97 (d, J = 8.9 Hz, 1H), 3.73 (t, J = 4.8 Hz, 4H), 3.54-3.50 (m, 4H), 3.49-3.45 (m, 2H), 2.93-2.76 (m, 2H).<br>MS(ESI$^-$): 594.3 for [M − H]$^-$. |
| 80 | N-(2,4-difluoro-3-(5-(6-thiomorpholinopyridin-3-yl)-1H-pyrrolo[2,3-b]pyridine-3-carbonyl)phenyl)-3,3,3-trifluoropropane-1-sulfonamide<br>C26H22F5N5O3S2/611.61 | $^1$H NMR (400 MHz, DMSO-d$_6$) δ 12.85 (d, J = 3.1 Hz, 1H), 10.03 (s, 1H), 8.65 (d, J = 2.3 Hz, 1H), 8.60 (d, J = 2.2 Hz, 1H), 8.49 (d, J = 2.6 Hz, 1H), 8.07 (d, J = 2.7 Hz, 1H), 7.92 (dd, J = 8.9, 2.6 Hz, 1H), 7.68 (td, J = 8.3, 6.2 Hz, 1H), 7.38 (t, J = 8.8 Hz, 1H), 6.98 (d, J = 8.9 Hz, 1H), 4.01-3.94 (m, 4H), 3.52-3.43 (m, 2H), 2.92-2.76 (m, 2H), 2.66-2.61 (m, 4H).<br>MS(ESI$^-$): 610.6 for [M − H]$^-$. |
| 81 | N-(3-(5-(6-(1,1-dioxidothio-morpholino)pyridin-3-yl)-1H-pyrrolo[2,3-b]pyridine-3-carbonyl)-2,4-difluorophenyl)-3,3,3-trifluoropropane-1-sulfonamide<br>C26H22F5N5O5S2/643.60 | $^1$H NMR (400 MHz, DMSO-d$_6$) δ 12.87 (d, J = 3.1 Hz, 1H), 10.03 (s, 1H), 8.67 (d, J = 2.3 Hz, 1H), 8.63 (d, J = 2.3 Hz, 1H), 8.54 (d, J = 2.6 Hz, 1H), 8.08 (d, J = 2.8 Hz, 1H), 8.01 (dd, J = 8.8, 2.6 Hz, 1H), 7.68 (td, J = 8.2, 6.1 Hz, 1H), 7.38 (t, J = 8.9 Hz, 1H), 7.17 (d, J = 8.9 Hz, 1H), 4.17-4.10 (m, 4H), 3.52-3.43 (m, 2H), 3.19-3.08 (m, 4H), 2.92-2.76 (m, 2H).<br>MS(ESI$^-$): 642.6 for [M − H]$^-$. |
| 82 | N-(3-(5-(4-cyclobutylphenyl)-1H-pyrrolo[2,3-b]pyridine-3-carbonyl)-2,4-difluorophenyl)-propane-1-sulfonamide<br>C27H25F2N3O3S/509.57 | $^1$H NMR (400 MHz, DMSO-d$_6$) δ 12.98 (s, 1H), 9.76 (s, 1H), 8.69 (d, J = 2.2 Hz, 1H), 8.59 (s, 1H), 8.22 (s, 1H), 7.67 (d, J = 8.1 Hz, 2H), 7.58 (dd, J = 14.9, 9.0 Hz, 1H), 7.38 (d, J = 8.1 Hz, 2H), 7.28 (t, J = 8.8 Hz, 1H), 3.67-3.53 (m, 1H), 3.17-3.07 (m, 2H), 2.39-2.29 (m, 2H), 2.14 (dd, J = 15.1, 6.0 Hz, 2H), 2.07-1.93 (m, 1H), 1.85 (d, J = 9.9 Hz, 1H), 1.74 (dd, J = 15.2, 7.5 Hz, 2H), 0.96 (t, J = 7.4 Hz, 3H).<br>MS(ESI$^+$): 510.2 for [M + H]$^+$ |
| 83 | N-(3-(5-(1H-imidazol-5-yl)-1H-pyrrolo[2,3-b]pyridine-3-carbonyl)-2,4-difluorophenyl)-propane-1-sulfonamide<br>C20H17F2N5O3S/445.44 | $^1$H NMR (400 MHz, DMSO-d$_6$) δ 8.91-8.87 (m, 1H), 8.80 (d, J = 2.1 Hz, 1H), 8.75-8.72 (m, 1H), 8.00 (s, 1H), 7.61-7.52 (m, 1H), 7.29-7.22 (m, 1H), 3.12-3.06 (m, 2H), 1.78-1.65 (m, 2H), 0.93 (t, J = 7.4 Hz, 3H).<br>MS(ESI$^+$): 446.0 for [M + H]$^+$ |
| 84 | N-(3-(5-(1H-pyrazol-5-yl)-1H-pyrrolo[2,3-b]pyridine-3-carbonyl)-2,4-difluorophenyl)-propane-1-sulfonamide<br>C20H17F2N5O3S/445.44 | $^1$H NMR (400 MHz, DMSO-d$_6$) δ 13.01 (s, 1H), 12.93 (s, 1H), 9.78 (s, 1H), 8.89 (s, 1H), 8.83 (s, 1H), 8.18 (s, 1H), 7.85 (s, 1H), 7.59 (dd, J = 14.8, 8.8 Hz, 1H), 7.28 (t, J = 8.5 Hz, 1H), 6.85 (s, 1H), 3.18-3.07 (m, 2H), 1.74 (dd, J = 14.9, 7.6 Hz, 2H), 0.96 (t, J = 7.3 Hz, 3H)<br>MS(ESI$^+$): 446.0 for [M + H]$^+$ |
| 85 | N-(3-(5-(1H-1,2,4-triazol-3-yl)-1H-pyrrolo[2,3-b]pyridine-3-carbonyl)-2,4-difluorophenyl)-propane-1-sulfonamide<br>C19H16F2N6O3S/446.43 | $^1$H NMR (400 MHz, DMSO-d$_6$) δ 8.93 (s, 1H), 8.74 (s, 1H), 8.30 (s, 1H), 8.11 (s, 1H), 7.62-7.52 (m, 1H), 7.28-7.22 (m, 1H), 3.17-3.04 (m, 2H), 1.80-1.65 (m, 3H), 0.96 (t, J = 7.5 Hz, 3H). |
| 86 | N-(3-(5-(1,3,4-thiadiazol-2-yl)-1H-pyrrolo[2,3-b]pyridine-3-carbonyl)-2,4-difluorophenyl)-propane-1-sulfonamide<br>C19H15F2N5O3S2/463.48 | $^1$H NMR (400 MHz, DMSO-d$_6$) δ 13.26 (s, 1H), 9.82 (s, 1H), 9.70 (s, 1H), 9.12-9.03 (m, 1H), 9.01 (s, 1H), 8.37 (s, 1H), 7.67-7.55 (m, 1H), 7.36-7.24 (m, 1H), 3.18-3.07 (m, 2H), 1.83-1.65 (m, 2H), 0.96 (t, J = 7.4 Hz, 3H).<br>MS(ESI$^+$): 464.50 for [M + H]$^+$ |
| 87 | N-(2,4-difluoro-3-(5-(2-(methylthio)thiazol-4-yl)-1H-pyrrolo[2,3-b]pyridine-3-carbonyl)phenyl)propane-1-sulfonamide<br>C21H18F2N4O3S3/508.58 | $^1$H NMR (400 MHz, DMSO-d$_6$) δ 13.01 (s, 1H), 9.77 (s, 1H), 9.00 (d, J = 2.0 Hz, 1H), 8.92 (s, 1H), 8.23 (s, 1H), 8.20 (s, 1H), 7.66-7.52 (m, 1H), 7.29 (t, J = 8.6 Hz, 1H), 3.18-3.05 (m, 2H), 1.73 (dq, J = 15.0, 7.4 Hz, 2H), 0.95 (t, J = 7.4 Hz, 3H). Calculated 508.05 for C22H18F2N4O3S.<br>Measured 509.0 for [M + H]$^+$ |

TABLE 3-continued

Examples 73-95 were prepared according to the procedure described for Example 72.

| | | |
|---|---|---|
| 88 | N-(2,4-difluoro-3-(5-(5-oxo-4,5-dihydropyrazin-2-yl)-1H-pyrrolo-[2,3-b]pyridine-3-carbonyl)-phenyl)propane-1-sulfonamide C21H17F2N5O4S/473.45 | $^1$H NMR (400 MHz, DMSO-d$_6$) δ 12.95 (s, 1H), 12.79-12.59 (m, 1H), 9.76 (s, 1H), 8.91 (s, 2H), 8.19 (d, J = 4.1 Hz, 2H), 7.58 (dd, J = 14.9, 8.9 Hz, 1H), 7.28 (t, J = 8.6 Hz, 1H), 3.19-3.06 (m, 2H), 1.84-1.64 (m, 2H), 0.96 (t, J = 7.4 Hz, 3H). |
| 89 | N-(2,4-difluoro-3-(5-(pyrazin-2-yl)-1H-pyrrolo[2,3-b]pyridine-3-carbonyl)phenyl)propane-1-sulfonamide C21H17F2N5O3S/457.46 | $^1$H NMR (600 MHz, DMSO-d$_6$) δ 13.11 (s, 1H), 9.78 (s, 1H), 9.37 (d, J = 1.2 Hz, 1H), 9.16 (s, 2H), 8.77 (dd, J = 2.2, 1.6 Hz, 1H), 8.65 (d, J = 2.4 Hz, 1H), 8.27 (s, 1H), 7.59 (td, J = 9.0, 6.0 Hz, 1H), 7.29 (t, J = 8.6 Hz, 1H), 3.14-3.10 (m, 2H), 1.78-1.69 (m, 2H), 0.95 (t, J = 7.4 Hz, 3H). Calculated exact mass: 457.1 MS(ESI$^-$): 456.3 for [M − H]$^-$. |
| 90 | N-(2,4-difluoro-3-(5-(pyrimidin-2-yl)-1H-pyrrolo[2,3-b]pyridine-3-carbonyl)phenyl)propane-1-sulfonamide C21H17F2N5O3S/457.46 | $^1$H NMR (600 MHz, DMSO-d$_6$) δ 13.09 (s, 1H), 9.79 (s, 1H), 9.42 (s, 1H), 9.39 (d, J = 2.0 Hz, 1H), 8.92 (d, J = 4.8 Hz, 2H), 8.21 (s, 1H), 7.58 (td, J = 9.0, 5.9 Hz, 1H), 7.46 (t, J = 4.9 Hz, 1H), 7.28 (t, J = 8.4 Hz, 1H), 3.12-3.08 (m, 2H), 1.75-1.68 (m, 2H), 0.93 (t, J = 7.5 Hz, 3H). Calculated exact mass: 457.1 MS(ESI$^-$): 456.3 for [M − H]$^-$. |
| 91 | N-(2,4-difluoro-3-(5-(pyrimidin-5-yl)-1H-pyrrolo[2,3-b]pyridine-3-carbonyl)phenyl)propane-1-sulfonamide C21H17F2N5O3S/457.46 | $^1$H NMR (600 MHz, DMSO-d$_6$) δ 13.04 (s, 1H), 9.76 (s, 1H), 9.17 (s, 1H), 9.14 (s, 2H), 8.74 (d, J = 2.2 Hz, 2H), 8.71 (s, 1H), 7.56 (td, J = 9.0, 5.9 Hz, 1H), 7.24 (t, J = 8.4 Hz, 1H), 3.10-3.04 (m, 2H), 1.73-1.66 (m, 2H), 0.92 (t, J = 7.4 Hz, 3H). Calculated exact mass: 457.1 MS(ESI$^-$): 456.3 for [M − H]$^-$. |
| 92 | N-(2,4-difluoro-3-(5-(2-methoxypyrimidin-5-yl)-1H-pyrrolo[2,3-b]pyridine-3-carbonyl)phenyl)-1-phenylmethanesulfonamide C26H19F2N5O4S/535.53 | $^1$H NMR (600 MHz, DMSO-d$_6$) δ 13.07 (d, J = 1.5 Hz, 1H), 9.82 (s, 1H), 9.02 (s, 2H), 8.74 (d, J = 2.2 Hz, 1H), 8.70 (s, 1H), 8.24 (d, J = 2.1 Hz, 1H), 7.51 (td, J = 9.0, 5.9 Hz, 1H), 7.40-7.38 (m, 2H), 7.36-7.33 (m, 3H), 7.24 (t, J = 8.5 Hz, 1H), 4.54 (s, 2H), 4.00 (s, 3H). Calculated exact mass: 535.1 MS(ESI$^-$): 534.0 for [M − H]$^-$. |
| 93 | N-(3-(5-(4-(dimethylphosphoryl)phenyl)-1H-pyrrolo[2,3-b]pyridine-3-carbonyl)-2,4-difluorophenyl)propane-1-sulfonamide C25H24F2N3O4PS/531.51 | $^1$H NMR (400 MHz, DMSO-d$_6$) δ 13.05 (s, 2H), 9.77 (s, 1H), 8.77 (d, J = 1.8 Hz, 1H), 8.69 (s, 1H), 8.27 (s, 1H), 7.97-7.86 (m, 4H), 7.59 (dd, J = 14.8, 8.9 Hz, 1H), 7.29 (t, J = 8.7 Hz, 1H), 3.18-3.07 (m, 2H), 1.73 (dd, J = 22.7, 10.4 Hz, 8H), 0.96 (t, J = 7.4 Hz, 3H). Calculated exact mass: 531.12 MS(ESI$^+$): 532.11 for [M + H]$^+$. |
| 94 | 3-(2,6-difluoro-3-(propylsulfonamido)benzoyl)-N-(2-hydroxyethoxy)-1H-pyrrolo[2,3-b]pyridine-5-carboxamide C20H20F2N4O6S/558.56 | $^1$H NMR (400 MHz, DMSO-d$_6$) δ 13.04 (s, 1H), 11.85 (s, 1H), 9.80 (s, 1H), 8.77 (d, J = 2.0 Hz, 1H), 8.68 (s, 1H), 8.26 (s, 1H), 7.89 (q, J = 8.4 Hz, 4H), 7.58 (dd, J = 14.9, 9.0 Hz, 1H), 7.28 (t, J = 8.7 Hz, 1H), 4.79 (s, 1H), 3.95 (t, J = 4.8 Hz, 2H), 3.63 (d, J = 4.7 Hz, 2H), 3.15-3.09 (m, 2H), 1.73 (dd, J = 15.1, 7.5 Hz, 2H), 0.96 (t, J = 7.4 Hz, 3H). Calculated exact mass: 558.14 MS(ESI$^+$): 559.0 for [M + H]$^+$. |
| 95 | N-(3-(5-(1,3-dimethyl-1-oxido-1l4-benzo[e][1,2]thiazin-6-yl)-1H-pyrrolo[2,3-b]pyridine-3-carbonyl)-2,4-difluorophenyl)propane-1-sulfonamide C27H24F2N4O4S2/570.63 | $^1$H NMR (400 MHz, DMSO-d$_6$) δ 13.07 (s, 1H), 9.79 (s, 1H), 8.79 (s, 1H), 8.72 (s, 1H), 8.28 (s, 1H), 8.20 (d, J = 8.4 Hz, 1H), 7.79 (d, J = 8.3 Hz, 1H), 7.73 (s, 1H), 7.29 (t, J = 8.8 Hz, 1H), 6.20 (s, 1H), 3.79 (s, 3H), 3.19-3.07 (m, 2H), 2.14 (s, 3H), 1.74 (dd, J = 15.0, 7.5 Hz, 2H), 0.96 (t, J = 7.4 Hz, 3H). Calculated exact mass: 570.12 MS(ESI$^+$): 571.05 for [M + H]$^+$. |

Example 96: Synthesis of 4-(3-(2,6-difluoro-3-(propylsulfonamido)benzoyl)-pyrrolo[2,3-b]pyridin-5-yl)benzenesulfonamide

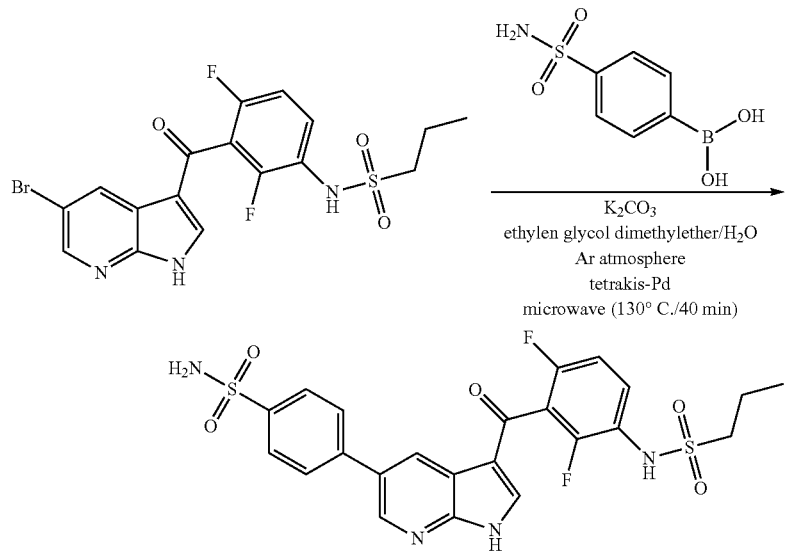

N-[3-(5-bromo-1H-pyrrolo[2,3-b]pyridine-3-carbonyl)-2,4-difluorophenyl]propane-1-sulfonamide (80.0 mg, 0.175 mmol), (4-sulfamoylphenyl)boronic acid (0.0456 g, 0.227 mmol) and Potassium Carbonate (0.0490 g, 0.349 mmol) were suspended in ethylene glycol dimethyl ether (1.60 mL)/water (0.400 mL) and degassed with argon for 5 min. Tetrakis Pd (0.0121 g, 0.0105 mmol) was added and the resulting mixture was heated in a microwave at 130° C. for 40 min. The crudes was passed through a celite pad, which was flushed with EtOAc. The organic phases were washed with water and brine, dried over Na2SO4 and the solvent was removed in vacuo. The product was purified via flash chromatography (Si2O, DCM/EtOAc 20%-50%).

Analytical Data:
$^1$H NMR (400 MHz, DMSO-$d_6$) δ 13.08 (d, J=2.3 Hz, 1H), 9.78 (s, 1H), 8.78 (d, J=2.2 Hz, 1H), 8.71 (s, 1H), 8.29 (d, J=2.6 Hz, 1H), 7.99 (d, J=8.6 Hz, 2H), 7.95 (d, J=8.7 Hz, 2H), 7.59 (td, J=9.0, 6.0 Hz, 1H), 7.45 (s, 2H), 7.32-7.25 (m, 1H), 3.17-3.09 (m, 2H), 1.80-1.67 (m, 2H), 0.96 (t, J=7.4 Hz, 3H).

Calculated exact mass for $C_{23}H_{20}F_2N_4O_5S_2$: 534.1 (molecular weight: 534.55)
MS(ESI$^-$): 532.7 for [M−H]$^-$.

Example 97: Synthesis of N-(2,4-difluoro-3-(5-(2-(trifluoromethyl)phenyl)-1H-pyrrolo[2,3-b]pyridine-3-carbonyl)phenyl)propane-1-sulfonamide

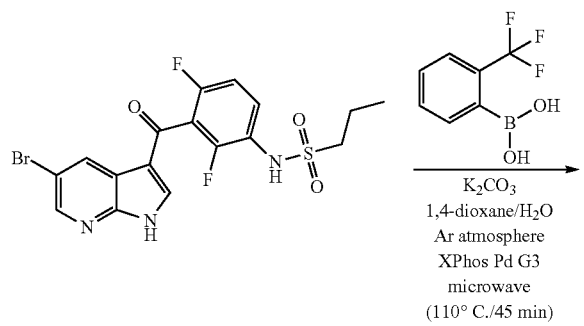

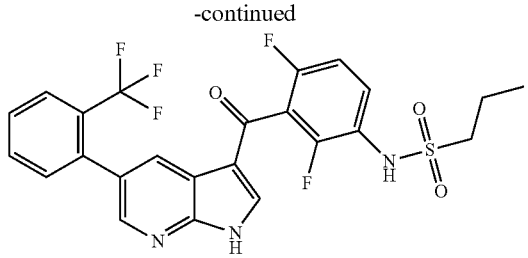

N-[3-(5-bromo-1H-pyrrolo[2,3-b]pyridine-3-carbonyl)-2,4-difluorophenyl]propane-1-sulfonamide (0.120 g, 0.262 mmol), [2-(trifluoromethyl)phenyl]boronic acid (0.0547 g, 0.288 mmol) and Potassium Carbonate (0.0734 g, 0.524 mmol) were suspended in 1,4-dioxane (0.900 mL) and water (0.450 mL) and degassed with argon for 5 min. XPhos Pd G3 (0.0111 g, 0.0131 mmol) was added and the mixture was heated to 110° C. in a microwave oven for 45 min at 50 W. The crude was filtered over a pad of Celite, flushed with EtOAc and the filtrate was washed with sat., aq. NH4Cl solution. The organic phase was dried over sodium sulfate, the solvent was removed under reduced pressure and the product was purified applying flash chromatography using DCM/MeOH (100/0 v/v to 97/3 v/v) as eluent.

Analytical Data:
$^1$H NMR (600 MHz, DMSO-$d_6$) δ 13.07 (s, 1H), 9.76 (s, 1H), 8.39 (s, 1H), 8.35 (d, J=1.7 Hz, 1H), 8.29 (d, J=1.5 Hz, 1H), 7.90 (d, J=7.9 Hz, 1H), 7.78 (t, J=7.5 Hz, 1H), 7.69 (t, J=7.7 Hz, 1H), 7.61-7.54 (m, 2H), 7.28 (t, J=8.6 Hz, 1H), 3.14-3.10 (m, 2H), 1.78-1.70 (m, 2H), 0.96 (t, J=7.4 Hz, 3H).

Calculated exact mass for $C_{24}H_{18}F_5N_3O_3S$: 523.1 (molecular weight: 523.48)
MS(ESI$^+$): 521.9 for [M−H]$^-$.

Example 98: Synthesis of N-(3-(5-(4-(dimethylamino)phenyl)-1H-pyrrolo[2,3-b]pyridine-3-carbonyl)-2,4-difluorophenyl)propane-1-sulfonamide

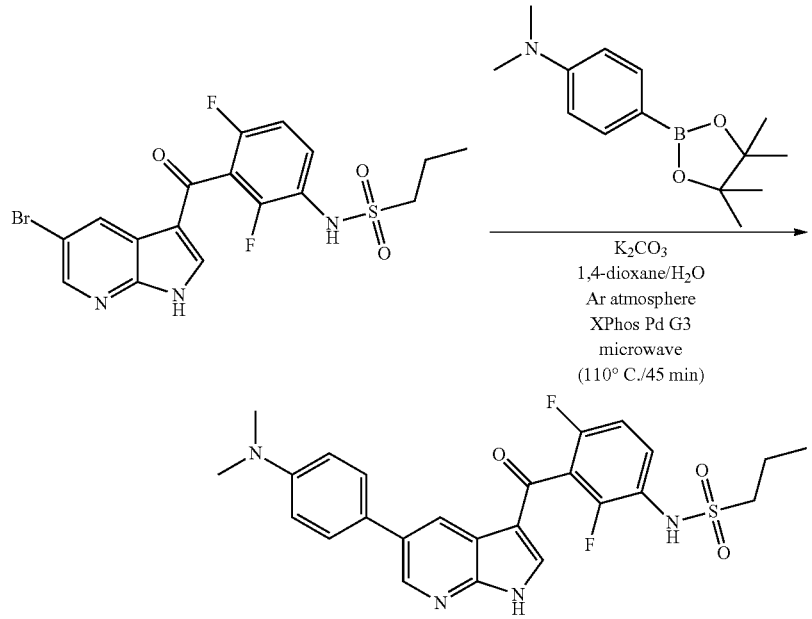

N-[3-(5-bromo-1H-pyrrolo[2,3-b]pyridine-3-carbonyl)-2,4-difluorophenyl]propane-1-sulfonamide (0.120 g, 0.262 mmol), N,N-dimethyl-4-(4,4,5,5-tetramethyl-1,3,2-dioxaborolan-2-yl)aniline (0.0712 g, 0.288 mmol) and potassium carbonate (0.0734 g, 0.524 mmol) were suspended in 1,4-dioxane (0.900 mL) and water (0.450 mL) and degassed with argon for 5 min. XPhos Pd G3 (0.0111 g, 0.0131 mmol) was added and the mixture was heated to 110° C. in a microwave oven for 45 min at 50 W. The crude was filtered over a pad of Celite, flushed with EtOAc and the filtrate was washed with sat. aq. NH$_4$Cl solution. The organic phase was dried over sodium sulfate, the solvent was removed under reduced pressure and the product was purified applying flash chromatography using DCM/MeOH (100/0 v/v to 95/5 v/v) as eluent.

Analytical Data:

$^1$H NMR (600 MHz, DMSO-d$_6$) δ 12.89 (s, 1H), 9.76 (s, 1H), 8.64 (d, J=2.2 Hz, 1H), 8.52 (s, 1H), 8.17 (s, 1H), 7.62-7.53 (m, 3H), 7.28 (t, J=8.4 Hz, 1H), 6.86 (d, J=8.8 Hz, 2H), 3.12 (dd, J=8.6, 6.7 Hz, 2H), 2.96 (s, 6H), 1.74 (dq, J=15.0, 7.5 Hz, 2H), 0.96 (t, J=7.4 Hz, 3H).

Calculated exact mass for C$_{25}$H$_{24}$F$_2$N$_4$O$_3$S: 498.2 (molecular weight: 498.55);

MS(ESI$^-$): 497.0 for [M−H]$^-$.

In analogy to Examples 96-98, compounds of Examples 99-123, given in Table 4, were prepared.

| Ex. | | Chemical structure |
|---|---|---|
| 99 | naphthalen-2-ylboronic acid | product structure |
| 100 | 1-Boc-pyrrol-3-ylboronic acid | product structure |

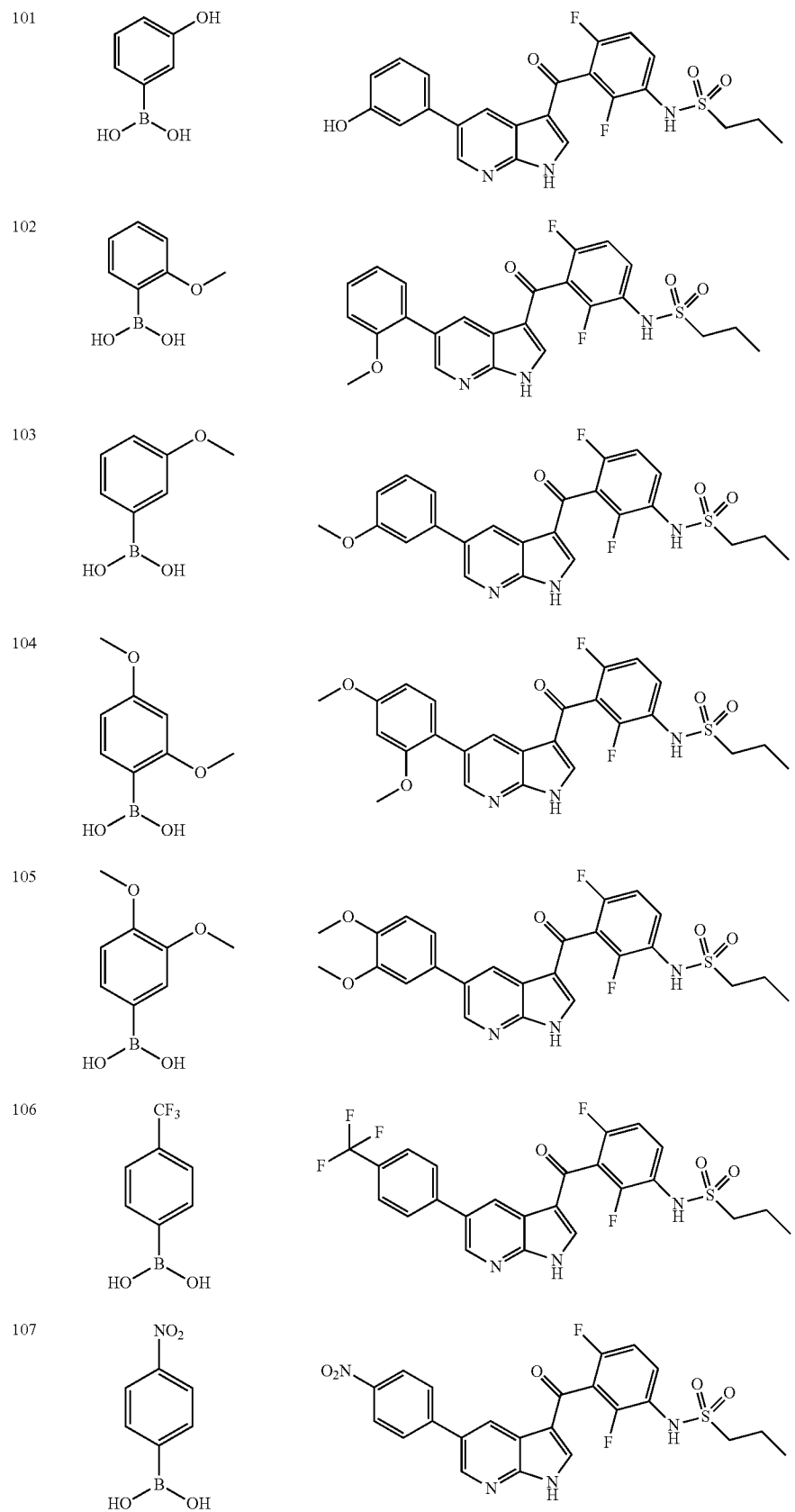

-continued
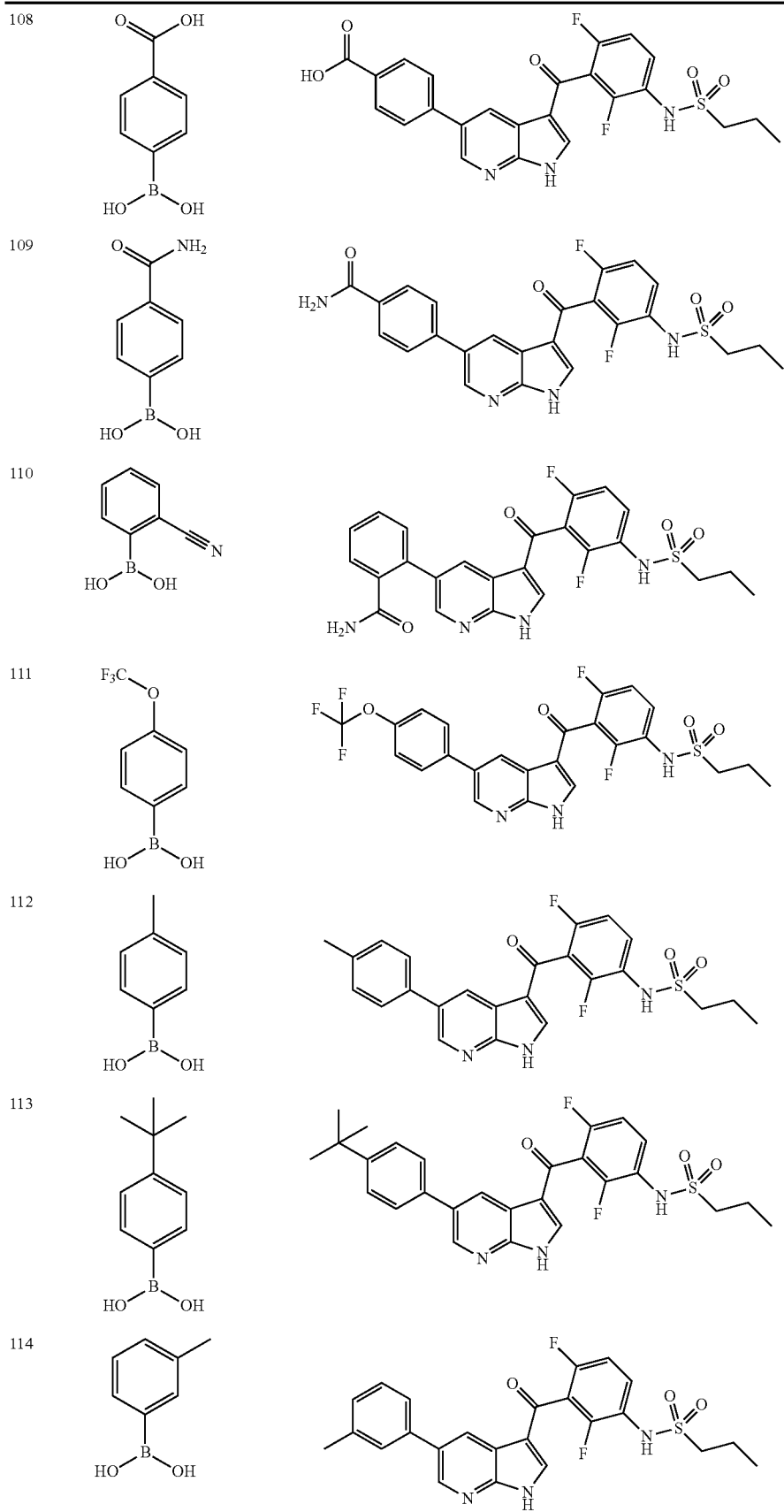

-continued
| 115 | 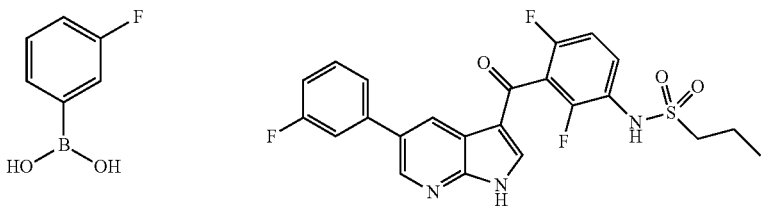 |
| 116 | 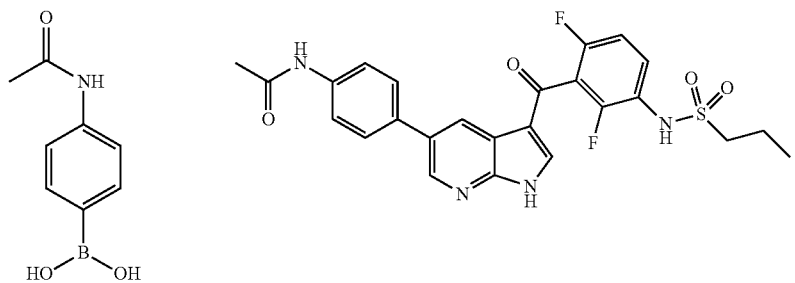 |
| 117 | 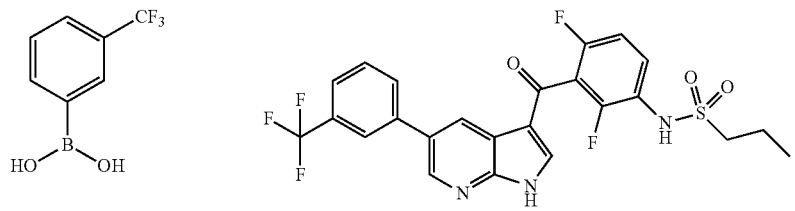 |
| 118 | 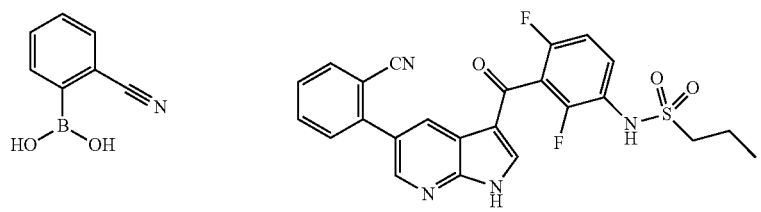 |
| 119 | 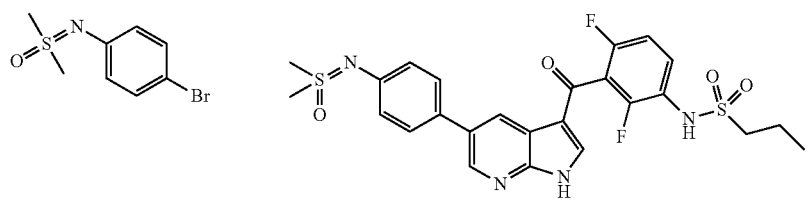 |
| 120 | 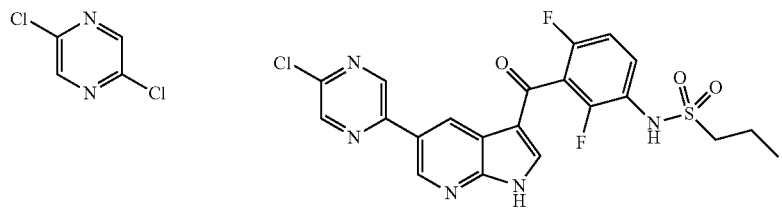 |

| | | |
|---|---|---|
| 121 | 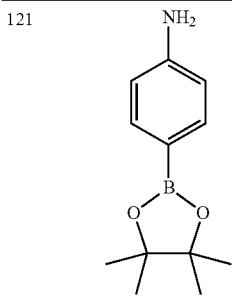 | 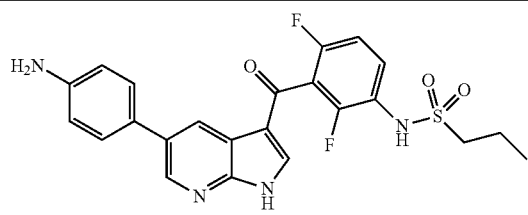 |
| 122 | 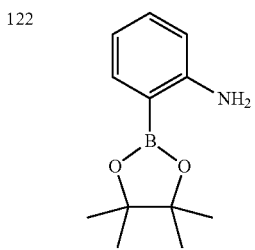 | 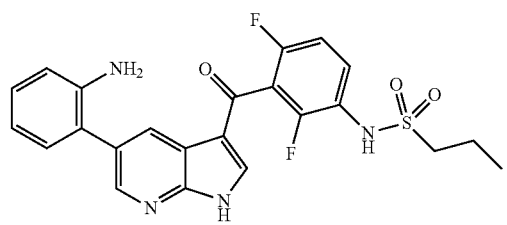 [SMILES: CCCS(=O)(=O)Nc1ccc(F)c(C(=O)c2c[nH]c3ncc(-c4ccccc4N)cc23)c1F] |

| Ex. | IUPAC-Name Formula/Molecular Weight | Analytical Data |
|---|---|---|
| 99 | N-(2,4-difluoro-3-(5-(naphthalen-2-yl)-1H-pyrrolo[2,3-b]pyridine-3-carbonyl)phenyl)propane-1-sulfonamide C27H21F2N3O3S/505.54 | $^1$H NMR (600 MHz, DMSO-$d_6$) δ 13.03 (s, 1H), 9.78 (s, 1H), 8.87 (d, J = 2.2 Hz, 1H), 8.79 (s, 1H), 8.33 (s, 1H), 8.26 (d, J = 1.5 Hz, 1H), 8.07 (d, J = 8.4 Hz, 2H), 7.98 (d, J = 7.9 Hz, 1H), 7.94 (dd, J = 8.5, 1.5 Hz, 1H), 7.63-7.53 (m, 3H), 7.30 (t, J = 8.5 Hz, 1H), 3.16-3.11 (m, 2H), 1.79-1.70 (m, 2H), 0.96 (t, J = 7.4 Hz, 3H). ESI-MS [M − H]$^-$: m/z calculated for C27H21F2N3O3S 504.1 found: 504.0. |
| 100 | N-(3-(5-(1H-pyrrol-3-yl)-1H-pyrrolo[2,3-b]pyridine-3-carbonyl)-2,4-difluorophenyl)propane-1-sulfonamide C21H18F2N4O3S/444.46 | $^1$H NMR (400 MHz, DMSO-$d_6$) δ 12.78 (s, 1H), 11.04 (s, 1H), 9.93 (s, 1H), 8.65 (d, J = 1.7 Hz, 1H), 8.44 (s, 1H), 8.08 (s, 1H), 7.57 (dd, J = 14.8, 8.9 Hz, 1H), 7.32 (s, 1H), 7.27 (t, J = 8.7 Hz, 1H), 6.86 (s, 1H), 6.50 (s, 1H), 3.18-3.02 (m, 2H), 1.73 (dq, J = 14.9, 7.3 Hz, 2H), 0.95 (t, J = 7.4 Hz, 3H). |
| 101 | N-(2,4-difluoro-3-(5-(3-hydroxyphenyl)-1H-pyrrolo[2,3-b]pyridine-3-carbonyl)phenyl)propane-1-sulfonamide C23H19F2N3O4S/471.48 | $^1$H NMR (600 MHz, DMSO-$d_6$) δ 12.98 (s, 1H), 9.76 (s, 1H), 9.61 (s, 1H), 8.65 (d, J = 2.2 Hz, 1H), 8.59 (s, 1H), 8.22 (s, 1H), 7.59 (td, J = 9.0, 5.9 Hz, 1H), 7.33-7.26 (m, 2H), 7.16 (d, J = 7.7 Hz, 1H), 7.11-7.09 (m, 1H), 6.82 (dd, J = 8.1, 1.7 Hz, 1H), 3.14-3.11 (m, 2H), 1.78-1.70 (m, 2H), 0.96 (t, J = 7.4 Hz, 3H). Calculated exact mass: 471.1 MS(ESI$^-$): 470.3 for [M − H]$^-$. |
| 102 | N-(2,4-difluoro-3-(5-(2-methoxyphenyl)-1H-pyrrolo[2,3-b]pyridine-3-carbonyl)phenyl)propane-1-sulfonamide C24H21F2N3O4S/485.51 | $^1$H NMR (600 MHz, DMSO-$d_6$) δ 12.94 (s, 1H), 9.76 (s, 1H), 8.48 (d, J = 1.8 Hz, 2H), 8.21 (s, 1H), 7.64-7.52 (m, 3H), 7.43-7.37 (m, 2H), 7.28 (t, J = 8.5 Hz, 1H), 7.17 (d, J = 8.1 Hz, 1H), 7.09 (td, J = 7.4, 0.8 Hz, 1H), 3.80 (s, 3H), 3.14-3.08 (m, 2H), 1.77-1.70 (m, 2H), 0.95 (t, J = 7.4 Hz, 3H). Calculated exact mass: 485.1 MS(ESI$^-$): 484.3 for [M − H]$^-$. |
| 103 | N-(2,4-difluoro-3-(5-(3-methoxyphenyl)-1H-pyrrolo[2,3-b]pyridine-3-carbonyl)phenyl)propane-1-sulfonamide C24H21F2N3O4S/485.51 | $^1$H NMR (600 MHz, DMSO-$d_6$) δ 13.00 (s, 1H), 9.77 (s, 1H), 8.71 (d, J = 2.2 Hz, 1H), 8.61 (s, 1H), 8.24 (s, 1H), 7.59 (td, J = 9.0, 5.9 Hz, 1H), 7.44 (t, J = 7.9 Hz, 1H), 7.31-7.25 (m, 3H), 6.99 (ddd, J = 8.2, 2.4, 0.6 Hz, 1H), 3.86 (s, 3H), 3.15-3.10 (m, 2H), 1.77-1.70 (m, 2H), 0.96 (t, J = 7.4 Hz, 3H). Calculated exact mass: 485.1 MS(ESI$^-$): 484.3 for [M − H]$^-$. |

| | | |
|---|---|---|
| 104 | N-(3-(5-(2,4-dimethoxyphenyl)-1H-pyrrolo[2,3-b]pyridine-3-carbonyl)-2,4-difluorophenyl)propane-1-sulfonamide C25H23F2N3O5S/515.53 | $^1$H NMR (600 MHz, DMSO-d$_6$) δ 12.90 (s, 1H), 9.76 (s, 1H), 8.43 (d, J = 2.0 Hz, 2H), 8.18 (d, J = 1.2 Hz, 1H), 7.58 (td, J = 9.0, 5.9 Hz, 1H), 7.31 (d, J = 8.3 Hz, 1H), 7.28 (t, J = 8.7 Hz, 1H), 6.72 (d, J = 2.4 Hz, 1H), 6.67 (dd, J = 8.4, 2.4 Hz, 1H), 3.83 (s, 3H), 3.79 (s, 3H), 3.13-3.08 (m, 2H), 177-1.69 (m, 2H), 0.95 (t, J = 7.4 Hz, 3H). Calculated exact mass: 515.1 MS(ESI$^-$): 514.3 for [M − H]$^-$. |
| 105 | N-(3-(5-(3,4-dimethoxyphenyl)-1H-pyrrolo[2,3-b]pyridine-3-carbonyl)-2,4-difluorophenyl)propane-1-sulfonamide C25H23F2N3O5S/515.53 | $^1$H NMR (600 MHz, DMSO-d$_6$) δ 12.96 (s, 1H), 9.76 (s, 1H), 8.70 (d, J = 2.2 Hz, 1H), 8.55 (s, 1H), 8.21 (s, 1H), 7.59 (td, J = 9.0, 6.0 Hz, 1H), 7.31-7.24 (m, 3H), 7.09 (d, J = 8.4 Hz, 1H), 3.88 (s, 3H), 3.82 (s, 3H), 3.14-3.10 (m, 2H), 1.80-1.63 (m, 2H), 0.96 (t, J = 7.4 Hz, 3H). Calculated exact mass: 515.1 MS(ESI$^-$): 514.3 for [M − H]$^-$. |
| 106 | N-(2,4-difluoro-3-(5-(4-(trifluoromethyl)phenyl)-1H-pyrrolo[2,3-b]pyridine-3-carbonyl)phenyl)propane-1-sulfonamide C24H18F5N3O3S/523.48 | $^1$H NMR (600 MHz, DMSO-d$_6$) δ 13.07 (s, 1H), 9.77 (s, 1H), 8.79 (d, J = 2.2 Hz, 1H), 8.72 (s, 1H), 8.28 (s, 1H), 8.01 (d, J = 8.1 Hz, 2H), 7.87 (d, J = 8.2 Hz, 2H), 7.60 (td, J = 9.0, 5.9 Hz, 1H), 7.29 (t, J = 8.3 Hz, 1H), 3.15-3.10 (m, 2H), 1.78-1.71 (m, 2H), 0.96 (t, J = 7.4 Hz, 3H). Calculated exact mass: 523.1 MS(ESI$^-$): 522.2 for [M − H]$^-$. |
| 107 | N-(2,4-difluoro-3-(5-(4-nitrophenyl)-1H-pyrrolo[2,3-b]pyridine-3-carbonyl)phenyl)propane-1-sulfonamide C23H18F2N4O5S/500.48 | $^1$H NMR (600 MHz, DMSO-d$_6$) δ 13.11 (s, 1H), 9.77 (s, 1H), 8.83 (d, J = 2.2 Hz, 1H), 8.77 (s, 1H), 8.35 (d, J = 8.8 Hz, 2H), 8.30 (s, 1H), 8.08 (d, J = 8.8 Hz, 2H), 7.57-7.53 (m, 1H), 7.29 (t, J = 8.3 Hz, 1H), 3.15-3.12 (m, 2H), 1.78-1.71 (m, 2H), 0.97 (t, J = 7.4 Hz, 3H). Calculated exact mass: 500.1 MS(ESI$^-$): 499.1 for [M − H]$^-$. |
| 108 | 4-(3-(2,6-difluoro-3-(propylsulfonamido)benzoyl)-1H-pyrrolo[2,3-b]pyridin-5-yl)benzoic acid C24H19F2N3O5S/499.49 | $^1$H NMR (600 MHz, DMSO-d$_6$) δ 13.06 (s, 2H), 9.77 (s, 1H), 8.79 (d, J = 2.2 Hz, 1H), 8.71 (s, 1H), 8.27 (s, 1H), 8.08 (d, J = 8.4 Hz, 2H), 7.90 (d, J = 8.3 Hz, 2H), 7.60 (td, J = 9.0, 5.9 Hz, 1H), 7.29 (t, J = 8.3 Hz, 1H), 3.15-3.11 (m, 2H), 178-1.69 (m, 2H), 0.96 (t, J = 7.4 Hz, 3H). Calculated exact mass: 499.1 MS(ESI$^-$): 498.1 for [M − H]$^-$. |
| 109 | 4-(3-(2,6-difluoro-3-(propylsulfonamido)benzoyl)-1H-pyrrolo[2,3-b]pyridin-5-yl)benzamide C24H20F2N4O4S/498.50 | $^1$H NMR (600 MHz, DMSO-d$_6$) δ 13.04 (d, J = 2.4 Hz, 1H), 9.77 (s, 1H), 8.78 (d, J = 2.2 Hz, 1H), 8.69 (s, 1H), 8.26 (d, J = 2.7 Hz, 1H), 8.07 (s, 1H), 8.03 (d, J = 8.4 Hz, 2H), 7.85 (d, J = 8.3 Hz, 2H), 7.59 (td, J = 9.0, 6.0 Hz, 1H), 7.41 (s, 1H), 7.29 (t, J = 8.4 Hz, 1H), 3.14-3.11 (m, 2H), 1.78-1.71 (m, 2H), 0.96 (t, J = 7.4 Hz, 3H). Calculated exact mass: 498.1 MS(ESI$^-$): 496.9 for [M − H]$^-$. |
| 110 | N-(3-(5-(2-cyanophenyl)-1H-pyrrolo[2,3-b]pyridine-3-carbonyl)-2,4-difluorophenyl)propane-1-sulfonamide C24H18F2N4O3S/480.49 | $^1$H NMR (600 MHz, DMSO-d$_6$) δ 12.96 (d, J = 2.0 Hz, 1H), 9.76 (s, 1H), 8.51 (s, 1H), 8.40 (d, J = 2.1 Hz, 1H), 8.20 (d, J = 2.7 Hz, 1H), 7.74 (s, 1H), 7.60-7.52 (m, 3H), 7.50-7.45 (m, 2H), 7.35 (s, 1H), 7.27 (t, J = 8.7 Hz, 1H), 3.16-3.08 (m, 2H), 1.79-1.69 (m, 2H), 0.97 (t, J = 7.4 Hz, 3H). Calculated exact mass: 498.1 MS(ESI$^-$): 496.6 for [M − H]$^-$. |
| 111 | N-(2,4-difluoro-3-(5-(4-(trifluoromethoxy)phenyl)-1H-pyrrolo[2,3-b]pyridine-3-carbonyl)phenyl)propane-1-sulfonamide C24H18F5N3O4S/539.48 | $^1$H NMR (600 MHz, DMSO-d$_6$) δ 13.03 (s, 1H), 9.76 (s, 1H), 8.73 (d, J = 2.2 Hz, 1H), 8.66 (s, 1H), 8.26 (s, 1H), 7.89 (d, J = 8.7 Hz, 2H), 7.59 (td, J = 9.0, 5.9 Hz, 1H), 7.51 (d, J = 8.1 Hz, 2H), 7.29 (t, J = 8.4 Hz, 1H), 3.15-3.10 (m, 2H), 178-1.71 (m, 2H), 0.96 (t, J = 7.4 Hz, 3H). Calculated exact mass: 539.1 MS(ESI$^-$): 537.8 for [M − H]$^-$. |

| # | Compound | Data |
|---|---|---|
| 112 | N-(2,4-difluoro-3-(5-(p-tolyl)-1H-pyrrolo[2,3-b]pyridine-3-carbonyl)phenyl)propane-1-sulfonamide<br>C24H21F2N3O3S/469.51 | $^1$H NMR (600 MHz, DMSO-d$_6$) δ 12.97 (s, 1H), 9.76 (s, 1H), 8.68 (d, J = 2.2 Hz, 1H), 8.59 (s, 1H), 8.22 (s, 1H), 7.64 (d, J = 8.0 Hz, 2H), 7.59 (td, J = 9.0, 5.9 Hz, 1H), 7.33 (d, J = 7.9 Hz, 2H), 7.28 (t, J = 8.5 Hz, 1H), 3.14-3.10 (m, 2H), 2.37 (s, 3H), 178-1.70 (m, 2H), 0.96 (t, J = 7.4 Hz, 3H).<br>Calculated exact mass: 469.1<br>MS(ESI$^-$): 468.0 for [M − H]$^-$. |
| 113 | N-(3-(5-(4-(tert-butyl)phenyl)-1H-pyrrolo[2,3-b]pyridine-3-carbonyl)-2,4-difluorophenyl)propane-1-sulfonamide<br>C27H27F2N3O3S/511.59 | $^1$H NMR (600 MHz, DMSO-d$_6$) δ 12.98 (s, 1H), 9.77 (s, 1H), 8.69 (d, J = 2.2 Hz, 1H), 8.60 (s, 1H), 8.22 (s, 1H), 7.67 (d, J = 8.3 Hz, 2H), 7.59 (td, J = 9.0, 6.0 Hz, 1H), 7.54 (d, J = 8.4 Hz, 2H), 7.29 (t, J = 8.5 Hz, 1H), 3.14-3.10 (m, 2H), 179-1.69 (m, 2H), 1.33 (s, 9H), 0.96 (t, J = 7.4 Hz, 3H).<br>Calculated exact mass: 511.2<br>MS(ESI$^-$): 509.9 for [M − H]$^-$. |
| 114 | N-(2,4-difluoro-3-(5-(m-tolyl)-1H-pyrrolo[2,3-b]pyridine-3-carbonyl)phenyl)propane-1-sulfonamide<br>C24H21F2N3O3S/469.51 | $^1$H NMR (600 MHz, DMSO-d$_6$) δ 12.98 (d, J = 1.8 Hz, 1H), 9.77 (s, 1H), 8.69 (d, J = 2.2 Hz, 1H), 8.61 (s, 1H), 8.23 (d, J = 2.5 Hz, 1H), 7.64-7.51 (m, 3H), 7.41 (t, J = 7.6 Hz, 1H), 7.29 (t, J = 8.6 Hz, 1H), 7.23 (d, J = 7.5 Hz, 1H), 3.14-3.10 (m, 2H), 2.42 (s, 3H), 1.78-1.71 (m, 2H), 0.96 (t, J = 7.4 Hz, 3H).<br>Calculated exact mass: 469.1<br>MS(ESI$^-$): 468.0 for [M − H]$^-$. |
| 115 | N-(2,4-difluoro-3-(5-(3-fluorophenyl)-1H-pyrrolo[2,3-b]pyridine-3-carbonyl)phenyl)propane-1-sulfonamide<br>C23H18F3N3O3S/473.47 | $^1$H NMR (600 MHz, DMSO-d$_6$) δ 13.03 (s, 1H), 9.77 (s, 1H), 8.74 (d, J = 2.2 Hz, 1H), 8.66 (s, 1H), 8.26 (d, J = 2.0 Hz, 1H), 7.65-7.54 (m, 4H), 7.29 (t, J = 8.7 Hz, 1H), 7.25 (td, J = 8.7, 2.2 Hz, 1H), 3.14-3.11 (m, 2H), 1.79-1.66 (m, 2H), 0.96 (t, J = 7.4 Hz, 3H).<br>Calculated exact mass: 473.1<br>MS(ESI$^-$): 472.0 for [M − H]$^-$. |
| 116 | N-(4-(3-(2,6-difluoro-3-(propylsulfonamido)benzoyl)-1H-pyrrolo[2,3-b]pyridin-5-yl)phenyl)acetamide<br>C25H22F2N4O4S/512.53 | $^1$H NMR (600 MHz, DMSO-d$_6$) δ 12.96 (s, 1H), 10.07 (s, 1H), 9.76 (s, 1H), 8.69 (d, J = 2.0 Hz, 1H), 8.59 (s, 1H), 8.21 (s, 1H), 7.74 (d, J = 8.5 Hz, 2H), 7.69 (d, J = 8.5 Hz, 2H), 7.62-7.55 (m, 1H), 7.28 (t, J = 8.6 Hz, 1H), 3.15-3.10 (m, 2H), 2.08 (s, 3H), 1.74 (dq, J = 14.9, 7.4 Hz, 2H), 0.96 (t, J = 7.4 Hz, 3H).<br>Calculated exact mass: 512.1<br>MS(ESI$^-$): 511.0 for [M − H]$^-$. |
| 117 | N-(2,4-difluoro-3-(5-(3-(trifluoromethyl)phenyl)-1H-pyrrolo[2,3-b]pyridine-3-carbonyl)phenyl)propane-1-sulfonamide<br>C24H18F5N3O3S/523.48 | $^1$H NMR (600 MHz, DMSO-d$_6$) δ 13.06 (s, 1H), 9.77 (s, 1H), 8.79 (d, J = 2.2 Hz, 1H), 8.70 (s, 1H), 8.27 (s, 1H), 8.08 (d, J = 7.2 Hz, 2H), 7.77 (dt, J = 15.3, 7.7 Hz, 2H), 7.59 (td, J = 9.0, 6.0 Hz, 1H), 7.29 (t, J = 8.6 Hz, 1H), 3.16-3.05 (m, 2H), 1.79-1.69 (m, 2H), 0.96 (t, J = 7.4 Hz, 3H).<br>Calculated exact mass: 523.1<br>MS(ESI$^-$): 522.0 for [M − H]$^-$. |
| 118 | N-(3-(5-(2-cyanophenyl)-1H-pyrrolo[2,3-b]pyridine-3-carbonyl)-2,4-difluorophenyl)propane-1-sulfonamide<br>C24H18F2N4O3S/480.49 | $^1$H NMR (600 MHz, DMSO-d$_6$) δ 13.14 (s, 1H), 9.77 (s, 1H), 8.64 (s, 1H), 8.61 (d, 2.2 Hz, 1H), 8.32 (s, 1H), 8.02 (dd, J = 7.8, 0.8 Hz, 1H), 7.85 (td, J = 7.7, 1.2 Hz, 1H), 7.77 (d, J = 7.4 Hz, 1H), 7.65 (td, J = 77, 1.0 Hz, 1H), 7.59 (td, J = 9.0, 5.9 Hz, 1H), 7.29 (t, J = 8.5 Hz, 1H), 3.15-3.10 (m, 2H), 1.78-1.70 (m, 2H), 0.96 (t, J = 7.4 Hz, 3H).<br>Calculated exact mass: 480.1<br>MS(ESI$^-$): 479.0 for [M − H]$^-$. |
| 119 | N-(3-(5-(4-((dimethyl(oxo)-l6-sulfaneylidene)amino)phenyl)-1H-pyrrolo[2,3-b]pyridine-3-carbonyl)-2,4-difluorophenyl)propane-1-sulfonamide<br>C25H24F2N4O4S2/546.61 | $^1$H NMR (400 MHz, DMSO-d$_6$) δ 12.94 (s, 1H), 9.77 (s, 1H), 8.65 (s, 1H), 8.55 (s, 1H), 8.20 (s, 1H), 7.57 (d, J = 8.1 Hz, 3H), 7.28 (t, J = 8.5 Hz, 1H), 7.07 (d, J = 8.2 Hz, 2H), 3.26 (s, 6H), 3.17-3.07 (m, 2H), 1.73 (d, J = 7.3 Hz, 2H), 0.96 (t, J = 7.3 Hz, 3H).<br>Calculated exact mass: 546.12; MS(ESI$^+$): 547.1 |
| 120 | N-(3-(5-(3-chloropyrazin-2-yl)-1H-pyrrolo[2,3-b]pyridine-3-carbonyl)-2,4-difluorophenyl)propane-1-sulfonamide<br>C21H16ClF2N5O3S/491.90 | $^1$H NMR (400 MHz, DMSO-d$_6$) δ 13.14 (s, 1H), 9.79 (s, 1H), 9.27 (s, 1H), 9.17 (s, 2H), 8.92 (s, 1H), 8.31 (s, 1H), 7.59 (dd, J = 14.9, 8.8 Hz, 1H), 7.29 (t, J = 8.7 Hz, 1H), 3.19-3.07 (m, 2H), 1.74 (dq, J = 14.9, 7.4 Hz, 2H), 0.96 (t, J = 7.4 Hz, 3H). |

-continued

| 121 | N-(3-(5-(4-aminophenyl)-1H-pyrrolo[2,3-b]pyridine-3-carbonyl)-2,4-difluorophenyl)propane-1-sulfonamide C23H20F2N4O3S/470.49 | $^1$H NMR (600 MHz, DMSO-d$_6$) δ 12.86 (s, 1H), 9.75 (s, 1H), 8.59 (d, J = 2.1 Hz, 1H), 8.47 (s, 1H), 8.15 (s, 1H), 7.58 (td, J = 8.9, 6.1 Hz, 1H), 7.41 (d, J = 8.2 Hz, 2H), 7.28 (t, J = 8.6 Hz, 1H), 6.70 (d, J = 8.4 Hz, 2H), 5.28 (s, 2H), 3.15-3.09 (m, 2H), 1.74 (dq, J = 15.0, 7.4 Hz, 2H), 0.96 (t, J = 7.4 Hz, 3H). Calculated exact mass: 470.1 MS(ESI$^-$): 469.0 for [M − H]$^-$. |
| --- | --- | --- |
| 122 | N-(3-(5-(2-aminophenyl)-1H-pyrrolo[2,3-b]pyridine-3-carbonyl)-2,4-difluorophenyl)propane-1-sulfonamide C23H20F2N4O3S/470.49 | $^1$H NMR (600 MHz, DMSO-d$_6$) δ 12.92 (s, 1H), 9.75 (s, 1H), 8.47 (s, 1H), 8.40 (d, J = 1.9 Hz, 1H), 8.19 (s, 1H), 7.58 (dd, J = 14.8, 8.9 Hz, 1H), 7.27 (t, J = 8.6 Hz, 1H), 7.12-7.08 (m, 1H), 7.05 (dd, J = 7.4, 1.1 Hz, 1H), 6.80 (d, J = 7.8 Hz, 1H), 6.68 (t, J = 7.3 Hz, 1H), 4.87 (s, 2H), 3.15-3.09 (m, 2H), 1.78-1.71 (m, 2H), 0.97 (t, J = 7.4 Hz, 3H). Calculated exact mass: 470.1 MS(ESI$^-$): 469.0 for [M − H]$^-$. |

Example 123: Synthesis of N-(3-(5-cyclobutyl-1-pyrrolo[2,3-b]pyridine-3-carbonyl)-2,4-difluorophenyl)propane-1-sulfonamide Example 123 was prepared according to the following route of synthesis:

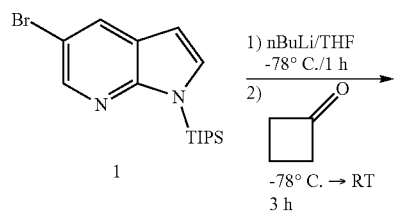

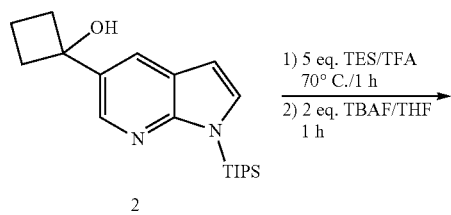

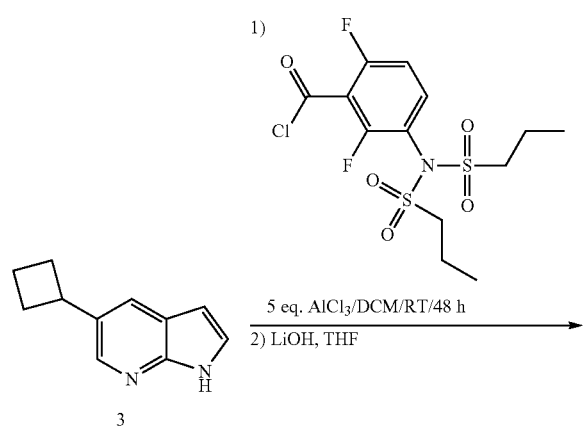

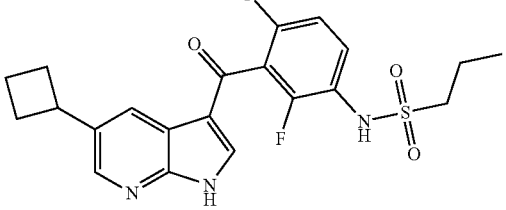

Analytical Data:

Chemical purity (HPLC/UV): 99.7%

MS(ESI$^+$): 434.20 (calculated exact mass for C21H21F2N3O3S: 433.13)

Synthesis of 5-substituted N-(2-fluorophenyl) alkyl-1-sulfonamide derivatives 5-substituted N-(2-fluoro-(1H-pyrrolo[2,3-b]pyridine-3-carbonyl)phenyl)alkyl-1-sulfonamide derivatives according to the formula

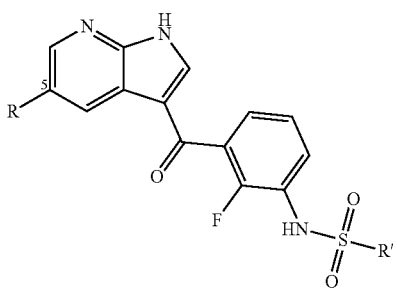

were prepared according to Example 124 which is described below.

Example 124: Synthesis of N-(3-(5-(4-chlorophenyl)-1H-pyrrolo[2,3-b]pyridine-3-carbonyl)-2-fluorophenyl)-1-phenylmethanesulfonamide

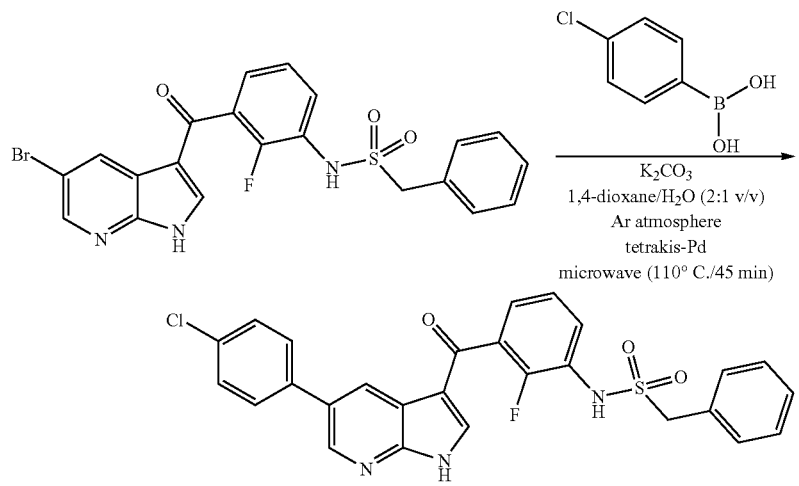

To a solution of N-[3-(5-bromo-1H-pyrrolo[2,3-b]pyridine-3-carbonyl)-2-fluorophenyl]-1-phenylmethanesulfonamide (0.1000 g, 0.205 mmol, prepared in analogy to Example 3) in 1,4-dioxane (0.700 mL) and water (0.350 mL) (4-chlorophenyl)boronic acid (0.0480 g, 0.307 mmol) and potassium carbonate (0.0574 g, 0.410 mmol) were added and the mixture was degassed with argon for 5 min. Tetrakis Pd (0.0237 g, 0.0205 mmol) was added and the reaction vial was irradiated for 45 min at 110° C. (50 W) in a microwave oven. After cooling to RT, the mixture was passed through a pad of Celite, which was washed with EtOAc (50 ml). The organic phase was washed with saturated, aqueous NH$_4$Cl solution and water and dried after washing with sodium sulfate. The product was purified applying flash chromatography using DCM/MeOH (0-3%) as eluent. N-[3-[5-(4-chlorophenyl)-1H-pyrrolo[2,3-b]pyridine-3-carbonyl]-2-fluorophenyl]-1-phenylmethanesulfonamide (0.0548 g, 0.0843 mmol, 41% yield) was obtained as off white solid.

Analytical Data:

$^1$H NMR (600 MHz, DMSO-d$_6$) δ 8.70 (d, J=2.2 Hz, 1H), 8.68 (d, J=2.2 Hz, 1H), 8.03 (s, 1H), 7.85 (dd, J=20.1, 8.4 Hz, 1H), 7.78 (dd, J=8.7, 2.4 Hz, 2H), 7.57 (d, J=8.5 Hz, 2H), 7.51 (td, J=7.9, 1.4 Hz, 1H), 7.39-7.31 (m, 5H), 7.24 (t, J=7.8 Hz, 1H), 4.51 (s, 2H).

Calculated exact mass for C$_{27}$H$_{19}$ClFN$_3$O$_3$S: (molecular weight: 519.98)

MS(ESI$^-$): 518.2 for [M−H]$^-$.

TABLE 5

Examples 125-133, prepared in analogy to Example 124.

| Ex. | | Chemical structure |
|---|---|---|
| 125 | ![structure] | ![structure] |
| 126 | ![structure] | ![structure] |

TABLE 5-continued
Examples 125-133, prepared in analogy to Example 124.
| 127 | 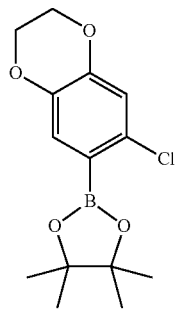 [SMILES: CC1(C)OB(c2cc3c(cc2Cl)OCCO3)OC1(C)C] | 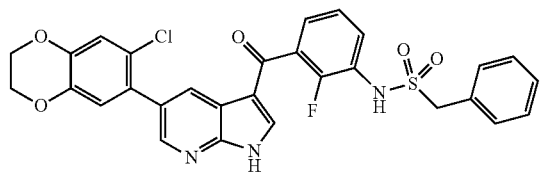 [SMILES: O=C(c1cccc(NS(=O)(=O)Cc2ccccc2)c1F)c1c[nH]c2ncc(-c3cc4c(cc3Cl)OCCO4)cc12] |
| 128 | 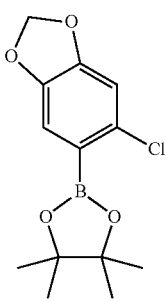 [SMILES: CC1(C)OB(c2cc3c(cc2Cl)OCO3)OC1(C)C] | 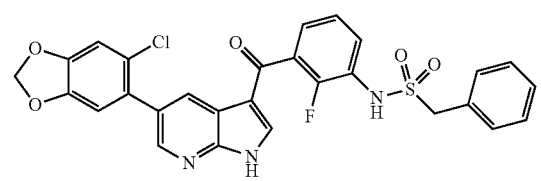 [SMILES: O=C(c1cccc(NS(=O)(=O)Cc2ccccc2)c1F)c1c[nH]c2ncc(-c3cc4c(cc3Cl)OCO4)cc12] |
| 129 | 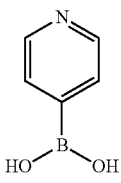 | 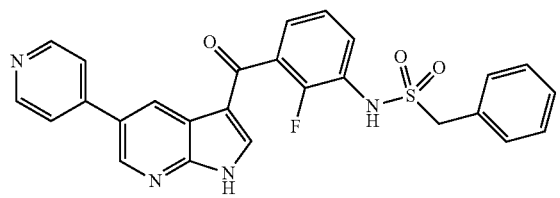 [SMILES: O=C(c1cccc(NS(=O)(=O)Cc2ccccc2)c1F)c1c[nH]c2ncc(-c3ccncc3)cc12] |
| 130 | 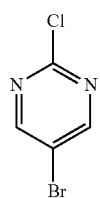 |  |
| 131 | 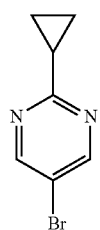 | 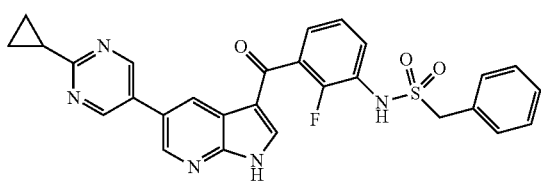 [SMILES: O=C(c1cccc(NS(=O)(=O)Cc2ccccc2)c1F)c1c[nH]c2ncc(-c3cnc(C4CC4)nc3)cc12] |
| 132 | 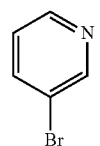 | 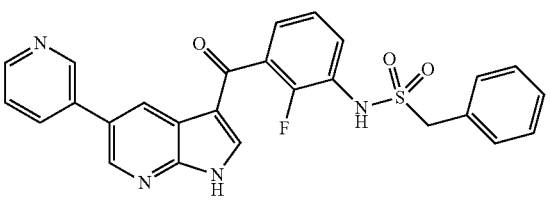 [SMILES: O=C(c1cccc(NS(=O)(=O)Cc2ccccc2)c1F)c1c[nH]c2ncc(-c3cccnc3)cc12] |

TABLE 5-continued

Examples 125-133, prepared in analogy to Example 124.

133 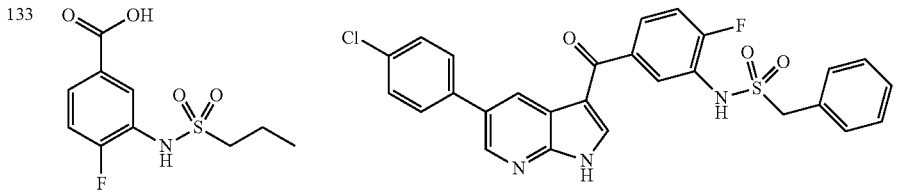

| Ex. | IUPAC-Name Formula/Molecular Weight | Analytical Data |
|---|---|---|
| 125 | N-(3-(5-(2-chloro-4-methoxyphenyl)-1H-pyrrolo[2,3-b]pyridine-3-carbonyl)-2-fluorophenyl)-1-phenylmethanesulfonamide $C_{28}H_{21}ClFN_3O_4S$/550.00 | $^1$H NMR (600 MHz, DMSO-$d_6$) δ 8.47 (d, J = 2.1 Hz, 1H), 8.38 (d, J = 2.1 Hz, 1H), 7.96 (s, 1H), 7.52 (td, J = 8.2, 1.5 Hz, 1H), 7.45 (d, J = 8.5 Hz, 1H), 7.34-7.26 (m, 6H), 7.20 (d, J = 2.6 Hz, 1H), 7.10 (t, J = 7.8 Hz, 1H), 7.06 (dd, 8.5, 2.6 Hz, 1H), 6.97 (t, J = 6.0 Hz, 1H), 4.26 (s, 2H), 3.84 (s, 3H). Calculated exact mass: 549.1 MS(ESI$^-$): 548.3 for [M − H]$^-$. |
| 126 | N-(2-fluoro-3-(5-(4-fluoro-2-methylphenyl)-1H-pyrrolo[2,3-b]pyridine-3-carbonyl)phenyl)-1-phenylmethanesulfonamide C28H21F2N3O3S/517.55 | $^1$H NMR (600 MHz, DMSO-$d_6$) δ 12.89 (s, 1H), 9.84 (s, 1H), 8.38 (d, J = 1.5 Hz, 1H), 8.35 (d, J = 1.5 Hz, 1H), 8.04 (s, 1H), 7.50 (t, J = 7.5 Hz, 1H), 7.41-7.33 (m, 7H), 7.26 (t, J = 7.9 Hz, 1H), 7.23 (dd, J = 10.1, 2.2 Hz, 1H), 7.14 (td, J = 8.4, 2.3 Hz, 1H), 4.55 (s, 2H), 2.27 (s, 3H). Calculated exact mass: 517.1 MS(ESI$^-$): 516.3 for [M − H]$^+$. |
| 127 | N-(3-(5-(7-chloro-2,3-dihydrobenzo[b][1,4]dioxin-6-yl)-1H-pyrrolo[2,3-b]pyridine-3-carbonyl)-2-fluorophenyl)-1-phenylmethanesulfonamide C29H21ClFN3O5S/578.01 | $^1$H NMR (600 MHz, DMSO-$d$,) 612.89 (s, 1H), 9.83 (s, 1H), 8.48 (d, J = 2.2 Hz, 1H), 8.38 (d, J = 2.2 Hz, 1H), 8.04 (s, 1H), 7.50 (td, J = 7.9, 1.5 Hz, 1H), 7.40-7.33 (m, 6H), 7.26 (t, J = 7.8 Hz, 1H), 7.14 (s, 1H), 7.04 (s, 1H), 4.55 (s, 2H), 4.32 (s, 4H). Calculated exact mass: 577.1 MS(ESI$^-$): 576.2 for [M − H]$^-$. |
| 128 | N-(3-(5-(6-chlorobenzo[d][1,3]dioxol-5-yl)-1H-pyrrolo[2,3-b]pyridine-3-carbonyl)-2-fluorophenyl)-1-phenylmethanesulfonamide C28H19ClFN3O5S/563.98 | $^1$H NMR (600 MHz, DMSO$_6$) δ 12.91 (s, 1H), 9.84 (s, 1H), 8.47 (d, J = 2.1 Hz, 1H), 8.37 (d, J = 2.2 Hz, 1H), 8.04 (s, 1H), 7.62 (ddd, J = 7.0, 5.6, 4.0 Hz, 1H), 7.50 (td, J = 7.9, 1.5 Hz, 1H), 7.40-7.33 (m, 5H), 7.28-7.24 (m, 2H), 7.13 (s, 1H), 6.15 (s, 2H), 4.55 (s, 2H). Calculated exact mass: 563.1 MS(ESI$^-$): 562.2 for [M − H]$^-$. |
| 129 | N-(2-fluoro-3-(5-(pyridin-4-yl)-1H-pyrrolo[2,3-b]pyridine-3-carbonyl)phenyl)-1-phenylmethanesulfonamide C26H19FN4O3S/486.52 | $^1$H NMR (600 MHz, DMSO-$d_6$) δ 12.99 (s, 1H), 9.86 (s, 1H), 8.83 (d, J = 2.3 Hz, 1H), 8.82 (d, J = 2.3 Hz, 1H), 8.68 (dd, J = 4.5, 1.6 Hz, 2H), 8.08 (s, 1H), 7.82 (dd, J = 4.5, 1.6 Hz, 2H), 7.51 (td, J = 7.9, 1.5 Hz, 1H), 7.42-7.34 (m, 6H), 7.28 (t, J = 7.8 Hz, 1H), 4.56 (s, 2H). Calculated exact mass: 486.1. MS(ESI$^-$): 485.2 for [M − H]$^-$. |
| 130 | N-(2-fluoro-3-(5-(2-methoxypyrimidin-5-yl)-1H-pyrrolo[2,3-b]pyridine-3-carbonyl)phenyl)-1-phenylmethanesulfonamide C26H20FN5O4S/517.54 | $^1$H NMR (600 MHz, DMSO-$d_6$) δ 12.94 (d, J = 1.9 Hz, 1H), 9.84 (s, 1H), 9.00 (s, 2H), 8.72 (d, J = 2.2 Hz, 1H), 8.71 (d, J = 2.2 Hz, 1H), 8.06 (d, J = 1.9 Hz, 1H), 7.51 (td, I = 7.9, 1.4 Hz, 1H), 7.41-7.37 (m, 3H), 7.37-7.34 (m, 3H), 7.27 (t, J = 7.8 Hz, 1H), 4.56 (s, 2H), 3.99 (s, 3H). Calculated exact mass: 517.1 MS(ESI$^-$): 516.2 for [M − H]$^-$. |
| 131 | N-(3-(5-(2-cyclopropylpyrimidin-5-yl)-1H-pyrrolo[2,3-b]pyridine-3-carbonyl)-2-fluorophenyl)-1-phenylmethanesulfonamide C28H22FN5O3S/527.57 | $^1$H NMR (600 MHz, DMSO-$d_6$) δ 12.96 (s, 1H), 9.85 (s, 1H), 9.02 (s, 2H), 8.74 (d, J = 2.2 Hz, 1H), 8.72 (d, J = 2.2 Hz, 1H), 8.07 (d, J = 1.1 Hz, 1H), 7.51 (td, J = 7.9, 1.4 Hz, 1H), 7.41-7.37 (m, 3H), 7.37-7.34 (m, 3H), 7.27 (t, J = 7.8 Hz, 1H), 4.56 (s, 2H), 2.28 (tt, J = 8.0, 4.8 Hz, 1H), 1.12-1.08 (m, 2H), 1.08-1.05 (m, 2H). Calculated exact mass: 527.1 MS(ESI$^-$): 526.3 for [M − H]$^-$. |

TABLE 5-continued

Examples 125-133, prepared in analogy to Example 124.

| | |
|---|---|
| 132 N-(2-fluoro-3-(5-(pyridin-3-yl)-1H-pyrrolo[2,3-b]pyridine-3-carbonyl)phenyl)-1-phenylmethanesulfonamide C26H19FN4O3S/486.52 | $^1$H NMR (600 MHz, DMSO-d$_6$) δ 12.95 (s, 1H), 9.85 (s, 1H), 8.97 (d, J = 1.9 Hz, 1H), 8.75 (d, J = 2.2 Hz, 1H), 8.72 (d, J = 2.2 Hz, 1H), 8.63 (dd, J = 4.7, 1.3 Hz, 1H), 8.20-8.16 (m, 1H), 8.07 (d, J = 1.3 Hz, 1H), 7.55 (dd, J = 7.8, 4.8 Hz, 1H), 7.51 (td, J = 7.9, 1.4 Hz, 1H), 7.41-7.37 (m, 3H), 7.37-7.34 (m, 3H), 7.28 (t, J = 7.8 Hz, 1H), 4.56 (s, 2H). Calculated exact mass. 486.1 MS(ESI$^-$): 485.1 for [M − H]$^-$. |
| 133 N-(5-(5-(4-chlorophenyl)-1H-pyrrolo[2,3-b]pyridine-3-carbonyl)-2-fluorophenyl)-1-phenylmethanesulfonamide C27H19ClFN3O3S/519.98 | $^1$H NMR (600 MHz, DMSO-d$_6$) δ 12.84 (s, 1H), 9.92 (s, 1H), 8.72 (d, J = 2.2 Hz, 1H), 8.68 (d, J = 2.2 Hz, 1H), 8.17 (s, 1H), 7.90 (dd, J = 7.7, 2.0 Hz, 1H), 7.77 (d, J = 8.5 Hz, 2H), 7.73 (ddd, J = 8.2, 4.5, 2.1 Hz, 1H), 7.57 (d, J = 8.5 Hz, 2H), 7.47 (dd, J = 10.0, 8.6 Hz, 1H), 3.18-3.14 (m, 2H), 1.80-1.73 (m, 2H), 0.98 (t, J = 7.4 Hz, 3H). Calculated exact mass: 519.08 MS(ESI$^-$): [M − H]$^-$. |

Example 134: Synthesis of N-(2,4-difluoro-3-(5-(3-hydroxyazetidine-1-yl)-1H-pyrrolo[2,3-b]pyridine-3-carbonyl)phenyl)propane-1-sulfonamide

Example 134: Synthesis of 3-(benzyloxy)azetidine

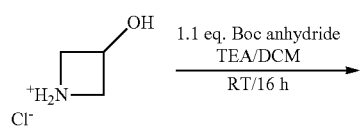

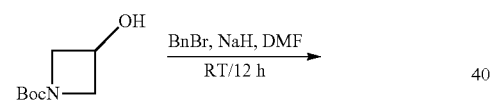

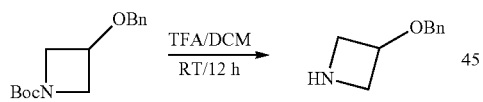

Example 134-2: N-(2,4-difluoro-3-(5-(3-hydroxyazetidin-1-yl)-1H-pyrrolo[2,3-b]pyridine-3-carbonyl)phenyl)propane-1-sulfonamide

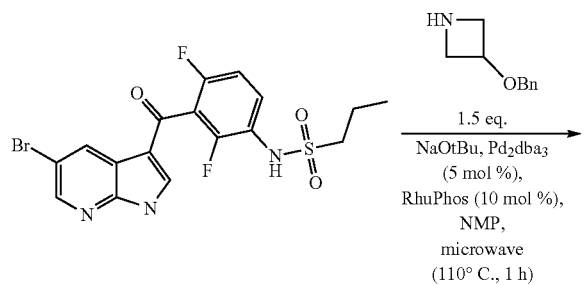

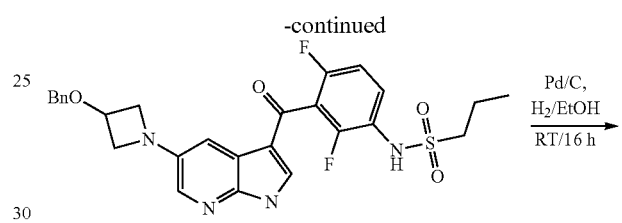

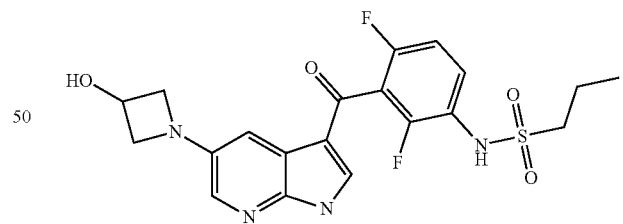

Example 82

Analytical Data:

$^1$H NMR (400 MHz, DMSO-d$_6$) δ 12.57 (s, 1H), 9.70 (s, 1H), 7.93 (s, 1H), 7.70 (d, J=2.6 Hz, 1H), 7.52 (td, J=9.0, 6.0 Hz, 1H), 7.38 (s, 1H), 7.22 (t, J=8.7 Hz, 1H), 4.59 (dt, J=11.3, 5.6 Hz, 1H), 4.14 (t, J=6.9 Hz, 2H), 3.55-3.52 (m, 3H), 3.13-3.03 (m, 2H), 1.70 (dq, J=15.0, 7.5 Hz, 2H), 0.93 (t, J=7.4 Hz, 3H).

Calculated exact mass: 450.12. MS(ESI'): 551.0 for [M+H]'.

Examples 135 and 136: Synthesis of N-(2,4-difluoro-3-(5-(4-oxopiperidin-1-yl)-1H-pyrrolo[2,3-b]pyridine-3-carbonyl)phenyl)propane-1-sulfonamide and N-(2,4-difluoro-3-(5-(4-hydroxypiperidin-1-yl)-1H-pyrrolo[2,3-b]pyridine-3-carbonyl)phenyl)propane-1-sulfonamide
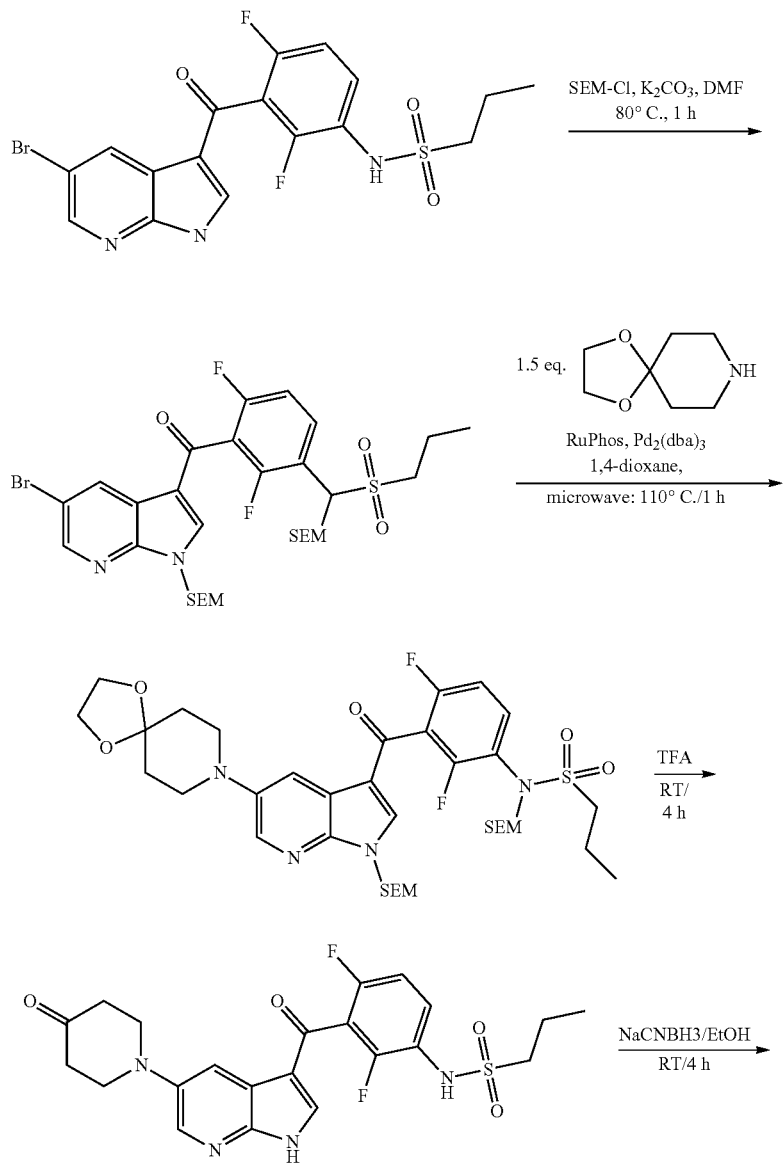

Analytical Data:

Example 135:

$^1$H NMR (400 MHz, CDCl$_3$) δ 10.23 (s, 1H), 8.38 (s, 1H), 8.31 (s, 1H), 7.70 (dd, J=16.1, 10.5 Hz, 2H), 7.07 (t, J=8.6 Hz, 1H), 6.60 (s, 1H), 3.67 (t, J=5.9 Hz, 4H), 3.17-3.09 (m, 2H), 2.68 (t, J=5.9 Hz, 4H), 1.92 (dd, J=15.3, 7.7 Hz, 2H), 1.08 (t, J=7.4 Hz, 3H).

Calculated exact mass: 476.13 for C$_{22}$H$_{22}$F$_2$N$_4$O$_4$S. MS(ESI$^+$): 477.1 for [M+H]$^+$.

Example 136:

$^1$H NMR (400 MHz, DMSO-d$_6$) δ 12.64 (s, 1H), 9.74 (s, 1H), 8.24 (d, J=2.7 Hz, 1H), 8.00 (s, 1H), 7.90 (s, 1H), 7.56 (dd, J=14.9, 8.9 Hz, 1H), 7.26 (t, J=8.4 Hz, 1H), 4.71 (d, J=4.2 Hz, 1H), 3.68-3.60 (m, 1H), 3.52-3.45 (m, 2H), 3.14-3.07 (m, 2H), 2.88 (t, J=10.0 Hz, 2H), 1.87 (s, 2H), 1.74 (dd, J=15.3, 7.6 Hz, 2H), 1.61-1.51 (m, 2H), 0.96 (t, J=7.4 Hz, 3H).

Calculated exact mass: 478.15 for C$_{22}$H$_{24}$F$_2$N$_4$O$_4$S. MS(ESI$^+$) 479.1 for [M+H]$^+$.

Example 137 Synthesis of 1-(3-(2,6-difluoro-3-(propylsulfonamido)benzoyl)-1H-pyrrolo[2,3-b]pyridin-5-yl)azetidine-3-carboxylic acid Example 137 was prepared in analogy to 134.

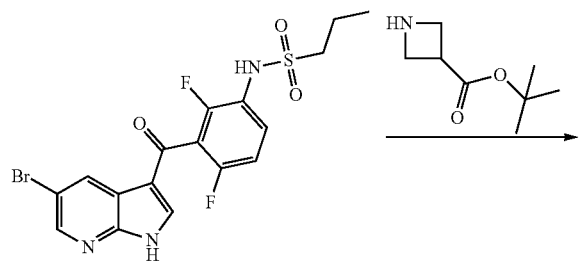

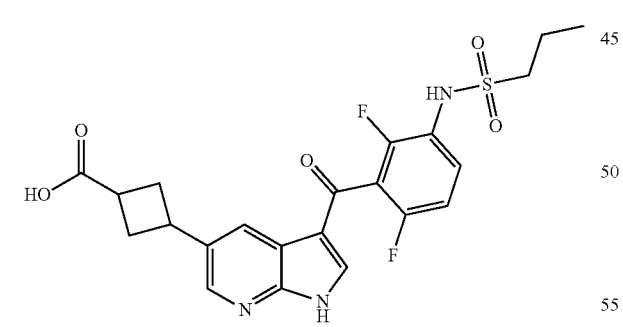

Analytical Data:

$^1$H NMR (400 MHz, DMSO-d$_6$) δ 12.63 (s, 1H), 9.73 (s, 1H), 7.98 (s, 1H), 7.76 (d, J=2.6 Hz, 1H), 7.55 (td, J=9.0, 6.0 Hz, 1H), 7.42 (s, 1H), 7.25 (t, J=8.6 Hz, 1H), 4.11 (t, J=7.8 Hz, 2H), 3.95 (t, J=6.5 Hz, 2H), 3.17-3.05 (m, 2H), 1.74 (dq, J=15.0, 7.5 Hz, 2H), 0.96 (t, J=7.4 Hz, 3H).

Calculated exact mass for C$_{21}$H$_{20}$F$_2$N$_4$O$_5$S: 478.11 (molecular weight: 478.47).

MS(ESI+): 479.1 for [M+H]$^+$.

Example 138: Synthesis of N-(3-(5-(2,6-dimethyl-morpholino)-1H-pyrrolo[2,3-b]pyridine-3-carbonyl)-2,4-difluorophenyl)propane-1-sulfonamide Example 138 was prepared in analogy to 134.

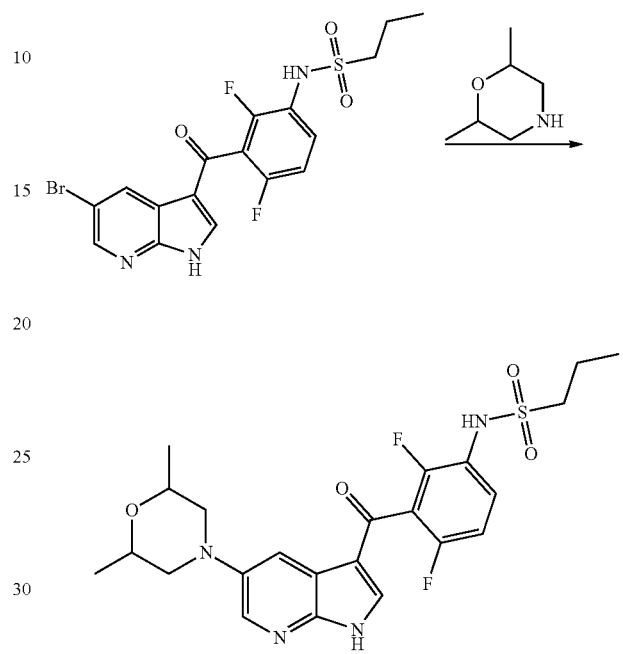

Analytical Data:

$^1$H NMR (400 MHz, DMSO-d$_6$) δ 12.67 (s, 1H), 9.75 (s, 1H), 8.28 (d, J=2.6 Hz, 1H), 8.01 (s, 1H), 7.88 (s, 1H), 7.554.9, 8.9 Hz, 1H), 7.25 (t, J=8.7 Hz, 1H), 4.11 (s, 1H), 3.84-3.72 (m, 2H), 3.57 (d, J=11.3 Hz (dd, J=1, 2H), 3.15-3.06 (m, 2H), 2.33 (t, J=11.0 Hz, 2H), 1.74 (dd, J=15.1, 7.5 Hz, 2H), 1.26 (d, J=6.4 Hz, 1H), 1.18 (d, J=6.2 Hz, 4H), 0.96 (t, J=7.4 Hz, 3H).

Calculated exact mass for C$_{23}$H$_{26}$F$_2$N$_4$O$_4$S: 492.16; molecular weight: 492.54.

MS(ESI$^+$): 493.1 for [M+H]$^+$.

Example 139: Synthesis of N-(2,4-difluoro-3-(5-(oxetan-3-ylamino-pyrrolo[2,3-b]pyridine-3-carbonyl)phenyl)propane-1-sulfonamide Example 139 was prepared in analogy to example 134.

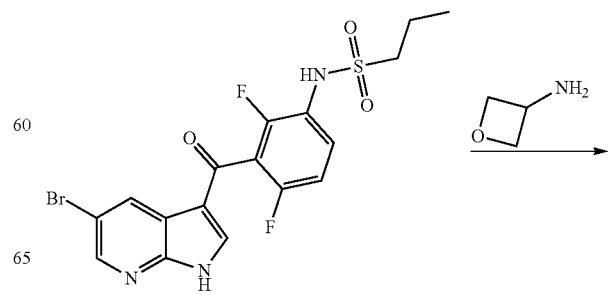

-continued

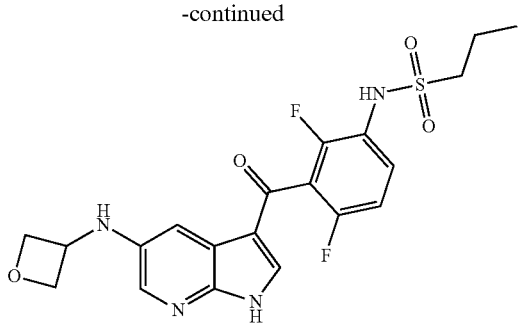

Analytical Data:

$^{1}$H NMR (400 MHz, DMSO-$d_{6}$) δ 12.54 (s, 1H), 9.73 (s, 1H), 7.91 (s, 1H), 7.83 (d, J=2.4 Hz, 1H), 7.55 (dd, J=14.9, 9.0 Hz, 1H), 7.40 (s, 1H), 7.25 (t, J=8.7 Hz, 1H), 4.88 (t, J=6.3 Hz, 2H), 4.57 (d, J=5.6 Hz, 1H), 4.44 (t, J=5.9 Hz, 2H), 3.12 (dd, J=17.4, 9.9 Hz, 2H), 1.74 (dq, J=15.0, 7.5 Hz, 2H), 0.96 (t, J=7.4 Hz, 3H)

Calculated exact mass for $C_{20}H_{20}F_{2}N_{4}O_{4}S$: 450.12 (molecular weight: 450.46)

MS(ESI'): 451.1 for [M+H]'.

Example 140: Synthesis of N-(2,4-difluoro-3-(5-(oxetan-3-ylamino) 1 i-pyrrolo[2,3-b]pyridine-3-carbonyl)phenyl)propane-1-sulfonamide Example 140 was prepared in analogy to 134.

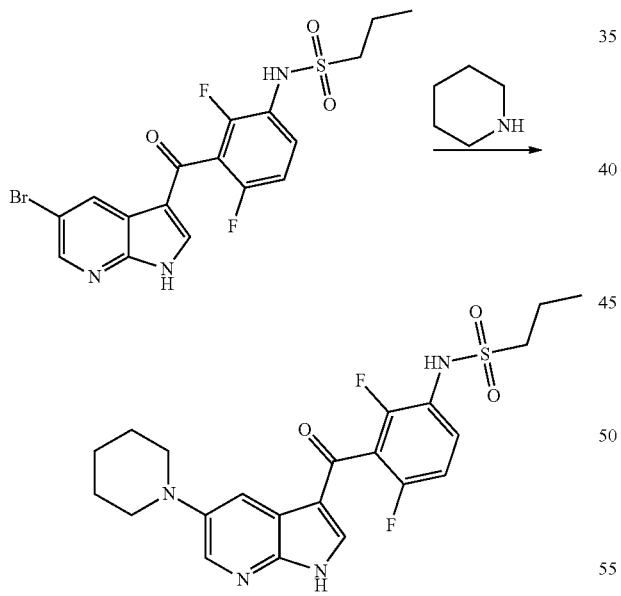

Analytical Data:

$^{1}$H NMR (400 MHz, DMSO-$d_{6}$) δ 12.82-12.67 (m, 1H), 9.75 (s, 1H), 8.31 (s, 1H), 8.06 (s, 1H), 7.56 (dd, J=14.9, 9.0 Hz, 1H), 7.26 (t, J=8.7 Hz, 1H), 3.22 (s, 4H), 3.16-3.06 (m, 2H), 1.83-1.64 (m, 6H), 1.63-1.51 (m, 2H), 0.96 (t, J=7.4 Hz, 3H).

Calculated exact mass for $C_{22}H_{24}F_{2}N_{4}O_{3}S$: 462.15 (molecular weight: 462.52)

MS(ESI$^{+}$): 463.1 for [M+H]$^{+}$.

Synthesis of 5-substituted N-(2,x-difluoro-3-(1-pyrrolo[2,3-b]pyridine-3-carbonyl)phenyl)alkyl-1-sulfonamide derivatives 5-Substituted N-(2,x-difluoro-3-(1H-pyrrolo[2,3-b]pyridine-3-carbonyl)phenyl)alkyl-1-sulfonamide derivatives according to the formula

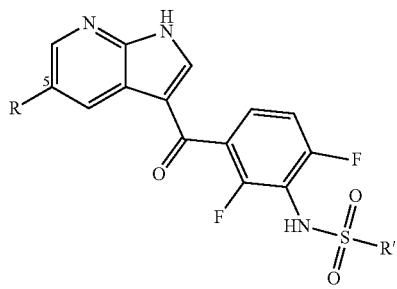

were prepared according to the following examples.

Example 141: Synthesis of N-3-(5-(2-cyclopropylpyrimidin-5-yl)-1H-pyrrolo[2,3-b]pyridine-3-carbonyl)-2,6-difluorophenyl) methanesulfonamide

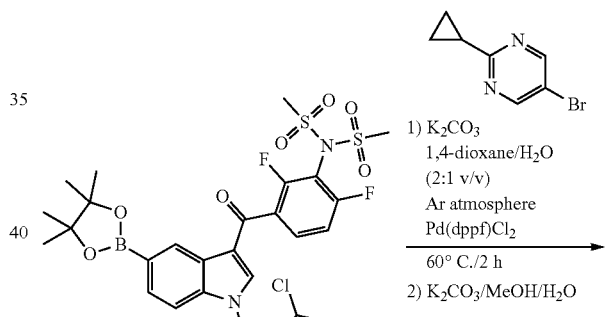

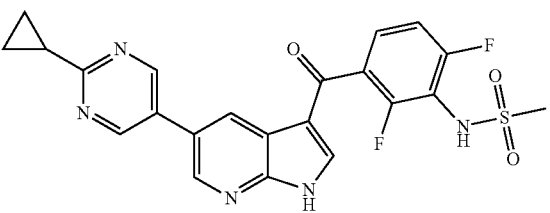

N-[3-[1-(2,6-dichlorobenzoyl)-5-(4,4,5,5-tetramethyl-1,3,2-dioxaborolan-2-yl)pyrrolo[2,3-b]pyridine-3-carbonyl]-2,6-difluorophenyl]-N-methylsulfonylmethanesulfonamide (150 mg, 0.206 mmol), 5-bromo-2-cyclopropylpyrimidine (0.0451 g, 0.227 mmol) and potassium carbonate (0.0578 g, 0.412 mmol) were dissolved in 1,4-dioxane (1.40 mL) and water (0.700 mL) and the mixture was degassed with argon. Pd(dppf)Cl$_2$ (0.00753 g, 0.0103 mmol)) was added and the mixture was heated to 60° C. for 2 h. The crude mixture was passed through a Celite pad, flushed with MeOH and EtOAc and the solvent was removed in vacuo. The residue was dissolved in MeOH, potassium carbonate (500 mg) was added and the suspension was stirred for 3 h at RT. Water was added, the pH adjusted to 6-8 with 1 N HCl$_{aq}$. and the aqueous phase was extracted with EtOAc. The organic layers were combined, dried over sodium sulfate and the solvent was removed under reduced pressure. The product was pre-purified via flash chromatography using DCM/EtOAc/MeOH (92/8/0-88/8/4) as eluent. Thereafter, the product was suspended in EtOAc and after addition of n-pentane, the product was filtered off and dried in vacuo (yield: 59 mg (60%), chemical purity (HPLC/UV): 98%)

Analytical Data:
$^1$H NMR (400 MHz, DMSO-d$_6$) δ 12.97 (s, 1H), 9.72 (s, 1H), 9.01 (s, 2H), 8.72 (s, 2H), 8.12 (d, J=2.6 Hz, 1H), 7.66 (q, J=7.6 Hz, 1H), 7.36 (t, J=8.9 Hz, 1H), 3.12 (s, 3H), 2.27 (td, J=8.0, 4.0 Hz, 1H), 1.13-1.01 (m, 4H).

Calculated exact mass for C$_{22}$H$_{17}$F$_2$N$_5$O$_3$S: 469.1 (molecular weight: 469.47)
MS (ESI$^-$): 468.3 for [M−H]$^-$.

Example 144: Synthesis of N-(2,6-difluoro-3-(5-(2-(trifluoromethyl)pyrimidin-5-yl)-1H-pyrrolo[2,3-b]pyridine-3-carbonyl)phenyl)-3,3,3-trifluoro-propane-1-sulfonamide N-[3-[1-(2,6-dichlorobenzoyl)-5-(4,4,5,5-tetramethyl-1,3,2-dioxaborolan-2-yl)pyrrolo[2,3-b]pyridine-3-carbonyl]-2,6-difluorophenyl]-3,3,3-trifluoro-N-(3,3,3-trifluoropropylsulfonyl)propane-1-sulfonamide (200 mg, 0.224 mmol, prepared in analogy to Example 4, Steps 4-1 and 4-2), 5-bromo-2-(trifluoromethyl)pyrimidine (56.0 mg, 0.247 mmol) and potassium carbonate (62.8 mg, 0.448 mmol) were dissolved in 1,4-dioxane (1.50 mL) and water (0.750 mL) and the mixture was degased with argon. Pd(dppf)Cl$_2$ (8.20 mg, 0.0112 mmol) was added and the mixture was heated to 60° C. for 2 h. The crude mixture was passed through a Celite pad, flushed with MeOH and EtOAc and the solvent was removed in vacuo. The residue was resolved in MeOH, potassium carbonate (500 mg) was added and the suspension was stirred for 3 h at rt. Water was added, the pH adjusted to 6-8 with 1 N HCl$_{aq}$. and the aqueous phase was extracted with EtOAc, the layers were separated and the organic layers were dried over sodium sulfate and the solvent was removed under reduced pressure. The product was pre-purified via flash chromatography using DCM/EtOAc/MeOH (92/8/0-88/8/4) as eluent. The pre-purified product was suspended in EtOAc and precipitated with n-pentane, filtered and dried in vacuo (yield: 52 mg (40%), chemical purity (HPLC/UV): 99%).

Analytical Data:
$^1$H NMR (400 MHz, DMSO-d$_6$) δ 13.09 (s, 1H), 10.05 (s, 1H), 9.50 (s, 2H), 8.89 (dd, J=9.9, 2.2 Hz, 2H), 8.21 (s, 1H), 7.76-7.64 (m, 1H), 7.40 (t, J=8.9 Hz, 1H), 3.53-3.43 (m, 2H), 2.91-2.76 (m, 2H).

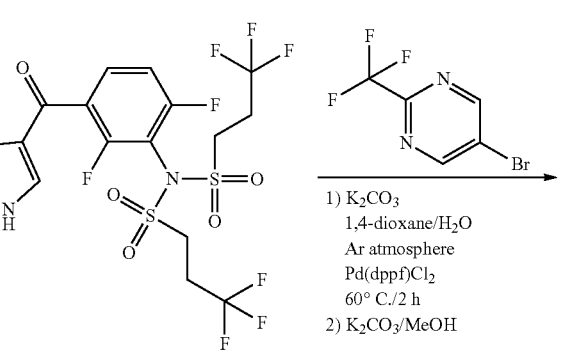

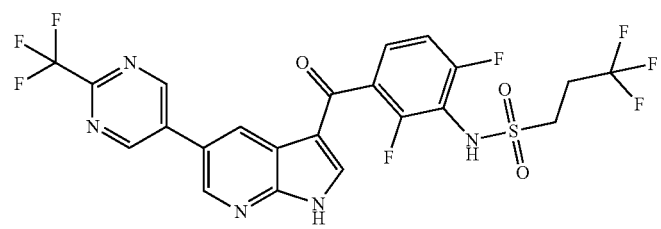

Example 143: Synthesis of N-(3-(5-(3-cyanophenyl)-1-pyrrolo[2,3-b]pyridine-3-carbonyl)-2,6-difluorophenyl)propane-1-sulfonamide

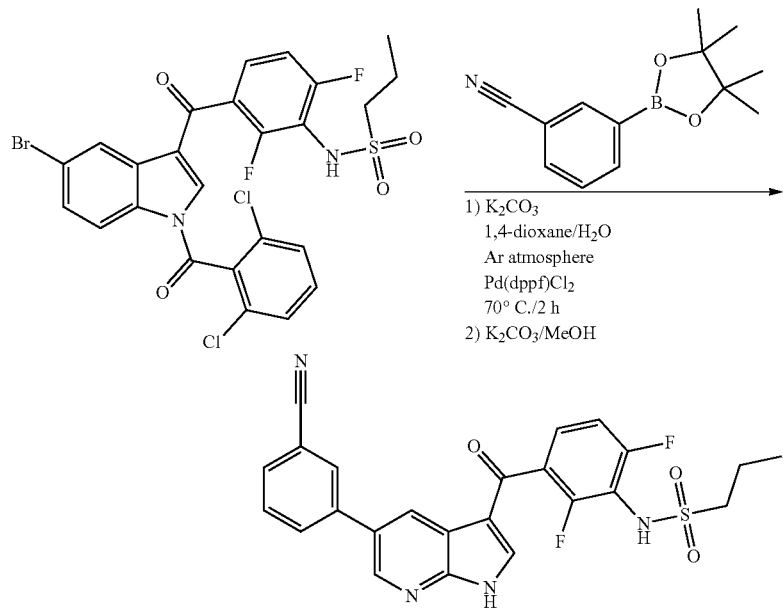

1) $K_2CO_3$
1,4-dioxane/$H_2O$
Ar atmosphere
Pd(dppf)$Cl_2$
70° C./2 h
2) $K_2CO_3$/MeOH N-[3-[5-bromo-1-(2,6-dichlorobenzoyl)pyrrolo[2,3-b]pyridine-3-carbonyl]-2,6-difluorophenyl]propane-1-sulfonamide (0.150 g, 0.238 mmol), 3-(4,4,5,5-tetramethyl-1,3,2-dioxaborolan-2-yl)benzonitrile (0.0599 g, 0.261 mmol) and potassium carbonate (0.0666 g, 0.475 mmol) were suspended in 1,4-dioxane (1.20 mL) and water (0.600 mL) and degassed with argon for 5 min. Pd(dppf)$Cl_2$ (0.0137 g, 0.0119 mmol) was added and the mixture was heated to 70° C. for 2 h. The crude was filtered through a pad of Celite, flushed with EtOAc and solvent was evaporated. The residue was suspended in MeOH (5 ml) and potassium carbonate (200 mg) was added. The mixture was stirred at RT until TLC revealed complete hydrolysis of the 2,6-dichlorobenzoyl protection group. After dilution with water, 1N HCl was added (pH 6-7) and the product was extracted with EtOAc (3×50 ml). The organic phase was dried over sodium sulfate, the solvent removed under reduced pressure and the product was purified applying flash chromatography using DCM/MeOH (100/0 v/v to 95/5 v/v) as eluent (yield: 52.8,g (45%); chemical purity (HPLC/UV): 97%).

Analytical Data:
$^1$H NMR (600 MHz, DMSO-$d_6$) δ 12.95 (s, 1H), 9.65 (s, 1H), 8.76 (d, J=1.9 Hz, 1H), 8.74 (d, J=1.9 Hz, 1H), 8.27 (s, 1H), 8.10 (s, 2H), 7.87 (d, J=7.6 Hz, 1H), 7.72 (t, J=7.8 Hz, 1H), 7.66 (dd, J=14.2, 7.6 Hz, 1H), 7.36 (t, J=8.8 Hz, 1H), 3.19-3.13 (m, 2H), 1.81 (dq, J=15.0, 7.4 Hz, 2H), 1.00 (t, J=7.4 Hz, 3H).

Calculated exact mass for $C_{24}H_{18}F_2N_4O_3S$: 480.1 (molecular weight: 480.49);
MS(ESI$^-$): 479.0 for [M−H]$^-$.

In analogy to Examples 141-143, the compound of Examples 144-238, given in Table 5, were prepared.

TABLE 5

Examples 144-238, prepared in analogy to Examples 141-143.

| Ex. | Reactant | Product | | Analytical Data |
|---|---|---|---|---|
| 144 | (pyridazine-Br structure) | (product structure) | N-(2,6-difluoro-3-(5-(pyridazin-4-yl)-1H-pyrrolo-[2,3-b]pyridine-3-carbonyl)phenyl)-propane-1-sulfonamide C21H17F2N5O3S/ 457.46 | $^1$H NMR (400 MHz, DMSO) δ 13.09 (s, 1H), 9.77 (d, J = 1.3 Hz, 1H), 9.67 (s, 1H), 9.33 (d, J = 5.5 Hz, 1H), 8.93 (dd, J = 8.2, 2.2 Hz, 2H), 8.22-8.14 (m, 2H), 7.67 (dd, J = 14.5, 7.7 Hz, 1H), 7.36 (t, J = 8.8 Hz, 1H), 3.21-3.10 (m, 2H), 1.81 (dq, J = 14.9, 7.4 Hz, 2H), 1.00 (t, J = 7.4 Hz, 3H) Calculated exact mass: 457.10 MS(ESI$^+$): 458.1 for [M + H]$^+$. |

TABLE 5-continued

Examples 144-238, prepared in analogy to Examples 141-143.

| Ex. | Reactant | Product | | Analytical Data |
|---|---|---|---|---|
| 145 | 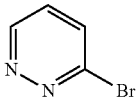 | 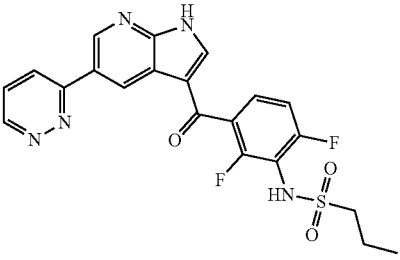 [SMILES: CCCS(=O)(=O)Nc1c(F)ccc(C(=O)c2c[nH]c3ncc(-c4cccnn4)cc23)c1F] | N-(2,6-difluoro-3-(5-(pyridazin-3-yl)-1H-pyrrolo[2,3-b]pyridine-3-carbonyl)phenyl)-propane-1-sulfonamide C21H17F2N5O3S/ 457.46 | $^{1}$H NMR (400 MHz, DMSO) δ 9.25 (dd, J = 6.6, 3.5 Hz, 2H), 9.14 (d, J = 2.0 Hz, 1H), 8.38 (d, J = 8.7 Hz, 1H), 8.13 (s, 1H), 7.83 (dd, J = 8.6, 4.9 Hz, 1H), 7.67-7.57 (m, 1H), 7.33 (t, J = 8.8 Hz, 1H), 3.15-3.09 (m, 2H), 1.79 (dt, J = 15.1, 7.6 Hz, 2H), 0.99 (t, J = 7.4 Hz, 3H). Calculated 457.10 for C21H17F2N5O3S. Measured 457.9 for [M + H]$^{+}$. |
| 146 | 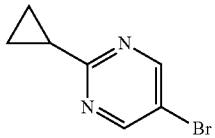 | 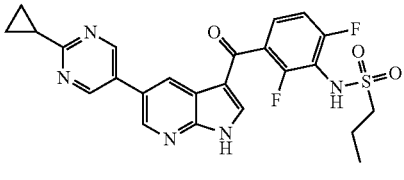 [SMILES: CCCS(=O)(=O)Nc1c(F)ccc(C(=O)c2c[nH]c3ncc(-c4cnc(C5CC5)nc4)cc23)c1F] | N-(3-(5-(2-cyclopropyl-pyrimidin-5-yl)-1H-pyrrolo[2,3-b]pyridine-3-carbonyl)-2,6-difluorophenyl)-propane-1-sulfonamide C24H21F2N5O3S/ 497.52 | $^{1}$H NMR (400 MHz, DMSO-d$_{6}$) δ 12.98 (s, 1H), 9.65 (s, 1H), 9.02 (s, 1H), 8.72 (d, J = 7.4 Hz, 1H), 8.11 (s, 1H), 7.72-7.59 (m, 1H), 7.42-7.31 (m, 1H), 3.21-3.11 (m, 1H), 2.31-2.24 (m, 1H), 1.81 (d, J = 7.6 Hz, 2H), 1.16-1.04 (m, 4H), 1.00 (t, J = 7.4 Hz, 3H). |
| 147 | 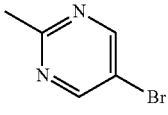 | 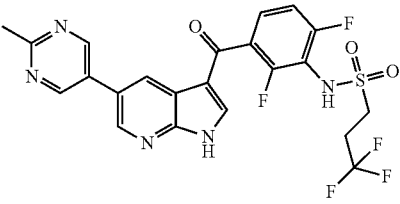 [SMILES: Cc1ncc(-c2cnc3[nH]cc(C(=O)c4ccc(F)c(NS(=O)(=O)CCC(F)(F)F)c4F)c3c2)cn1] | N-(2,6-difluoro-3-(5-(2-methyl-pyrimidin-5-yl)-1H-pyrrolo[2,3-b]pyridine-3-carbonyl)phenyl)-3,3,3-trifluoropropane-1-sulfonamide C22H16F5N5O3S/ 525.45 | $^{1}$H NMR (400 MHz, DMSO-d$_{6}$) δ 13.07 (s, 1H), 10.04 (s, 1H), 9.49 (s, 2H), 8.90 (d, J = 2.3 Hz, 1H), 8.87 (d, J = 2.3 Hz, 1H), 8.20 (s, 1H), 7.70 (td, J = 8.3, 6.2 Hz, 1H), 7.39 (t, J = 8.8 Hz, 1H), 3.51-3.43 (m, 2H), 2.91-2.76 (m, 2H). |
| 148 | 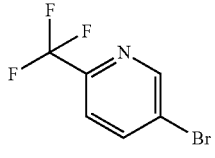 | 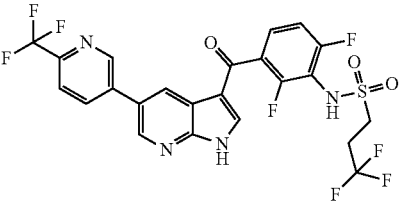 [SMILES: O=C(c1ccc(F)c(NS(=O)(=O)CCC(F)(F)F)c1F)c1c[nH]c2ncc(-c3ccc(C(F)(F)F)nc3)cc12] | N-(2,6-difluoro-3-(5-(6-(trifluoromethyl)pyridin-3-yl)-1H-pyrrolo[2,3-b]pyridine-3-carbonyl)phenyl)-3,3,3-trifluoropropane-1-sulfonamide C23H14F8N4O3S/ 578.44 | $^{1}$H NMR (400 MHz, DMSO-d$_{6}$) δ 13.03 (d, J = 3.0 Hz, 1H), 10.04 (s, 1H), 9.18 (d, J = 2.3 Hz, 1H), 8.83 (d, J = 2.3 Hz, 1H), 8.81 (d, J = 2.3 Hz, 1H), 8.48 (dd, J = 8.1, 2.3 Hz, 1H), 8.18 (s, 1H), 8.03 (d, J = 8.2 Hz, 1H), 7.70 (td, J = 8.2, 6.1 Hz, 1H), 7.39 (td, J = 9.0, 1.4 Hz, 1H), 3.52-3.44 (m, 2H), 2.91-2.77 (m, 2H). MS(ESI):. Measured 577.3 for [M − H]$^{−}$. |
| 149 | 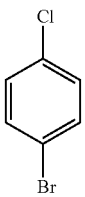 | 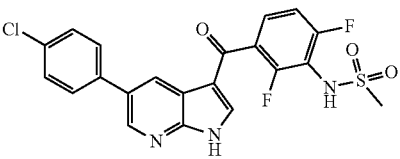 [SMILES: CS(=O)(=O)Nc1c(F)ccc(C(=O)c2c[nH]c3ncc(-c4ccc(Cl)cc4)cc23)c1F] | N-(3-(5-(4-chlorophenyl)-1H-pyrrolo[2,3-b]pyridine-3-carbonyl)-2,6-difluorophenyl)-methanesulfonamide C21H14ClF2N3O3S/ 461.87 | $^{1}$H NMR (400 MHz, DMSO-d$_{6}$) δ 12.91 (s, 1H), 9.72 (s, 1H), 8.69 (q, J = 2.3 Hz, 2H), 8.10 (d, J = 1.5 Hz, 1H), 7.78 (d, J = 8.6 Hz, 2H), 7.66 (td, J = 8.3, 6.2 Hz, 1H), 7.57 (d, J = 8.5 Hz, 2H), 7.36 (td, J = 8.9, 1.4 Hz, 1H), 3.12 (s, |

TABLE 5-continued

Examples 144-238, prepared in analogy to Examples 141-143.

| Ex. | Reactant | Product | | Analytical Data |
|---|---|---|---|---|
| | | | | 3H). Calculated exact mass: 461.0 MS(ESI⁻): 460.3 for [M − H]⁻. |
| 150 | Cl-C₆H₄-Br | | N-(3-(5-(4-chlorophenyl)-1H-pyrrolo[2,3-b]pyridine-3-carbonyl)-2,6-difluorophenyl)-3,3,3-trifluoropropane-1-sulfonamide C23H15ClF5N3O3S/ 543.89 | $^1$H NMR (400 MHz, DMSO-d$_6$) δ 12.91 (d, J = 3.1 Hz, 1H), 10.03 (s, 1H), 8.69 (q, J = 2.3 Hz, 2H), 8.11 (s, 1H), 7.78 (d, J = 8.5 Hz, 2H), 7.69 (td, J = 8.3, 6.2 Hz, 1H), 7.57 (d, J = 8.5 Hz, 2H), 7.38 (td, J = 9.0, 1.4 Hz, 1H), 3.51-3.44 (m, 2H), 2.92-2.76 (m, 2H). Calculated exact mass: 543.0 MS(ESI⁻): 542.2 for [M − H]⁻. |
| 151 | | | N-(2,6-difluoro-3-(5-(4-(S-methyl-sulfonimidoyl)phenyl)-1H-pyrrolo[2,3-b]pyridine-3-carbonyl)phenyl)propane-1-sulfonamide C24H22F2N4O4S2/ 532.58 | $^1$H NMR (400 MHz, DMSO-d$_6$) δ 12.97 (s, 1H), 9.65 (s, 1H), 8.77 (d, J = 4.4 Hz, 2H), 8.12 (s, 1H), 8.05 (d, J = 8.3 Hz, 2H), 7.99 (d, J = 8.2 Hz, 2H), 7.66 (dd, J = 14.2, 7.5 Hz, 1H), 7.36 (t, J = 8.8 Hz, 1H), 4.28 (s, 1H), 3.22-3.02 (m, 5H), 1.81 (dd, J = 15.1, 7.5 Hz, 2H), 1.00 (t, J = 7.4 Hz, 3H). Calculated exact mass: 532.11 MS(ESI⁺): 533.98 for [M + H]⁺ |
| 152 | | | N-(3-(5-(2-chloro-4-hydroxyphenyl)-1H-pyrrolo[2,3-b]pyridine-3-carbonyl)-2,6-difluorophenyl)propane-1-sulfonamide C23H18ClF2N3O4S/ 505.92 | $^1$H NMR (600 MHz, DMSO-d$_6$) δ 12.89 (s, 1H), 10.07 (s, 1H), 9.64 (s, 1H), 8.46 (d, J = 2.1 Hz, 1H), 8.38 (d, J = 1.4 Hz, 1H), 8.06 (d, J = 1.3 Hz, 1H), 7.65 (dd, J = 14.4, 7.7 Hz, 1H), 7.34 (t, J = 8.2 Hz, 2H), 6.99 (d, J = 2.4 Hz, 1H), 6.88 (dd, J = 8.4, 2.4 Hz, 1H), 3.18-3.13 (m, 2H), 1.81 (dq, J = 15.0, 7.5 Hz, 2H), 1.00 (t, J = 7.4 Hz, 3H). Calculated exact mass: 505.1 MS(ESI⁻): 504.0 for [M − H]⁻. |
| 153 | | | N-(3-(5-(2-chloro-4-(2,3-dihydroxypropoxy)phenyl)-1H-pyrrolo[2,3-b]pyridine-3-carbonyl)-2,6-difluorophenyl)propane-1-sulfonamide C26H24ClF2N3O6S/ 580.00 | $^1$H NMR (600 MHz, DMSO-d$_6$) δ 12.91 (s, 1H), 9.64 (s, 1H), 8.49 (d, J = 1.9 Hz, 1H), 8.40 (d, J = 2.0 Hz, 1H), 8.08 (s, 1H), 7.65 (dd, J = 14.3, 7.6 Hz, 1H), 7.45 (d, J = 8.5 Hz, 1H), 7.35 (t, J = 8.7 Hz, 1H), 7.21 (d, J = 2.4 Hz, 1H), 7.07 (dd, J = 8.5, 2.4 Hz, 1H), 5.01 (d, J = 5.1 Hz, 1H), 4.70 |

TABLE 5-continued

Examples 144-238, prepared in analogy to Examples 141-143.

| Ex. | Reactant | Product | | Analytical Data |
|---|---|---|---|---|
| | | | | (t, J = 5.6 Hz, 1H), 4.11 (dd, J = 10.0, 3.9 Hz, 1H), 3.97 (dd, J = 10.0, 6.2 Hz, 1H), 3.83 (dq, J = 10.8, 5.5 Hz, 1H), 3.47 (t, J = 5.6 Hz, 2H), 3.18-3.12 (m, 2H), 1.81 (dq, J = 14.9, 7.4 Hz, 2H), 1.00 (t, J = 7.4 Hz, 3H). Calculated exact mass: 579.1 MS(ESI⁻): 578.0 for [M − H]⁻. |
| 154 | 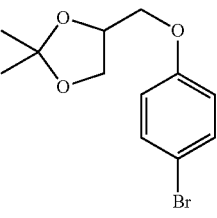 | 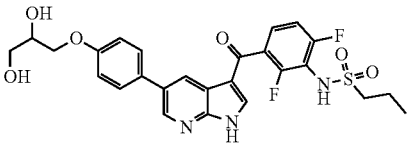 [SMILES: CCCS(=O)(=O)Nc1c(F)ccc(C(=O)c2c[nH]c3ncc(-c4ccc(OCC(O)CO)cc4)cc23)c1F] | N-(3-(5-(4-(2,3-dihydroxypropoxy)phenyl)-1H-pyrrolo[2,3-b]pyridine-3-carbonyl)-2,6-difluorophenyl)-propane-1-sulfonamide C26H25F2N3O6S/ 545.56 | ¹H NMR (600 MHz, DMSO-d₆) δ 12.84 (s, 1H), 9.65 (s, 1H), 8.65 (d, J = 2.2 Hz, 1H), 8.62 (d, J = 2.2 Hz, 1H), 8.04 (s, 1H), 7.65 (dd, J = 17.8, 8.2 Hz, 3H), 7.35 (t, J = 8.7 Hz, 1H), 7.09 (d, J = 8.7 Hz, 2H), 4.98 (d, J = 5.2 Hz, 1H), 4.69 (t, J = 5.6 Hz, 1H), 4.07 (dd, J = 9.9, 4.2 Hz, 1H), 3.93 (dd, J = 9.9, 6.2 Hz, 1H), 3.83 (dq, J = 10.9, 5.6 Hz, 1H), 3.48 (t, J = 5.6 Hz, 2H), 3.18-3.13 (m, 2H), 1.85-1.77 (m, 2H), 1.00 (t, J = 7.4 Hz, 3H). Calculated exact mass: 545.1 MS(ESI⁻): 544.2 for [M − H]⁻. |
| 155 | 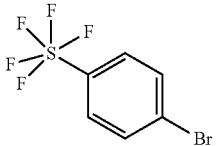 | 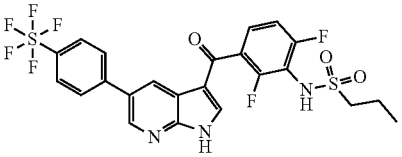 [SMILES: CCCS(=O)(=O)Nc1c(F)ccc(C(=O)c2c[nH]c3ncc(-c4ccc(S(F)(F)(F)(F)F)cc4)cc23)c1F] | N-(2,6-difluoro-3-(5-(4-(pentafluoro-l6-sulfaneyl)phenyl)-1H-pyrrolo[2,3-b]pyridine-3-carbonyl)phenyl)-propane-1-sulfonamide C23H18F7N3O3S2/ 581.52 | ¹H NMR (400 MHz, DMSO-d₆) δ 12.99 (s, 1H), 9.66 (s, 1H), 8.83-8.72 (m, 2H), 8.12 (s, 1H), 8.02 (q, J = 9.1 Hz, 4H), 7.72-7.60 (m, J = 6.7 Hz, 1H), 7.36 (t, J = 8.9 Hz, 1H), 3.21-3.11 (m, 2H), 1.81 (dd, J = 15.2, 7.5 Hz, 2H), 1.00 (t, J = 7.4 Hz, 3H). Calculated exact mass: 581.07 MS(ESI⁺): 582.00 for [M + H]⁺. |
| 156 | 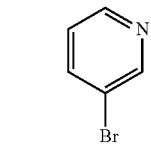 | 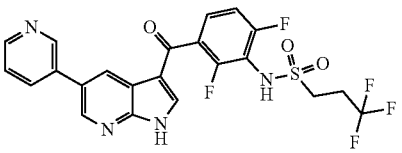 [SMILES: O=C(c1ccc(F)c(NS(=O)(=O)CCC(F)(F)F)c1F)c1c[nH]c2ncc(-c3cccnc3)cc12] | N-(2,6-difluoro-3-(5-(pyridin-3-yl)-1H-pyrrolo[2,3-b]pyridine-3-carbonyl)phenyl)-3,3,3-trifluoro-propane-1-sulfonamide C22H15F5N4O3S/ 510.44 | ¹H NMR (400 MHz, DMSO-d₆) δ 12.96 (s, 1H), 10.02 (s, 1H), 8.96 (s, 1H), 8.74 (d, J = 2.3 Hz, 1H), 8.72 (d, J = 2.3 Hz, 1H), 8.63 (d, J = 4.8 Hz, 1H), 8.17 (dt, J = 8.0, 2.0 Hz, 1H), 8.14 (s, 1H), 7.69 (td, J = 8.2, 6.1 Hz, 1H), 7.54 (dd, J = 7.9, 4.7 Hz, 1H), 7.38 (t, J = 8.8 Hz, 1H), 3.51-3.43 (m, 2H), 2.92-2.74 (m, 2H). Calculated exact mass: 510.1 MS(ESI⁻): 509.3 for [M − H]⁻. |

TABLE 5-continued

Examples 144-238, prepared in analogy to Examples 141-143.

| Ex. | Reactant | Product | | Analytical Data |
|---|---|---|---|---|
| 157 | 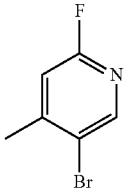 | 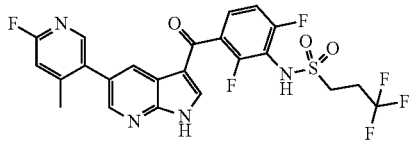 [SMILES: Cc1cc(F)ncc1-c1cnc2[nH]cc(C(=O)c3ccc(F)c(NS(=O)(=O)CCC(F)(F)F)c3F)c2c1] | N-(2,6-difluoro-3-(5-(6-fluoro-4-methylpyridin-3-yl)-1H-pyrrolo-[2,3-b]pyridine-3-carbonyl)phenyl)-3,3,3-trifluoro-propane-1-sulfon-amide C23H16F6N4O3S/ 542.46 | $^1$H NMR (600 MHz, DMSO-d$_6$) δ 12.97 (d, J = 1.3 Hz, 1H), 10.03 (s, 1H), 8.45 (d, J = 2.1 Hz, 1H), 8.41 (d, J = 2.1 Hz, 1H), 8.15 (s, 2H), 7.69 (dd, J = 14.4, 7.8 Hz, 1H), 7.38 (t, J = 8.7 Hz, 1H), 7.23 (s, 1H), 3.50-3.44 (m, 2H), 2.89-2.77 (m, 2H), 2.33 (s, 3H). Calculated exact mass: 542.1 MS(ESI$^-$): 540.9 for [M − H]$^-$. |
| 158 | 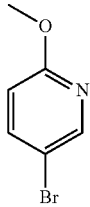 | 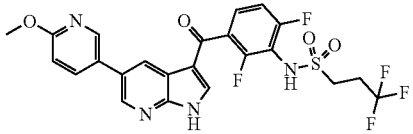 [SMILES: COc1ccc(-c2cnc3[nH]cc(C(=O)c4ccc(F)c(NS(=O)(=O)CCC(F)(F)F)c4F)c3c2)cn1] | N-(2,6-difluoro-3-(5-(6-methoxy-pyridin-3-yl)-1H-pyrrolo[2,3-b]pyridine-3-carbonyl)phenyl)-3,3,3-trifluoro-propane-1-sulfon-amide C23H17F5N4O4S/ 540.47 | $^1$H NMR (600 MHz, DMSO-d$_6$) δ 12.91 (d, J = 2.0 Hz, 1H), 10.04 (s, 1H), 8.67 (d, J = 2.2 Hz, 1H), 8.64 (d, J = 2.2 Hz, 1H), 8.53 (d, J = 2.5 Hz, 1H), 8.11 (d, J = 1.9 Hz, 1H), 8.09 (dd, J = 8.6, 2.6 Hz, 1H), 7.69 (dd, J = 14.5, 7.8 Hz, 1H), 7.38 (t, J = 8.8 Hz, 1H), 6.96 (dd, J = 8.6, 0.3 Hz, 1H), 3.92 (s, 3H), 3.49-3.45 (m, 2H), 2.88-2.79 (m, 2H). Calculated exact mass: 540.1 MS(ESI$^-$): 539.0 for [M − H]$^-$. |
| 159 | 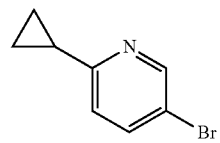 |  | N-(3-(5-(6-cyclo-propylpyridin-3-yl)-1H-pyrrolo-[2,3-b]pyridine-3-carbonyl)-2,6-difluorophenyl)-propane-1-sulfon-amide C25H22F2N4O3S/ 496.53 | $^1$H NMR (400 MHz, DMSO-d$_6$) δ 12.92 (s, 1H), 9.65 (szzz, 1H), 8.76 (s, 1H), 8.72-8.60 (m, J = 14.3 Hz, 2H), 8.08 (s, 1H), 8.04-7.98 (m, 1H), 7.71-7.58 (m, 1H), 7.43 (d, J = 8.0 Hz, 1H), 7.39-7.30 (m, 1H), 3.21-3.10 (m, 2H), 2.23-2.11 (m, 1H), 1.88-1.74 (m, 2H), 1.10-0.89 (m, 7H). Calculated exact mass: 496.14 MS(ESI$^+$): 497.10 for [M + H] |
| 160 | 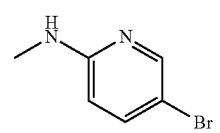 |  | N-(2,6-difluoro-3-(5-(6-(methyl-amino)pyridin-3-yl)-1H-pyrrolo-[2,3-b]pyridine-3-carbonyl)phenyl)-propane-1-sulfon-amide C23H21F2N5O3S/ 485.51 | $^1$H NMR (400 MHz, DMSO-d$_6$) δ 12.82 (s, 1H), 9.65 (s, 1H), 8.57 (d, J = 21.7 Hz, 2H), 8.36 (s, 1H), 8.02 (s, 1H), 7.81-7.73 (m, 1H), 7.69-7.58 (m, 1H), 7.38-7.30 (m, 1H), 6.72-6.64 (m, 1H), 6.62-6.56 (m, 1H), 3.15 (s, 3H), 2.83 (d, J = 4.3 Hz, 3H), 1.88-1.75 (m, 2H), 1.00 (t, J = 7.0 Hz, 3H) |

TABLE 5-continued

Examples 144-238, prepared in analogy to Examples 141-143.

| Ex. | Reactant | Product | | Analytical Data |
|---|---|---|---|---|
| | | | | Calculated exact mass: 485.13<br>MS(ESI+): 486.0 for [M + H]+ |
| 161 | 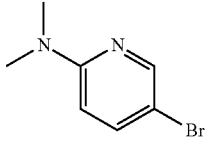 |  | N-(3-(5-(6-(dimethylamino)-pyridin-3-yl)-1H-pyrrolo[2,3-b]pyridine-3-carbonyl)-2,6-difluorophenyl)-propane-1-sulfon-amide<br>C24H23F2N5OS/499.54 | 1H NMR (400 MHz, DMSO-d6) δ 12.84-12.76 (m, 1H), 9.65-9.57 (m, 1H), 8.59 (s, 1H), 8.54 (s, 1H), 8.43 (s, 1H), 7.99 (s, 1H), 7.90-7.82 (m, 1H), 7.64-7.57 (m, 1H), 7.35-7.27 (m, 1H), 6.78-6.72 (m, 1H), 3.12 (s, 2H), 3.05 (s, 6H), 1.85-1.73 (m, 2H), 0.96 (t, J = 7.4 Hz, 3H). Calculated exact mass: 499.15<br>MS(ESI+): 500.10 for [M + H]+ |
| 162 | 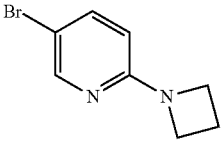 |  | N-(3-(5-(6-(azetidin-1-yl)-pyridin-3-yl)-1H-pyrrolo[2,3-b]pyridine-3-carbonyl)-2,6-difluorophenyl)-propane-1-sulfon-amide<br>C25H23F2N5O3S/511.55 | 1H NMR (400 MHz, DMSO-d6) δ 12.84 (s, 1H), 9.65 (s, 1H), 8.62 (d, J = 2.1 Hz, 1H), 8.56 (d, J = 2.1 Hz, 1H), 8.42 (d, J = 1.8 Hz, 1H), 8.03 (s, 1H), 7.89 (dd, J = 8.6, 2.4 Hz, 1H), 7.64 (d, J = 7.2 Hz, 1H), 7.35 (s, 1H), 6.49 (d, J = 8.6 Hz, 1H), 4.00 (t, J = 7.4 Hz, 4H), 3.21-3.08 (m, 2H), 2.41-2.28 (m, 2H), 1.81 (dd, J = 15.1, 7.6 Hz, 2H), 1.00 (t, J = 7.4 Hz, 3H). Calculated exact mass: 511.15<br>MS(ESI+): 512.10 for [M + H]+ |
| 163 | 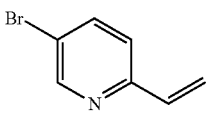 |  | N-(2,6-difluoro-3-(5-(6-vinylpyridin-3-yl)-1H-pyrrolo-[2,3-b]pyridine-3-carbonyl)phenyl)-propane-1-sulfon-amide<br>C24H20F2N4O3S/482.51 | 1H NMR (400 MHz, DMSO-d6) δ 12.97 (s, 1H), 9.67 (s, 1H), 8.94 (s, 1H), 8.74 (d, J = 16.3 Hz, 2H), 8.17 (d, J = 6.4 Hz, 1H), 8.11 (s, 1H), 7.66 (s, 2H), 7.36 (s, 1H), 6.99-6.81 (m, 1H), 6.31 (d, J = 17.6 Hz, 1H), 5.52 (d, J = 10.5 Hz, 1H), 3.16 (s, 2H), 1.82 (s, 2H), 0.99 (s, 3H). Calculated exact mass: 482.12<br>MS(ESI+): 483.0 for [M + H]+ |
| 164 | 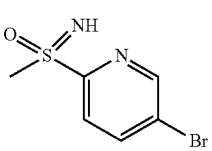 |  | N-(2,6-difluoro-3-(5-(6-(S-methyl-sulfonimidoyl)-pyridin-3-yl)-1H-pyrrolo[2,3-b]-pyridine-3-carbonyl)phenyl)-propane-1-sulfon-amide | 1H NMR (400 MHz, DMSO-d6) δ 13.02 (s, 1H), 9.66 (s, 1H), 9.18-9.05 (m, 1H), 8.94-8.68 (m, 2H), 8.55-8.41 (m, 1H), 8.29-8.01 (m, 2H), 7.74-7.58 (m, 1H), 7.45-7.28 (m, 1H), |

TABLE 5-continued

Examples 144-238, prepared in analogy to Examples 141-143.

| Ex. | Reactant | Product | | Analytical Data |
|---|---|---|---|---|
| | | | C23H21F2N5O4S2/ 533.57 | 4.50 (s, 1H), 3.25-2.88 (m, 5H), 1.93-1.68 (m, 2H), 0.99 (t, 3H). Calculated exact mass: 533.10 MS(ESI+): 534.0 for [M + H]+ |
| 165 | 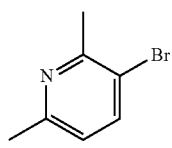 |  | N-(3-(5-(2,6-dimethylpyridin-3-yl)-1H-pyrrolo-[2,3-b]pyridine-3-carbonyl)-2,6-difluorophenyl)-propane-1-sulfonamide C24H22F2N4O3S/ 484.52 | $^1$H NMR (400 MHz, DMSO-$d_6$) δ 13.11-12.71 (m, 2H), 8.40 (d, J = 5.8 Hz, 2H), 8.09 (s, 1H), 7.70-7.56 (m, 2H), 7.34 (t, J = 8.8 Hz, 1H), 7.20 (d, J = 7.7 Hz, 1H), 3.21-3.00 (m, 5H), 1.81 (dd, J = 15.0, 7.5 Hz, 2H), 1.00 (t, J = 7.3 Hz, 3H). Calculated exact mass: 484.14 MS(ESI+): 485.0 for [M + H]+. |
| 166 | 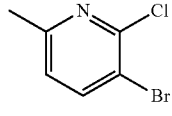 |  | N-(3-(5-(2-chloro-6-methylpyridin-3-yl)-1H-pyrrolo-[2,3-b]pyridine-3-carbonyl)-2,6-difluorophenyl)-propane-1-sulfonamide C23H19ClF2N4O3S/ 504.94 | $^1$H NMR (400 MHz, DMSO-$d_6$) δ 12.99 (s, 1H), 9.66 (s, 1H), 8.54 (d, J = 1.9 Hz, 1H), 8.45 (d, J = 1.9 Hz, 1H), 8.12 (s, 1H), 7.91 (d, J = 7.7 Hz, 1H), 7.70-7.62 (m, 1H), 7.44 (d, J = 7.7 Hz, 1H), 7.35 (t, J = 8.8 Hz, 1H), 3.20-3.10 (m, 2H), 1.81 (dd, J = 15.0, 7.4 Hz, 2H), 1.00 (t, J = 7.4 Hz, 3H). Calculated exact mass: 504.08 MS(ESI+): 505.05 for [M + H]+ |
| 167 | 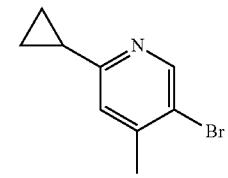 |  | N-(3-(5-(6-cyclopropyl-4-methyl-pyridin-3-yl)-1H-pyrrolo[2,3-b]pyridine-3-carbonyl)-2,6-difluorophenyl)-propane-1-sulfonamide C26H24F2N4O3S/ 510.56 | $^1$H NMR (400 MHz, DMSO-$d_6$) δ 12.94 (s, 1H), 9.66 (s, 1H), 8.39 (d, J = 7.3 Hz, 2H), 8.27 (s, 1H), 8.09 (s, 1H), 7.64 (dd, J = 14.5, 7.4 Hz, 1H), 7.34 (t, J = 8.9 Hz, 1H), 7.29 (s, 1H), 3.20-3.09 (m, 2H), 2.25 (s, 3H), 2.11 (dt, J = 12.8, 6.5 Hz, 1H), 1.86-1.72 (m, 2H), 1.40-1.38 (m, 1H), 1.05-0.91 (m, 7H). Calculated exact mass: 510.15 MS(ESI+): 511.10 for [M + H]+ |
| 168 | 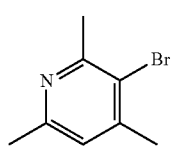 | 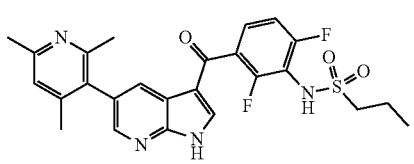 [SMILES: CCCS(=O)(=O)Nc1c(F)ccc(C(=O)c2c[nH]c3ncc(-c4c(C)cc(C)nc4C)cc23)c1F] | N-(2,6-difluoro-3-(5-(2,4,6-trimethylpyridin-3-yl)-1H-pyrrolo-[2,3-b]pyridine-3-carbonyl)phenyl)-propane-1-sulfonamide C25H24F2N4O3S/ 498.55 | $^1$H NMR (400 MHz, DMSO-$d_6$) δ 12.93 (s, 1H), 9.87-9.51 (m, 1H), 8.27 (d, J = 2.0 Hz, 1H), 8.21 (d, J = 1.9 Hz, 1H), 8.08 (s, 1H), 7.71-7.61 (m, 1H), 7.34 (t, J = 9.0 Hz, 1H), 7.09 (s, 1H), 3.20-3.10 (m, 2H), 2.45 (s, 3H), 2.16 (s, |

TABLE 5-continued

Examples 144-238, prepared in analogy to Examples 141-143.

| Ex. | Reactant | Product | | Analytical Data |
|---|---|---|---|---|
| | | | | 3H), 1.98 (s, 3H), 1.81 (dd, J = 15.1, 7.5 Hz, 2H), 1.00 (t, J = 7.4 Hz, 3H). Calculated exact mass: 498.15 MS(ESI+): 499.05 for [M + H]+ |
| 169 | 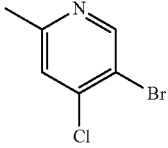 | 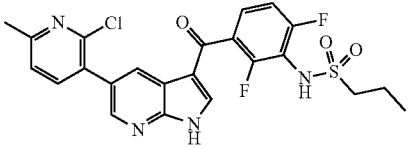 [SMILES: CCCS(=O)(=O)Nc1c(F)ccc(C(=O)c2c[nH]c3ncc(-c4ccc(C)nc4Cl)cc23)c1F] | N-(3-(5-(2-chloro-6-methylpyridin-3-yl)-1H-pyrrolo-[2,3-b]pyridine-3-carbonyl)-2,6-difluorophenyl)-propane-1-sulfonamide C23H19ClF2N4O3S/ 504.94 | 1H NMR (400 MHz, DMSO-d6) δ 13.00 (s, 1H), 9.65 (s, 1H), 8.56 (s, 2H), 8.46 (d, J = 1.4 Hz, 1H), 8.13 (s, 1H), 7.74-7.58 (m, 2H), 7.35 (t, J = 8.8 Hz, 1H), 3.21-3.09 (m, 2H), 2.56 (s, 3H), 1.80 (dt, J = 14.5, 7.4 Hz, 2H), 1.00 (t, J = 7.4 Hz, 3H). Calculated exact mass; 504.08 MS(ESI+): 505.1 for [M + H]+ |
| 170 | 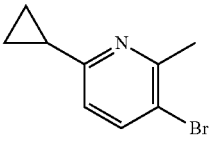 |  | N-(3-(5-(6-cyclopropyl-2-methyl-pyridin-3-yl)-1H-pyrrolo[2,3-b]pyridine-3-carbonyl)-2,6-difluorophenyl)-propane-1-sulfonamide C26H24F2N4O3S/ 510.56 | 1H NMR (400 MHz, DMSO-d6) δ 12.91 (s, 1H), 9.64 (s, 1H), 8.39 (d, J = 3.0 Hz, 2H), 8.08 (s, 1H), 7.69-7.59 (m, 1H), 7.56 (d, J = 7.8 Hz, 1H), 7.34 (t, J = 9.0 Hz, 1H), 7.22 (d, J = 7.8 Hz, 1H), 3.20-3.09 (m, 2H), 2.38 (s, 3H), 2.18-2.08 (m, 1H), 1.80 (dt, J = 15.5, 7.8 Hz, 2H), 1.05-0.91 (m, 7H). Calculated exact mass: 510.15 MS(ESI+): 511.10 for [M + H]+ |
| 171 | 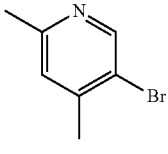 |  | N-(3-(5-(4,6-dimethylpyridin-3-yl)-1H-pyrrolo-[2,3-b]pyridine-3-carbonyl)-2,6-difluorophenyl)-propane-1-sulfonamide C24H22F2N4O3S/ 484.52 | 1H NMR (400 MHz, DMSO-d6) δ 12.94 (s, 1H), 9.65 (s, 1H), 8.41 (d, J = 2.1 Hz, 1H), 8.39 (d, J = 2.1 Hz, 1H), 8.32 (s, 1H), 8.10 (s, 1H), 7.64 (d, J = 7.1 Hz, 1H), 7.34 (t, J = 8.7 Hz, 1H), 7.26 (s, 1H), 3.30 (s, 3H), 3.19-3.10 (m, 2H), 2.26 (s, 3H), 1.87-1.75 (m, 2H), 0.99 (t, J = 7.4 Hz, 3H). |
| 172 | 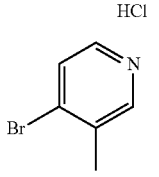 | 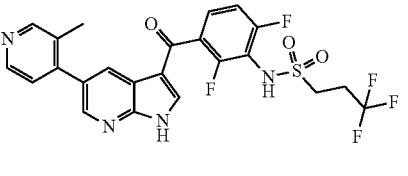 [SMILES: Cc1cnccc1-c1cnc2[nH]cc(C(=O)c3ccc(F)c(NS(=O)(=O)CCC(F)(F)F)c3F)c2c1] | N-(2,6-difluoro-3-(5-(3-methyl-pyridin-4-yl)-1H-pyrrolo[2,3-b]pyridine-3-carbonyl)phenyl)-3,3,3-trifluoro-propane-1-sulfonamide C23H17F5N4O3S/ 524.47 | 1H NMR (600 MHz, DMSO-d6) δ 12.98 (s, 1H), 9.75 (s, 1H), 8.56 (s, 1H), 8.52-8.43 (m, 3H), 8.12 (s, 1H), 7.64 (dd, J = 13.0, 7.5 Hz, 1H), 7.39-7.31 (m, 2H), 3.17-3.10 (m 2H), 2.30 (s, 3H), 1.85-1.76 (m, 2H), 1.00 (t, J = 7.1 Hz, |

TABLE 5-continued

Examples 144-238, prepared in analogy to Examples 141-143.

| Ex. | Reactant | Product | | Analytical Data |
|---|---|---|---|---|
| | | | | 3H). Calculated exact mass: 524.1 MS(ESI⁻): 523.0 for [M − H]⁻. |
| 173 | 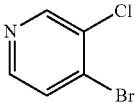 | 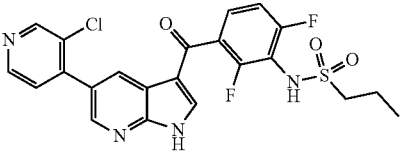 [SMILES: CCCS(=O)(=O)Nc1c(F)ccc(C(=O)c2c[nH]c3ncc(-c4ccncc4Cl)cc23)c1F] | N-(3-(5-(3-chloro-pyridin-4-yl)-1H-pyrrolo[2,3-b]pyridine-3-carbonyl)-2,6-difluorophenyl)-propane-1-sulfonamide C22H17ClF2N4O3S/ 490.91 | ¹H NMR (400 MHz, DMSO-d₆) δ 13.04 (s, 1H), 9.64 (s, 1H), 8.80 (s, 1H), 8.66-8.62 (m, 2H), 8.53 (d, J = 2.1 Hz, 1H), 7.71-7.61 (m, 2H), 7.35 (t, 1H), 3.21-3.10 (m, 2H), 1.87-1.75 (m, 2H), 1.00 (t, J = 7.4 Hz, 3H). Calculated exact mass: 490.07 MS(ESI⁺): 491.00 for [M + H]⁺ |
| 174 | 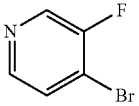 |  | N-(2,6-difluoro-3-(5-(3-fluoropyridin-4-yl)-1H-pyrrolo-[2,3-b]pyridine-3-carbonyl)phenyl)-propane-1-sulfonamide C22H17F3N4O3S/ 474.46 | ¹H NMR (400 MHz, DMSO-d₆) δ 13.03 (s, 1H), 9.65 (s, 1H), 8.77 (s, 1H), 8.72 (d, J = 2.2 Hz, 1H), 8.69 (s, 1H), 8.56 (d, J = 4.8 Hz, 1H), 8.15 (s, 1H), 7.79 (s, 1H), 7.72-7.63 (m, 1H), 7.36 (s, 1H), 3.22-3.10 (m, 2H), 1.89-1.73 (m, 2H), 1.00 (t, J = 7.4 Hz, 3H). Calculated exact mass: 474.10 MS(ESI⁺): 475.00 for [M + H]⁺ |
| 175 | 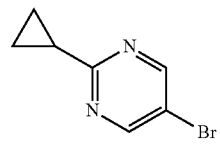 | 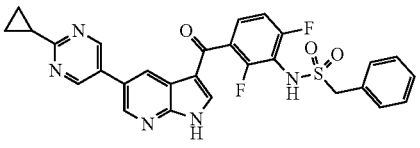 [SMILES: O=C(c1ccc(F)c(NS(=O)(=O)Cc2ccccc2)c1F)c1c[nH]c2ncc(-c3cnc(C4CC4)nc3)cc12] | N-(3-(5-(2-cyclo-propylpyrimidin-5-yl)-1H-pyrrolo-[2,3-b]pyridine-3-carbonyl)-2,6-difluorophenyl)-1-phenylmethane-sulfonamide C28H21F2N5O3S/ 545.56 | ¹H NMR (400 MHz, DMSO-d₆) δ 12.99 (s, 1H), 9.75 (s, 1H), 9.02 (s, 2H), 8.73 (s, 2H), 8.12 (s, 1H), 7.69-7.59 (m, 1H), 7.47-7.42 (m, 2H), 7.41-7.31 (m, 4H), 4.52 (s, 2H), 2.35-2.22 (m, 1H), 1.15-1.02 (m, 4H). Calculated exact mass: 545.13 MS(ESI⁺): 545.95 for [M + H]⁺ |
| 176 | 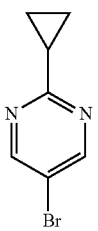 | 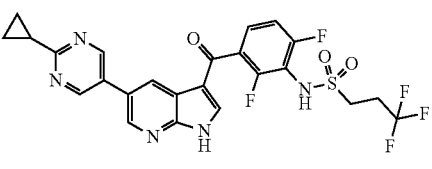 [SMILES: O=C(c1ccc(F)c(NS(=O)(=O)CCC(F)(F)F)c1F)c1c[nH]c2ncc(-c3cnc(C4CC4)nc3)cc12] | N-(3-(5-(2-cyclo-propylpyrimidin-5-yl)-1H-pyrrolo-[2,3-b]pyridine-3-carbonyl)-2,6-difluorophenyl)-3,3,3-trifluoro-propane-1-sulfonamide C24H18F5N5OS/ 551.49 | ¹H NMR (400 MHz, DMSO-d₆) δ 12.97 (d, J = 3.1 Hz, 1H), 10.03 (s, 1H), 9.01 (s, 2H), 8.75-8.68 (m, 2H), 8.14 (d, J = 2.6 Hz, 1H), 7.69 (td, J = 8.2, 6.1 Hz, 1H), 7.39 (t, J = 8.8 Hz, 1H), 3.52-3.43 (m, 2H), 2.84 (dtd, J = 11.6, 8.5, 4.4 Hz, 2H), 2.28 (tt, J = 7.8, 4.9 Hz, 1H), 1.12-1.04 (m, 4H). Calculated exact mass: 551.1 MS(ESI⁻): 550.3 for [M − H]⁻. |

TABLE 5-continued

Examples 144-238, prepared in analogy to Examples 141-143.

| Ex. | Reactant | Product | | Analytical Data |
|---|---|---|---|---|
| 177 | (2-methylamino-5-bromopyrimidine) | (structure) | N-(2,6-difluoro-3-(5-(2-(methylamino)pyrimidin-5-yl)-1H-pyrrolo[2,3-b]pyridine-3-carbonyl)phenyl)-3,3,3-trifluoropropane-1-sulfonamide C22H17F5N6O3S/ 540.47 | $^1$H NMR (400 MHz, DMSO-d$_6$) δ 12.88 (s, 1H), 10.04 (s, 1H), 8.67 (s, 2H), 8.63 (s, 1H), 8.59 (s, 1H), 8.09 (s, 1H), 7.68 (dd, J = 14.2, 7.3 Hz, 1H), 7.38 (t, J = 8.7 Hz, 1H), 7.30 (dd, J = 9.2, 4.7 Hz, 1H), 3.52-3.43 (m, 2H), 2.95-2.77 (m, 5H). Calculated exact mass: 540.1 MS(ESI$^-$): 539.3 for [M − H]$^-$. |
| 178 | (2-dimethylamino-5-bromopyrimidine) | (structure) | N-(3-(5-(2-(dimethylamino)pyrimidin-5-yl)-1H-pyrrolo[2,3-b]pyridine-3-carbonyl)-2,6-difluorophenyl)-3,3,3-trifluoropropane-1-sulfonamide C23H19F5N6O3S/ 554.50 | $^1$H NMR (400 MHz, DMSO-d$_6$) δ 12.89 (d, J = 2.4 Hz, 1H), 10.04 (s, 1H), 8.73 (s, 2H), 8.63 (d, J = 2.1 Hz, 1H), 8.59 (d, J = 2.1 Hz, 1H), 8.09 (d, J = 1.8 Hz, 1H), 7.68 (dd, J = 14.5, 7.8 Hz, 1H), 7.38 (t, J = 8.8 Hz, 1H), 3.52-3.42 (m, 2H), 3.19 (s, 6H), 2.91-2.76 (m, 2H). Calculated exact mass: 554.1 MS(ESI$^-$): 553.4 for [M − H]$^-$. |
| 179 | (2-pyrrolidin-1-yl-5-bromopyrimidine) | (structure) | N-(2,6-difluoro-3-(5-(2-(pyrrolidin-1-yl)pyrimidin-5-yl)-1H-pyrrolo[2,3-b]pyridine-3-carbonyl)phenyl)-3,3,3-trifluoropropane-1-sulfonamide C25H21F5N6O3S/ 580.53 | $^1$H NMR (600 MHz, DMSO-d$_6$) δ 12.95 (s, 1H), 10.47 (s, 1H), 8.72 (s, 2H), 8.62 (d, J = 2.2 Hz, 1H), 8.58 (d, J = 2.2 Hz, 1H), 8.07 (s, 1H), 7.66 (dd, J = 14.4, 7.6 Hz, 1H), 7.37 (t, J = 8.8 Hz, 1H), 3.55 (t, J = 6.6 Hz, 4H), 3.48-3.44 (m, 2H), 2.89-2.79 (m, 2H), 1.99-1.94 (m, 4H). Calculated exact mass: 580.1 MS(ESI$^-$): 579.2 for [M − H]$^-$. |
| 180 | (2-azetidin-1-yl-5-bromopyrimidine) | (structure) | N-(3(5-(2-(azetidin-1-yl)pyrimidin-5-yl)-1H-pyrrolo[2,3-b]pyridine-3-carbonyl)-2,6-difluorophenyl)-3,3,3-trifluoropropane-1-sulfonamide C24H19F5N6O3S/ 566.51 | $^1$H NMR (600 MHz, DMSO-d$_6$) δ 12.89 (s, 1H), 10.03 (s, 1H), 8.72 (s, 2H), 8.62 (d, J = 2.2 Hz, 1H), 8.58 (d, J = 2.2 Hz, 1H), 8.09 (s, 1H), 7.65 (dd, J = 14.3, 7.5 Hz, 1H), 7.36 (t, J = 8.8 Hz, 1H), 4.11 (t, J = 7.5 Hz, 4H), 3.47-3.42 (m, 2H), 2.88-2.78 (m, 2H), 2.38-2.32 (m, 2H). Calculated exact mass: 566.1 MS(ESI$^-$): 565.1 for [M − H]$^-$. |

TABLE 5-continued

Examples 144-238, prepared in analogy to Examples 141-143.

| Ex. | Reactant | Product | Analytical Data |
|---|---|---|---|
| 181 | (structure) | N-(2,6-difluoro-3-(5-(2-(piperidin-1-yl)pyrimidin-5-yl)-1H-pyrrolo[2,3-b]pyridine-3-carbonyl)phenyl)-3,3,3-trifluoropropane-1-sulfonamide C26H23F5N6O3S/ 594.56 | $^{1}$H NMR (600 MHz, DMSO-$d_6$) δ 12.88 (d, J = 2.4 Hz, 1H), 10.03 (s, 1H), 8.72 (s, 2H), 8.64 (d, J = 2.2 Hz, 1H), 8.59 (d, J = 2.1 Hz, 1H), 8.09 (d, J = 2.2 Hz, 1H), 7.67 (dd, J = 14.3, 7.7 Hz, 1H), 7.38 (t, J = 8.8 Hz, 1H), 3.83-3.79 (m, 4H), 3.49-3.44 (m, 2H), 2.88-2.79 (m, 2H), 1.66 (dt, J = 11.5, 5.8 Hz, 2H), 1.58-1.53 (m, 4H). Calculated exact mass: 594.2 MS(ESI$^-$): 593.0 for [M − H]$^-$. |
| 182 | (structure) | N-(3-(5-(2-cyclopropylamino)-pyrimidin-5-yl)-1H-pyrrolo[2,3-b]pyridine-3-carbonyl)-2,6-difluorophenyl)-3,3,3-trifluoropropane-1-sulfonamide C24H19F5N6O3S/ 566.51 | $^{1}$H NMR (600 MHz, DMSO-$d_6$) δ 12.88 (s, 1H), 10.04 (s, 1H), 8.69 (s, 2H), 8.63 (d, J = 2.2 Hz, 1H), 8.60 (d, J = 2.2 Hz, 1H), 8.08 (s, 1H), 7.66 (dd, J = 14.4, 7.7 Hz, 1H), 7.59 (d, J = 3.5 Hz, 1H), 7.37 (t, J = 8.8 Hz, 1H), 3.48-3.44 (m, 2H), 2.88-2.79 (m, 2H), 2.79-2.74 (m, 1H), 0.72-0.68 (m, 2H), 0.53-0.49 (m, 2H). Calculated exact mass: 566.1 MS(ESI$^-$): 565.1 for [M − H]$^-$. |
| 183 | (structure) | N-(3-(5-(2-cyclopropylpyrimidin-5-yl)-1H-pyrrolo[2,3-b]pyridine-3-carbonyl)-2,6-difluorophenyl)-ethanesulfonamide C23H19F2N5O3S/ 483.49 | $^{1}$H NMR (400 MHz, DMSO-$d_6$) δ 12.97 (s, 1H), 9.64 (s, 1H), 9.02 (s, 2H), 8.72 (d, J = 6.0 Hz, 2H), 8.11 (s, 1H), 7.65 (dd, J = 14.5, 7.5 Hz, 1H), 7.35 (t, J = 8.8 Hz, 1H), 3.18 (dd, J = 13.5, 6.2 Hz, 2H), 2.35-2.22 (m, 1H), 1.32 (t, J = 7.2 Hz, 2H), 1.16-1.00 (m, 3H). Calculated exact mass: 483.12 MS(ESI$^+$): 484.40 for [M + H]$^+$ |
| 184 | (structure) | N-(2,6-difluoro-3-(5-(2-(trifluoromethyl)pyrimidin-5-yl)-1H-pyrrolo[2,3-b]pyridine-3-carbonyl)phenyl)-propane-1-sulfonamide C22H16F5N5O3S/ 525.45 | $^{1}$H NMR (400 MHz, DMSO-$d_6$) δ 13.07 (s, 1H), 9.65 (s, 1H), 9.49 (s, 2H), 8.89 (d, J = 6.2 Hz, 2H), 8.17 (s, 1H), 7.67 (dd, J = 14.5 7.5 Hz, 1H), 7.36 (t, J = 8.9 Hz, 1H), 3.22-3.01 (m, 2H), 1.91-1.70 (m, 2H), 1.14-0.83 (m, 3H). Calculated exact mass: 525.09 MS(ESI$^+$): 526.0 for [M + H]$^+$ |

TABLE 5-continued

Examples 144-238, prepared in analogy to Examples 141-143.

| Ex. | Reactant | Product | Analytical Data |
|---|---|---|---|
| 185 | Boc-piperazine-pyrimidine-Br | N-(2,6-difluoro-3-(5-(2-(piperazin-1-yl)pyrimidin-5-yl)-1H-pyrrolo-[2,3-b]pyridine-3-carbonyl)phenyl)-propane-1-sulfonamide C25H25F2N7O3S/ 541.58 | $^1$H NMR (400 MHz, DMSO-$d_6$) δ 12.95 (s, 2H), 9.67 (s, 1H), 8.84 (s, 2H), 8.67 (s, 1H), 8.64 (s, 1H), 8.08 (s, 1H), 7.64 (d, J = 6.7 Hz, 1H), 7.36 (t, J = 8.8 Hz, 1H), 4.12-3.98 (m, 4H), 3.56 (s, 2H), 3.28-3.08 (m, 5H), 1.81 (dd, J = 15.1, 7.5 Hz, 2H), 1.00 (t, J = 7.4 Hz, 3H). Calculated exact mass: 541.17 MS(ESI$^+$): 542.05 for [M + H]$^+$ |
| 186 | 2-methyl-4-chloro-5-bromopyrimidine | N-(3-(5-(4-chloro-2-methylpyrimidin-5-yl)-1H-pyrrolo-[2,3-b]pyridine-3-carbonyl)-2,6-difluorophenyl)-propane-1-sulfonamide C22H18ClF2N5O3S/ 505.92 | $^1$H NMR (400 MHz, DMSO-$d_6$) δ 13.10-12.97 (m, 1H), 9.72-9.59 (m, 1H), 8.84 (s, 1H), 8.62 (d, J = 2.1 Hz, 1H), 8.51 (d, J = 2.1 Hz, 1H), 8.15 (s, 1H), 7.73-7.59 (m, 1H), 7.40-7.29 (m, 1H), 3.21-3.08 (m, 2H), 2.70 (s, 3H), 1.81 (d, J = 7.6 Hz, 2H), 1.00 (t, J = 7.4 Hz, 3H). Calculated exact mass: 505.08 MS(ESI$^+$): 506.0 for [M + H]$^+$ |
| 187 | 2-methoxyethylamino-pyrimidine-Br | N-(2,6-difluoro-3-(5-(2-((2-methoxyethyl)-amino)pyrimidin-5-yl)-1H-pyrrolo-[2,3-b]pyridine-3-carbonyl)phenyl)-propane-1-sulfonamide C24H24F2N6O4S/ 530.55 | $^1$H NMR (400 MHz, DMSO-$d_6$) δ 12.91 (s, 1H), 9.66 (s, 1H), 8.78 (s, 2H), 8.65 (d, J = 2.0 Hz, 1H), 8.61 (s, 1H), 7.71-7.59 (m, J = 6.8 Hz, 1H), 7.35 (t, J = 8.6 Hz, 1H), 3.77 (d, J = 4.6 Hz, 4H), 3.70 (d, J = 4.6 Hz, 4H), 3.20-3.08 (m, 2H), 1.81 (dd, J = 15.0, 7.5 Hz, 2H), 0.99 (t, J = 7.4 Hz, 3H). Calculated exact mass: 530.15 MS(ESI$^+$): 531.10 for [M + H]$^+$ |
| 188 | morpholino-pyrimidine-Br | N-(2,6-difluoro-3-(5-(2-morpholino-pyrimidin-5-yl)-1H-pyrrolo[2,3-b]-pyridine-3-carbonyl)-phenyl)propane-1-sulfonamide C25H24F2N6O4S/ 542.56 | $^1$H NMR (400 MHz, DMSO-$d_6$) δ 12.91 (s, 1H), 9.66 (s, 1H), 8.78 (s, 2H), 8.65 (d, J = 2.0 Hz, 1H), 8.61 (s, 1H), 8.07 (s, 1H), 7.65 (d, J = 6.8 Hz, 1H), 7.35 (t, J = 8.6 Hz, 1H), 3.77 (d, J = 4.6 Hz, 4H), 3.70 (d, J = 4.6 Hz, 4H), 3.22-3.09 (m, 2H), 1.81 (dd, J = 15.0, 7.5 Hz, 2H), 0.99 (t, J = 7.4 Hz, 3H). Calculated exact mass: 542.15 MS(ESI$^+$): 543.10 for [M + H]$^+$ |

TABLE 5-continued

Examples 144-238, prepared in analogy to Examples 141-143.

| Ex. | Reactant | Product | Analytical Data |
|---|---|---|---|
| 189 | | N-(3-(5-(2-cyano-pyrimidin-5-yl)-1H-pyrrolo[2,3-b]pyridine-3-carbonyl)-2,6-difluorophenyl)-propane-1-sulfonamide C22H16F2N6O3S/ 482.47 | $^1$H NMR (400 MHz, DMSO-$d_6$) δ 13.08 (s, 1H), 9.65 (s, 1H), 9.48 (s, 1H), 8.90 (d, J = 7.2 Hz, 1H), 8.17 (s, 1H), 7.72-7.60 (m, 1H), 7.42-7.29 (m, 1H), 3.20-3.08 (m, 2H), 1.81 (d, J = 7.6 Hz, 2H), 1.00 (t, J = 7.4 Hz, 3H). Calculated exact mass: 482.10 MS(ESI$^+$): 483.05 for [M + H]$^+$ |
| 190 | | 5-(3-(2,4-difluoro-3-(propylsulfon-amido)benzoyl)-1H-pyrrolo[2,3-b]pyridin-5-yl)-pyrimidine-2-carboxamide C22H18F2N6O4S/ 500.48 | $^1$H NMR (400 MHz, DMSO-$d_6$) δ 13.05 (s, 1H), 9.66 (s, 1H), 9.35 (s, 2H), 8.86 (d, J = 2.1 Hz, 2H), 8.27 (s, 1H), 8.15 (s, 1H), 7.84 (s, 1H), 7.73-7.62 (m, 1H), 7.36 (t, J = 8.9 Hz, 1H), 3.20-3.11 (m, 2H), 1.81 (dd, J = 15.1, 7.5 Hz, 2H), 1.00 (t, J = 7.4 Hz, 3H). Calculated exact mass: 500.11 MS(ESI$^+$): 501.05 for [M + H]$^+$ |
| 191 | | N-(2,6-difluoro-3-(5-(2-(pyrrolidin-1-yl)pyrimidin-5-yl)-1H-pyrrolo-[2,3-b]pyridine-3-carbonyl)phenyl)-propane-1-sulfonamide C25H24F2N6O3S/ 526.56 | $^1$H NMR (400 MHz, DMSO-$d_6$) δ 12.89 (s, 1H), 9.65 (s, 1H), 8.72 (s, 2H), 8.63 (d, J = 1.9 Hz, 1H), 8.58 (s, 1H), 8.06 (s, 1H), 7.64 (d, J = 7.4 Hz, 1H), 7.35 (t, J = 8.9 Hz, 1H), 3.56 (d, J = 6.4 Hz, 4H), 3.20-3.10 (m, 2H), 1.98 (d, J = 6.3 Hz, 4H), 1.81 (dd, J = 15.1, 7.5 Hz, 2H), 1.00 (t, J = 7.4 Hz, 3H). Calculated exact mass: 526.16 MS(ESI$^+$): 527.05 for [M + H]$^+$ |
| 192 | | N-(2,6-difluoro-3-(5-(2-((3-methoxy-propyl)amino)-pyrimidin-5-yl)-1H-pyrrolo[2,3-b]-pyridine-3-carbonyl)-phenyl)propane-1-sulfonamide C25H26F2N6O4S/ 544.58 | $^1$H NMR (400 MHz, DMSO-$d_6$) δ 12.86 (s, 1H), 9.64 (s, 1H), 8.64 (s, 1H), 8.58 (d, J = 18.8 Hz, 2H), 8.04 (s, 1H), 7.69-7.58 (m, 1H), 7.41-7.27 (m, 2H), 3.48-3.33 (m, 4H), 3.23 (s, 3H), 3.19-3.09 (m, 2H), 1.87-1.72 (m, 4H), 0.98 (t, J = 7.3 Hz, 3H). Calculated exact mass: 544.17 MS(ESI$^+$): 545.05 for [M + H]$^+$ |
| 193 | | N-(2,6-difluoro-3-(5-(2-isopropyl-pyrimidin-5-yl)-1H-pyrrolo[2,3-b]pyridine-3-carbonyl)phenyl)-propane-1-sulfonamide | $^1$H NMR (400 MHz, DMSO-$d_6$) δ 13.00 (s, 1H), 9.66 (s, 1H), 9.13 (s, 2H), 8.75 (d, J = 7.6 Hz, 2H), 8.12 (s, 1H), 7.65 (s, 1H), 7.41-7.30 (m, 1H), 3.26-3.19 (m, 1H), |

TABLE 5-continued

Examples 144-238, prepared in analogy to Examples 141-143.

| Ex. | Reactant | Product | Analytical Data |
|---|---|---|---|
| | | C24H23F2N5O3S/ 499.54 | 3.19-3.07 (m, 2H), 1.93-1.70 (m, 2H), 1.34 (d, J = 6.5 Hz, 6H), 1.00 (d, J = 6.7 Hz, 3H). Calculated exact mass: 499.15 MS(ESI+): 499.99 for [M + H]+. |
| 194 | | N-(2,6-difluoro-3-(5-(2-(4-methyl-piperazin-1-yl)-pyrimidin-5-yl)-1H-pyrrolo[2,3-b]pyridine-3-carbonyl)phenyl)-propane-1-sulfon-amide C26H27F2N7O3S/ 555.60 | $^1$H NMR (400 MHz, DMSO-d$_6$) δ 12.90 (s, 1H), 9.67 (s, 1H), 8.76 (s, 2H), 8.62 (d, J = 17.9 Hz, 2H), 8.06 (s, 1H), 7.72-7.58 (m, 1H), 7.40-7.30 (m, 1H), 3.81 (s, 4H), 3.20-3.10 (m, 2H), 2.43 (s, 3H), 2.26 (s, 2H), 1.90-1.74 (m, 2H), 1.00 (t, J = 7.4 Hz, 3H). Calculated exact mass: 555.19 MS(ESI+): 556.05 for [M + H]+ |
| 195 | | N-(2,6-difluoro-3-(5-(2-(methylthio)-pyrimidin-5-yl)-1H-pyrrolo[2,3-b]pyridine-3-carbonyl)phenyl)-propane-1-sulfon-amide C22H19F2N5O3S2/ 503.54 | $^1$H NMR (400 MHz, DMSO-d$_6$) δ 12.97 (s, 1H), 9.67 (s, 1H), 9.05 (s, 2H), 8.74 (d, J = 3.8 Hz, 2H), 8.11 (s, 1H), 7.61 (d, J = 6.9 Hz, 1H), 7.33 (t, J = 8.9 Hz, 1H), 3.19-3.07 (m, 2H), 2.56 (s, 3H), 1.79 (dt, J = 14.4, 7.2 Hz, 2H), 0.99 (t, J = 7.4 Hz, 3H). Calculated exact mass: 503.09 MS(ESI+): 504.00 for [M + H]+ |
| 196 | | N-(3-(5-(2-(tert-butyl)pyrimidin-5-yl)-1H-pyrrolo-[2,3-b]pyridine-3-carbonyl)-2,6-difluorophenyl)-propane-1-sulfon-amide C25H25F2N5O3S/ 513.56 | $^1$H NMR (400 MHz, DMSO-d$_6$) δ 13.00 (s, 1H), 9.66 (s, 1H), 9.14 (s, 2H), 8.75 (d, J = 7.9 Hz, 2H), 8.12 (s, 1H), 7.66 (dd, J = 14.4, 7.6 Hz, 1H), 7.36 (t, J = 8.9 Hz, 1H), 3.20-3.10 (m, 2H), 1.81 (dd, J = 15.0, 7.5 Hz, 2H), 1.42 (s, 9H), 1.00 (t, J = 7.4 Hz, 2H). Calculated exact mass: 513.16 MS(ESI+): 514.10 for [M + H]+ |
| 197 | | N-(2,6-difluoro-3-(5-(2-(isopropyl-thio)pyrimidin-5-yl)-1H-pyrrolo-[2,3-b]pyridine-3-carbonyl)phenyl)-propane-1-sulfon-amide C24H23F2N5O3S2/ 531.60 | $^1$H NMR (400 MHz, DMSO-d$_6$) δ 13.00 (s, 1H), 9.67 (s, 1H), 9.04 (s, 2H), 8.74 (d, J = 3.3 Hz, 2H), 8.11 (s, 1H), 7.66-7.54 (m, 1H), 7.33 (s, 1H), 4.00-3.90 (m, 1H), 3.18-3.06 (m, 2H), 1.90-1.70 (m, 2H), 1.42 (d, J = 6.7 Hz, 6H), 0.99 (t, J = 7.3 Hz, 3H). Calculated exact mass: 531.12 |

TABLE 5-continued

Examples 144-238, prepared in analogy to Examples 141-143.

| Ex. | Reactant | Product | Analytical Data |
|---|---|---|---|
| 198 | (structure) | N-(2,6-difluoro-3-(5-(2-(4-(2-hydroxyethyl)piperazin-1-yl)pyrimidin-5-yl)-1H-pyrrolo-[2,3-b]pyridine-3-carbonyl)phenyl)-propane-1-sulfonamide C27H29F2N7O4S/ 585.63 | MS(ESI+): 532.0 [M + H]+ $^1$H NMR (400 MHz, DMSO-d$_6$) δ 12.89 (s, 1H), 9.65 (s, 1H), 8.75 (s, 2H), 8.64 (s, 1H), 8.59 (s, 1H), 8.06 (s, 1H), 7.70-7.58 (m, 1H), 7.38-7.28 (m, 1H), 4.52-4.40 (m, 1H), 3.80 (s, 3H), 3.60-3.49 (m, 2H), 3.20-3.10 (m, 2H), 2.46 (s, 2H), 2.41-2.41 (m, 1H), 1.88-1.73 (m, 2H), 1.00 (t, J = 7.4 Hz, 3H). Calculated exact mass: 585.20 MS(ESI+): 586.05 for [M + H]+ |
| 199 | (structure) | N-(3-(5-(2-(azetidin-1-yl)pyrimidin-5-yl)-1H-pyrrolo-[2,3-b]pyridine-3-carbonyl)-2,6-difluorophenyl)-propane-1-sulfonamide C24H22F2N6O3S/ 512.54 | $^1$H NMR (400 MHz, DMSO-d$_6$) δ 12.89 (s, 1H), 9.65 (s, 1H), 8.72 (s, 2H), 8.63 (d, J = 2.1 Hz, 1H), 8.58 (d, J = 2.0 Hz, 1H), 8.06 (s, 1H), 7.64 (dd, J = 14.5, 7.7 Hz, 1H), 7.35 (t, J = 8.8 Hz, 1H), 4.11 (t, J = 7.5 Hz, 4H), 3.20-3.11 (m, 2H), 2.35 (dt, J = 14.7, 7.3 Hz, 2H), 1.82 (dt, J = 15.0, 7.4 Hz, 2H), 1.00 (t, J = 7.4 Hz, 3H) Calculated exact mass; 512.14 MS(ESI+): 513.10 for [M + H]+ |
| 200 | (structure) | N-(3-(5-(2-(3-(dimethylamino)-propoxy)pyrimidin-5-yl)-1H-pyrrolo-[2,3-b]pyridine-3-carbonyl)-2,6-difluorophenyl)-propane-1-sulfonamide C26H28F2N6O4S/ 558.60 | $^1$H NMR (400 MHz, DMSO-d$_6$) δ 12.98-12.89 (m, 1H), 8.98 (s, 2H), 8.77-8.63 (m, 2H), 8.13-8.07 (m, 1H), 7.66-7.56 (m, 1H), 7.36-7.29 (m, 1H), 4.46-4.35 (m, 2H), 3.18-3.07 (m, 2H), 2.46-2.37 (m, 2H), 2.20 (s, 6H), 1.98-1.87 (m, 2H), 1.87-1.74 (m, 2H), 0.99 (s, 3H). Calculated exact mass: 558.19 MS(ESI+): 559.05 for [M + H]+ |
| 201 | (structure) | N-(2,6-difluoro-3-(5-(2-((2-hydroxyethyl)amino)-pyrimidin-5-yl)-1H-pyrrolo[2,3-b]pyridine-3-carbonyl)phenyl)-propane-1-sulfonamide C23H22F2N6O4S/ 516.52 | $^1$H NMR (600 MHz, DMSO-d$_6$) δ 12.88 (d, J = 2.7 Hz, 1H), 9.65 (s, 1H), 8.66 (s, 2H), 8.63 (d, J = 2.2 Hz, 1H), 8.58 (d, J = 2.1 Hz, 1H), 8.05 (d, J = 2.2 Hz, 1H), 7.65 (dd, J = 14.4, 7.7 Hz, 1H), 7.35 (t, J = 8.8 Hz, 1H), 7.27 (s, 1H), 3.56 (t, J = 6.3 Hz, 2H), 3.42 (dd, J = |

TABLE 5-continued

Examples 144-238, prepared in analogy to Examples 141-143.

| Ex. | Reactant | Product | Analytical Data |
|---|---|---|---|
| | | | 9.8, 6.0 Hz, 2H), 3.17-3.14 (m, 2H), 1.85-1.77 (m, 2H), 1.00 (t, J = 7.4 Hz, 3H). Calculated exact mass: 516.1 MS(ESI⁻): 515.0 for [M − H]⁻. |
| 201 | | | N-(2,6-difluoro-3-(5-(2-((2-hydroxyethyl)(methyl)amino)pyrimidin-5-yl)-1H-pyrrolo[2,3-b]pyridine-3-carbonyl)phenyl)propane-1-sulfonamide C24H24F2N6O4S/ 530.55 | ¹H NMR (600 MHz, DMSO-d₆) δ 12.88 (s, 1H), 9.65 (s, 1H), 8.72 (s, 2H), 8.63 (d, J = 2.2 Hz, 1H), 8.58 (d, J = 2.2 Hz, 1H), 8.05 (s, 1H), 7.65 (dd, J = 14.4, 7.7 Hz, 1H), 7.35 (t, J = 8.7 Hz, 1H), 4.73 (t, J = 5.4 Hz, 1H), 3.73 (t, J = 6.2 Hz, 2H), 3.63 (q, J = 6.0 Hz, 2H), 3.21 (s, 3H), 3.18-3.12 (m, 2H), 1.85-1.76 (m, 2H), 1.00 (t, J = 7.4 Hz, 3H). Calculated exact mass: 530.2 MS(ESI⁻): 528.9 for [M − H]⁻. |
| 203 | | | (S)-N-(2,6-difluoro-3-(5-(2-(3-hydroxypyrrolidin-1-yl)pyrimidin-5-yl)-1H-pyrrolo[2,3-b]pyridine-3-carbonyl)phenyl)propane-1-sulfonamide C25H24F2N6O4S/ 542.56 | ¹H NMR (600 MHz, DMSO-d₆) δ 12.88 (s, 1H), 9.65 (s, 1H), 8.72 (s, 2H), 8.63 (d, J = 2.2 Hz, 1H), 8.58 (d, J = 2.1 Hz, 1H), 8.05 (s, 1H), 7.65 (dd, J = 14.4, 7.7 Hz, 1H), 7.35 (t, J = 8.7 Hz, 1H), 4.99 (d, J = 3.5 Hz, 1H), 4.41 (s, 1H), 3.68-3.63 (m, 1H), 3.62-3.56 (m, 2H), 3.51 (d, J = 11.6 Hz, 1H), 3.17-3.14 (m, 2H), 2.07-2.01 (m, 1H), 1.95-1.89 (m, 1H), 1.85-1.77 (m, 2H), 1.00 (t, J = 7.4 Hz, 3H). Calculated exact mass: 542.2 MS(ESI⁻): 540.9 for [M − H]⁻. |
| 204 | | | (R)-N-(2,6-difluoro-3-(5-(2-(3-hydroxypyrrolidin-1-yl)pyrimidin-5-yl)-1H-pyrrolo[2,3-b]pyridine-3-carbonyl)phenyl)propane-1-sulfonamide C25H24F2N6O4S/ 542.56 | ¹H NMR (600 MHz, DMSO-d₆) δ 12.88 (d, J = 2.6 Hz, 1H), 9.65 (s, 1H), 8.72 (s, 2H), 8.63 (d, J = 2.2 Hz, 1H), 8.58 (d, J = 2.0 Hz, 1H), 8.05 (d, J = 2.2 Hz, 1H), 7.65 (dd, J = 14.4, 7.7 Hz, 1H), 7.35 (t, J = 8.8 Hz, 1H), 4.99 (s, 1H), 4.41 (s, 1H), 3.68-3.63 (m, 1H), 3.62-3.56 (m, 2H), 3.51 (d, J = 11.6 Hz, 1H), 3.18-3.14 (m, 2H), 2.04 (dtd, J = 13.2, 8.9, 4.6 Hz, 1H), 1.94-1.89 (m, 1H), 1.85-1.78 (m, |

TABLE 5-continued

Examples 144-238, prepared in analogy to Examples 141-143.

| Ex. | Reactant | Product | | Analytical Data |
|---|---|---|---|---|
| | | | | 2H), 1.00 (t, J = 7.4 Hz, 3H). Calculated exact mass: 542.2 MS(ESI⁻): 540.9 for [M − H]⁻. |
| 205 | 3-hydroxy-1-(5-bromopyrimidin-2-yl)azetidine | | N-(2,6-difluoro-3-(5-(2-(3-hydroxy-azetidin-1-yl)-pyrimidin-5-yl)-1H-pyrrolo[2,3-b]pyridine-3-carbonyl)phenyl)-propane-1-sulfon-amide C24H22F2N6O4S/ 528.53 | $^1$H NMR (600 MHz, DMSO-d$_6$) δ 12.89 (d, J = 2.6 Hz, 1H), 9.65 (s, 1H), 8.72 (s, 2H), 8.63 (d, J = 2.2 Hz, 1H), 8.58 (d, J = 2.1 Hz, 1H), 8.06 (d, J = 2.1 Hz, 1H), 7.64 (dd, J = 14.4, 7.7 Hz, 1H), 7.35 (t, J = 8.7 Hz, 1H), 5.73 (d, J = 6.5 Hz, 1H), 4.63-4.57 (m, 1H), 4.32-4.28 (m, 2H), 3.85 (dd, J = 9.9, 4.5 Hz, 2H), 3.17-3.13 (m, 2H), 1.81 (dq, J = 15.0, 7.5 Hz, 2H), 1.00 (t, J = 7.4 Hz, 3H). Calculated exact mass: 528.1 MS(ESI⁻): 527.1 for [M − H]⁻. |
| 206 | 5-bromo-2-ethylpyrimidine | | N-(3-(5-(2-ethyl-pyrimidin-5-yl)-1H-pyrrolo[2,3-b]pyridine-3-carbonyl)-2,6-difluorophenyl)-propane-1-sulfon-amide C23H21F2N5O3S/ 485.51 | $^1$H NMR (400 MHz, DMSO-d$_6$) δ 12.99 (szzz, 2H), 9.65 (s, 2H), 9.12 (s, 2H), 8.78-8.75 (m, 1H), 8.75-8.72 (m, 1H), 8.12 (s, 1H), 7.69-7.62 (m, 1H), 7.39-7.31 (m, 1H), 3.21-3.10 (m, 2H), 3.04-2.93 (m, 2H), 1.86-1.75 (m, 2H), 1.34 (t, 3H), 1.00 (t, 3H). Calculated exact mass: 485.13 MS(ESI⁺): 486.05 for [M + H]⁺ |
| 207 | 5-bromo-2-(fluoromethyl)pyrimidine | | N-(2,6-difluoro-3-(5-(2-(fluoromethyl)-pyrimidin-5-yl)-1H-pyrrolo[2,3-b]pyridine-3-carbonyl)phenyl)-propane-1-sulfon-amide C22H18F3N5O3S/ 489.47 | $^1$H NMR (400 MHz, DMSO-d$_6$) δ 13.03 (s, 1H), 9.66 (s, 1H), 9.28 (s, 2H), 8.81 (s, 2H), 8.14 (s, 1H), 7.70-7.60 (m, 1H), 7.40-7.32 (m, 1H), 5.61 (d, J = 46.5 Hz, 2H), 3.21-3.07 (m, 2H), 1.91-1.73 (m, 2H), 1.08-0.92 (m, 3H). Calculated exact mass: 489.11 MS(ESI⁺): 490.05 for [M + H]⁺ |
| 208 | 5-bromo-2-((trimethylsilyl)ethynyl)pyrimidine | | N-(3-(5-(2-ethynyl-pyrimidin-5-yl)-1H-pyrrolo[2,3-b]pyridine-3-carbonyl)-2,6-difluorophenyl)-propane-1-sulfon-amide C23H17F2N5O3S/ 481.48 | $^1$H NMR (400 MHz, DMSO-d$_6$) δ 13.04 (s, 1H), 9.66 (s, 1H), 9.24 (s, 2H), 8.82 (s, 2H), 8.15 (s, 1H), 7.66 (d, J = 7.1 Hz, 1H), 7.36 (t, J = 8.8 Hz, 1H), 4.48 (s, 1H), 3.22-3.09 (m, 2H), 1.89-1.74 (m, 2H), 1.00 (t, J = 7.4 |

TABLE 5-continued

Examples 144-238, prepared in analogy to Examples 141-143.

| Ex. | Reactant | Product | Analytical Data |
|---|---|---|---|
| | | | Hz, 3H). Calculated exact mass: 481.10 MS(ESI⁻): 480.0 for [M − H]⁻ |
| 209 | 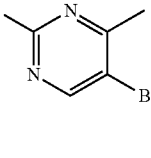 | 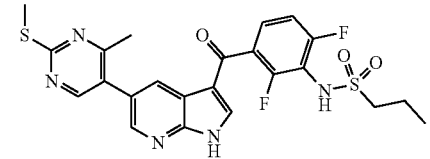 [SMILES: CCCS(=O)(=O)Nc1c(F)ccc(C(=O)c2c[nH]c3ncc(-c4cnc(SC)nc4C)cc23)c1F] N-(2,6-difluoro-3-(5-(4-methyl-2-(methylthio)-pyrimidin-5-yl)-1H-pyrrolo[2,3-b]pyridine-3-carbonyl)phenyl)-propane-1-sulfon-amide C23H21F2N5O3S2/ 517.57 | $^1$H NMR (400 MHz, DMSO-$d_6$) δ 12.97 (s, 1H), 9.64 (s, 1H), 8.53 (s, 1H), 8.48-8.46 (m, 1H), 8.45-8.43 (m, 1H), 8.11 (s, 1H), 7.68-7.58 (m, 1H), 7.34 (t, 1H), 3.19-3.08 (m, 2H), 2.54 (s, 2H), 2.41 (s, 3H), 1.86-1.70 (m, 2M), 0.98 (t, J = 7.4 Hz, 3H). Calculated exact mass: 517.11 MS(ESI⁺): 518.05 for [M + H]⁺ |
| 210 | 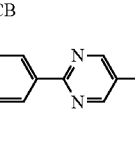 DCB | 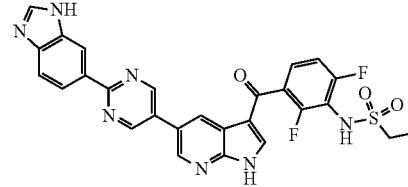 N-(3-(5-(2-(1H-benzo[d]imidazol-6-yl)pyrimidin-5-yl)-1H-pyrrolo-[2,3-b]pyridine-3-carbonyl)-2,6-difluorophenyl)-propane-1-sulfonamide C28H21F2N7O3S/ 573.58 | $^1$H NMR (400 MHz, DMSO-$d_6$) δ 13.02 (s, 1H), 12.70 (s, 1H), 9.30 (s, 2H), 8.85 (d, J = 9.6 Hz, 2H), 8.80-8.63 (m, 1H), 8.47-8.30 (m, 2H), 8.14 (s, 1H), 7.83-7.74 (m, 1H), 7.70-7.62 (m, 1H), 7.40-7.32 (m, 1H), 3.22-3.11 (m, 2H), 1.88-1.72 (m, 2H), 1.00 (t, J = 7.4 Hz, 3H). Calculated exact mass: 573.14 MS(ESI⁺): 574.05 for [M + H]⁺. |
| 211 | 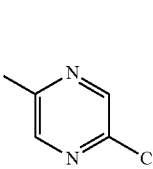 | 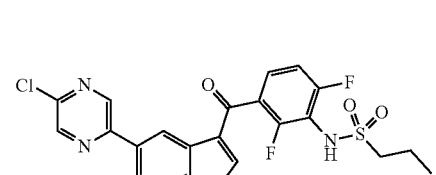 N-(3-(5-(5-chloro-pyrazin-2-yl)-1H-pyrrolo[2,3-b]pyridine-3-carbonyl)-2,6-difluorophenyl)-propane-1-sulfon-amide C21H16ClF2N5O3S/ 491.90 | $^1$H NMR (400 MHz, DMSO-$d_6$) δ 9.25 (d, J = 1.3 Hz, 1H), 9.20 (d, J = 2.2 Hz, 1H), 9.14 (d, J = 2.2 Hz, 1H), 8.92 (d, J = 1.3 Hz, 1H), 8.10 (s, 1H), 7.54-7.44 (m, 1H), 7.30-7.22 (m, 1H), 3.11-2.99 (m, 2H), 1.85-1.72 (m, 2H), 0.98 (t, J = 7.4 Hz, 3H). Calculated exact mass: 491.06 MS(ESI⁺): 492.05 for [M + H]⁺ |
| 212 | 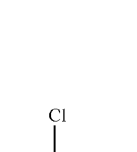 | 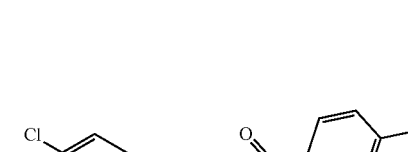 (3-amino-2,4-difluorophenyl)-(5-(4-chloro-phenyl)-1H-pyrrolo[2,3-b]-pyridin-3-yl)-methanone C20H12ClF2N3O/ 383.78 | $^1$H NMR (700 MHz, DMSO-$d_6$) δ 12.81 (s, 1H), 8.67 (d, J = 2.2 Hz, 1H), 8.67 (d, J = 2.2 Hz, 1H), 8.05 (s, 1H), 7.79-7.76 (m, 2H), 7.58-7.55 (m, 2H), 7.03 (t, J = 9.4 Hz, 1H), 6.76 (dd, J = 14.0, 7.6 Hz, 1H), 5.45 (s, 2H). Calculated exact mass: 383.1 MS(ESI⁻): 381.9 for [M − H]⁻. |

TABLE 5-continued

Examples 144-238, prepared in analogy to Examples 141-143.

| Ex. | Reactant | Product | | Analytical Data |
|---|---|---|---|---|
| 213 | 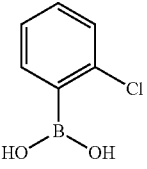 | 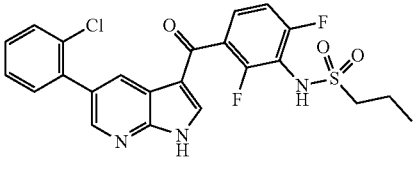 [SMILES: CCCS(=O)(=O)Nc1c(F)ccc(C(=O)c2c[nH]c3ncc(-c4ccccc4Cl)cc23)c1F] | N-(3-(5-(2-chlorophenyl)-1H-pyrrolo[2,3-b]pyridine-3-carbonyl)-2,6-difluorophenyl)-propane-1-sulfonamide C23H18ClF2N3O3S/ 489.92 | $^1$H NMR (700 MHz, DMSO-$d_6$) δ 12.96 (s, 1H), 9.65 (s, 1H), 8.53 (d, J = 2.2 Hz, 1H), 8.44 (d, J = 2.2 Hz, 1H), 8.11 (s, 1H), 7.66 (dd, J = 14.4, 7.7 Hz, 1H), 7.64 (dd, J = 7.4, 1.8 Hz, 1H), 7.55 (dd, J = 7.1, 2.1 Hz, 1H), 7.48 (pd, J = 7.4, 1.7 Hz, 2H), 7.35 (t, J = 8.8 Hz, 1H), 3.17-3.14 (m, 2H), 1.84-1.78 (m, 2H), 1.00 (t, J = 7.4 Hz, 3H). Calculated exact mass: 489.1 MS(ESI$^-$): 487.8 for [M − H]$^-$. |
| 214 | 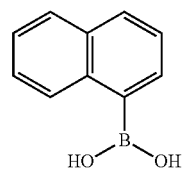 |  | N-(2,6-difluoro-3-(5-(naphthalen-1-yl)-1H-pyrrolo-[2,3-b]pyridine-3-carbonyl)phenyl)-methanesulfonamide C25H17F2N3O3S/ 477.49 | $^1$H NMR (700 MHz, DMSO-$d_6$) δ 12.99 (s, 1H), 9.66 (s, 1H), 8.56 (d, J = 2.0 Hz, 1H), 8.49 (d, 2.0 Hz, 1H), 8.13 (s, 1H), 8.05 (d, J = 8.1 Hz, 1H), 8.03 (d, J = 8.2 Hz, 1H), 7.80 (d, J = 8.4 Hz, 1H), 7.67 (dd, J = 14.4, 7.7 Hz, 1H), 7.64 (dd, J = 8.1, 7.1 Hz, 1H), 7.58 (ddd, J = 8.0, 6.7, 0.9 Hz, 1H), 7.56-7.52 (m, 2H), 7.35 (t, J = 8.8 Hz, 1H), 3.17-3.13 (m, 2H), 1.84-1.78 (m, 2H), 1.00 (t, J = 7.4 Hz, 3H). Calculated exact mass: 505.1 MS(ESI$^-$): 504.0 for [M − H]$^-$. |
| 215 | 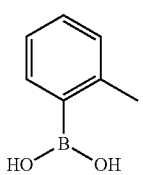 | 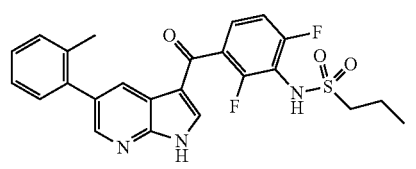 [SMILES: CCCS(=O)(=O)Nc1c(F)ccc(C(=O)c2c[nH]c3ncc(-c4ccccc4C)cc23)c1F] | N-(2,6-difluoro-3-(5-(o-tolyl)-1H-pyrrolo[2,3-b]-pyridine-3-carbonyl)phenyl)-propane-1-sulfonamide C24H21F2N3O3S/ 469.51 | $^1$H NMR (600 MHz, DMSO-$d_6$) δ 13.00 (d, J = 2.0 Hz, 1H), 9.76 (s, 1H), 8.39 (d, J = 2.1 Hz, 1H), 8.35 (s, 1H), 8.24 (d, J = 2.7 Hz, 1H), 7.64-7.53 (m, 2H), 7.37-7.30 (m, 4H), 7.28 (t, J = 8.5 Hz, 1H), 3.15-3.06 (m, 2H), 2.26 (s, 3H), 1.78-1.69 (m, 2H), 0.96 (t, J = 7.4 Hz, 3H). Calculated exact mass: 469.1 MS(ESI$^-$): 468.0 for [M − H]$^-$. |

TABLE 5-continued

Examples 144-238, prepared in analogy to Examples 141-143.

| Ex. | Reactant | Product | Analytical Data |
|---|---|---|---|
| 216 | (4-fluorophenyl)boronic acid | N-(2,6-difluoro-3-(5-(4-fluorophenyl)-1H-pyrrolo[2,3-b]pyridine-3-carbonyl)phenyl)-propane-1-sulfonamide C23H18F3N3O3S/ 473.47 | $^1$H NMR (600 MHz, DMSO-d$_6$) δ 12.89 (s, 1H), 9.65 (s, 1H), 8.67 (d, J = 2.2 Hz, 1H), 8.65 (d, J = 2.2 Hz, 1H), 8.07 (s, 1H), 7.80-7.76 (m, 2H), 7.66 (dd, J = 14.4, 7.7 Hz, 1H), 7.38-7.32 (m, 3H), 3.19-3.12 (m, 2H), 1.85-1.77 (m, 2H), 1.00 (t, J = 7.4 Hz, 3H). Calculated exact mass: 473.1 MS(ESI$^-$): 472.0 for [M − H]$^-$. |
| 217 | (4-fluoro-2-methylphenyl)boronic acid | N-(2,6-difluoro-3-(5-(4-fluoro-2-methylphenyl)-1H-pyrrolo[2,3-b]pyridine-3-carbonyl)phenyl)-propane-1-sulfonamide C24H20F3N3O3S/ 487.50 | $^1$H NMR (600 MHz, DMSO-d$_6$) δ 12.90 (s, 1H), 9.64 (s, 1H), 8.38 (d, J = 2.2 Hz, 1H), 8.35 (d, J = 2.1 Hz, 1H), 8.08 (s, 1H), 7.65 (dd, J = 14.4, 7.7 Hz, 1H), 7.37-7.29 (m, 2H), 7.23 (dd, J = 10.1, 2.6 Hz, 1H), 7.14 (td, J = 8.5, 2.7 Hz, 1H), 3.18-3.12 (m, 2H), 2.26 (s, 3H), 1.85-1.77 (m, 2H), 1.00 (t, J = 7.4 Hz, 3H). Calculated exact mass: 487.1 MS(ESI$^-$): 486.0 for [M − H]$^-$. |
| 218 | (2-chloro-4-methoxyphenyl)boronic acid | N-(3-(5-(2-chloro-4-methoxyphenyl)-1H-pyrrolo[2,3-b]pyridine-3-carbonyl)-2,6-difluorophenyl)-propane-1-sulfonamide C24H20ClF2N3O4S/ 519.95 | H NMR (600 MHz, DMSO-d$_6$) δ 12.91 (s, 1H), 9.64 (s, 1H), 8.49 (d, J = 2.2 Hz, 1H), 8.39 (d, J = 2.2 Hz, 1H), 8.08 (s, 1H), 7.65 (dd, J = 14.4, 7.7 Hz, 1H), 7.46 (d, J = 8.5 Hz, 1H), 7.34 (t, J = 8.8 Hz, 1H), 7.21 (d, J = 2.6 Hz, 1H), 7.07 (dd, J = 8.5, 2.6 Hz, 1H), 3.85 (s, 3H), 3.18-3.13 (m, 2H), 1.85-1.77 (m, 2H), 1.00 (t, J = 7.4 Hz, 3H). Calculated exact mass: 519.1 MS(ESI$^-$): 517.9 for [M − H]$^-$. |
| 219 | (4-(1H-tetrazol-5-yl)phenyl)boronic acid | N-(3-(5-(4-(1H-tetrazol-5-yl)-phenyl)-1H-pyrrolo[2,3-b]-pyridine-3-carbonyl)-2,6-difluorophenyl)-propane-1-sulfonamide C24H19F2N7O3S/ 523.52 | $^1$H NMR (700 MHz, DMSO-d$_6$) δ 12.94 (s, 1H), 9.64 (br. s., 2H), 8.77 (d, J = 1.9 Hz, 1H), 8.75 (d, J = 2.1 Hz, 1H), 8.16 (d, J = 8.0 Hz, 2H), 8.09 (s, 1H), 7.89 (d, J = 8.2 Hz, 2H), 7.67 (dd, J = 14.3, 7.7 Hz, 1H), 7.36 (t, J = 8.7 Hz, 1H), 3.18-3.14 (m, 2H), 1.82 (dq, J = |

TABLE 5-continued

Examples 144-238, prepared in analogy to Examples 141-143.

| Ex. | Reactant | Product | | Analytical Data |
|---|---|---|---|---|
| | | | | 15.0, 7.4 Hz, 2H), 1.00 (t, J = 7.4 Hz, 3H). Calculated exact mass: 523.1 MS(ESI⁻): 522.0 for [M − H]⁻. |
| 220 | 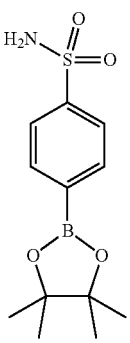 | 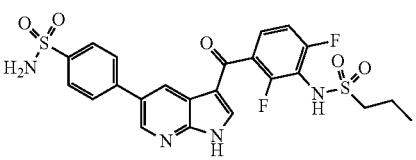 [SMILES: CCCS(=O)(=O)Nc1c(F)ccc(C(=O)c2c[nH]c3ncc(-c4ccc(S(N)(=O)=O)cc4)cc23)c1F] | 4-(3-(2,4-difluoro-3-(propylsulfon-amido)benzoyl)-1H-pyrrolo[2,3-b]pyridin-5-yl)-benzenesulfon-amide C23H20F2N4O5S2/ 534.55 | ¹H NMR (600 MHz, DMSO-d₆) δ 12.96 (s, 1H), 9.65 (s, 1H), 8.77 (d, J = 2.2 Hz, 1H), 8.75 (d, J = 2.2 Hz, 1H), 8.11 (s, 1H), 7.98-7.94 (m, 4H), 7.66 (dd, J = 14.4, 7.7 Hz, 1H), 7.43 (s, 2H), 7.36 (t, J = 8.7 Hz, 1H), 3.18-3.14 (m, 2H), 1.85-1.78 (m, 2H), 1.00 (t, J = 7.4 Hz, 3H). Calculated exact mass: 534.1 MS(ESI⁻): 533.0 for [M − H]⁻. |
| 221 | 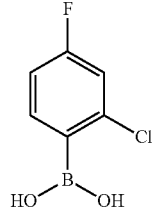 |  | N-(3-(5-(2-chloro-4-fluorophenyl)-1H-pyrrolo[2,3-b]pyridine-3-carbonyl)-2,6-difluorophenyl)-propane-1-sulfon-amide C23H17ClF3N3O3S/ 507.91 | ¹H NMR (700 MHz, DMSO-d₆) δ 12.97 (s, 1H), 9.65 (s, 1H), 8.51 (d, J = 2.2 Hz, 1H), 8.42 (d, J = 2.2 Hz, 1H), 8.11 (s, 1H), 7.68-7.62 (m, 2H), 7.61 (dd, J = 8.5, 6.2 Hz, 1H), 7.39-7.33 (m, 2H), 3.17-3.13 (m, 2H), 1.84-1.78 (m, 2H), 1.00 (t, J = 7.4 Hz, 3H). Calculated exact mass: 507.1 MS(ESI⁻): 506.0 for [M − H]⁻. |
| 222 | 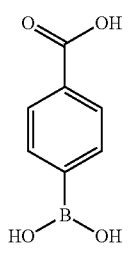 |  | 4-(3-(2,4-difluoro-3-(propylsulfon-amido)benzoyl)-1H-pyrrolo[2,3-b]pyridin-5-yl)-benzoic acid C24H19F2N3O5S/ 499.49 | ¹H NMR (700 MHz, DMSO-d₆) δ 12.96 (s, 2H), 9.66 (s, 1H), 8.77 (d, J = 2.2 Hz, 1H), 8.75 (d, J = 2.2 Hz, 1H), 8.11 (s, 1H), 8.08 (d, J = 8.3 Hz, 2H), 7.89 (d, J = 8.4 Hz, 2H), 7.67 (dd, J = 14.3, 7.7 Hz, 1H), 7.36 (t, J = 8.7 Hz, 1H), 3.18-3.14 (m, 2H), 1.84-1.78 (m, 2H), 1.00 (t, J = 7.4 Hz, 3H). Calculated exact mass: 499.1 MS(ESI⁻): 497.9 for [M − H]⁻. |
| 223 | 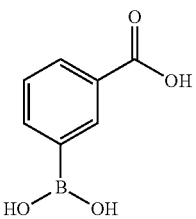 | 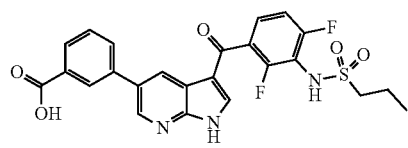 [SMILES: CCCS(=O)(=O)Nc1c(F)ccc(C(=O)c2c[nH]c3ncc(-c4cccc(C(=O)O)c4)cc23)c1F] | 3-(3-(2,4-difluoro-3-(propylsulfon-amido)benzoyl)-1H-pyrrolo[2,3-b]pyridin-5-yl)-benzoic acid C24H19F2N3O5S/ 499.49 | ¹H NMR (600 MHz, DMSO-d₆) δ 13.06 (s, 1H), 9.80 (s, 1H), 8.75 (d, J = 2.2 Hz, 1H), 8.68 (s, 1H), 8.27-8.24 (m, 2H), 8.03 (d, J = 7.7 Hz, 1H), 8.01-7.98 (m, 1H), 7.66 (t, J = 7.7 Hz, 1H), 7.59 (td, J = 9.0, 5.9 Hz, 1H), 7.29 (t, J = 8.3 Hz, |

TABLE 5-continued

Examples 144-238, prepared in analogy to Examples 141-143.

| Ex. | Reactant | Product | | Analytical Data |
|---|---|---|---|---|
| | | | | 1H), 3.14-3.11 (m, 2H), 1.78-1.70 (m, 2H), 0.96 (t, J = 7.4 Hz, 3H). Calculated exact mass: 499.1 MS(ESI⁻): 498.1 for [M − H]⁻. |
| 224 | | | 2-(3-(2,4-difluoro-3-(propylsulfon-amido)benzoyl)-1H-pyrrolo[2,3-b]pyridin-5-yl)-benzoic acid C24H19F2N3O5S/ 499.49 | ¹H NMR (600 MHz, DMSO-d₆) δ 12.98 (s, 1H), 12.89 (s, 1H), 9.76 (s, 1H), 8.40 (s, 1H), 8.35 (d, J = 2.2 Hz, 1H), 8.22 (s, 1H), 7.86 (dd, J = 7.7, 1.1 Hz, 1H), 7.65 (td, J = 7.5, 1.3 Hz, 1H), 7.58 (td, J = 9.0, 5.9 Hz, 1H), 7.55-7.50 (m, 2H), 7.28 (t, J = 8.4 Hz, 1H), 3.14-3.10 (m, 2H), 1.78-1.71 (m, 2H), 0.97 (t, J = 7.4 Hz, 3H). Calculated exact mass: 499.1 MS(ESI⁻): 498.0 for [M − H]⁻. |
| 225 | | | N-(3-(5-(4-chloro-2-methylphenyl)-1H-pyrrolo[2,3-b]pyridine-3-carbonyl)-2,6-difluorophenyl)-propane-1-sulfon-amide C24H20ClF2N3O3S/ 503.95 | ¹H NMR (400 MHz, DMSO-d₆) δ 12.92 (s, 1H), 9.64 (s, 1H), 8.37 (dd, J = 10.3, 2.1 Hz, 2H), 8.09 (s, 1H), 7.69-7.60 (m, 1H), 7.46 (s, 1H), 7.41-7.26 (m, 3H), 3.17-3.11 (m, 2H), 1.81 (dd, J = 15.1, 7.6 Hz, 2H), 1.00 (t, J = 7.4 Hz, 3H). Calculated exact mass 503.09 MS(ESI⁺): 504.05 for [M + H]⁺. |
| 226 | | | N-(3-(5-(2-chloro-4-methoxyphenyl)-1H-pyrrolo[2,3-b]pyridine-3-carbonyl)-2,6-difluorophenyl)-butane-1-sulfon-amide C25H22ClF2N3O4S/ 533.97 | ¹H NMR (600 MHz, DMSO-d₆) δ 12.92 (s, 1H), 9.66 (s, 1H), 8.48 (d, J = 2.1 Hz, 1H), 8.39 (d, J = 2.1 Hz, 1H), 8.08 (s, 1H), 7.65 (dd, J = 14.3, 7.7 Hz, 1H), 7.46 (d, J = 8.5 Hz, 1H), 7.35 (t, J = 8.8 Hz, 1H), 7.21 (d, J = 2.5 Hz, 1H), 7.07 (dd, J = 8.5, 2.6 Hz, 1H), 3.85 (s, 3H), 3.19-3.13 (m, 2H), 1.77 (dt, J = 15.3, 7.7 Hz, 2H), 1.46-1.36 (m, 2H), 0.89 (t, J = 7.4 Hz, 3H). Calculated exact mass: 533.1 MS(ESI⁻): 532.0 for [M − H]⁻. |

TABLE 5-continued

Examples 144-238, prepared in analogy to Examples 141-143.

| Ex. | Reactant | Product | Analytical Data |
|---|---|---|---|
| 227 | (4-fluoro-2-methylphenyl)boronic acid | N-(2,6-difluoro-3-(5-(4-fluoro-2-methylphenyl)-1H-pyrrolo[2,3-b]pyridine-3-carbonyl)phenyl)butane-1-sulfonamide C25H22F3N3O3S/ 501.52 | $^1$H NMR (600 MHz, DMSO-$d_6$) δ 12.90 (s, 1H), 9.64 (s, 1H), 8.38 (d, J = 2.1 Hz, 1H), 8.35 (d, J = 2.1 Hz, 1H), 8.08 (s, 1H), 7.65 (dd, J = 14.4, 7.7 Hz, 1H), 7.36-7.32 (m, 2H), 7.23 (dd, J = 10.1, 2.6 Hz, 1H), 7.14 (td, J = 8.5, 2.7 Hz, 1H), 3.19-3.13 (m, 2H), 2.26 (s, 3H), 1.80-1.73 (m, 2H), 1.45-1.37 (m, 2H), 0.89 (t, J = 7.4 Hz, 3H). Calculated exact mass: 501.1 MS(ESI$^-$): 500.1 for [M − H]$^-$. |
| 228 | pyridin-3-ylboronic acid | N-(2,6-difluoro-3-(5-(pyridin-3-yl)-1H-pyrrolo[2,3-b]pyridine-3-carbonyl)phenyl)methanesulfonamide C20H14F2N4O3S/ 428.41 | $^1$H NMR (400 MHz, DMSO-$d_6$) δ 12.96 (s, 1H), 9.74 (s, 1H), 8.82-8.68 (m, 2H), 8.63 (d, J = 3.8 Hz, 1H), 8.18 (d, J = 7.9 Hz, 1H), 8.12 (s, 1H), 7.65 (dd, J = 14.2, 7.4 Hz, 1H), 7.55 (dd, J = 7.8, 4.7 Hz, 1H), 7.36 (t, J = 8.8 Hz, 1H), 3.11 (s, 3H). Calculated exact mass: 428.08 MS(ESI$^+$): for [M + H]$^+$ |
| 229 | (6-methylpyridin-3-yl)boronic acid | N-(2,6-difluoro-3-(5-(6-methylpyridin-3-yl)-1H-pyrrolo[2,3-b]pyridine-3-carbonyl)phenyl)propane-1-sulfonamide C23H20F2N4O3S/ 470.49 | $^1$H NMR (400 MHz, DMSO-$d_6$) δ 12.90 (s, 1H), 9.63 (s, 1H), 8.78 (s, 1H), 8.66 (d, J = 12.0 Hz, 2H), 8.06 (s, 1H), 8.05-8.00 (m, 1H), 7.68-7.58 (m, 1H), 7.40-7.28 (m, 2H), 3.19-3.06 (m, 2H), 2.51 (s, 3H), 1.78 (d, J = 7.6 Hz, 2H), 0.96 (t, J = 7.4 Hz, 3H). Calculated exact mass: 470.12 MS(ESI$^+$): 471.10 for [M + H]$^+$ |
| 230 | (6-(trifluoromethyl)pyridin-3-yl)boronic acid | N-(2,6-difluoro-3-(5-(6-(trifluoromethyl)pyridin-3-yl)-1H-pyrrolo[2,3-b]pyridine-3-carbonyl)phenyl)propane-1-sulfonamide C23H17F5N4O3S/ 524.47 | $^1$H NMR (400 MHz, DMSO-$d_6$) δ 13.03 (s, 1H), 9.66 (s, 1H), 9.19 (s, 1H), 8.82 (dd, J = 9.2, 2.0 Hz, 2H), 8.49 (d, J = 8.1 Hz, 1H), 8.15 (s, 1H), 8.04 (d, J = 8.2 Hz, 1H), 7.67 (dd, J = 14.5, 7.6 Hz, 1H), 7.36 (t, J = 8.8 Hz, 1H), 3.21-3.11 (m, 2H), 1.81 (dq, J = 14.6, 7.2 Hz, 2H), 1.00 (t, J = 7.4 Hz, 3H). Calculated exact mass: 524.09 |

TABLE 5-continued

Examples 144-238, prepared in analogy to Examples 141-143.

| Ex. | Reactant | Product | Analytical Data |
|---|---|---|---|
| | | | MS(ESI$^+$): 525.00 for [M + H]$^+$ |
| 231 | pyridin-4-yl boronic acid | N-(2,6-difluoro-3-(5-(pyridin-4-yl)-1H-pyrrolo[2,3-b]pyridine-3-carbonyl)phenyl)ethanesulfonamide C21H16F2N4O3S/ 442.44 | $^1$H NMR (600 MHz, DMSO-d$_6$) δ 13.00 (s, 1H), 9.66 (s, 1H), 8.83 (d, J = 2.2 Hz, 1H), 8.80 (d, J = 2.3 Hz, 1H), 8.68 (d, J = 4.8 Hz, 2H), 8.12 (s, 1H), 7.81 (dd, J = 4.6, 1.5 Hz, 2H), 7.67 (dd, J = 14.4, 7.7 Hz, 1H), 7.36 (t, J = 8.8 Hz, 1H), 3.19 (q, J = 7.3 Hz, 2H), 1.33 (t, J = 7.3 Hz, 3H). Calculated exact mass: 442.1 MS(ESI$^-$): 441.1 for [M − H]$^-$. |
| 232 | pyridin-3-yl B(OH)$_2$ | N-(2,6-difluoro-3-(5-(pyridin-3-yl)-1H-pyrrolo[2,3-b]pyridine-3-carbonyl)phenyl)propane-1-sulfonamide C22H18F2N4O3S/ 456.47 | $^1$H NMR (400 MHz, dmso) δ 12.96 (s, 1H), 9.81 (s, 1H), 8.96 (s, 1H), 8.73 (dd, J = 11.4, 2.1 Hz, 2H), 8.66-8.60 (m, 1H), 8.18 (d, J = 7.9 Hz, 1H), 8.11 (s, 1H), 7.63 (dd, J = 14.5, 7.5 Hz, 1H), 7.55 (dd, J = 7.7, 4.9 Hz, 1H), 7.34 (t, J = 8.9 Hz, 1H), 3.19-3.08 (m, 2H), 1.80 (dq, J = 14.9, 7.4 Hz, 2H), 0.99 (t, J = 7.4 Hz, 3H). Calculated exact mass: 456. MS(ESI$^+$): 457.00 for [M + H]$^+$. |
| 233 | pyridin-4-yl B(OH)$_2$ | N-(2,6-difluoro-3-(5-(pyridin-4-yl)-1H-pyrrolo[2,3-b]pyridine-3-carbonyl)phenyl)propane-1-sulfonamide C22H18F2N4O3S/ 456.47 | $^1$H NMR (400 MHz, dmso) δ 13.07-12.84 (m, 1H), 10.05-9.75 (m, 1H), 8.82 (dd, J = 9.5, 2.2 Hz, 2H), 8.68 (d, J = 5.9 Hz, 2H), 8.13 (s, 1H), 7.82 (d, J = 6.0 Hz, 2H), 7.64 (dd, J = 14.5, 7.5 Hz, 1H), 7.35 (t, J = 8.7 Hz, 1H), 3.18-3.11 (m, 2H), 1.81 (dd, J = 15.1, 7.6 Hz, 2H), 0.99 (t, J = 7.4 Hz, 3H). Calculated exact mass: 456.11 MS(ESI$^+$): 457.1 for [M + H]$^+$. |
| 234 | pyridin-4-yl boronic acid | N-(2,6-difluoro-3-(5-(pyridin-4-yl)-1H-pyrrolo[2,3-b]pyridine-3-carbonyl)phenyl)methanesulfonamide C20H14F2N4O3S/ 428.41 | $^1$H NMR (400 MHz, DMSO-d$_6$) δ 13.00 (s, 1H), 9.73 (s, 1H), 8.82 (dd, J = 7.0, 2.2 Hz, 2H), 8.76-8.57 (m, 2H), 8.14 (s, 1H), 7.82 (dd, J = 4.6, 1.5 Hz, 2H), 7.65 (dd, J = 14.4, 7.7 Hz, 1H), |

TABLE 5-continued

Examples 144-238, prepared in analogy to Examples 141-143.

| Ex. | Reactant | Product | | Analytical Data |
|---|---|---|---|---|
| | | | | 7.35 (t, J = 8.8 Hz, 1H), 3.10 (s, 3H). |
| 235 | 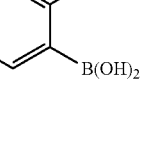 | 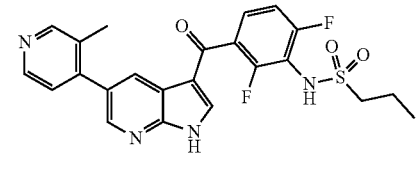 [SMILES: CCCS(=O)(=O)Nc1c(F)ccc(C(=O)c2c[nH]c3ncc(-c4ccncc4C)cc23)c1F] | N-(2,6-difluoro-3-(5-(3-methyl-pyridin-4-yl)-1H-pyrrolo[2,3-b]pyridine-3-carbonyl)phenyl)-propane-1-sulfon-amide C23H20F2N4O3S/ 470.49 | 1H NMR (400 MHz, DMSO-d6) δ 12.96 (s, 1H), 9.66 (s, 1H), 8.52 (d, J = 4.1 Hz, 1H), 8.44 (d, J = 4.3 Hz, 2H), 8.11 (s, 1H), 7.73 (d, J = 7.4 Hz, 1H), 7.66 (dd, J = 14.3, 7.5 Hz, 1H), 7.40-7.31 (m, 2H), 3.21-3.10 (m, 2H), 2.46 (s, 3H), 1.81 (dd, J = 15.0, 7.4 Hz, 2H), 1.00 (t, J = 7.4 Hz, 3H). Calculated exact mass: 470.12 MS(ESI+): 471.0 for [M + H]+ |
| 236 | 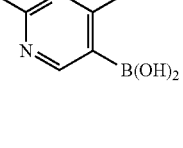 |  | N-(3-(5-(2,4-dimethoxy-pyrimidin-5-yl)-1H-pyrrolo[2,3-b]pyridine-3-carbonyl)-2,6-difluorophenyl)-propane-1-sulfon-amide C23H21F2N5O5S/ 517.51 | 1H NMR (400 MHz, DMSO-d6) δ 12.91 (s, 1H), 9.65 (s, 1H), 8.57 (d, J = 1.6 Hz, 1H), 8.50 (d, J = 1.9 Hz, 1H), 8.47 (s, 1H), 8.08 (s, 1H), 7.65 (d, J = 6.9 Hz, 1H), 7.35 (t, J = 8.8 Hz, 1H), 3.97 (s, 6H), 3.20-3.10 (m, 2H), 1.80 (dd, J = 15.1, 7.5 Hz, 2H), 0.99 (t, J = 7.4 Hz, 3H). Calculated exact mass: 517.12 MS(ESI+): 518.0 for [M + H]+ |
| 237 | 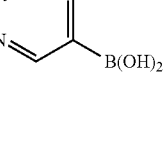 |  | N-(3-(5-(2-chloro-pyrimidin-5-yl)-1H-pyrrolo[2,3-b]pyridine-3-carbonyl)-2,6-difluorophenyl)-propane-1-sulfon-amide C21H16ClF2N5O3S/ 491.90 | 1H NMR (400 MHz, DMSO-d6) δ 13.02 (s, 1H), 9.64 (s, 1H), 9.23 (d, J = 26.5 Hz, 2H), 8.76 (t, J = 15.3 Hz, 2H), 8.13 (s, 1H), 7.64 (dd, J = 14.4, 7.6 Hz, 1H), 7.34 (t, J = 8.8 Hz, 1H), 3.15 (dd, J = 14.6, 7.1 Hz, 2H), 1.78 (dt, J = 14.8, 7.4 Hz, 2H), 0.98 (t, J = 7.4 Hz, 3H). Calculated exact mass: 491.06 MS(ESI+): 492.00 for [M + H]+ |
| 238 | 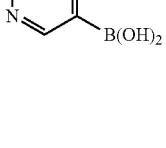 | 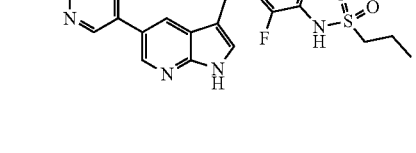 | N-(2,6-difluoro-3-(5-(2-methoxy-pyrimidin-5-yl)-1H-pyrrolo[2,3-b]pyridine-3-carbonyl)phenyl)-propane-1-sulfon-amide C22H19F2N5O4S/ 487.48 | 1H NMR (400 MHz, DMSO-d6) δ 12.95 (s, 1H), 9.64 (s, 1H), 8.99 (s, 2H), 8.69 (d, J = 5.4 Hz, 2H), 8.09 (s, 1H), 7.64 (dd, J = 14.1, 7.4 Hz, 1H), 7.34 (t, J = 8.8 Hz, 1H), 4.00 (d, J = 20.7 Hz, 2H), 3.20-3.06 (m, 2H), 1.79 (dd, J = 15.0, 7.5 Hz, 2H), 0.98 (t, J = 7.3 Hz, 3H). Calculated |

TABLE 5-continued

Examples 144-238, prepared in analogy to Examples 141-143.

| Ex. | Reactant | Product | Analytical Data |
|---|---|---|---|
| | | | exact mass: 487.11<br>MS(ESI+): 488.00<br>for [M + H]+ |

Example 239: Synthesis of N-(3-(5-cyclobutyl-1H-pyrrolo[2,3-b]pyridine-3-carbonyl)-2,6-difluorophenyl)propane-1-sulfonamide Example 240: Synthesis of N-(2,6-difluoro-3-(5-(pyridin-4-yl)-1H-pyrrolo[2,3-b]pyridine-3-carbonyl)phenyl)-1-phenylethanesulfonamide

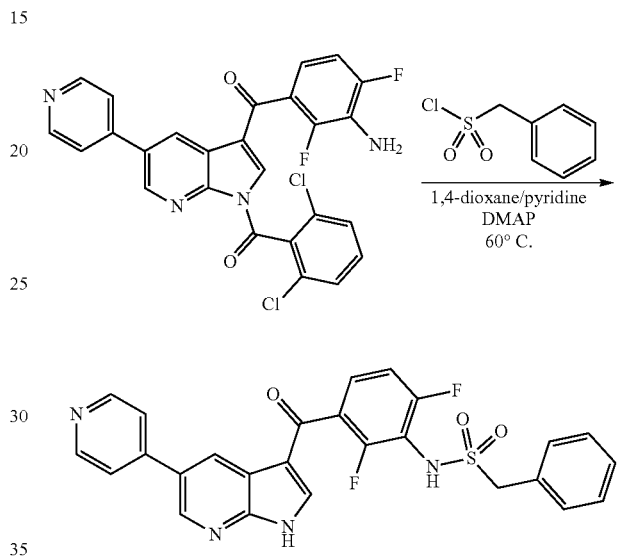

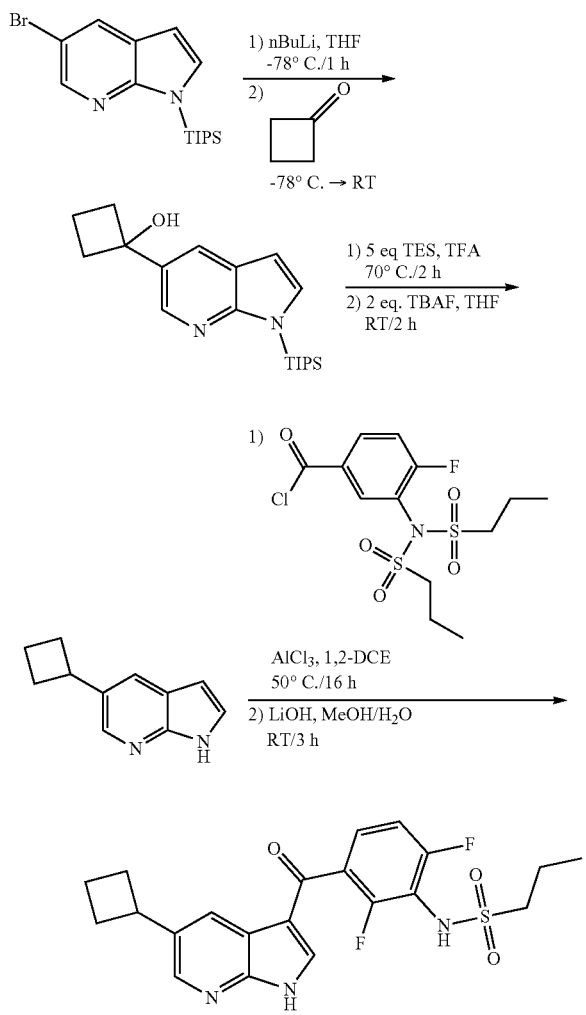

To a solution of (3-amino-2,4-difluorophenyl)-[1-(2,6-dichlorobenzoyl)-5-pyridin-4-ylpyrrolo[2,3-b]pyridin-3-yl]methanone (0.200 g, 0.382 mmol) in 1,4-dioxane (0.637 mL) and pyridine (0.637 mL) was added phenylmethanesulfonyl chloride (0.109 g, 0.573 mmol) and 4-Dimethylaminopyridine (0.00467 g, 0.0382 mmol) successively. The mixture was stirred at 60° C. until TLC revealed completion of the reaction. The crude was diluted with EtOAc (50 ml) and washed with 1M HCl (aq., 20 ml) twice. The organic phase was dried over sodium sulfate and the solvent was removed in vacuo. The product was purified applying flash chromatography using DCM/MeOH (0-5%) as eluent. N-[2,6-difluoro-3-(5-pyridin-4-yl-1H-pyrrolo[2,3-b]pyridine-3-carbonyl)phenyl]-1-phenylmethanesulfonamide (0.0840 g, 0.1550 mmol, 41% yield) was obtained as a off white solid (yield: 84 mg (40%), chemical purity (HPLC/UV): 93%).

Analytical Data:

$^1$H NMR (600 MHz, DMSO-d$_6$) δ 13.01 (s, 1H), 9.75 (s, 1H), 8.83 (dd, J=5.4, 2.2 Hz, 2H), 8.68 (dd, J=4.5, 1.6 Hz, 2H), 8.14 (s, 1H), 7.82 (dd, J=4.5, 1.6 Hz, 2H), 7.68 (dd, J=14.4, 7.7 Hz, 1H), 7.45 (dd, J=7.8, 1.5 Hz, 2H), 7.41-7.35 (m, 4H), 4.54 (s, 2H).

Calculated exact mass: 504.1 for C$_{26}$H$_{18}$F$_2$N$_4$O$_3$S (molecular weight: 504.51) MS(ESI$^-$): 503.2 for [M−H]$^-$.

Analytical Data:

$^1$H NMR (400 MHz, DMSO-d$_6$) δ 12.69 (s, 1H), 9.65 (s, 1H), 8.36 (s, 1H), 8.27 (s, 1H), 7.96 (s, 1H), 7.70-7.56 (m, 1H), 7.33 (t, J=8.9 Hz, 1H), 3.80-3.60 (m, 1H), 3.20-3.11 (m, 2H), 2.44-2.29 (m, 3H), 2.25-2.11 (m, 2H), 2.10-1.97 (m, 1H), 1.88 (d, J=9.1 Hz, 1H), 1.81 (dd, J=15.2, 7.6 Hz, 2H), 1.00 (t, J=7.4 Hz, 3H).

Calculated exact mass: 433.13 for C$_{21}$H$_{21}$F$_2$N$_3$O$_3$S (molecular weight: 433.47)

MS(ESI$^+$): 434.2 for [M+H]$^+$

Examples 241 and 242: Synthesis of N-(2,4-difluoro-3-(5-(piperidin-4-yl)-1-pyrrolo[2,3-b]pyridine-3-carbonyl)phenyl)propane-1-sulfonamide and N-(2,4-difluoro-3-(5-(1,2,3,4-tetrahydropyridin-4-yl)-1-pyrrolo[2,3-b]pyridine-3-carbonyl)phenyl)propane-1-sulfonamide

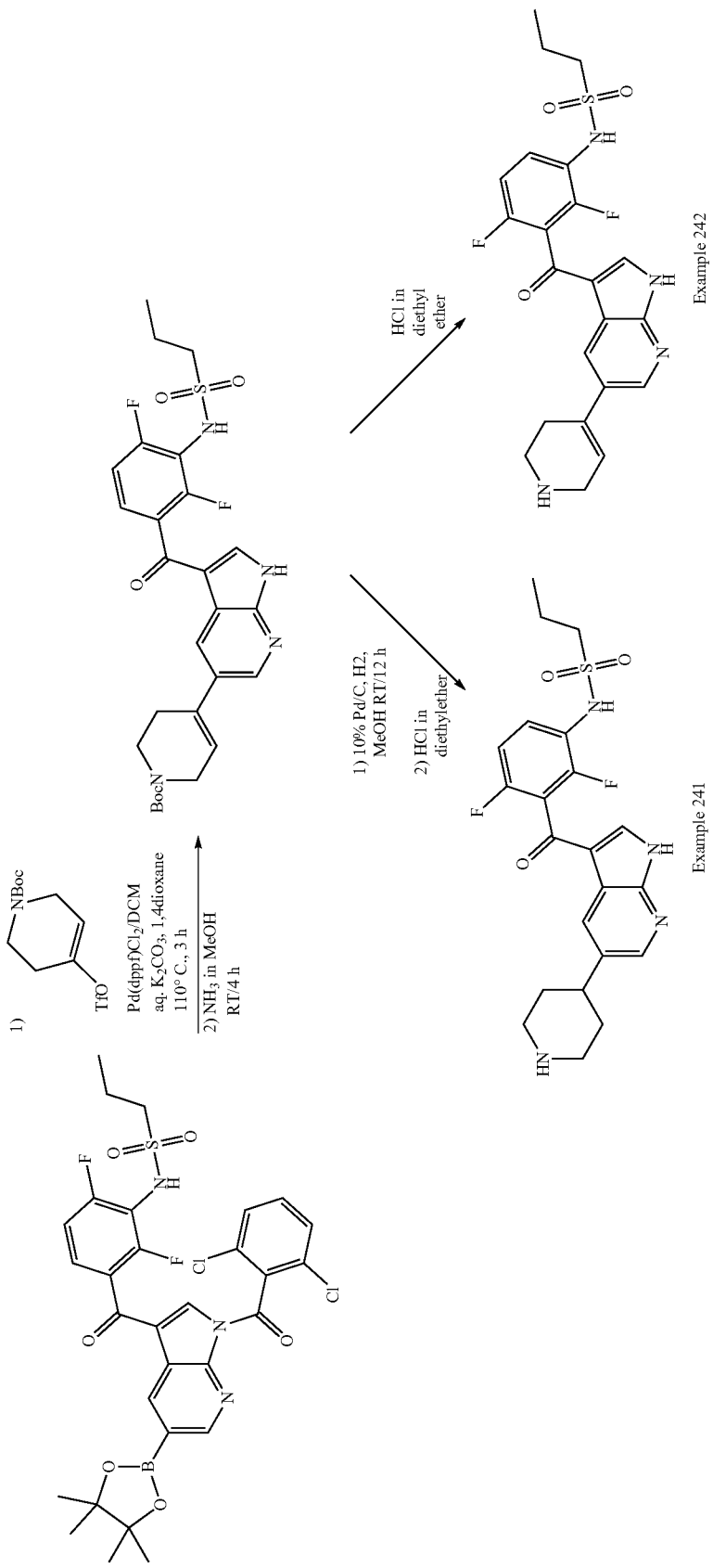

Analytical Data:

Example 241:

1H NMR (400 MHz, DMSO-d6) δ 8.36-8.32 (m, 1H), 8.32-8.29 (m, 1H), 8.09 (s, 1H), 7.56-7.48 (m, 1H), 7.20-7.13 (m, 1H), 3.06-2.99 (m, 3H), 2.98-2.84 (m, 4H), 1.99-1.89 (m, 2H), 1.89-1.78 (m, 2H), 1.77-1.66 (m, 2H), 0.95 (t, J=7.4 Hz, 3H).

Calculated exact mass: 460.14 for C22H24F2N4O3S (molecular weight: 462.52)

MS(ESI+): 463.20 for [M+H]+

Example 242:

$^1$H NMR (400 MHz, DMSO-$d_6$) δ 8.54 (d, J=1.9 Hz, 1H), 8.41 (s, 1H), 8.31 (s, 1H), 8.14 (s, 1H), 7.61 7.49 (m, 1H), 7.22 (t, J=8.7 Hz, 1H), 6.28 (s, 1H), 3.61 (s, 2H), 3.18 (t, J=5.6 Hz, 2H), 3.12-3.02 (m, 2H), 2.62 (s, 2H), 1.73 (dd, J=15.2, 7.6 Hz, 2H), 0.95 (t, J=7.4 Hz, 3H).

Calculated exact mass: 460.14 for C22H22F2N4O3S (molecular weight: 460.50)

MS(ESI$^+$): 461.20 for [M+H]$^+$.

Example 243: Biological Activity

Example 243-1: Binding Assays

The kinase activities of the compounds of the invention were measured using KINOMEscan™ Profiling Service at DiscoveRx Corporation, 42501 Albrae St. Fremont, CA 94538, USA which is based on a competition binding assay that quantitatively measures the ability of a compound to compete with an immobilized, active-site directed ligand. The assay was performed by combining three components: DNA-tagged kinase; immobilized ligand; and a test compound. The ability of the test compound to compete with the immobilized ligand was measured via quantitative PCR of the DNA tag. The technology is described in detail in Fabian, M. A. et al. A small molecule-kinase interaction map for clinical kinase inhibitors. Nat. Biotechnol., 23, 329-336 (2005) and in Karaman, M. W. et al. A quantitative analysis of kinase inhibitor selectivity. Nat. Biotechnol., 26, 127-132 (2008).

For investigation of the affinity to MKK4, BRaf, MKK7 and JNK1, the kinases were produced in HEK-293 cells and subsequently tagged with DNA for qPCR detection. Streptavidin-coated magnetic beads were treated with biotinylated small molecule ligands for 30 minutes at RT to generate affinity resins for kinase assays. The liganded beads were blocked with excess biotin and washed with blocking buffer (SEABLOCK™ (Pierce), 1% BSA, 0.05% TWEEN®20, 1 mM DTT) to remove unbound ligand and to reduce non-specific binding. Binding reactions were assembled by combining kinases, liganded affinity beads, and test compounds in 1× binding buffer (20% SEABLOCK™, 0.17×PBS, 0.05% TWEEN®20, 6 mM DTT). All reactions were performed in polystyrene 96-well plates in a final volume of 0.135 mL. The assay plates were incubated at RT with shaking for 1 hour and the affinity beads were washed with wash buffer (1×PBS, 0.05% TWEEN®20). The beads were then re-suspended in elution buffer (1×PBS, 0.05% EEN®20, 0.5 11M non-biotinylated affinity ligand) and incubated at RT with shaking for 30 minutes. The kinase concentration in the eluates was measured by qPCR.

Average Z' values and standard deviations were calculated for each kinase based on fourteen control wells per experiment in over 135 independent experiments spanning a period of sixteen months. Average Z'=0.71.

Potency of Test Compounds:

The compounds were screened at the indicated concentrations and results for binding interactions are reported as [% of control], where lower numbers indicate stronger binding, i.e. higher potency.

Details regarding the kinases tested are given in table 6 below.

The test compounds were provided as 10 mM stock solutions. The test solutions at indicated final concentrations were prepared at DiscoverX. The results are given in table 7.

TABLE 6

|  | BRaf | MKK4 | MKK7 | JNK1 |
|---|---|---|---|---|
| Group |  | STE | STE | CMCG |
| Kinase Construct |  | Partial Length | Full Length | Full length |
| Accession Number |  | NP_003001.1 | NP_660186.1 | NP_002741.1 |
| Species |  | Human | Human | Human |
| Kinase Form |  | Wild Type | Wild Type | Wild Type |
| Expression System |  | Mammalian | Mammalian | Mammalian |
| Amino Acid Start/Stop |  | S84/D399 | M1/R419 | M1/Q384 |
| Average Z' Panel |  | 0.67 | 0.78 | 0.79 |

Binding Affinity to MKK4 and Selectivity against BRaf, MKK7 and JNK1

Potency of representative examples against the protein kinases MKK4, BRaf, MKK7 and JNK1 expressed as residual percent of control binding (PoC), was determined at a concentration of 100 nM. The determined potencies are categorized as follows:

| PoC @ 100 nM | category |
|---|---|
| PoC < 1 | +++ |
| 1 ≤ PoC < 3 | ++ |
| 3 ≤ PoC < 30 | + |
| 30 ≤ PoC | ◯ |

The binding selectivity of representative examples against the protein kinases BRaf, MKK7 and JNK1, altogether denominated as "off-targets" is determined by the ratios of PoC (off-target)/PoC (MKK4). The ratios are categorized as follows:

| Ratio | category |
|---|---|
| Ratio > 100 | +++ |
| 100 ≥ ratio > 10 | ++ |
| 10 ≥ ratio > 3 | + |
| 3 ≥ Ratio | ◯ |

TABLE 7

Binding affinity of representative Examples to MKK4 and selectivity against BRaf, MKK7 and JNK1, based on binding affinities, expressed as % of control.

| Example | MKK4 [% Ctrl @ 100 nM] | selectivity based on % Ctrl @100 nM vs. Braf | vs. MKK7 | vs. JNK1 |
|---|---|---|---|---|
| 2b | ○ | ○ | ○ | ○ |
| 2c | +++ | +++ | +++ | +++ |
| 2d | + | + | + | + |
| 2f | + | ○ | + | + |
| 13 | ○ | ○ | ○ | ○ |
| 14 | ○ | ○ | ○ | ○ |
| 15 | ○ | ○ | ○ | ○ |
| 16 | ○ | ○ | ○ | ○ |
| 17 | ○ | ○ | ○ | ○ |
| 18 | + | ○ | + | + |
| 19 | + | ++ | ++ | ++ |
| 20 | + | + | ++ | ++ |
| 21 | ++ | ++ | ++ | ++ |
| 22 | + | ○ | ++ | ++ |
| 23 | + | ○ | ++ | + |
| 24 | + | ○ | ++ | + |
| 25 | + | ○ | + | + |
| 26 | ++ | ++ | ++ | ++ |
| 27 | +++ | +++ | +++ | +++ |
| 28 | ++ | ++ | ++ | ++ |
| 29 | + | ○ | ++ | ++ |
| 30 | +++ | ++ | +++ | +++ |
| 31 | +++ | ○ | +++ | +++ |
| 32 | + | ○ | + | + |
| 33 | + | ++ | ++ | ++ |
| 34 | + | ++ | ++ | ++ |
| 35 | +++ | + | +++ | +++ |
| 36 | ++ | ++ | ++ | ++ |
| 37 | + | + | + | + |
| 38 | + | + | + | + |
| 39 | + | + | ++ | ++ |
| 40 | +++ | +++ | +++ | +++ |
| 41 | ++ | ++ | ++ | ++ |
| 42 | + | + | + | + |
| 43 | + | + | + | + |
| 44 | + | ++ | ++ | ++ |
| 45 | +++ | + | +++ | +++ |
| 46 | +++ | +++ | +++ | +++ |
| 47 | ++ | + | ++ | ++ |
| 48 | + | ○ | ++ | ++ |
| 49 | +++ | ○ | +++ | +++ |
| 50 | +++ | ○ | +++ | +++ |
| 51 | + | ○ | + | ○ |
| 52 | + | ○ | ++ | ++ |
| 53 | +++ | + | +++ | +++ |
| 58 | +++ | ++ | +++ | +++ |
| 59 | +++ | ○ | +++ | +++ |
| 60 | + | ++ | ++ | ++ |
| 61 | ○ | ○ | + | + |
| 62 | ○ | ○ | ○ | ○ |
| 63 | ○ | ○ | ○ | ○ |
| 64 | ○ | ○ | ○ | ○ |
| 65 | ○ | ○ | ○ | ○ |
| 66 | ○ | ○ | ○ | ○ |
| 67 | ○ | ○ | ○ | ○ |
| 68 | + | ○ | + | + |
| 69 | + | ++ | ++ | ++ |
| 77 | +++ | ○ | +++ | +++ |
| 79 | +++ | +++ | +++ | +++ |
| 81 | +++ | +++ | +++ | +++ |
| 82 | +++ | +++ | +++ | +++ |
| 83 | +++ | ○ | +++ | +++ |
| 84 | +++ | ○ | +++ | +++ |
| 85 | + | ○ | ++ | ++ |
| 86 | + | ○ | ++ | ++ |
| 87 | ○ | ○ | ○ | ○ |
| 88 | +++ | + | +++ | +++ |
| 100 | + | ○ | ++ | ++ |
| 101 | ++ | ○ | ++ | ++ |
| 102 | ++ | ++ | ++ | ++ |
| 103 | + | ○ | ++ | ++ |
| 104 | + | + | ++ | ++ |
| 105 | ++ | ○ | ++ | ++ |
| 106 | + | ○ | + | + |
| 107 | + | + | ++ | ++ |
| 108 | +++ | ++ | +++ | +++ |
| 109 | +++ | + | +++ | +++ |
| 110 | ○ | ○ | ○ | ○ |
| 111 | ○ | ○ | ○ | ○ |
| 120 | + | ○ | ++ | ++ |
| 123 | +++ | ++ | +++ | +++ |
| 124 | + | ++ | ++ | ++ |
| 125 | ++ | ++ | ++ | ++ |
| 126 | + | ++ | ++ | ++ |
| 127 | ++ | ++ | ++ | ++ |
| 128 | ++ | ++ | ++ | ++ |
| 129 | +++ | +++ | +++ | +++ |
| 146 | +++ | +++ | +++ | +++ |
| 148 | +++ | +++ | +++ | +++ |
| 156 | +++ | +++ | +++ | +++ |
| 157 | +++ | +++ | +++ | +++ |
| 158 | +++ | +++ | +++ | +++ |
| 159 | +++ | +++ | +++ | +++ |
| 160 | +++ | +++ | +++ | +++ |
| 161 | +++ | +++ | +++ | +++ |
| 162 | +++ | +++ | +++ | +++ |
| 163 | +++ | +++ | +++ | +++ |
| 175 | +++ | +++ | +++ | +++ |
| 176 | +++ | +++ | +++ | +++ |
| 177 | +++ | +++ | +++ | +++ |
| 178 | +++ | +++ | +++ | +++ |
| 179 | +++ | +++ | +++ | +++ |
| 180 | +++ | +++ | +++ | +++ |
| 181 | +++ | +++ | +++ | +++ |
| 182 | +++ | +++ | +++ | +++ |
| 183 | +++ | +++ | +++ | +++ |
| 184 | +++ | +++ | +++ | +++ |
| 211 | +++ | +++ | +++ | +++ |
| 228 | +++ | +++ | +++ | +++ |
| 229 | +++ | +++ | +++ | +++ |
| 230 | +++ | +++ | +++ | +++ |
| 231 | +++ | +++ | +++ | +++ |
| 232 | +++ | +++ | +++ | +++ |
| 233 | +++ | +++ | +++ | +++ |
| 234 | +++ | +++ | +++ | +++ |
| 240 | +++ | +++ | +++ | +++ |
| 241 | + | ○ | + | + |
| 242 | + | ○ | + | + |

Example 243-2: Enzyme Assays

The kinase activities of the compounds of the invention were measured using the 33PanQinase® Assay Service provided by ProQinase GmbH, Freiburg, Germany. Details of the assay conditions are disclosed on the website of ProQinase (https://www.proginase.com/products-services-biochemical-assay-services/kinase-assays). In brief, all kinase assays were performed in 96-well FlashPlates™ from PerkinElmer (Boston, MA, USA) in a 50 μl reaction volume. The reaction cocktail was pipetted in four steps in the following order:
  20 μl of assay buffer (standard buffer)
  5 μl of ATP solution (in H$_2$O)
  5 μl of test compound (in 10% DMSO)
  20 μl enzyme/subtrate mix The assay for all protein kinases contained 70 mM HEPES-NaOH pH7.5, 3 mM MgCl$_2$, 3 mM MnCl$_2$, 3 μM Na-orthovanadate, 1.2 mM DTT, 50 μg/ml PEG20000, ATP (variable concentrations, corresponding to the apparent ATP-Km of the respective kinase), [γ-33P]-ATP (approx. 8×1005 cpm per well), protein kinase and substrate.

The reaction cocktails were incubated at 30° C. for 60 minutes. The reaction is stopped with 50 μl of 2% (v/v) $H_3PO_4$, plates were aspirated and washed two times with 200 μl 0.9% (w/v) NaCl. Incorporation of $^{33}Pi$ was determined with a microplate scintillation counter (Microbeta, Wallac).

All assays were performed with a BeckmanCoulter/SA-GIAN™ Core System.

In case of single concentration assays, the potency of the test compound is expressed as % residual activity. For determination of IC50-values, serial dilutions in the final concentration range between 100 μM and 3 nM (10 concentrations) were tested. The fitting model for the IC50 determinations was "Sigmoidal response (variable slope)" with parameters "top" fixed at 100% and "bottom" at 0%. The fitting method used was a least-squares fit.

MKK4 Potency:

Inhibition potency against MKK4 is categorized as follows:

Assay at single concentration (100 nM):

| | category |
|---|---|
| Residual activity < 50%: | +++ |
| 50% ≤ Residual activity < 70%: | ++, |
| 70% ≤ Residual activity < 90% | + |
| Residual activity ≥ 90% | ○ |

Assays with determination of $IC_{50}$-values:

| | category |
|---|---|
| $IC_{50}$ < 100 nM: | +++ |
| 100 nM < $IC_{50}$ < 1 μM: | ++ |
| 1μM < $IC_{50}$ < 10 μM: | + |
| $IC_{50}$ > 10 μM: | ○ |

Selectivity of test compounds against BRaf, JNK1 and MKK7, altogether denominated as off-targets was calculated by the ratio of IC50 (off-target)/IC50 (MKK4) and categorized as follows:

| | Category |
|---|---|
| $IC_{50}$(off-target)/$IC_{50}$(MKK4) > 100 | +++ |
| 100 ≥ $IC_{50}$(off-target)/$IC_{50}$(MKK4) > 10 | ++ |
| 10 ≥ $IC_{50}$(off-target)/$IC_{50}$(MKK4) > 3 | + |
| 3 ≥ $IC_{50}$(off-target)/$IC_{50}$(MKK4) | ○ |

TABLE 8

Biochemical potency of representative Examples to MKK4 and selectivity against BRaf, MKK7 and JNK1, based on inhibition of enzyme activity at a single concentration or on $IC_{50}$-values.

| | | Potency | Selectivity | | |
|---|---|---|---|---|---|
| Example | assay | MKK4 | Braf | JNK1 | IVIKK7 |
| 2b | 100 nM | + | N/D | N/D | N/D |
| 2c | IC50 | +++ | ++ | ++ | +++ |
| 2d | 100 nM | + | N/D | N/D | N/D |
| 2e | IC50 | ++ | ++ | + | +++ |
| 2f | 100 nM | + | N/D | N/D | N/D |
| 2g | IC50 | ++ | ○ | + | +++ |
| 2h | IC50 | ++ | + | ++ | ++ |
| 27 | IC50 | ++ | ○ | ○ | +++ |
| 32 | 100 nM | + | N/D | N/D | N/D |
| 33 | 100 nM | + | N/D | N/D | N/D |
| 34 | 100 nM | + | N/D | N/D | N/D |
| 35 | 100 nM | ++ | N/D | N/D | N/D |
| 36 | 100 nM | + | N/D | N/D | N/D |
| 37 | 100 nM | + | N/D | N/D | N/D |
| 38 | 100 nM | + | N/D | N/D | N/D |
| 39 | 100 nM | + | N/D | N/D | N/D |
| 40 | 100 nM | + | N/D | N/D | N/D |
| 41 | 100 nM | + | N/D | N/D | N/D |
| 42 | 100 nM | + | N/D | N/D | N/D |
| 43 | 100 nM | + | N/D | N/D | N/D |
| 44 | 100 nM | + | N/D | N/D | N/D |
| 45 | IC50 | ++ | ○ | ++ | +++ |
| 46 | IC50 | ++ | + | + | +++ |
| 47 | IC50 | + | N/D | N/D | N/D |
| 48 | IC50 | + | ○ | ○ | ++ |
| 49 | IC50 | + | N/D | ++ | ++ |
| 50 | IC50 | ++ | ○ | ○ | +++ |
| 51 | 100 nM | + | N/D | N/D | N/D |
| 52 | 100 nM | + | N/D | N/D | N/D |
| 53 | IC50 | ++ | ○ | ○ | +++ |
| 54 | IC50 | ++ | ○ | ○ | +++ |
| 55 | IC50 | ++ | ○ | + | +++ |
| 56 | IC50 | ++ | ○ | ○ | +++ |
| 57 | IC50 | ++ | ○ | ○ | +++ |
| 58 | IC50 | ++ | N/D | ○ | ++ |
| 59 | IC50 | ++ | ○ | + | +++ |
| 60 | IC50 | + | N/D | N/D | N/D |
| 61 | 100 nM | ○ | N/D | N/D | N/D |
| 62 | 100 nM | ○ | N/D | N/D | N/D |
| 63 | 100 nM | ++ | N/D | N/D | N/D |
| 64 | 100 nM | + | N/D | N/D | N/D |
| 65 | 100 nM | ○ | N/D | N/D | N/D |
| 66 | 100 nM | ○ | N/D | N/D | N/D |
| 67 | 100 nM | ○ | N/D | N/D | N/D |
| 68 | 100 nM | + | N/D | N/D | N/D |
| 69 | 100 nM | ++ | N/D | N/D | N/D |
| 70 | IC50 | ++ | ○ | ++ | +++ |
| 71 | IC50 | + | ○ | ○ | ++ |
| 74 | IC50 | ++ | ○ | + | +++ |
| 75 | IC50 | ++ | ○ | + | +++ |
| 76 | IC50 | ++ | ○ | + | +++ |
| 77 | IC50 | ++ | ○ | + | +++ |
| 78 | IC50 | ++ | ○ | + | +++ |
| 79 | IC50 | +++ | + | ++ | +++ |
| 80 | IC50 | +++ | ++ | ++ | +++ |
| 81 | IC50 | +++ | + | ++ | +++ |
| 82 | IC50 | ++ | ○ | + | +++ |
| 83 | IC50 | ++ | N/D | ○ | ++· |
| 84 | IC50 | ++ | N/D | ○ | +++ |
| 85 | IC50 | + | N/D | ○ | ++ |
| 86 | IC50 | + | N/D | ○ | ++ |
| 87 | IC50 | ○ | N/D | ○ | ○ |
| 88 | IC50 | ++ | N/D | ○ | ++ |
| 89 | IC50 | + | ○ | ○ | ++ |
| 90 | IC50 | + | ○ | ○ | ++ |
| 91 | IC50 | + | ○ | ○ | ++ |
| 92 | IC50 | + | ○ | ○ | ++ |
| 92 | IC50 | ++ | + | + | +++ |
| 93 | IC50 | ++ | ○ | ++ | +++ |
| 94 | IC50 | +++ | ○ | + | +++ |
| 95 | IC50 | ++ | ○ | ○ | +++ |
| 96 | 100 nM | ++ | N/D | N/D | N/D |
| 97 | IC50 | ++ | ○ | + | +++ |
| 98 | IC50 | + | ○ | + | ++ |
| 99 | IC50 | ++ | ○ | ○ | +++ |
| 100 | IC50 | ○ | N/D | ○ | ○ |

TABLE 8-continued

Biochemical potency of representative Examples to MKK4 and selectivity against BRaf, MKK7 and JNK1, based on inhibition of enzyme activity at a single concentration or on $IC_{50}$-values.

| Example | assay | Potency MKK4 | Selectivity Braf | JNK1 | IVIKK7 |
|---|---|---|---|---|---|
| 101 | IC50 | ++ | ○ | ○ | +++ |
| 102 | IC50 | ++ | ○ | + | +++ |
| 103 | IC50 | ++ | ○ | + | +++ |
| 105 | IC50 | ++ | ○ | ++ | +++ |
| 106 | IC50 | ++ | ○ | + | +++ |
| 107 | IC50 | ++ | ○ | + | +++ |
| 108 | IC50 | +++ | ○ | + | +++ |
| 109 | IC50 | ++ | ○ | + | +++ |
| 110 | IC50 | ++ | ○ | + | +++ |
| 111 | IC50 | ++ | ○ | + | +++ |
| 113 | IC50 | ++ | ○ | + | +++ |
| 114 | IC50 | ++ | ○ | + | +++ |
| 115 | IC50 | ++ | ○ | + | +++ |
| 116 | IC50 | ++ | ○ | ○ | +++ |
| 117 | IC50 | + | ○ | ○ | +++ |
| 118 | IC50 | ++ | ○ | + | +++ |
| 119 | IC50 | ++ | ○ | ○ | +++ |
| 120 | IC50 | ++ | N/D | ○ | ++ |
| 121 | IC50 | ++ | ○ | ○ | +++ |
| 122 | IC50 | ++ | ○ | ○ | +++ |
| 123 | IC50 | ++ | N/D | ○ | +++ |
| 124 | IC50 | ++ | +++ | ○ | +++ |
| 125 | IC50 | ++ | +++ | + | +++ |
| 126 | IC50 | ++ | +++ | + | +++ |
| 127 | IC50 | ++ | +++ | + | +++ |
| 128 | IC50 | ++ | +++ | + | +++ |
| 129 | IC50 | ++ | ++ | + | +++ |
| 130 | IC50 | ++ | ++ | ++ | +++ |
| 131 | IC50 | ++ | ++ | ++ | +++ |
| 132 | IC50 | ++ | ++ | ○ | +++ |
| 133 | IC50 | ++ | ++ | ○ | +++ |
| 134 | IC50 | + | ○ | ○ | ++ |
| 135 | IC50 | + | ○ | ○ | ++ |
| 136 | IC50 | + | ○ | ○ | ++ |
| 137 | IC50 | ++ | ○ | + | +++ |
| 138 | IC50 | + | ○ | ○ | ++ |
| 140 | IC50 | + | ○ | ○ | ++ |
| 141 | IC50 | ++ | ++ | +++ | +++ |
| 142 | IC50 | +++ | +++ | ++·+ | +++ |
| 143 | IC50 | +++ | +++ | ++ | +++ |
| 144 | IC50 | +++ | ++ | +++ | +++ |
| 145 | IC50 | ++ | ++ | ++ | +++ |
| 146 | IC50 | +++ | +++ | +++ | +++ |
| 147 | IC50 | +++ | ++ | +++ | +++ |
| 148 | IC50 | +++ | ++ | +++ | +++ |
| 149 | IC50 | ++ | ++ | ++ | +++ |
| 150 | IC50 | +++ | +++ | +++ | +++ |
| 151 | IC50 | ++ | ++ | ++ | +++ |
| 152 | IC50 | +++ | +++ | ++ | +++ |
| 153 | IC50 | +++ | +++ | ++ | +++ |
| 154 | IC50 | +++ | ++ | ++ | +++ |
| 155 | IC50 | ++·+ | +++ | ++ | +++ |
| 156 | IC50 | +++ | ++ | +++ | +++ |
| 157 | IC50 | +++ | +++ | +++ | +++ |
| 158 | IC50 | +++ | ++ | +++ | +++ |
| 159 | IC50 | +++ | ++ | +++ | +++ |
| 160 | IC50 | +++ | ++ | ++ | +++ |
| 161 | IC50 | +++ | ++ | ++ | +++ |
| 162 | IC50 | ++ | ++ | ++ | +++ |
| 163 | IC50 | +++ | ++ | ++ | +++ |
| 164 | IC50 | +++ | ++ | ++ | +++ |
| 165 | IC50 | +++ | +++ | +++ | +++ |
| 166 | IC50 | +++ | +++ | +++ | +++ |
| 167 | IC50 | +++ | +++ | +++ | +++ |
| 168 | IC50 | ++ | +++ | ++ | +++ |
| 169 | IC50 | +++ | +++ | +++ | +++ |
| 170 | IC50 | +++ | +++ | +++ | +++ |
| 171 | IC50 | +++ | +++ | +++ | +++ |
| 172 | IC50 | +++ | +++ | +++ | +++ |
| 173 | IC50 | +++ | +++ | ++ | +++ |
| 175 | IC50 | +++ | ++ | + | +++ |
| 176 | IC50 | +++ | ++ | +++ | +++ |
| 177 | IC50 | +++ | N/D | +++ | +++ |
| 178 | IC50 | +++ | N/D | +++ | +++ |
| 179 | IC50 | +++ | +++ | +++ | +++ |
| 180 | IC50 | +++ | +++ | +++ | +++ |
| 181 | IC50 | ++ | +++ | ++ | +++ |
| 182 | IC50 | +++ | +++ | +++ | +++ |
| 183 | IC50 | ++ | +++ | +++ | +++ |
| 184 | IC50 | ++ | +++ | ++ | +++ |
| 185 | IC50 | ++ | + | ++ | +++ |
| 186 | IC50 | +++ | +++ | +++ | +++ |
| 187 | IC50 | ++ | +++ | +++ | +++ |
| 188 | IC50 | +++ | +++ | +++ | +++ |
| 189 | IC50 | ++ | ++ | ++ | +++ |
| 190 | IC50 | +++ | +++ | +++ | +++ |
| 191 | IC50 | ++ | +++ | +++ | +++ |
| 192 | IC50 | ++ | +++ | ++ | +++ |
| 193 | IC50 | +++ | ++ | +++ | +++ |
| 194 | IC50 | ++ | ++ | ++ | +++ |
| 195 | IC50 | +++ | +++ | +++ | +++ |
| 196 | IC50 | +++ | +++ | +++ | +++ |
| 197 | IC50 | ++ | +++ | ++ | +++ |
| 198 | IC50 | ++ | ++ | ++ | +++ |
| 199 | IC50 | +++ | ++ | ++ | +++ |
| 200 | IC50 | + | + | + | +++ |
| 201 | IC50 | +++ | +++ | +++ | +++ |
| 202 | IC50 | +++ | ++ | +++ | +++ |
| 203 | IC50 | +++ | ++ | +++ | +++ |
| 204 | IC50 | ++ | ++ | +++ | +++ |
| 205 | IC50 | ++ | ++ | ++ | +++ |
| 206 | IC50 | +++ | +++ | +++ | +++ |
| 207 | IC50 | ++ | +++ | ++ | +++ |
| 208 | IC50 | +++ | ++ | +++ | ++ |
| 209 | IC50 | +++ | +++ | +++ | +++ |
| 210 | IC50 | + | ++ | + | ++ |
| 211 | IC50 | ++ | +++ | ++ | +++ |
| 212 | IC50 | ++ | + | ○ | +++ |
| 213 | IC50 | +++ | +++ | ++ | +++ |
| 214 | IC50 | ++ | +++ | ++ | +++ |
| 215 | IC50 | ++ | ○ | + | +++ |
| 216 | IC50 | +++ | +++ | +++ | +++ |
| 217 | IC50 | +++ | +++ | +++ | +++ |
| 218 | IC50 | +++ | +++ | ++ | +++ |
| 219 | IC50 | ++·+ | +++ | ++ | +++ |
| 220 | IC50 | +++ | ++ | ++ | +++ |
| 221 | IC50 | +++ | +++ | ++ | +++ |
| 222 | IC50 | +++ | +++ | ++ | +++ |
| 223 | IC50 | +++ | + | ++ | +++ |
| 224 | IC50 | + | ○ | ○ | ++ |
| 225 | IC50 | +++ | +++ | ++ | +++ |
| 226 | IC50 | +++ | +++ | ++ | +++ |
| 227 | IC50 | +++ | +++ | +++ | +++ |
| 228 | IC50 | ++ | N/D | ++ | ++ |
| 229 | IC50 | +++ | +++ | +++ | +++ |
| 230 | IC50 | +++ | +++ | +++ | +++ |
| 231 | IC50 | +++ | ++ | ++ | +++ |
| 232 | IC50 | +++ | +++ | ++ | +++ |
| 233 | IC50 | +++ | ++ | +++ | +++ |
| 234 | IC50 | +++ | N/D | +++ | +++ |
| 235 | IC50 | +++ | +++ | +++ | +++ |
| 236 | IC50 | +++ | +++ | +++ | +++ |
| 237 | IC50 | +++· | +++ | +++ | +++ |
| 238 | IC50 | +++ | +++ | +++ | +++ |
| 239 | IC50 | +++ | +++ | ++ | +++ |
| 240 | IC50 | +++ | +++ | + | +++ |
| 241 | IC50 | + | N/D | ○ | + |
| 242 | IC50 | ○ | N/D | ○ | ++ |

The invention claimed is:
1. A compound having formula (Id)

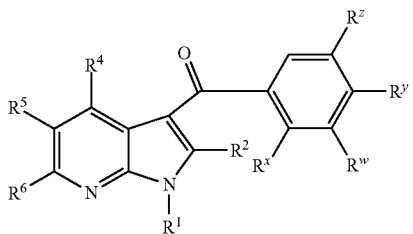

wherein
$R^1$ is H or alkyl;
$R^2$ is H or alkyl;
$R^4$ is H, or alkyl;
$R^6$ is H, or alkyl;
$R^w$ is —$NR^{10}SO_2R^{12}$;
$R^{10}$ is H, alkyl, or phenylalkyl;
$R^{12}$ is H, alkyl, haloalkyl or phenylalkyl, wherein the phenyl group is optionally substituted with 1 or 2 groups independently selected from alkyl and halogen;
$R^x$, $R^y$, and $R^z$ are selected from:
a) $R^x$ and $R^y$ are F and $R^z$ is H; and
b) $R^x$, $R^y$ and $R^z$ are F;
$R^5$ is selected from
(a) phenyl which is substituted with 1, 2 or 3 groups independently selected from
halogen,
alkyl,
alkoxy,
alkoxy wherein the alkyl group is substituted with 1, 2 or 3 hydroxy groups,
haloalkyl,
hydroxy,
—$SO_2NR^{10}R^{10}$,
—$CO_2R^{10}$,
—CN,
—$SF_5$,
—($NR^{10}$=)S(=O)-alkyl (S-alkyl sulfonimidoyl), and
1H- or 2H-tetrazolyl;
(b) naphthyl;
(c) a heteroaromatic 5- or 6-membered monocyclic group having 1 or 2 heteroatoms independently selected from O, N and S, wherein the heteroaromatic group is optionally substituted with 1, 2 or 3 groups independently selected from
alkyl,
haloalkyl,
cycloalkyl,
halogen,
hydroxy,
alkoxy, which is optionally substituted with —$NR^{10}R^{10}$,
—CN,
alkenyl,
alkynyl,
$R^{10}R^{10}$N—CO—)
alkyl-S(=O)(=$NR^{10}$)—,
cycloalkyl-$NR^{10}$—,
alkyl-$NR^{10}$—, wherein the alkyl group is substituted with hydroxy or alkoxy,
alkylsulfanyl,
benzimidazolyl,
and a non-aromatic heterocyclic 4-, 5- or 6-membered monocyclic group having 1 or 2 heteroatoms independently selected from O, and N, which heterocyclic group is optionally substituted with alkyl, hydroxyalkyl or hydroxy; and
(d) cycloalkyl,
or a pharmaceutically acceptable salt, solvate or optical isomer thereof.

2. The compound of claim 1 having formula (Ia)

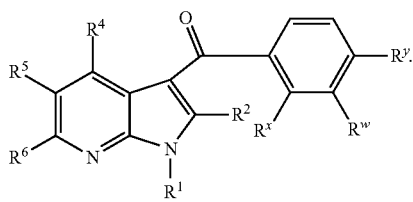

or a pharmaceutically acceptable salt, solvate or optical isomer thereof.

3. The compound of claim 2, wherein $R^5$ is selected from
(a) phenyl substituted with 1, 2 or 3 groups independently selected from
halogen,
alkyl,
alkoxy,
alkoxy wherein the alkyl group is substituted with 1, 2 or 3 hydroxy groups,
hydroxy,
—$SO_2NR^{10}R^{10}$,
—$CO_2R^{10}$,
CN,
—$SF_5$,)
alkyl-S(=O)(=$NR^{10}$)— (S-alkyl sulfonimidoyl), and
1H- or 2H-tetrazolyl,
(b) naphthyl;
(c) a heteroaromatic 5- or 6-membered monocyclic group having 1 or 2 heteroatoms independently selected from O, N and S, wherein the heteroaromatic group is optionally substituted with 1, 2 or 3 groups independently selected from
alkyl,
haloalkyl,
cycloalkyl,
—$NR^{10}R^{10}$,
halogen,
hydroxy,
alkoxy, which is optionally substituted with —$NR^{10}R^{10}$,
—CN,
alkenyl,
alkynyl,
$R^{10}R^{10}$N—CO—,
alkyl-S(=O)(=$NR^{10}$)—,
cycloalkyl-$NR^{10}$,
alkyl-$NR^{10}$—, wherein the alkyl group is substituted with hydroxy or alkoxy,
alkyl sulfanyl,
benzimidazolyl,
and a non-aromatic heterocyclic 4-, 5- or 6-membered monocyclic group having 1 or 2 heteroatoms independently selected from O, and N, which heterocyclic group is optionally substituted with alkyl, hydroxyalkyl or hydroxy, (d) cycloalkyl;

or a pharmaceutically acceptable salt, solvate or optical isomer thereof.

4. The compound of claim 1, wherein R¹, R², R⁴ and R⁶ are H, or a pharmaceutically acceptable salt, solvate or optical isomer thereof.

5. The compound of claim 1 selected from

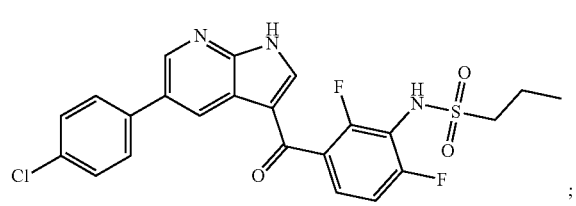
;

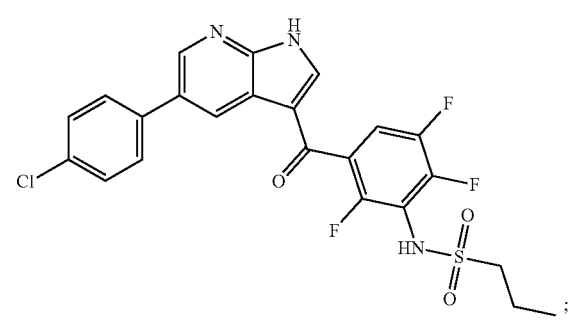
;

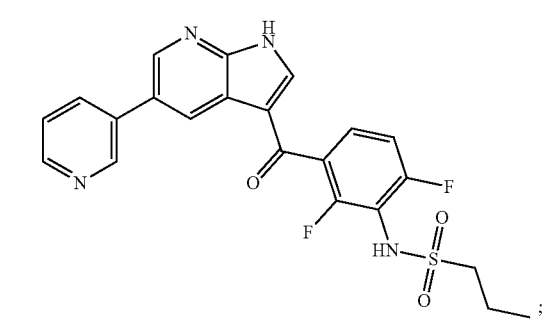
;

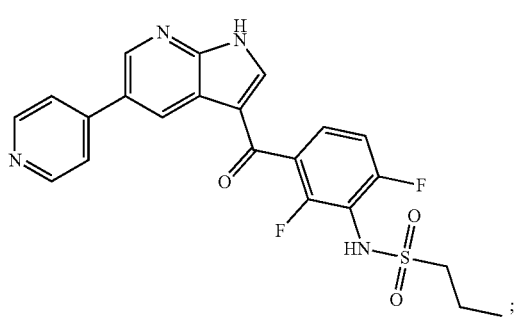
;

-continued

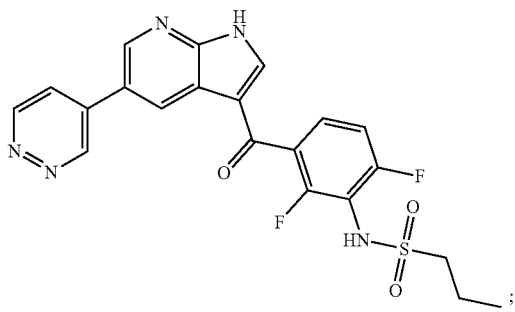
;

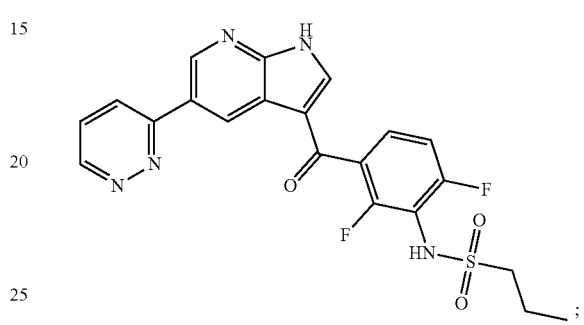
;

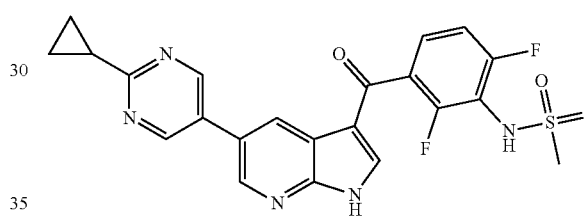
;

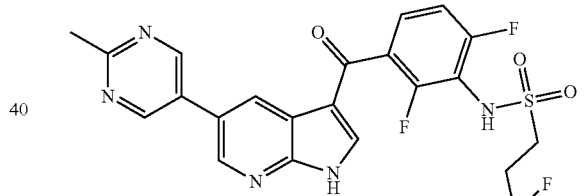
;

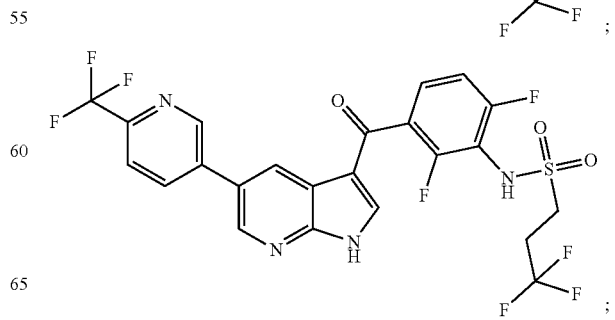
;

233
-continued
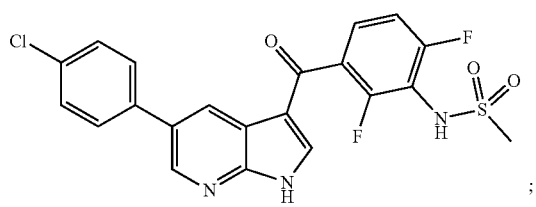
;
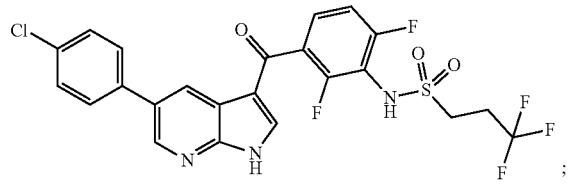
;
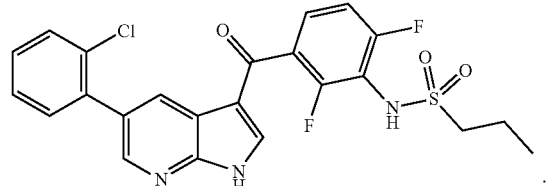
;
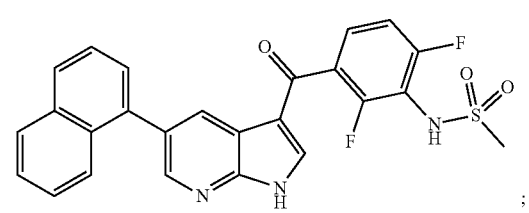
;
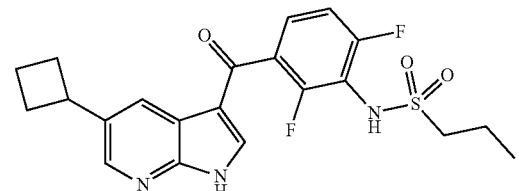
;
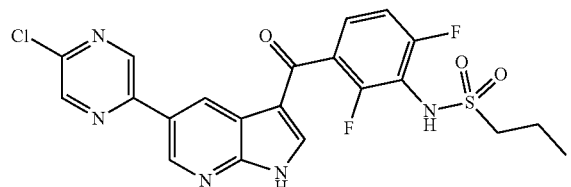
;
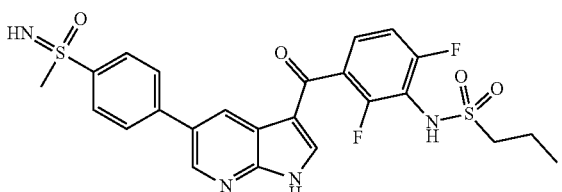
;
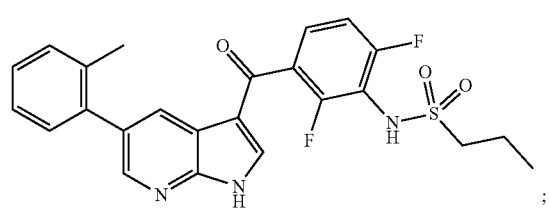
;
234
-continued
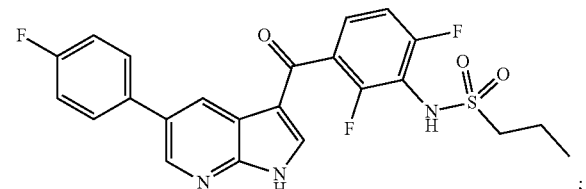
;
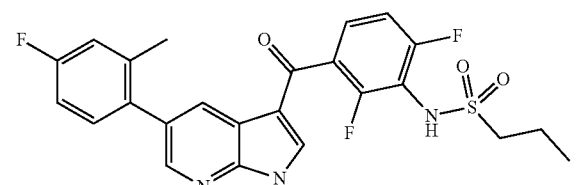
;
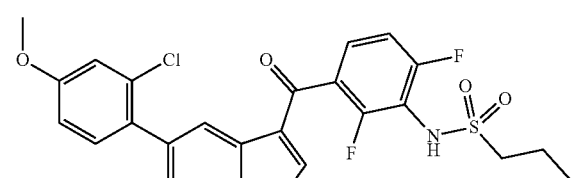
;

235
-continued
;
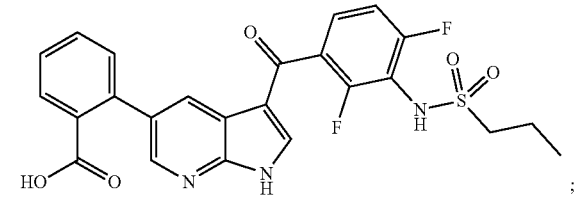
;
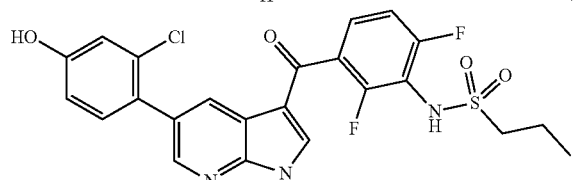
;
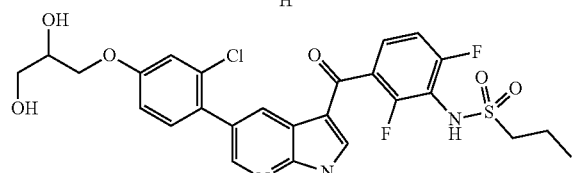
;
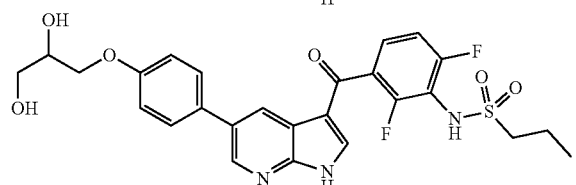
;
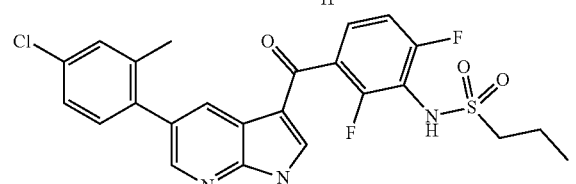
;
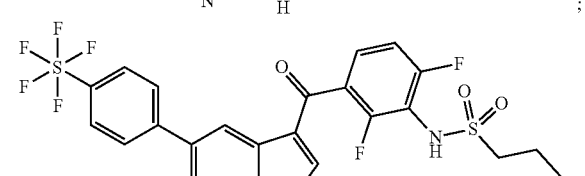
;
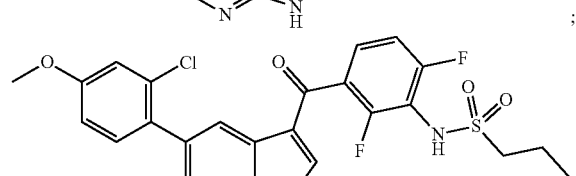
;
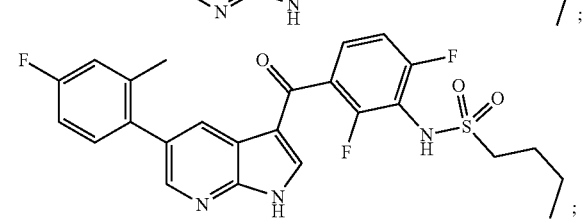
;
236
-continued
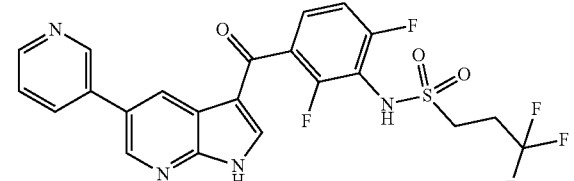
;
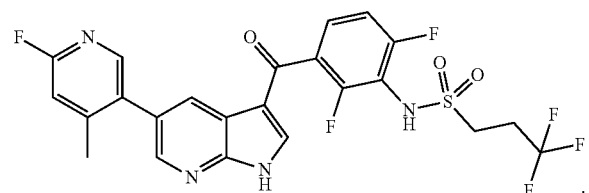
;
;
;
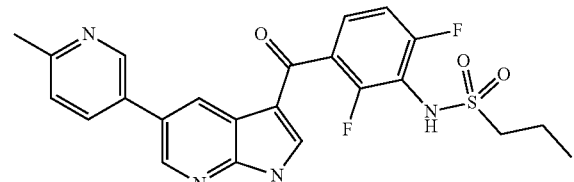
;
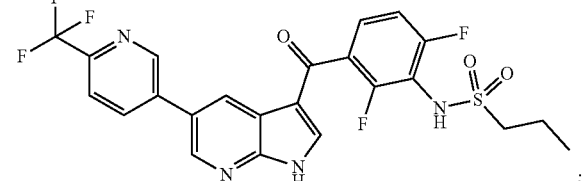
;
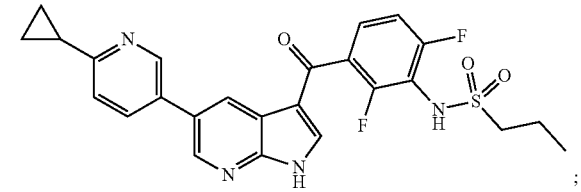
;
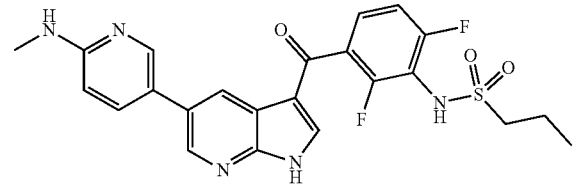
;

237
-continued
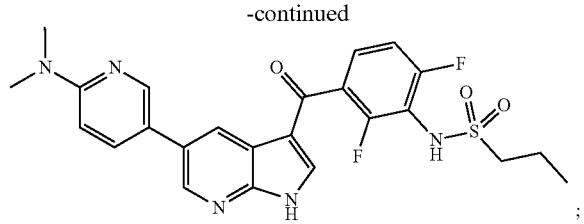
;
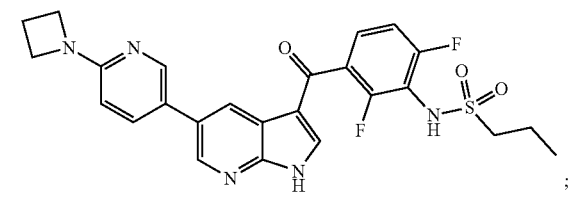
;
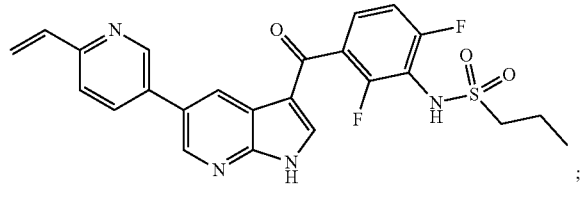
;
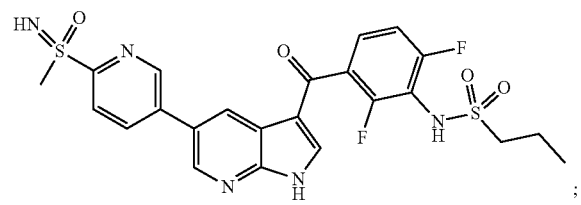
;
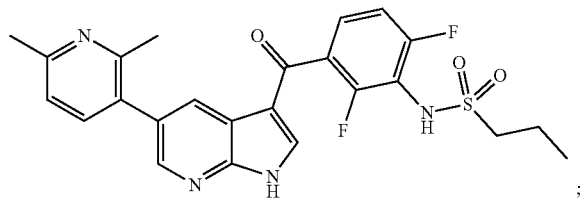
;
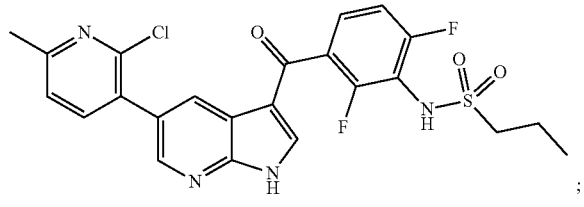
;
;
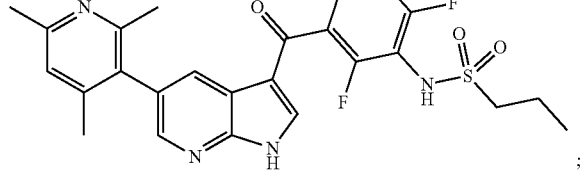
;
238
-continued
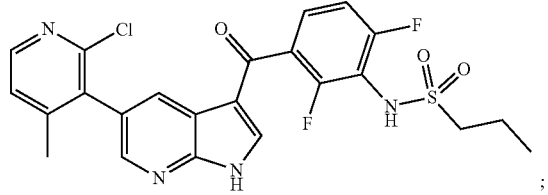
;
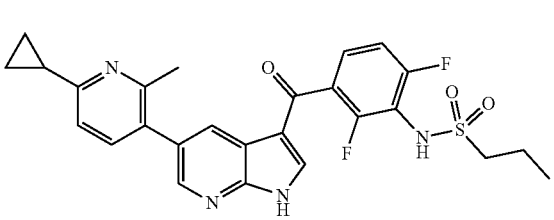
;
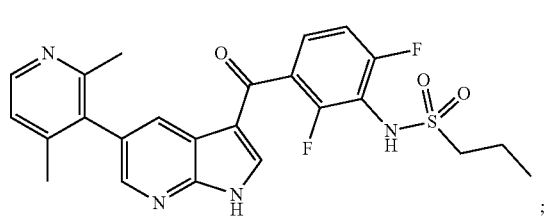
;
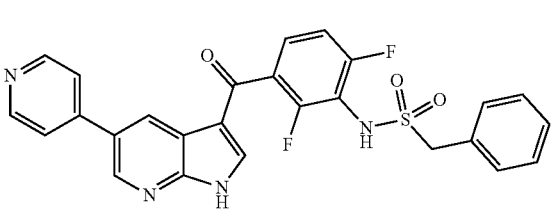
;
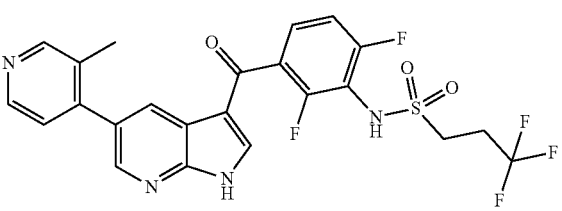
;
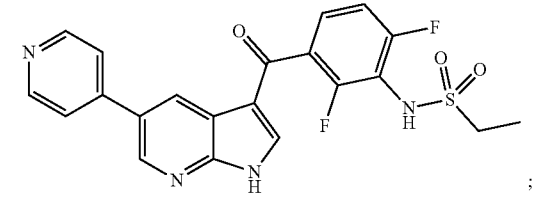
;
;
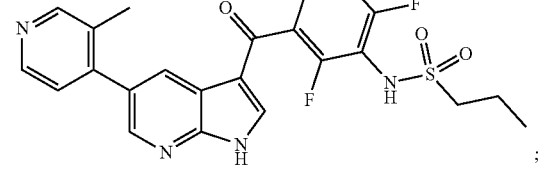
;

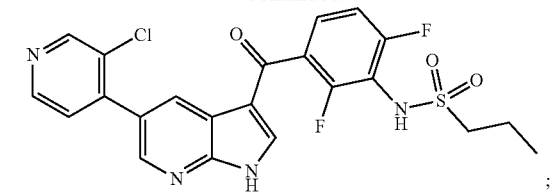
;
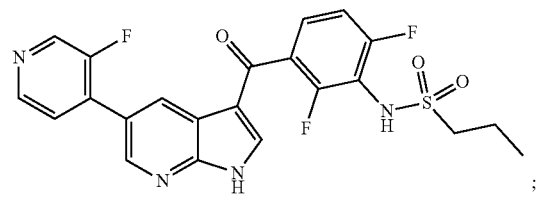
;
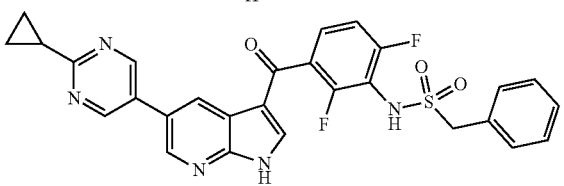
;
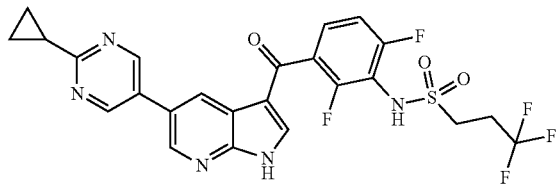
;
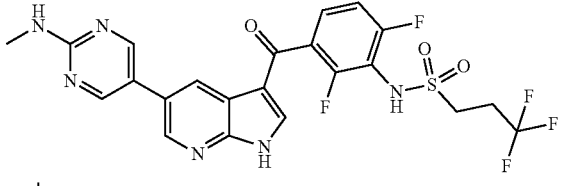
;
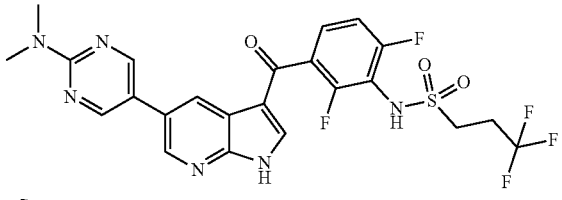
;
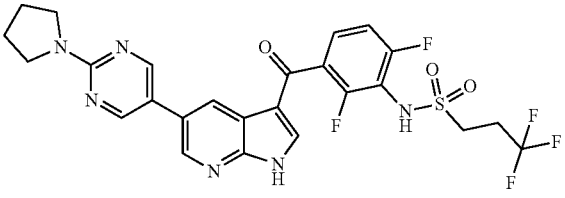
;
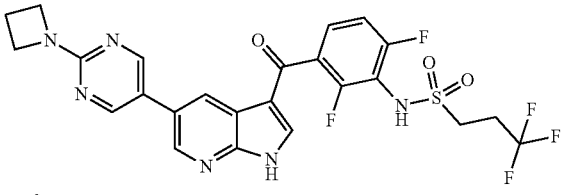
;
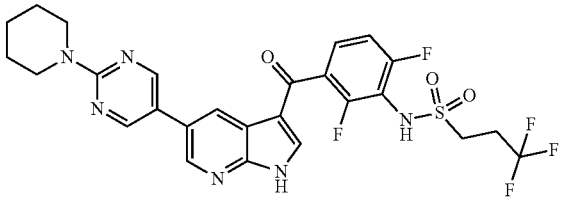
;
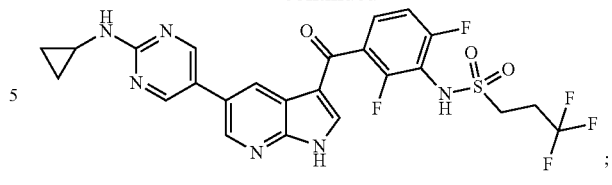
;
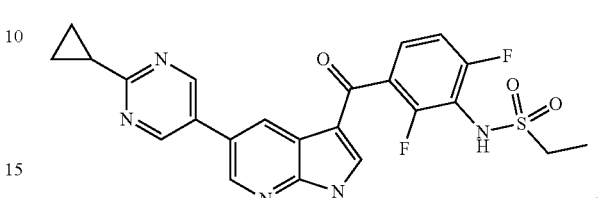
;
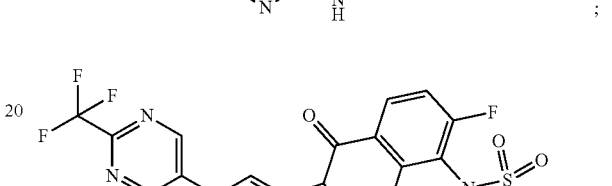
;
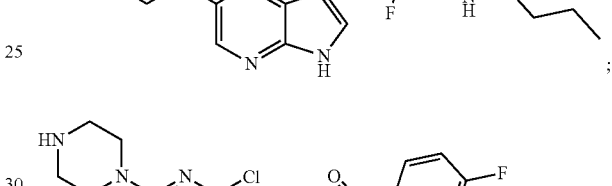
;
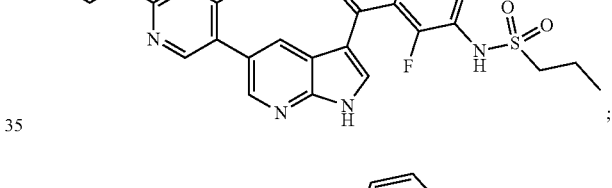
;
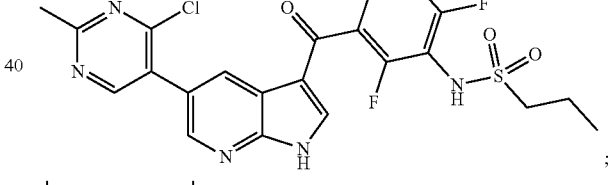
;
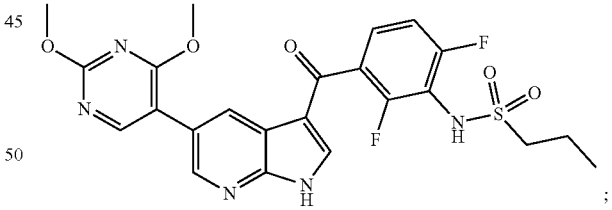
;
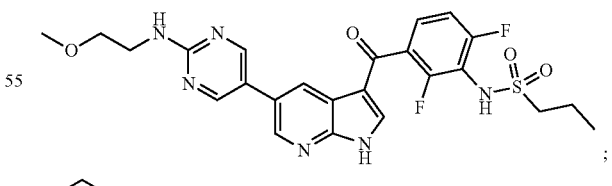
;
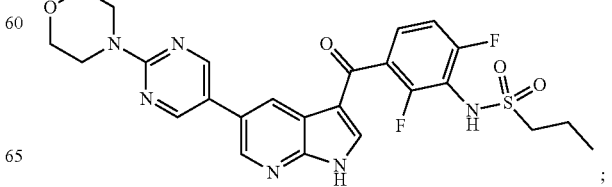
;

-continued

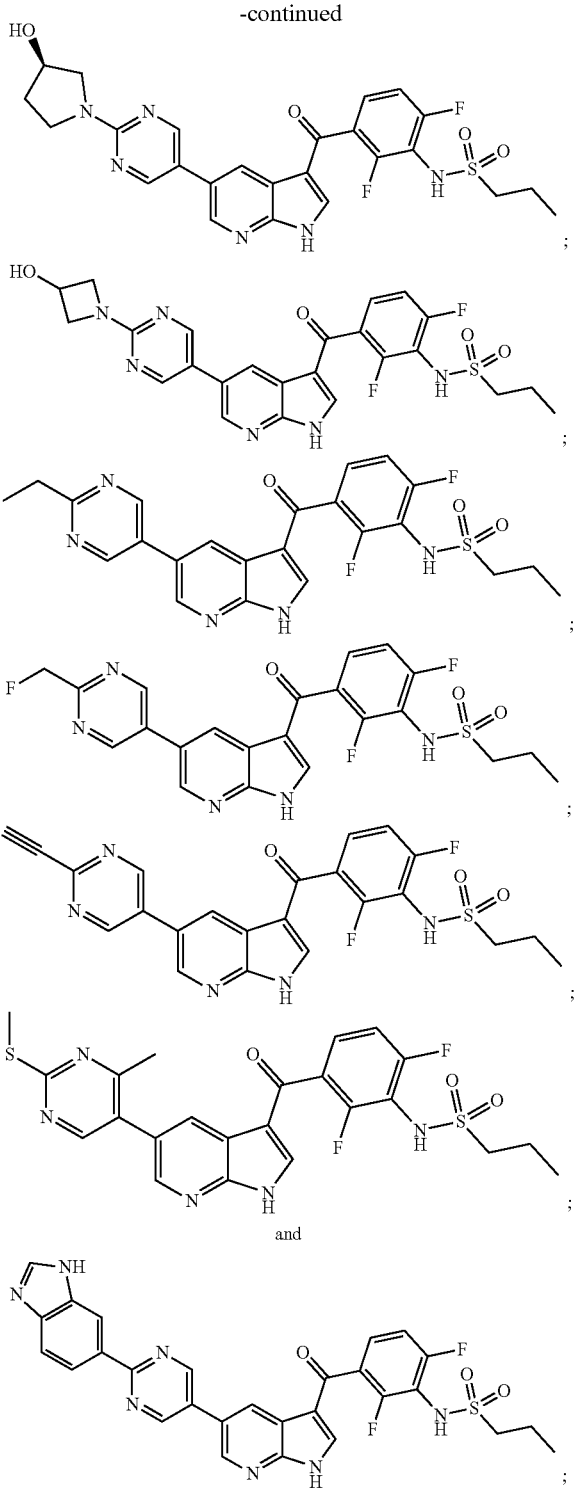

or a pharmaceutically acceptable salt, solvate or optical isomer thereof.

6. A pharmaceutical composition comprising a compound of claim 1 or a pharmaceutically acceptable salt, solvate or optical isomer thereof.

7. A method of selectively inhibiting protein kinase MKK4 over protein kinases JNK1 and MKK7 which comprises administering an effective amount of a compound of claim 1 or a pharmaceutically acceptable salt, solvate or optical isomer thereof to a subject in need thereof.

8. A method of promoting liver regeneration or preventing hepatocyte death which comprises administering an effective amount of a compound of claim 1 or a pharmaceutically acceptable salt, solvate or optical isomer thereof to a subject in need thereof.

9. The compound of claim 3, wherein the heteroaromatic 5- or 6-membered monocyclic group is selected from pyridyl and pyrimidinyl which group is optionally substituted with 1, 2 or 3 groups independently selected from
alkyl,
haloalkyl,
cycloalkyl,
—NR$^{10}$R$^{10}$,
halogen,
hydroxy,
alkoxy, which is optionally substituted with —NR$^{10}$R$^{10}$, —CN,
alkenyl,
alkynyl,
R$^{10}$R$^{10}$N—CO—,
alkyl-S(=O)(=NR$^{10}$)—,
cycloalkyl-NR$^{10}$—,
alkyl-NR$^{10}$—, wherein the alkyl group is substituted with hydroxy or alkoxy,
alkyl sulfanyl,
benzimidazolyl,
and
a non-aromatic heterocyclic 4-, 5- or 6-membered monocyclic group having 1 or 2 heteroatoms independently selected from O, and N, which heterocyclic group is optionally substituted with alkyl, hydroxyalkyl or hydroxy,
or a pharmaceutically acceptable salt, solvate or optical isomer thereof.

10. The compound of claim 9, wherein the heteroaromatic 5- or 6-membered monocyclic group is pyridyl which is optionally substituted with 1, 2 or 3 groups independently selected from halogen, alkyl, alkoxy, haloalkyl, cycloalkyl, —NR$^{10}$R$^{10}$ cycloalkyl-NR$^{10}$—, alkenyl, and alkyl-S(=O)(=NR$^{10}$)—, or a pharmaceutically acceptable salt, solvate or optical isomer thereof.

11. The compound of claim 9, wherein the heteroaromatic 5- or 6-membered monocyclic group is pyrimidinyl which is optionally substituted with 1 or 2 groups independently selected from
alkyl,
alkoxy which is optionally substituted with —NR$^{10}$R$^{10}$,
halogen,
alkyl-NR$^{10}$—, wherein the alkyl group is substituted with hydroxy or alkoxy,
—NR$^{10}$R$^{10}$,
haloalkyl,
cycloalkyl,
alkenyl,
—CN,
alkyl sulfanyl,
—NR$^{10}$R$^{10}$N—CO—,
cycloalkyl-NR$^{10}$—,
benzimidazolyl and
a non-aromatic heterocyclic 4-, 5- or 6-membered monocyclic group having 1 or 2 heteroatoms independently selected from O, and N, which heterocyclic group is optionally substituted with alkyl, hydroxyalkyl or hydroxyl, or a pharmaceutically acceptable salt, solvate or optical isomer thereof.

12. The compound of claim 11, wherein the pyrimidinyl is substituted with cycloalkyl, or a pharmaceutically acceptable salt, solvate or optical isomer thereof.

13. The compound of claim 11, wherein the pyrimidinyl is bound in the 5-position to the 1H-pyrrolo[2,3-b]pyridine and is substituted in the 2-position, or a pharmaceutically acceptable salt, solvate or optical isomer thereof.

14. The compound of claim 1, wherein $R^{12}$ is $C_1$-$C_4$-alkyl, $C_1$-$C_4$-haloalkyl, or benzyl, or a pharmaceutically acceptable salt, solvate or optical isomer thereof.

15. The compound of claim 4, wherein $R^{12}$ is $C_1$-$C_4$-alkyl, or a pharmaceutically acceptable salt, solvate or optical isomer thereof.

16. The compound of claim 1 having the formula

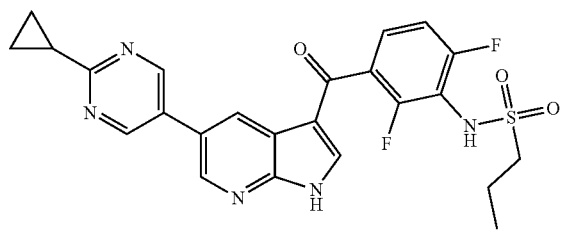 [SMILES: CCCS(=O)(=O)Nc1c(F)ccc(C(=O)c2c[nH]c3ncc(-c4cnc(C5CC5)nc4)cc23)c1F]

or a pharmaceutically acceptable salt or solvate thereof.

17. The compound of claim 1 having the formula

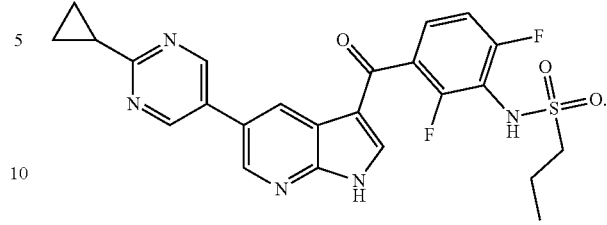

18. The compound of claim 1 having the formula

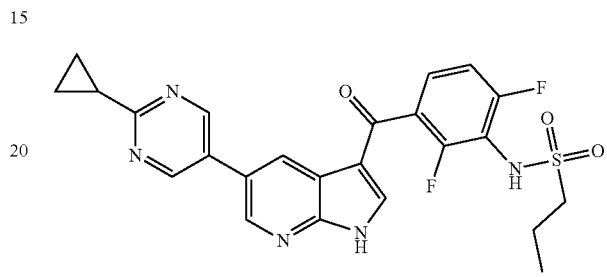

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 11,912,701 B2 | Page 1 of 2 |
| APPLICATION NO. | : 17/260519 | |
| DATED | : February 27, 2024 | |
| INVENTOR(S) | : Wolfgang Albrecht et al. | |

It is certified that error appears in the above-identified patent and that said Letters Patent is hereby corrected as shown below:

In the Claims

Column 229, Line 41, Claim 1, please delete "(S-alkyl sulfonimidoyl)," and insert
-- (S-alkylsulfonimidoyl), --;

Column 229, Lines 52-53, Claim 1, please delete "cycloalkyl, halogen," and insert -- cycloalkyl, $NR^{10}R^{10}$, halogen, --;

Column 229, Line 60, Claim 1, please delete "$R^{10}R^{10}N\text{-CO-}$)" and insert -- $R^{10}R^{10}N\text{-CO-}$, --;

Column 230, Line 37, Claim 3, please delete "-SF5,)" and insert -- -SF5, --;

Column 230, Line 38, Claim 3, please delete "(S-alkyl sulfonimidoyl)," and insert
-- (S-alkylsulfonimidoyl), --;

Column 230, Line 65, Claim 3, please delete "alkyl sulfanyl" and insert -- alkylsulfanyl --;

Column 240, Lines 28-35, Claim 5, please delete

"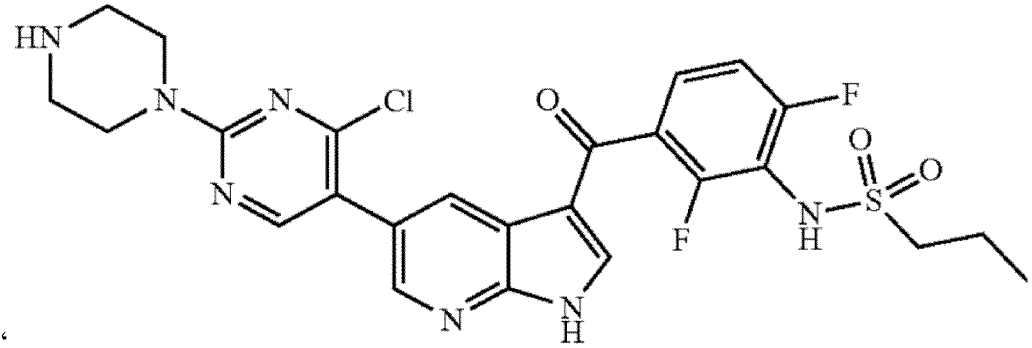" and insert

Signed and Sealed this
Twenty-fourth Day of September, 2024

Katherine Kelly Vidal
*Director of the United States Patent and Trademark Office*

CERTIFICATE OF CORRECTION (continued)
U.S. Pat. No. 11,912,701 B2

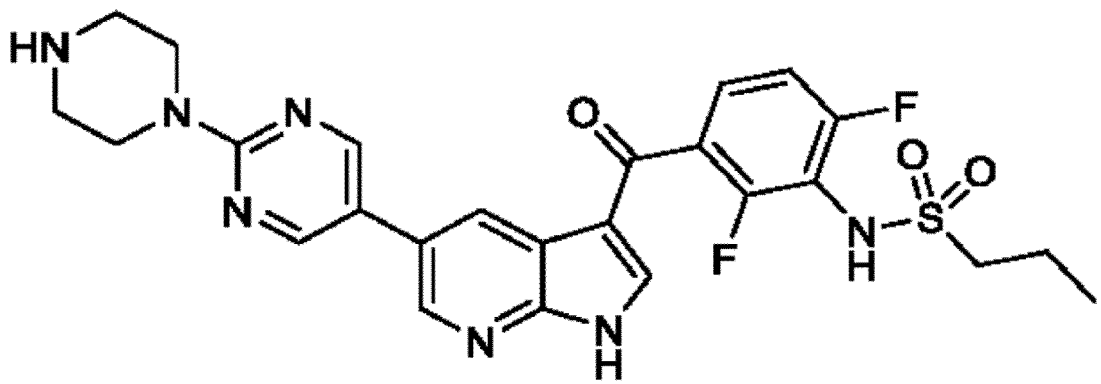

-- --;

Column 244, Line 10, Claim 9, please delete "which group is option" and insert -- which is option --;

Column 244, Line 58, Claim 11, please delete "alkyl sulfanyl" and insert -- alkylsulfanyl --;

Column 244, Line 59, Claim 11, please delete "-$NR^{10}R^{10}$-N-CO-" and insert
-- -$NR^{10}R^{10}$,
$R^{10}R^{10}$N-CO-, --; therefor.